US012527857B2

(12) United States Patent
Boyington et al.

(10) Patent No.: US 12,527,857 B2
(45) Date of Patent: *Jan. 20, 2026

(54) STABILIZED GROUP 2 INFLUENZA HEMAGGLUTININ STEM REGION TRIMERS AND USES THEREOF

(71) Applicant: The United States of America, as represented by the Secretary, Department of Health and Human Services, Bethesda, MD (US)

(72) Inventors: Jeffrey C. Boyington, Clarksburg, MD (US); Barney S. Graham, Smyrna, GA (US); John R. Mascola, Rockville, MD (US); Hadi M. Yassine, Doha (QA); Kizzmekia S. Corbett, Wheaton, MD (US); Syed M. Moin, Laurel, MD (US); Lingshu Wang, North Potomac, MD (US); Masaru Kanekiyo, Chevy Chase, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/491,193

(22) Filed: Oct. 20, 2023

(65) Prior Publication Data

US 2024/0050554 A1 Feb. 15, 2024

Related U.S. Application Data

(63) Continuation of application No. 17/742,201, filed on May 11, 2022, now Pat. No. 11,793,871, which is a continuation of application No. 16/329,592, filed as application No. PCT/US2017/049894 on Sep. 1, 2017, now Pat. No. 11,338,033.

(60) Provisional application No. 62/383,267, filed on Sep. 2, 2016.

(51) Int. Cl.

| | |
|---|---|
| ***A61K 39/145*** | (2006.01) |
| ***A61K 39/12*** | (2006.01) |
| ***A61P 31/16*** | (2006.01) |
| ***C07K 14/005*** | (2006.01) |
| ***C07K 14/195*** | (2006.01) |
| *A61K 39/00* | (2006.01) |

(52) U.S. Cl.

CPC ............ *A61K 39/145* (2013.01); *A61K 39/12* (2013.01); *A61P 31/16* (2018.01); *C07K 14/005* (2013.01); *C07K 14/195* (2013.01); *A61K 2039/55555* (2013.01); *C07K 2319/00* (2013.01); *C12N 2760/16122* (2013.01); *C12N 2760/16134* (2013.01)

(58) Field of Classification Search

CPC ... A61K 39/145; A61P 31/16; C07K 2319/00; C12N 2760/16134

See application file for complete search history.

(56) References Cited

U.S. PATENT DOCUMENTS

| | | | | |
|---|---|---|---|---|
| 7,094,598 | B2 | 8/2006 | Nabel et al. | |
| 7,097,841 | B2 | 8/2006 | Cater et al. | |
| 7,608,268 | B2 | 10/2009 | Carter et al. | |
| 9,441,019 | B2 | 9/2016 | Nabel et al. | |
| 9,452,211 | B2 | 9/2016 | Meijberg et al. | |
| 9,969,778 | B2 | 5/2018 | Meijberg et al. | |
| 10,137,190 | B2 | 11/2018 | Nabel et al. | |
| 11,338,033 | B2 * | 5/2022 | Boyington ........... | C07K 14/005 |
| 11,793,871 | B2 * | 10/2023 | Boyington ........... | C07K 14/195 |
| 2002/0054882 | A1 | 5/2002 | Okuno et al. | |
| 2003/0211996 | A1 | 11/2003 | Gowans et al. | |
| 2005/0042229 | A1 | 2/2005 | Yang et al. | |
| 2005/0108791 | A1 | 5/2005 | Edgerton | |
| 2006/0251679 | A1 | 11/2006 | Carter et al. | |
| 2007/0082054 | A1 | 4/2007 | Van Der Mooter et al. | |
| 2007/0224205 | A1 | 9/2007 | Powell et al. | |
| 2008/0299151 | A1 | 12/2008 | Fomsgaard | |
| 2009/0233377 | A1 | 9/2009 | Iwahori | |
| 2010/0137412 | A1 | 6/2010 | Zhou et al. | |
| 2010/0285982 | A1 | 11/2010 | Golding et al. | |
| 2010/0297174 | A1 | 11/2010 | Garcia-Sastre et al. | |

(Continued)

FOREIGN PATENT DOCUMENTS

| | | | |
|---|---|---|---|
| CN | 1668637 | A | 9/2005 |
| CN | 1694895 | A | 11/2005 |

(Continued)

OTHER PUBLICATIONS

A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.

(Continued)

*Primary Examiner* — Bao Q Li

(74) *Attorney, Agent, or Firm* — Klarquist Sparkman, LLP

(57) ABSTRACT

Vaccines that elicit broadly protective anti-influenza antibodies. The vaccines comprise nanoparticles that display HA trimers from Group 2 influenza virus on their surface. The nanoparticles are fusion proteins comprising a monomeric subunit (e.g., ferritin) joined to stabilized stem regions of Group 2 influenza virus HA proteins. The fusion proteins self-assemble to form the HA-displaying nanoparticles. Also provided are fusion proteins, and nucleic acid molecules encoding such proteins, and assays using nanoparticles of the invention to detect anti-influenza antibodies.

16 Claims, 92 Drawing Sheets

Specification includes a Sequence Listing.

(56) References Cited

U.S. PATENT DOCUMENTS

| | | | |
|---|---|---|---|
| 2011/0038025 A1 | 2/2011 | Naitou et al. |
| 2011/0059130 A1 | 3/2011 | Yusibov |
| 2011/0177122 A1 | 7/2011 | Nabel et al. |
| 2011/0212128 A1 | 9/2011 | Galarza et al. |
| 2014/0072958 A1 | 3/2014 | Nabel et al. |
| 2016/0303224 A1 | 10/2016 | Kanekiyo et al. |
| 2018/0021258 A1 | 1/2018 | Graham et al. |

FOREIGN PATENT DOCUMENTS

| | | | |
|---|---|---|---|
| CN | 103957891 A | 7/2014 |
| CN | 104185476 A | 12/2014 |
| CN | 105263516 A | 1/2016 |
| CN | 105849270 A | 8/2016 |
| EP | 1504037 B1 | 12/2009 |
| JP | 2015-502353 A | 1/2015 |
| JP | 2015-519348 A | 7/2015 |
| JP | 2016-525889 A | 9/2016 |
| WO | WO 2003/094849 A2 | 11/2003 |
| WO | WO 2004/007538 A2 | 1/2004 |
| WO | WO 2004/020454 A2 | 3/2004 |
| WO | WO 2009/109428 A2 | 9/2009 |
| WO | WO 2010/036948 A2 | 4/2010 |
| WO | WO 2010/117786 A1 | 10/2010 |
| WO | WO 2011/035422 A1 | 3/2011 |
| WO | WO 2011/044152 A1 | 4/2011 |
| WO | WO 2012/082634 A1 | 6/2012 |
| WO | WO 2012/162428 A1 | 11/2012 |
| WO | WO 2013/043729 A1 | 3/2013 |
| WO | WO 2013/044203 A2 | 3/2013 |
| WO | WO 2013/079473 A1 | 6/2013 |
| WO | WO 2013/177444 A2 | 11/2013 |
| WO | WO 2014/099931 A1 | 6/2014 |
| WO | WO 2014/191435 A1 | 12/2014 |
| WO | WO 2015/054639 A1 | 4/2015 |
| WO | WO 2015/063085 A1 | 5/2015 |
| WO | WO 2015/183969 A1 | 12/2015 |
| WO | WO 2016/005482 A1 | 1/2016 |
| WO | WO 2016/021209 A1 | 2/2016 |
| WO | WO 2018/005558 A1 | 1/2018 |
| WO | WO 2021/231729 A1 | 11/2021 |

OTHER PUBLICATIONS

GenBank Accession No. 3EGM_A submitted Sep. 11, 2008, 2 pages.

GenBank Accession No. AAP34324, submitted May 1, 2003, 2 pages.

Bachmann et al., "Neutralizing antiviral B cell responses," *Annu Rev Immunol.* 15: 235-270, 1997.

Benton et al., "Influenza hemagglutinin membrane anchor," *Proc Natl Acad Sci USA* 115.40: 10112-10117, Oct. 2018.

Bernacchioni et al. "Loop Electrostatics Modulates the Intersubunit Interactions in Ferritin," *ACS Chemical Biology* 9: 2517-2525, 2014.

Caton et al., "The antigenic structure of the influenza virus A/PR/8/34 hemagglutinin (H1 subtype)," *Cell* 31: 417-427, 1982.

Cohen et al., "Ferritin as an Endogenous MRI Reporter for Non-invasive Imaging Neoplasia of Gene Expression in C6 Glioma Tumors," *Neoplasia* 7.2: 109-117, Feb. 2005.

COLT38, UniProtKB COLT38_9INFB, Sep. 21, 2011 [online]. [Retrieved on Feb. 26, 2013]. Retrieved from the internet <URL: http://www.uniprot.org/uniprot/COLT38.txt?version=18>.

Corbett et al., "Design of Nanoparticulate Group 2 Influenza Virus Hemagglutinin Stem Antigens that Activate Unmuted Ancestor B Cell Receptors of Broadly Neutralizing Antibody Lineages," *mBio* 10.1: e02810-18, Jan./Feb. 2019 (27 pages).

Corti et al., "Heterosubtypic neutralizing antibodies are produced by individuals immunized with a seasonal influenza vaccine," *J Clin Invest.* 120: 1663-1673, 2010.

Corti et al., "A neutralizing antibody selected from plasma cells that binds to group 1 and group 2 influenza A hemagglutinins," *Science* 333: 850-856, 2011.

Dintzis et al., "Molecular determinants of immunogenicity: the immunon model of immune response," *Proc Natl Acad Sci USA* 73: 3671-3675, 1976.

Ehrenmann et al., "Amino Acids," *IMGT Aide-memoire: IMGT®, the International ImMunoGeneTics Information System®*, created Apr. 20, 2004, retrieved from internet <https://www.imgt.org/IMGTeducation/Aide-memoire/_UK/aminoacids/IMGTclasses.html>.

Ekiert et al., "A highly conserved neutralizing epitope on group 2 influenza A viruses," *Science* 333: 843-850, 2011.

Ekiert et al., "Antibody recognition of a highly conserved influenza virus epitope," *Science* 324: 246-251, 2009.

Greenstone et al., "Chimeric papillomavirus virus-like particles elicit antitumor immunity against the E7 oncoprotein in an HPV16 tumor model," *Proc. Natl. Acad. Sci. USA* 95: 1800-1805, Feb. 1998.

Harrison, "The Structure and Function of Ferritin," *Biochemical Education* 14.4: 154-162, 1986.

Haynes Jr., "Influenza virus-like particle vaccines," *Expert Rev Vaccines* 8: 435-445, 2009.

He et al., "Presenting native-like trimeric HIV-1 antigens with self-assembling nanoparticles," *Nature Communications* 7: 12041, Jun. 2016 (15 pages).

International Preliminary Report on Patentability for International (PCT) Patent Application No. PCT/US2017/049894, dated Mar. 14, 2019 (8 pages).

International Search Report and Written Opinion for PCT/US2017/049894, ISA European Patent Office, mailed Nov. 20, 2017 (11 pages).

Joyce et al., "Vaccine-Induced Antibodies that Neutralize Group 1 and Group 2 Influenza A Viruses," *Cell* 166.3: 609-623, Jul. 2016.

Kanekiyo et al., "Self-assembling influenza nanoparticle vaccines elicit broadly neutralizing H1N1 antibodies", *Nature* 499.7456: 102-106, Jul. 4, 2013.

Kanekiyo et al., "Rational Design of an Epstein-Barr Virus Vaccine Targeting the Receptor-Binding Site," *Cell* 162.5: 1090-1100, Aug. 2015.

Kang et al., "Influenza vaccines based on virus-like particles", *Virus Research* 143.2: 140-146, Aug. 2009.

Kashyap et al., "Combinatorial antibody libraries from survivors of the Turkish H5N1 avian influenza outbreak reveal virus neutralization strategies," *Proc Natl Acad Sci USA* 105: 5986-5991, 2008.

Kong et al., "Protective immunity to lethal challenge of the 1918 pandemic influenza virus by vaccination," *Proc Natl Acad Sci USA* 103: 15987-15991, 2006.

Kossovsky et al., "Nanocrystalline Epstein-Barr virus decoys," *Journal of Applied Biomaterials* 2.4: 251-259, Jan. 1991.

Krammer and Palese, "Influenza Virus Hemagglutinin Stalk-Based Antibodies and Vaccines," *Curr Opin Virol.* 3.5: 521-530, Oct. 2013.

Krause et al., "A broadly neutralizing human monoclonal antibody that recognizes a conserved, novel epitope on the globular head of the influenza H1N1 virus hemagglutinin," *J Virol* 85: 10905-10908, 2011.

Lambert et al., "Influenza vaccines for the future," *N Engl J Med.* 363: 2036-2044, 2010.

Lee et al., "Adaptations of nanoscale viruses and other protein cages for medical applications", *Nanomedicine*, 2.3: 137-149, Sep. 2006.

Lee et al., "Viruses and Virus-Like Protein Assemblies—Chemically Programmable Nanoscale Building Blocks," *Nano Res.* 2: 349-364, 2009.

Li et al., "Ferritin nanoparticle technology: A new platform for antigen presentation and vaccine development," Industrial Biotechnol 2, 143-147 (2006).

Lopez-Sagaseta et al., "Self-assembling protein nanoparticles in the design of vaccines," *Computational and Structural Biotechnology Journal* 14: 58-68, 2016.

Meldrum et al., "Magnetoferritin: in vitro synthesis of a novel magnetic protein," *Science* 257: 522-523, 1992.

Nabel et al., "Induction of unnatural immunity: prospects for a broadly protective universal influenza vaccine," *Nat Med.* 16: 1389-1391, 2010.

(56) References Cited

OTHER PUBLICATIONS

Ni et al., "Structural Insights into the Membrane Fusion Mechanism Mediated by Influenza Virus Hemagglutinin," *Biochemistry* 53.5: 846-854, 2014.
Okuno et al., "A common neutralizing epitope conserved between the hemagglutinins of influenza A virus H1 and H2 strains," *J Virol.* 67: 2552-2558, 1993.
Pulford et al., "Expression of the Epstein-Barr Virus Envelope Fusion Glycoprotein GB85 Gene by a Recombinant Baculovirus," *J Gen Virol.* 75.11: 3241-3248, Nov. 1994.
Roldao et al., "Virus-like particles in vaccine development," *Expert Rev Vaccines* 9: 1149-1176, 2010.
Ruiss et al., "A Virus-Like Particle-Based Epstein-Barr Virus Vaccine," *J Virol.* 85.24: 13105-13113, Dec. 2011.
Scorza et al., "Universal influenza vaccines: Shifting to better vaccines," *Vaccine* 34.26: 2926-2933, Mar. 2016.
Sheridan, "Flu vaccine makers upgrade technology—and pray for time," *Nat Biotechnol* 27: 489-491, 2009.
Steel et al., "Influenza Virus Vaccine Based on the Conserved Hemagglutinin Stalk Domain," *MBIO, American Society for Microbiology* 1.1: e00018-10, May 2010 (9 pages).
Sui et al., "Structural and functional bases for broad-spectrum neutralization of avian and human influenza A viruses," *Nat Struct Mol Biol.* 16: 265-273, 2009.
Treanor et al., "Safety and immunogenicity of a recombinant hemagglutinin vaccine for H5 influenza in humans," *Vaccine* 19: 1732-1737, 2001.
Treanor, "Safety and immunogenicity of a baculovirus-expressed hemagglutinin influenza vaccine: a randomized controlled trial," *JAMA* 297.14: 1577-1582, Apr. 2007.
Vallhov et al., "Exosomes Containing Glycoprotein 350 Released by EBV-Transformed B Cells Selectively Target B Cells through CD21 and Block EBV Infection in Vitro," *J Immunol.* 186.1: 73-82, Jan. 2011.
Wang et al., "Broadly protective monoclonal antibodies against H3 influenza viruses following sequential immunization with different hemagglutinins," *PLoS Pathog.* 6.2: e1000796, 2010 (9 pages).
Wei et al., "Cross-neutralization of 1918 and 2009 influenza viruses: role of glycans in viral evolution and vaccine design," *Sci Transl Med.* 2.24: 24ra21, 2010 (17 pages).
Wei et al., "Induction of broadly neutralizing H1N1 influenza antibodies by vaccination," *Science* 329: 1060-1064, 2010.
Wei et al., "Comparative efficacy of neutralizing antibodies elicited by recombinant hemagglutinin proteins from avian H5N1 influenza virus," *J Virol.* 82: 6200-6208, 2008.
Whittle Jr. et al., "Broadly neutralizing human antibody that recognizes the receptor-binding pocket of influenza virus hemagglutinin," *Proc Natl Acad Sci USA* 108: 14216-14221, 2011.
WHO Reference on Animal Influenza Diagnosis and Surveillance, 2002, Department of Communicable Disease Surveillance and Response, World Health Organization.
Wu et al., "Mammalian expression of virus-like particles for advanced mimicry of authentic influenza virus," *PLoS One* 5: e9784, 2010 (17 pages).
Xiong et al., "PCR-based accurate synthesis of long DNA sequences," *Nat Protoc.* 1.2: 791-797, 2006.
Yamashita et al., "Ferritin in the field of nanodevices," *Biochim Biophys Acta* 1800: 846-857, 2010.
Yang et al., "Immunization by avian H5 influenza hemagglutinin mutants with altered receptor binding specificity," *Science* 317: 825-828, 2007.
Yassine et al., "Hemagglutinin-stem nanoparticles generate heterosubtypic influenza protection," *Nature Medicine* 21.9: 1065-1070, Sep. 2015.
Zhang et al., "Self-Assembly in the Ferritin Nano-Cage Protein Super Family," *Int. J. Mol. Sci.* 12: 5406-5421, 2011.
Zhang et al., "Universal Influenza Vaccines, a Dream to Be Realized Soon," *Viruses* 6: 1974-1991, 2014.

* cited by examiner

HA stabilized stem gp41 ferritin nanoparticles

FIG. 3A

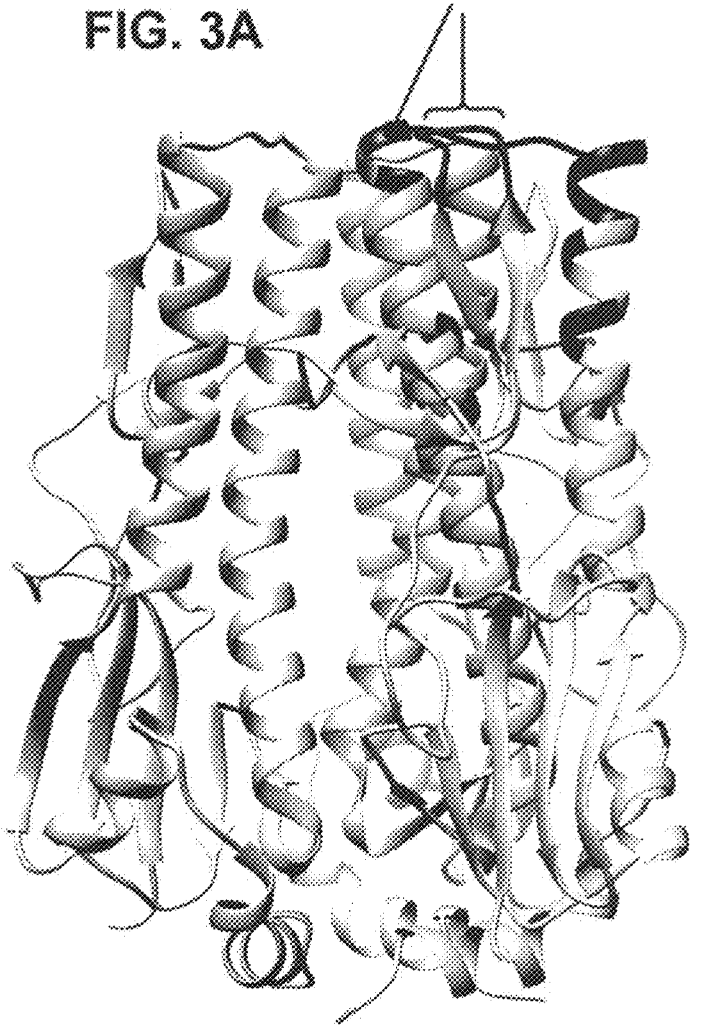

FIG. 3B

```
>H3-SS-np_231
MKTIIALSYILCLVFAQKLPGNDNSTATLCLGHHAVPNGTIVK
TITNDQIEVTNATELVFPGCGVLKLATGMRNVPEKQTRGIFGA
IAGFIENGWEGMVDGWYGFRHQNSEGIGQAADLKSTQAAINQI
NGMVNRVIALMAQGGPDCMLAELLVAILLNQHVIDLTDSEMRKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHAKKLIIFLNENNVPVQLTSIS
APEHKFEGLTQIFQKAYEHEQHISESINNIVDHAIKSKDHATF
NFLQWYVAEQHEEEVLFKDILDKIELIGNENHGLYLADQYVKG
IAKSRKSGS
```

FIG. 4A
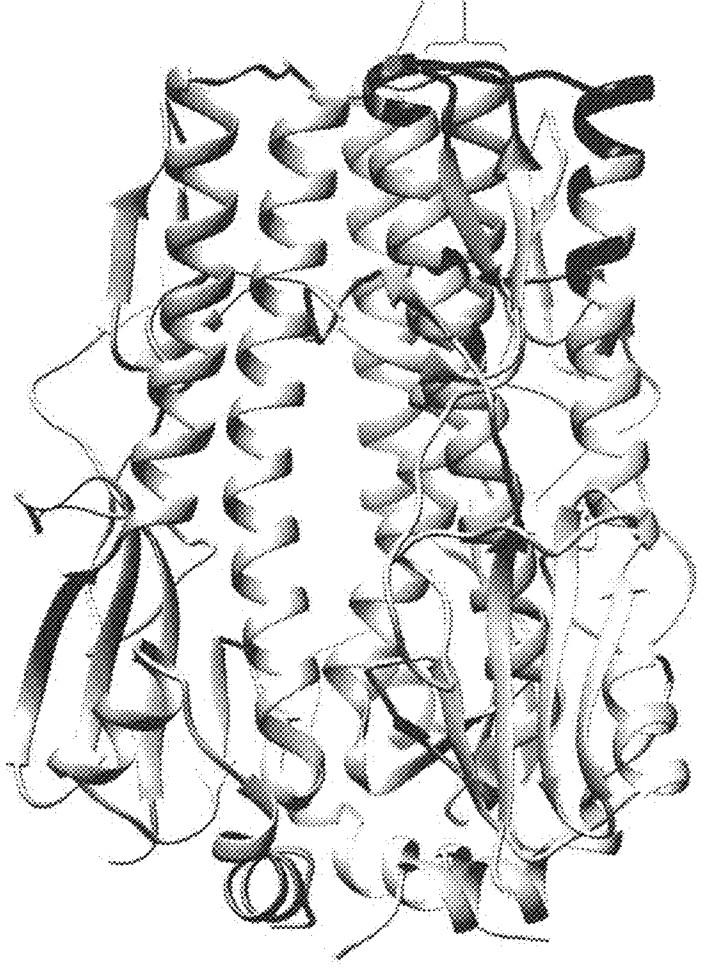
FIG. 4B
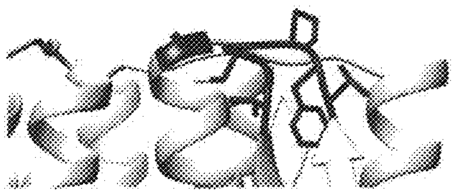
FIG 4C
Variations of the loop that replace the HA head
| | |
|---|---|
| TELVFPGCGVLKL | (H3 #231, H7 #16) |
| TELVFPGC-VLKL | (H3 #262, H7 #18) |
| TELVFP-CGVLKL | (H3 #264, H7 #20) |
| TELVFPNCGVLKL | (H3 #296, H7 #21) |
| TELCFNGIC-LKL | (H3 #249, H7 #27) |

>H3-SS-np_231
MKTIIALSYILCLVFAQKLPGNDNSTATLCLGHHAVPNGTIVK
TITNDQIEVTNATELVFPGCGVLKLATGMRNVPEKQTRGIFGA
IAGFIENGWEGMVDGWYGFRHQNSEGIGQAADLKSTQAAINQI
NGMVNRVIALMAQGGPDCMLAELLVAILNQHVIDLTDSEMRKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHAKKLIIFLNENNVPVQLTSIS
APEHKFEGLTQIFQKAYEHEQHISESINNIVDHAIKSKDHATF
NFLQWYVAEQHEEEVLFKDILDKIELIGNENHGLYLADQYVKG
IAKSRKSGS

FIG. 4D

FIG. 5A

HA2 membrane distal region between helices A and C replaced with short linker (GGPD)

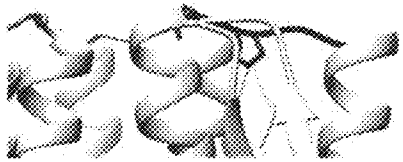

FIG. 5B

FIG. 5C

>H3-SS-np_231
MKTIIALSYILCLVFAQKLPGNDNSTATLCLGHHAVPNGTIVK
TITNDQIEVTNATELVFPGCGVLKLATGMRNVPEKQTRGIFGA
IAGFIENGWEGMVDGWYGFRHQNSEGIGQAADLKSTQAAINQI
NGMVNRVIALMAQGGPDCMLAELLVAILNQHVIDLTDSEMRKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHAKKLIIFLNENNVPVQLTSIS
APEHKFEGLTQIFQKAYEHEQHISESINNIVDHAIKSKDHATF
NFLQWYVAEQHEEEVLFKDILDKIELIGNENHGLYLADQYVKG
IAKSRKSGS

FIG. 6A

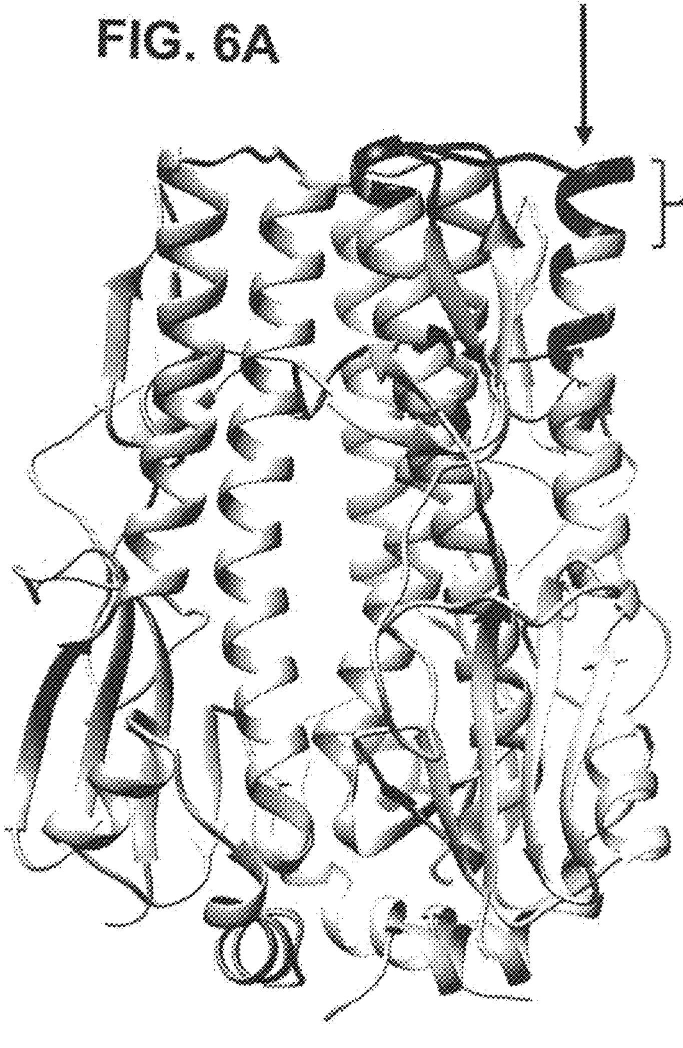

FIG. 6B

3. Five residue HA2 helix A extension (ALMAQ)

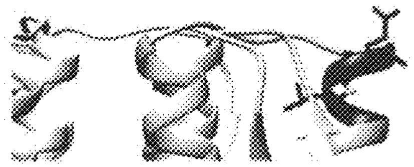

FIG. 6C

>H3-SS-np_231
MKTIIALSYILCLVFAQKLPGNDNSTATLCLGHHAVPNGTIVK
TITNDQIEVTNATELVFPGCGVLKLATGMRNVPEKQTRGIFGA
IAGFIENGWEGMVDGWYGFRHQNSEGIGQAADLKSTQAAINQI
NGMVNRVIALMAQGGPDCMLAELLVAILNQHVIDLTDSEMRKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHAKKLIIFLNENNVPVQLTSIS
APEHKFEGLTQIFQKAYEHEQHISESINNIVDHAIKSKDHATF
NFLQWYVAEQHEEEVLFKDILDKIELIGNENHGLYLADQYVKG
IAKSRKSGS

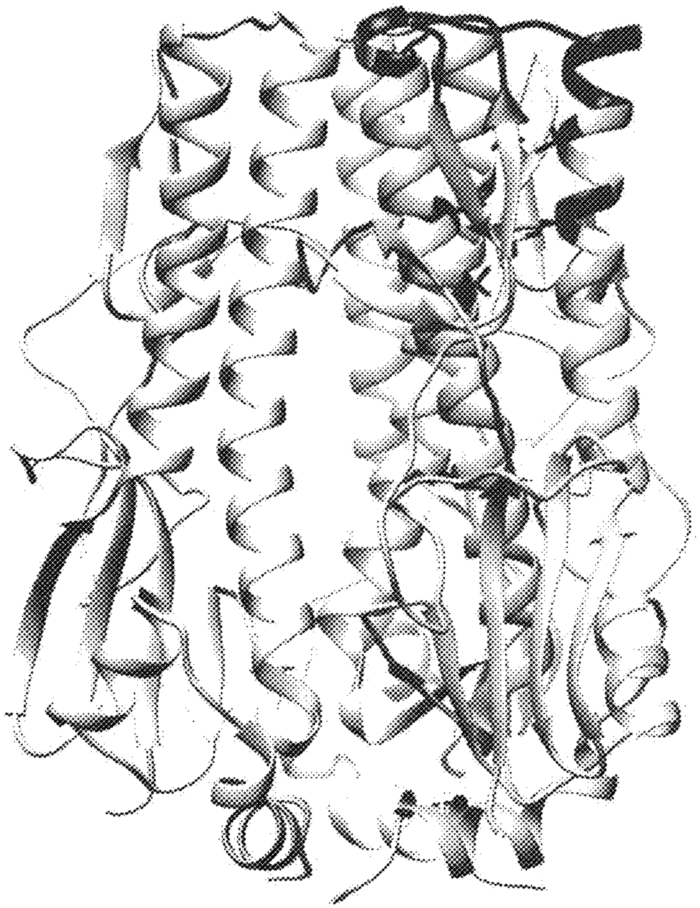

FIG. 7A

>H3-SS-np_231
MKTIIALSYILCLVFAQKLPGNDNSTATLCLGHHAVPNGTIVK
TITNDQIEVTNATELVFPGCGVLKLATGMRNVPEKQTRGIFGA
IAGFIENGWEGMVDGWYGFRHQNSEGIGQAADLKSTQAAINQI
NGMVNRVIALMAQGGPDCMLAELLVAILLNQHVIDLTDSEMRKL
FERTKKQLRENAEDMGNGCFKIYHKCDNACIGSIRNGTYDHDV
YRDEALNNRFQIKSGGDIIKLLNEQVNKEMQSSNLYMSMSSWC
YTHSLDGAGLFLFDHAAEEYEHAKKLIIFLNENNVPVQLTSIS
APEHKFEGLTQIFQKAYEHEQHISESINNIVDHAIKSKDHATF
NFLQWYVAEQHEEEVLFKDILDKIELIGNENHGLYLADQYVKG
IAKSRKSGS

FIG. 7B

Superose 6 10/30 gel filtration profile

Negative stain EM 2D class averages

| | EC50 (ug/ml) | |
|---|---|---|
| mAb | H1-SS-np | H3-SS-np_231 |
| D25 | --- | --- |
| CR8020 | 15.56 | 0.02 |
| CT149 | 0.03 | 0.03 |
| F16 | 0.14 | 0.08 |

| Fab | $K_D$ (M) | $K_D$ Error | $k_{on}$(1/Ms) |
|---|---|---|---|
| CT149 | 2.69E-09 | 2.66E-10 | 1.06E+06 |
| CR9114 | 6.41E-11 | 1.29E-09 | 2.00E+05 |

231

249

256

258

262 FIG. 11E
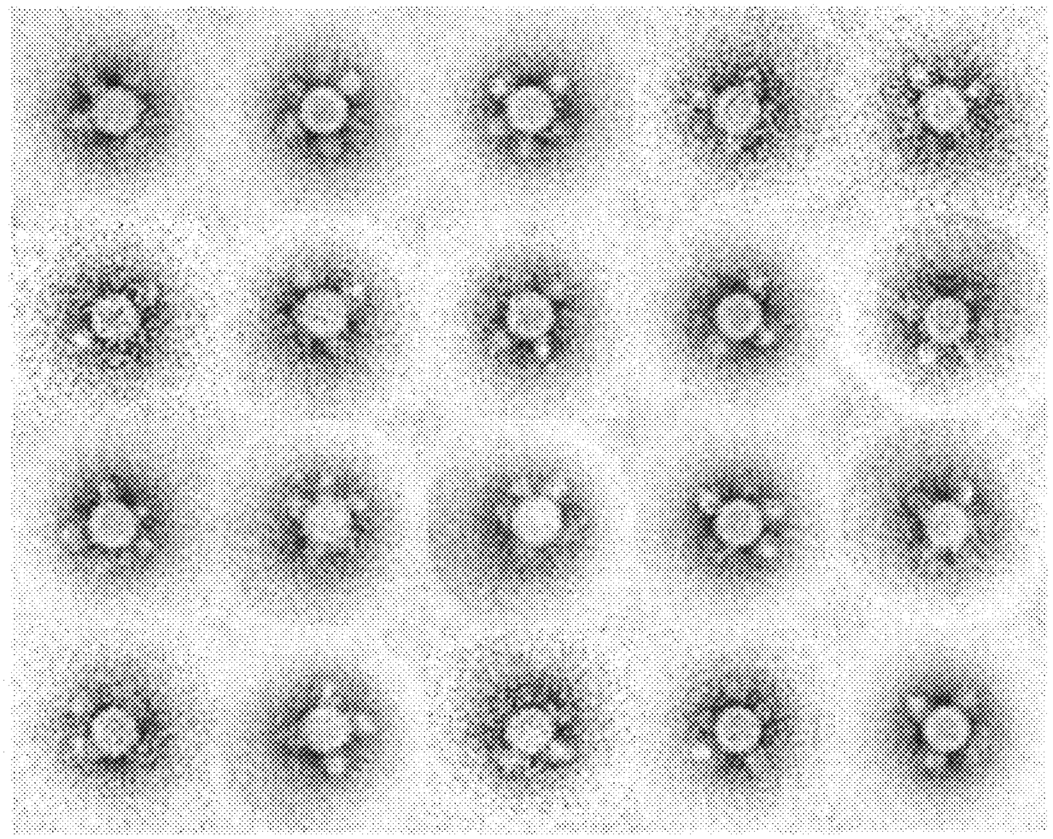
264 FIG. 11F
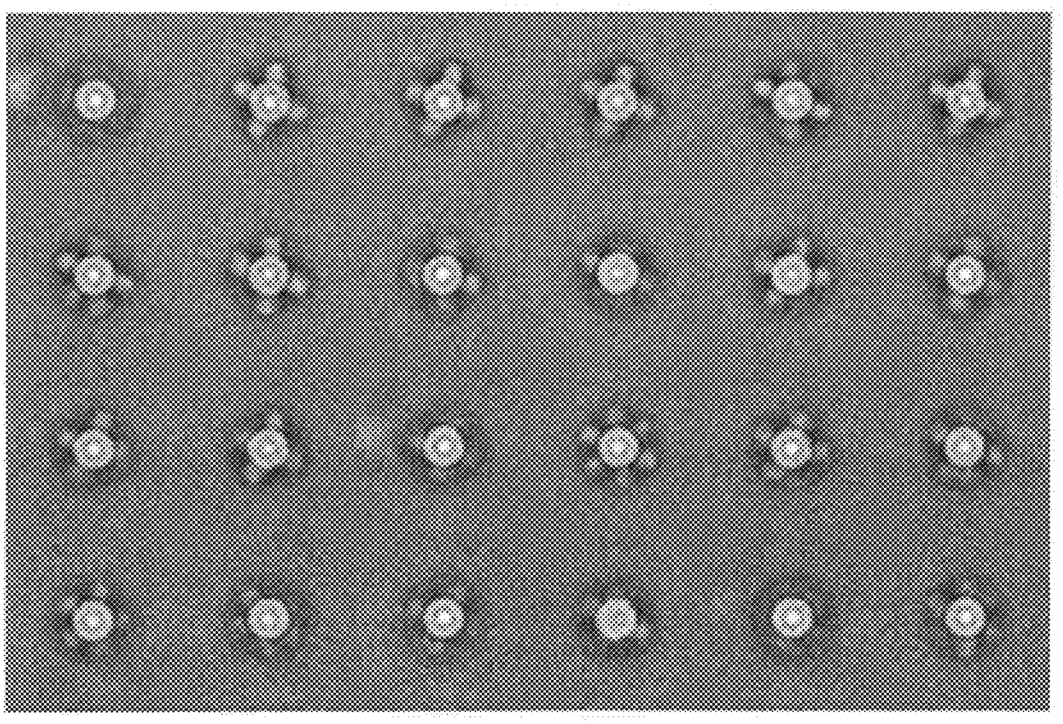

| H3-SS-np# | Antibody $EC_{50}$ (μg/ml) CR8020 | CT149 | FI6 |
|---|---|---|---|
| **249** | 0.036 | 0.013 | 0.024 |
| **256** | 0.050 | 0.020 | 0.022 |
| **258** | 0.060 | 0.140 | 0.028 |
| **262** | 0.039 | 0.019 | 0.022 |
| **264** | 0.041 | 0.010 | 0.026 |

ELISA characterization of H3-SS-np designs 235-265

| | | | | | | | | | | | | | |
|---|---|---|---|---|---|---|---|---|---|---|---|---|---|
| | | 96-well transfection Test - H3SSnp constructs #235 - #265 - ELISA Plate Key | | | | | | | | | | | |
| | | 1 | 2 | 3 | 4 | 5 | 6 | 7 | 8 | 9 | 10 | 11 | 12 |
| ELISA Plate key | A | neg. ctrl | FL H3 Np | H1-SS-np | 190 | 231 | 235 | 236 | 237 | 238 | 239 | 240 | 241 |
| | B | 242 | 243 | 244 | 245 | 246 | 247 | 248 | 249 | 250 | 251 | 252 | 253 |
| | C | 254 | 255 | 256 | 257 | 258 | 259 | 260 | 261 | 262 | 263 | 264 | 265 |
| | D | empty np | FL H3 Np | H1-SS-np | 231 | | | | | | | | |

| | | | | | | | | | | | | | |
|---|---|---|---|---|---|---|---|---|---|---|---|---|---|
| | | 96-well transfection Test - H3SSnp constructs #235 - #265 - Kinetic ELISA (5 minutes \| 8 reads) | | | | | | | | | | | |
| | | 1 | 2 | 3 | 4 | 5 | 6 | 7 | 8 | 9 | 10 | 11 | 12 |
| D25 (neg. ctrl) | A | 0.28 | -0.05 | 0.41 | 0.00 | 0.20 | 0.28 | 0.22 | 0.53 | 0.45 | 0.20 | 0.57 | -0.29 |
| | B | 0.22 | -0.12 | 0.30 | 0.29 | 0.08 | 0.40 | 0.41 | 1.53 | 0.19 | -0.54 | 0.11 | 0.00 |
| | C | 0.42 | 0.42 | 0.09 | 0.31 | 0.27 | 0.43 | 0.41 | 0.14 | 0.66 | 0.00 | 0.11 | 0.15 |
| | D | 0.21 | 0.49 | 0.37 | 0.28 | 0.64 | 0.56 | 0.59 | -0.09 | 0.39 | 0.48 | 0.82 | NoFit |
| FI6 | A | 0.46 | 1.79 | 5.79 | 0.85 | 2.65 | 0.39 | 0.41 | 0.63 | 0.67 | 0.87 | 2.41 | 0.88 |
| | B | 0.52 | 0.51 | 0.40 | 0.15 | 0.45 | 0.58 | -0.12 | 4.08 | 0.05 | 0.73 | 0.58 | 0.54 |
| | C | 0.59 | 0.40 | 8.89 | 0.26 | 2.38 | 2.46 | 2.46 | 3.80 | 3.55 | 0.87 | 3.88 | 7.33 |
| | D | 0.45 | 23.62 | 69.48 | 29.20 | 0.59 | 0.67 | NoFit | 0.46 | 0.49 | 0.80 | 0.55 | 0.41 |

| | | | | | | | | | | | | | |
|---|---|---|---|---|---|---|---|---|---|---|---|---|---|
| | | 96-well transfection Test - H3SSnp constructs #235 - #265 - Kinetic ELISA (5 minutes \| 8 reads) | | | | | | | | | | | |
| | | 1 | 2 | 3 | 4 | 5 | 6 | 7 | 8 | 9 | 10 | 11 | 12 |
| D25 (neg. ctrl) | A | 0.65 | 0.53 | 0.25 | 0.40 | 0.24 | 0.30 | 0.52 | 0.28 | 0.72 | 0.20 | 0.50 | 0.74 |
| | B | 0.49 | 0.42 | 0.38 | 0.43 | 0.33 | 0.34 | 0.27 | 0.42 | 5.34 | 0.60 | 0.81 | 0.68 |
| | C | 0.31 | 0.54 | -3.05 | 0.41 | 0.31 | 0.07 | 0.78 | 0.49 | 0.66 | 0.37 | 0.45 | 1.13 |
| | D | 1.42 | 1.05 | 1.21 | 1.36 | 0.39 | 0.33 | 0.43 | 0.77 | 1.13 | -0.14 | -2.21 | 2.33 |
| CT149 | A | 0.52 | 3.56 | 3.59 | 1.07 | 3.66 | 1.17 | 0.28 | 1.96 | 0.16 | 2.34 | 0.73 | -1.76 |
| | B | 0.09 | -0.33 | 0.31 | 0.29 | 0.34 | 0.43 | 0.07 | 12.43 | 0.33 | 0.66 | 0.29 | 1.48 |
| | C | 0.08 | -0.01 | 8.28 | 0.41 | 4.35 | 5.12 | 5.61 | 7.62 | 7.48 | 3.75 | 8.66 | 10.32 |
| | D | 0.39 | 11.20 | 115.53 | 75.59 | 0.25 | 0.08 | 0.36 | 0.18 | 0.12 | 0.67 | 0.57 | 0.25 |

Purified Protein Controls in row D: Ferritin nanoparticle (Empty np), Full length H3-np (FL H3 Np), H1-SS-np and H3-SS-np 231
Positive > 2.35

FIG. 13A

ELISA characterization of H3-SS-np designs 266-296

| | | 1 | 2 | 3 | 4 | 5 | 6 | 7 | 8 | 9 | 10 | 11 | 12 |
|---|---|---|---|---|---|---|---|---|---|---|---|---|---|
| Key | A | neg. ctrl | H1-SS-np | 231 | 266 | 267 | 268 | 269 | 270 | 271 | 272 | 273 | 274 |
| | B | 275 | 276 | 277 | 278 | 279 | 280 | 281 | 282 | 283 | 284 | 285 | 286 |
| | C | 287 | 288 | 289 | 290 | 291 | 292 | 293 | 294 | 295 | 231 protein | | |
| | | 1 | 2 | 3 | 4 | 5 | 6 | 7 | 8 | 9 | 10 | 11 | 12 |
| D25 (neg. ctrl) | A | NoFit | -0.1 | -0.3 | NoFit | 0.0 | 0.2 | -0.2 | 0.1 | 0.7 | -0.1 | -0.2 | 1.2 |
| | B | 0.5 | 0.2 | 0.3 | NoFit | 0.3 | NoFit | 0.5 | 1.9 | 0.2 | 0.5 | 0.2 | 0.3 |
| | C | -1.2 | 0.5 | NoFit | 0.0 | 0.3 | NoFit | -0.3 | 0.3 | -3.1 | 0.3 | | |
| | | 1 | 2 | 3 | 4 | 5 | 6 | 7 | 8 | 9 | 10 | 11 | 12 |
| CT149 | A | 0.1 | 1.2 | 1.2 | 4.9 | 5.2 | 5.5 | 4.9 | 2.5 | 1.5 | 3.2 | 0.7 | 1.8 |
| | B | 0.6 | 0.6 | 0.9 | 0.8 | 2.1 | 0.4 | 1.6 | 0.6 | 0.3 | 0.5 | 0.1 | -3.9 |
| | C | 2.1 | 3.1 | 3.6 | 0.5 | 2.2 | 1.8 | 2.1 | 1.8 | 1.9 | 26.0 | | |

Positive ≥ 1.5

FIG. 13B

>H3-SS_LS-01 (#231, LS N102D to remove glycan)

MKTIIALSYILCLVFAQKLPGNDNSTATLCLGHHAVPNGTIVKTITNDQ
IEVTNATEIVFPGCGVLKLATGMRNVPEKQTRGIFGAIAGFIENGWEGM
VDGWYGFRHQNSEGIGQAADLKSTQAAINQINGMVNRVIALMAQGGPDC
YLAELLVALLNQHVIDLTDSEMRKLFERTKKQLRENAEDMGNGCFKIYH
KCDNACIGSIRNGTYDHDVYRDEALNNRFQIKAGPPGGMQIYEGKLTAE
GLRFGIVASRFNHALVDRLVEGAIDCIVRHGGREEDITLVRVPGSWEIP
VAAGELARKEDIDAVIAIGVLIRGATPHFDYIASEVSKGLADLSLELRK
PITFGVITADTLEQAIERAGTKHGNKGWEAALSAIEMANLFKSLR

FIG. 17

| | H3-SS-LS-01 | H3-SS-LS-02 | H3-SS-LS-03 | H3-SS-LS-04 | H1-SS-np |
|---|---|---|---|---|---|
| IC50 | 0.07853 | 0.07698 | 0.02964 | 0.02494 | 0.03721 |

| | H3-SS-LS-01 | H3-SS-LS-02 | H3-SS-LS-03 | H3-SS-LS-04 |
|---|---|---|---|---|
| IC50 | 0.08182 | 0.08213 | 0.08877 | 0.09565 |

>H7-SS-np_016 (H7 equivalent of H3 #231)

MNTQILVFALIAIIPTNADKICLGHHAVSNGTKVNTLTERGVEVVNAT

* *
ELVFPGCGVLKLATGMKNVPEIPKGRGLFGAIAGFIENGWEGLIDGWY
GFRHQNAQGEGTAADYKSTQSAIDQITGMVNRVIALMAQGGPDCYLAE
LLVAMINQHVIDLADSEMDKLYERVKRQLRENAEEDGTGCFEIFHKCD
DDCMASIRNNTYDHSKYREEAMQNRIQIDSGGDIIKLLNEQVNKEMQS
SNLYMSMSSWCYTHSLDGAGLFLFDHAAEEYEHAKKLIIFLNENNVPV
QLTSISAPEHKFEGLTQIFQKAYEHEQHISESINNIVDHAIKSKDHAT
FNFLQWYVAEQHEEEVLFKDILDKIELIGNENHGLYLADQYVKGIAKS
RKSGS

FIG. 23

H1-SS-np (control)

H7-SS-16

H7-SS-18

H7-SS-20

H7-SS-21

H7-SS-23

H7-SS-25

H7-SS-26

| design | Antibody $IC_{50}$ (μg/ml) FI6 | CT149 | CR8020 |
|---|---|---|---|
| H7-SS-np16 | 0.039 | 0.024 | 0.089 |
| H7-SS-np18 | 0.039 | 0.024 | 0.069 |
| H7-SS-np20 | 0.045 | 0.024 | 0.084 |
| H7-SS-np21 | 0.038 | 0.024 | 0.101 |
| H7-SS-np23 | 0.052 | 0.022 | 0.135 |
| H7-SS-np25 | 0.039 | 0.070 | 0.086 |
| H7-SS-np26 | 0.038 | 0.096 | 0.071 |
| H1-SS-np | 0.032 | 0.037 | ND |

FIG. 26D $K_d$: 7.82E-09 M
$K_{on}$: 1.88E+05 $M^{-1}s^{-1}$
$K_{off}$: 1.47E-03 $s^{-1}$ $K_d$: 1.01E-08 M
$K_{on}$: 1.69E+05 $M^{-1}s^{-1}$
$K_{off}$: 1.71E-03 $s^{-1}$ $K_d$: 9.11E-09 M
$K_{on}$: 1.66E+05 $M^{-1}s^{-1}$
$K_{off}$: 1.51E-03 $s^{-1}$ $K_d$: 1.08E-08 M
$K_{on}$: 1.54E+05 $M^{-1}s^{-1}$
$K_{off}$: 1.66E-03 $s^{-1}$ >H10N8-SS-np_02 (H10ssF_2) (SEQ ID NO:103)
MYKIVVIIALLGAVKGLDKICLGHHAVANGTIVKTLTNEQEEVTNATELVFPGCVLMLATGMRNVPELIQGRGLFGAIAGFLENGWEGMVDGWY
GFRHQNAQGTGQAADYKSTQAAIDQITCMVNRVVALMAQGGPDCMLAELLVAMLNQHVIDMADSEMSNLYERVRKQLRQNAEEDGKGCFEIYHA
CDDSCMESIRNNTYDHSQYREEALLNRLNINSGGDIIKLLNEQVNKEMQSSNLYMSMSSWCYTHSLDGAGLFLFDHAAEEYEHAKKLIIFLNEN
NVPVQLTSISAPEHKFEGLTQIFQKAYEHEQHISESINNIVDHAIKSKDHATFNFLQWYVAEQHEEEVLFKDILDKIELIGNENHGLYLADQYV
KGIAKSRKSGS >H10N8-SS-np_03 (H10ssF_3) (SEQ ID NO:104)
MYKIVVIIALLGAVKGLDKICLGHHAVANGTIVKTLTNEQEEVTNATELVFPCGVLMLATGMRNVPELIQGRGLFGAIAGFLENGWEGMVDGWY
GFRHQNAQGTGQAADYKSTQAAIDQITCMVNRVVALMAQGGPDCMLAELLVAMLNQHVIDMADSEMSNLYERVRKQLRQNAEEDGKGCFEIYHA
CDDSCMESIRNNTYDHSQYREEALLNRLNINSGGDIIKLLNEQVNKEMQSSNLYMSMSSWCYTHSLDGAGLFLFDHAAEEYEHAKKLIIFLNEN
NVPVQLTSISAPEHKFEGLTQIFQKAYEHEQHISESINNIVDHAIKSKDHATFNFLQWYVAEQHEEEVLFKDILDKIELIGNENHGLYLADQYV
KGIAKSRKSGS >H10N8-SS-np_04 (H10ssF_4) (SEQ ID NO:105)
MYKIVVIIALLGAVKGLDKICLGHHAVANGTIVKTLTNEQEEVTNATELVFPGCGVLMLATGMRNVPELIQGRGLFGAIAGFLENGWEGMVDGWY
GFRHQNAQGTGQAADYKSTQAAIDQITCMVNRVVELMEQGGPDCMLAELLVAMLNQHVIDMADSEMSNLYERVRKQLRQNAEEDGKGCFEIYHAC
DDSCMESIRNNTYDHSQYREEALLNRLNINSGGDIIKLLNEQVNKEMQSSNLYMSMSSWCYTHSLDGAGLFLFDHAAEEYEHAKKLIIFLNENNV
PVQLTSISAPEHKFEGLTQIFQKAYEHEQHISESINNIVDHAIKSKDHATFNFLQWYVAEQHEEEVLFKDILDKIELIGNENHGLYLADQYVKGI
AKSRKSGS >H10N8-SS-np_05 (H10ssF_5) (SEQ ID NO:106)
MYKIVVIIALLGAVKGLDKICLGHHAVANGTIVKTLTNEQEEVTNATELVFPGCGVLMLATGMRNVPELIQGRGLFGAIAGFLENGWEGMVDGWY
GFRHQNAQGTGQAADYKSTQAAIDQITCMVNRVVALMAQGPPDCMLAELLVAMLNQHVIDMADSEMSNLYERVRKQLRQNAEEDGKGCFEIYHAC
DDSCMESIRNNTYDHSQYREEALLNRLNINSGGDIIKLLNEQVNKEMQSSNLYMSMSSWCYTHSLDGAGLFLFDHAAEEYEHAKKLIIFLNENNV
PVQLTSISAPEHKFEGLTQIFQKAYEHEQHISESINNIVDHAIKSKDHATFNFLQWYVAEQHEEEVLFKDILDKIELIGNENHGLYLADQYVKGI
AKSRKSGS

FIG. 31

Average Core Size: 13.5 ± 0.3 nm
Average Spike Size: 6.5 ± 0.4 nm

Average Core Size: 13.5 ± 0.5 nm
Average Spike Size: 7.1 ± 0.8 nm

Average Core Size: 14.4 ± 0.3 nm
Average Spike Size: 6.6 ± 0.5 nm

Average Core Size: 13.9 ± 0.3 nm
Average Spike Size: 6.4 ± 0.7 nm

Average Core Size: 13.2 ± 0.7 nm
Average Spike Size: 6.8 ± 0.5 nm

| Nanoparticle | Antibody $IC_{50}$ (mg/ml) FI6 | CT149 | CR8020 |
|---|---|---|---|
| Empty | ND | ND | ND |
| H1ssF | 0.002 | 0.004 | ND |
| H7ssF26 | 0.01 | 0.007 | 0.02 |
| H10ssF2 | 0.02 | 0.004 | 0.01 |
| H10ssF3 | 0.02 | 0.004 | 0.01 |
| H10ssF4 | 0.01 | 0.005 | 0.01 |
| H10ssF5 | 0.02 | 0.004 | 0.01 |

ND, not detected

>H3-SS-np_231 SEQ ID NO:46
MKTIIALSYILCLVFAQKLPGNDNSTATLCLGHHAVPNGTIVKTITNDQIEVTNATELVFPGCGVLKLATGMRNVPEKQTRGIFGAIAGFIENGWEGMVDGWY
GFRHQNSEGIGQAADLKSTQAAINQINGMVNRVIALMAQGGPDCMIAELLVALINQHVIDLTDSEMSKLFERTKKQLRENAEDMGNGCFKIYHKCDNACIGSI
RNGTYDHDVYRDEALNNRFQIKSGGDIIKLLNEQVNKEMCSSNLYMSMSSWCYTHSLDGAGLFLFDHAAEEYEHAKKLIIFLNENNVPVQLTSISAPEHKFEG
LTQIFQKAYEHEQHISESINNIVDHAIKSKDHATFNFLQWYVAEQHEEEVLFKDILDKIELIGNENHGLYLADQYVKGIAKSRKSGS

>H3-SS-np_249 SEQ ID NO:47
MKTIIALSYILCLVFAQKLPGNDNSTATLCLGHHAVPNGTIVKTITNDQIEVTNATELCFNGICLKLATGMRNVPEKQTRGIFGAIAGFIENGWEGMVDGWY
GFRHQNSEGIGQAADLKSTQAAINQINGMVNRVIALMAQGGPDAMIAELLVALINQHVIDLTDSEMSKLFERTKKQLRENAEDMGNGCFKIYHKCDNACIGS
IRNGTYDHDVYRDEALNNRFQIKSGGDIIKLLNEQVNKEMCSSNLYMSMSSWCYTHSLDGAGLFLFDHAAEEYEHAKKLIIFLNENNVPVQLTSISAPEHKF
EGLTQIFQKAYEHEQHISESINNIVDHAIKSKDHATFNFLQWYVAEQHEEEVLFKDILDKIELIGNENHGLYLADQYVKGIAKSRKSGS

>H3-SS-np_256 SEQ ID NO:48
MKTIIALSYILCLVFAQKLPGNDNSTATLCLGHHAVPNGTIVKTITNDQIEVTNATELVFPGCGVLKLATGMRNVPEKQTRGIFGAIAGFIENGWEGMVDGWY
GFRHQNSEGIGQAADLKSTQAAINQINGMVNRVIELMEQGGPDCMIAELLVALINQHVIDLTDSEMSKLFERTKKQLRENAEDMGNGCFKIYHKCDNACIGSI
RNGTYDHDVYRDEALNNRFQIKSGGDIIKLLNEQVNKEMCSSNLYMSMSSWCYTHSLDGAGLFLFDHAAEEYEHAKKLIIFLNENNVPVQLTSISAPEHKFEG
LTQIFQKAYEHEQHISESINNIVDHAIKSKDHATFNFLQWYVAEQHEEEVLFKDILDKIELIGNENHGLYLADQYVKGIAKSRKSGS

>H3-SS-np_258 SEQ ID NO:49
MKTIIALSYILCLVFAQKLPGNDNSTATLCLGHHAVPNCTIVKTITNDQIEVTNATELVFPGCGVLKLATGMRCVPEKQTRGIFGAIAGFIENGWEGMVDGWY
GFRHQNSEGIGQAADLKSTQAAINQINGMVNRVIELMEQGGPDCMIAELLVALINQHVIDLTDSEMSKLFERTKKQLRENAEDMGNGCFKIYHKCDNACIGSI
RNGTYDHDVYRDEALNNRFQIKSGGDIIKLLNEQVNKEMCSSNLYMSMSSWCYTHSLDGAGLFLFDHAAEEYEHAKKLIIFLNENNVPVQLTSISAPEHKFEG
LTQIFQKAYEHEQHISESINNIVDHAIKSKDHATFNFLQWYVAEQHEEEVLFKDILDKIELIGNENHGLYLADQYVKGIAKSRKSGS

FIG. 38

>H7-SS-np_020 (H7ssF_20) SEQ ID NO:93
MNTQILVFALIAIIPTNADKICLGHHAVSNGTKVNTLTERGVEVVNATELVFPCGVLKLATGMKNVPEIPKGRGLFGAIAGFIENGWEGLIDGW
YGFRHQNAQGEGTAADYKSTQSAIDQITGMVNRVIALMAQGGPDCYLAELLVAMLNQHVIDLADSEMDKLYERVKRQLRENAEEDGTGCFEIFH
KCDDDCMASIRNNTYDHSKYREEAMQNRIQIDSGGDIIKLLNEQVNKEMQSSNLYMSMSSWCYTHSLDGAGLFLFDHAAEEYEHAKKLIIFLNE
NNVPVQLTSISAPEHKFEGLTQIFQKAYEHEQHISESINNIVDHAIKSKDHATFNFLQWYVAEQHEEEVLFKDILDKIELIGNENHGLYLADQY
VKGIAKSRKSGS

>H7-SS-np_023 (H7ssF_23) SEQ ID NO:95
MNTQILVFALIAIIPTNADKICLGHHAVSNGTKVNTLTERGVEVVNATELVFPGCGVLKLATGMKNVPEIPKGRGLFGAIAGFIENGWEGLIDGW
YGFRHQNAQGEGTAADYKSTQSAIDQITGMVNRVIALMAQGPPDCYLAELLVAMLNQHVIDLADSEMDKLYERVKRQLRENAEEDGTGCFEIFHK
CDDDCMASIRNNTYDHSKYREEAMQNRIQIDSGGDIIKLLNEQVNKEMQSSNLYMSMSSWCYTHSLDGAGLFLFDHAAEEYEHAKKLIIFLNENN
VPVQLTSISAPEHKFEGLTQIFQKAYEHEQHISESINNIVDHAIKSKDHATFNFLQWYVAEQHEEEVLFKDILDKIELIGNENHGLYLADQYVKG
IAKSRKSGS

>H7-SS-np_025 (H7ssF_25) SEQ ID NO:96
MNTQILVFALIAIIPTNADKICLGHHAVSNGTKVNTLTERGVEVVNATELVFPGCGVLKLATGMKNVPEIPKGRGLFGAIAGFIENGWEGLIDGW
YGFRHQNAQGEGTAADYKSTQSAIDQITGMVNRVIALMEEGGPDCYLAELLVAMLNQHVIDLADSEMDKLYERVKRQLRENAEEDGTGCFEIFHK
CDDDCMASIRNNTYDHSKYREEAMQNRIQIDSGGDIIKLLNEQVNKEMQSSNLYMSMSSWCYTHSLDGAGLFLFDHAAEEYEHAKKLIIFLNENN
VPVQLTSISAPEHKFEGLTQIFQKAYEHEQHISESINNIVDHAIKSKDHATFNFLQWYVAEQHEEEVLFKDILDKIELIGNENHGLYLADQYVKG
IAKSRKSGS

>H7-SS-np_026 (H7ssF_26) SEQ ID NO:97
MNTQILVFALIAIIPTNADKICLGHHAVSNGTKVNTLTERGVEVVNATELVFPGCGVLKLATGMKNVPEIPKGRGLFGAIAGFIENGWEGLIDGWY
GFRHQNAQGEGTAADYKSTQSAIDQITGMVNKVIELMEQGGPDCYLAELLVAMLNQHVIDLADSEMDKLYERVKRQLRENAEEDGTGCFEIFHKCD
DDCMASIRNNTYDHSKYREEAMQNRIQIDSGGDIIKLLNEQVNKEMQSSNLYMSMSSWCYTHSLDGAGLFLFDHAAEEYEHAKKLIIFLNENNVPV
QLTSISAPEHKFEGLTQIFQKAYEHEQHISESINNIVDHAIKSKDHATFNFLQWYVAEQHEEEVLFKDILDKIELIGNENHGLYLADQYVKGIAKS
RKSGS

FIG. 39

>H3-SS-np_256 (H3ssF_256) SEQ ID NO:48
MKTIIALSYILCLVFAQKLPGNDNSTATLCLGHHAVPNGTIVKTITNDQIEVTNATELVFPGCGVLKLATGMRNVPEKQTRGIFGAIAGFIENGWEGMVDGWY
GFRHQNSEGIGQAADLKSTQAAINQINGMVNRVIELMEQGGPDCYLAELLVALLNQHVIDLTDSEMRKLFERTKKQLRENAEDMGNGCFKIYHKCDNACIGSI
RNGTYDHDVYRDEALNNRFQIK

>H3-SS-np_258 (H3ssF_258) SEQ ID NO:49
MKTIIALSYILCLVFAQKLPGNDNSTATLCLGHHAVPNCTIVKTITNDQIEVTNATELVFPGCGVLKLATGMRCVPEKQTRGIFGAIAGFIENGWEGMVDGWY
GFRHQNSEGIGQAADLKSTQAAINQINGMVNRVIELMEQGGPDCNIAELLVALLNQHVIDLTDSEMRKLFERTKKQLRENAEDMGNGCFKIYHKCDNACIGSI
RNGTYDHDVYRDEALNNRFQIK

>H7-SS-np_026 (H7ssF_26) SEQ ID NO:97
MNTQILVFALIAIIPTNADKICLGHHAVSNGTKVNTLTERGVEVVNATELVFPGCGVIKLATGMKNVPEIPKGRGLFGAIAGFIENGWEGLIDGWY
GFRHQNAQGEGTAADYKSTQSAIDQITGMVNRVIELMEQGGPDCNLAELLVAMLNQHVIDLADSEMDKLYERVKRQLRENAEEDGTGCFEIFHKCD
DDCMASIRNNTYDHSKYREEAMQNRIQID

>H10N8-SS-np_02 (H10ssF_2) (SEQ ID NO:103)
MYKIVVIIALLGAVKGLDKICLGHHAVANGTIVKTLTNEQEEVTNATELVFPGCVIMLATGMRNVPELIQGRGLFGAIAGFLENGWEGMVDGWY
GFRHQNAQGTGQAADYKSTQAAIDQITGMVNRVVALMAQGGPDCYLAELLVAMLNQHVIDMADSEMRNLYERVRKQLRQNAEEDGKGCFEIYHA
CDDSCMESIRNNTYDHSQYREEALLNRLNIN

>H10N8-SS-np_03 (H10ssF_3) (SEQ ID NO:104)
MYKIVVIIALLGAVKGLDKICLGHHAVANGTIVKTLTNEQEEVTNATELVFPCGVLMLATGMRNVPELIQGRGLFGAIAGFLENGWEGMVDGWY
GFRHQNAQGTGQAADYKSTQAAIDQITGMVNRVVALMAQGGPDCYLAELLVAMLNQHVIDMADSEMRNLYERVRKQLRQNAEEDGKGCFEIYHA
CDDSCMESIRNNTYDHSQYREEALLNRLNIN

>H10N8-SS-np_04 (H10ssF_4) (SEQ ID NO:105)
MYKIVVIIALLGAVKGLDKICLGHHAVANGTIVKTLTNEQEEVTNATELVFPGCGVLMLATGMRNVPELIQGRGLFGAIAGFLENGWEGMVDGWY
GFRHQNAQGTGQAADYKSTQAAIDQITGMVNRVVELMEQGGPDCYLAELLVAMLNQHVIDMADSEMRNLYERVRKQLRQNAEEDGKGCFEIYHAC
DDSCMESIRNNTYDHSQYREEALLNRLNIN

FIG. 41

SEQUENCE LISTING

```
Sequence total quantity: 160
SEQ ID NO: 1           moltype = AA  length = 168
FEATURE                Location/Qualifiers
source                 1..168
                       mol_type = protein
                       organism = Helicobacter pylori
SEQUENCE: 1
MLSDIIKLLN EQVNKEMQSS NLYMSMSSWC YTHSLDGAGL FLFDHAAEEY EHAKKLIIFL  60
NENNVPVQLT SISAPEHKFE GLTQIFQKAY EHEQHISESI NNIVDHAIKS KDHATFNFLQ  120
WYVAEQHEEE VLFKDILDKI ELIGNENHGL YLADQYVKGI AKSRKSGS              168

SEQ ID NO: 2           moltype = AA  length = 165
FEATURE                Location/Qualifiers
REGION                 1..165
                       note = Synthetic
source                 1..165
                       mol_type = protein
                       organism = synthetic construct
SEQUENCE: 2
DIIKLLNEQV NKEMQSSNLY MSMSSWCYTH SLDGAGLFLF DHAAEEYEHA KKLIIFLNEN  60
NVPVQLTSIS APEHKFEGLT QIFQKAYEHE QHISESINNI VDHAIKSKDH ATFNFLQWYV  120
AEQHEEEVLF KDILDKIELI GNENHGLYLA DQYVKGIAKS RKSGS                 165

SEQ ID NO: 3           moltype = AA  length = 154
FEATURE                Location/Qualifiers
source                 1..154
                       mol_type = protein
                       organism = Aquifex aeolicus
SEQUENCE: 3
MQIYEGKLTA EGLRFGIVAS RFNHALVDRL VEGAIDCIVR HGGREEDITL VRVPGSWEIP  60
VAAGELARKE DIDAVIAIGV LIRGATPHFD YIASEVSKGL ADLSLELRKP ITFGVITADT  120
LEQAIERAGT KHGNKGWEAA LSAIEMANLF KSLR                             154

SEQ ID NO: 4           moltype = AA  length = 566
FEATURE                Location/Qualifiers
source                 1..566
                       mol_type = protein
                       organism = Influenza virus A
SEQUENCE: 4
MKTIIALSYI LCLVFAQKLP GNDNSTATLC LGHHAVPNGT IVKTITNDQI EVTNATELVQ  60
SSSTGGICDS PHQILDGENC TLIDALLGDP QCDGFQNKKW DLFVERSKAY SNCYPYDVPD  120
YASLRSLVAS SGTLEFNNES FNWTGVTQNG TSSACKRRSN NSFFSRLNWL THLKFKYPAL  180
NVTMPNNEKF DKLYIWGVHH PGTDNDQISL YAQASGRITV STKRSQQTVI PNIGSRPRVR  240
DIPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGIGQA ADLKSTQAAI NQINGKLNRL IGKTNEKFHQ IEKEFSEVEG  420
RIQDLEKYVE DTKVDLWSYN AELLVALENQ HTIDLTDSEM NKLFERTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                      566

SEQ ID NO: 5           moltype = AA  length = 184
FEATURE                Location/Qualifiers
source                 1..184
                       mol_type = protein
                       organism = Influenza virus A
SEQUENCE: 5
MKTIIALSYI LCLVFAQKLP GNDNSTATLC LGHHAVPNGT IVKTITNDQI EVTNATELVQ  60
SSSTGEICDN PHQILDGENC TLIDALLGDP QCDGFQNKKW DLFVERSKAY SNCYPYDVPD  120
YASLRSLVAS SGTLEFNNES FNWTGVTQNG TSSACIRRSN SSFFSRLNWL THLNFKYPAL  180
NVTM                                                              184

SEQ ID NO: 6           moltype = AA  length = 188
FEATURE                Location/Qualifiers
source                 1..188
                       mol_type = protein
                       organism = Influenza virus A
SEQUENCE: 6
MKTIIALSYI LCLVFAQKLP GNDNSTATLC LGHHAVPNGT IVKTITNDQI EVTNATELVQ  60
SSSTGEICDS PHQILDGENC TLIDALLGDP QCDGFQNKKW DLFVERSKAY SNCYPYDVPD  120
YASLRSLVAS SGTLEFNNES FNWTGVTQNG TSSACIRRSN NSFFSRLNWL THLNFKYPAL  180
NVTMPNNE                                                          188

SEQ ID NO: 7           moltype = AA  length = 220
FEATURE                Location/Qualifiers
source                 1..220
                       mol_type = protein
                       organism = Influenza virus A
SEQUENCE: 7
```

```
MKTIIALSYI LCLVFAQKLP GNDNSTATLC LGHHAVPNGT IVKTITNDQI EVTNATELVQ  60
SSSTGEICDN PHQILDGENC TLIDALLGDP QCDGFQNKKW DLFVERSKAY SNCYPYDVPD  120
YASLRSLVAS SGTLEFNNES FNWTGVTQNG TSSACIRRSN SSFFSRLNWL THLNFKYPAL  180
NVTMPNNEQF DKLYIWGVHH PGTDKDQIFL YAQSSGRITV                        220

SEQ ID NO: 8            moltype = AA  length = 227
FEATURE                 Location/Qualifiers
source                  1..227
                        mol_type = protein
                        organism = Influenza virus A
SEQUENCE: 8
MKTIIALSYI LCLVFAQKLP GNDNSTATLC LGHHAVPNGT IVKTITNDQI EVTNATELVQ  60
SSSTGEICDN PHQILDGENC TLIDALLGDP QCDGFQNKKW DLFVERSKAY SNCYPYDVPD  120
YASLRSLVAS SGTLEFNNES FNWTGVTQNG TSSACIRRSN SSFFSRLNWL THLNFKYPAL  180
NVTMPNNEQF DKLYIWGVHH PGTDKDQIFL YAQSSGRITV STKRSQQ                227

SEQ ID NO: 9            moltype = AA  length = 251
FEATURE                 Location/Qualifiers
source                  1..251
                        mol_type = protein
                        organism = Influenza virus A
SEQUENCE: 9
MKTIIALSYI LCLVFAQKLP GNDNSTATLC LGHHAVPNGT IVKTITNDQI EVTNATELVQ  60
SSSTGEICDS PHQILDGKNC TLIDALLGDP QCDGFQNKKW DLFVERSKAY SNCYPFDVPD  120
YASLRSLVAS SGTLEFNNES FNWTGVTQNG TSSACIRRSK SSFFSRLNWL THLNFKYPAL  180
NVTMPNDEQF DKLYIWGVHH PGTDKDQIFL YAQASGRITV STKRSQQTVI PNIGSRPRIR  240
NIPSRISIYW G                                                       251

SEQ ID NO: 10           moltype = AA  length = 388
FEATURE                 Location/Qualifiers
source                  1..388
                        mol_type = protein
                        organism = Influenza virus A
SEQUENCE: 10
MKTIIALSYI LCLVFAQKLP GNDNSTATLC LGHHAVPNGT IVKTITNDQI EVTNATELVQ  60
SSSTGEICDS PHQILDGENC TLIDALLGDP QCDGFQNKKW DLFVERSKAY SNCYPYDVPD  120
YASLRSLVAS SGTLEFNNES FNWTGVTQNG TSSACIRRSN SSFFSRLNWL THLNFKYPAL  180
NVTMPNNEQF DKLYIWGVHH PGTDKDQIFL YAQSSGRITV STKRSQQAVI PNIGSRPRIR  240
NIPSRISIYW TIVKPGDILL INSTGNLIAP RGYFKIRSGK SSIMRSDAPI GKCNSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQA                                     388

SEQ ID NO: 11           moltype = AA  length = 372
FEATURE                 Location/Qualifiers
source                  1..372
                        mol_type = protein
                        organism = Influenza virus A
SEQUENCE: 11
MKTIIALSYI LCLVFAQKLP GNDNSTATLC LGHHAVPNGT IVKTITNDQI EVTNATELVQ  60
ISSTGGICDS PHQILDGENC TLIDALLGDP QCDGFQNKKW DLFVERSKAY SNCYPYDVPD  120
YASLRSLVAS SGTLEFNNES FDWTGVTQNG TSSACKRRSN KSFFSRLNWL THLKYKYPAL  180
NVTMPNNEKF DKLYIWGVHH PGTDSDQISL YAQASGRITV STKRSQQTVI PNIGSRPRVR  240
DVSSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQ                                                      372

SEQ ID NO: 12           moltype = AA  length = 400
FEATURE                 Location/Qualifiers
source                  1..400
                        mol_type = protein
                        organism = Influenza virus A
SEQUENCE: 12
MKTIIALSYI LCLVFAQKLP GNDNSTATLC LGHHAVPNGT IVKTITNDQI EVTNATELVQ  60
NSSIGEICDS PHQILDGENC TLIDALLGDP QCDGFQNKKW DLFVERSKAY SNCYPYDVPD  120
YASLRSLVAS SGTLEFNNES FNWSGVTQNG TSSACMRRSN SSFFSRLNWL THLNFKYPAL  180
NVTMPNNEQF DKLYIWGVHH PGTDKDQIFL YAQSSGRITV STKRSQQAVI PNIGSRPRIR  240
NIPSRISIYW TIVKPGDILL INSTGNLIAP RGYFKIRSGK SSIMRSDAPI GKCNSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL                        400

SEQ ID NO: 13           moltype = AA  length = 400
FEATURE                 Location/Qualifiers
source                  1..400
                        mol_type = protein
                        organism = Influenza virus A
SEQUENCE: 13
MKTIIALSYI LCLVFAQKLP GNDNSTATLC LGHHAVPNGT IVKTITNDQI EVTNATELVQ  60
SSSTGEICDS PHQILDGENC TLIDALLGDP QCDGFQNKKW DLFVERSKAY SSCYPYDVPD  120
YASLRSLVAS SGTLEFNNES FNWTGVTQNG TSSACIRRSN SSFFSRLNWL THLNFKYPAL  180
```

```
NVTMPNNEQF DKLYIWGVHH PGTDKDQIFL YAQSSGRITV STKRSQQAVI PNIGSRPRIR  240
NIPSRISIYW TIVKPGDILL INSTGNLIAP RGYFKIRSGK SSIMRSDAPI GKCNSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL                        400

SEQ ID NO: 14          moltype = AA  length = 400
FEATURE                Location/Qualifiers
source                 1..400
                       mol_type = protein
                       organism = Influenza virus A
SEQUENCE: 14
MKTIIALSYI LCLVFAQKLP GNDNSTATLC LGHHAVPNGT IVKTITNDQI EVTNATELVQ  60
SSSAGEICDS PHHILDGENC TLIDALLGDP QCDGFQNKKW DLFVERSRAY SNCYPYDVPD  120
YASLRSLVAS SGTLEFNNES FNWTGVTQNG TSSACIRRSN NSFFSRLNWL THLNFKYPAL  180
NVTMPNNEQF DKLYIWGVHH PGTDKDQIFL YAQASGRITV STKRSQQAVI PNIGSRPRVR  240
NIPSRISIYW TIVKPGDILL INSTGNLIAP RGYFKIRSGK SSIMRSDAPI GKCNSECITP  300
NGSIPNDKPF QNVNRITYGA CPRYVKQSTL KLATGMRNVP EKQTRGIFGA IAGFIENGWE  360
GMMDGWYGFR HQNSEGRGQA ADLKSTQAAI DQINGKLNRL                        400

SEQ ID NO: 15          moltype = AA  length = 372
FEATURE                Location/Qualifiers
source                 1..372
                       mol_type = protein
                       organism = Influenza virus A
SEQUENCE: 15
MKTIIALSYI LCLVFAQKLP GNDNSTATLC LGHHAVPNGT IVKTITNDQI EVTNATELVQ  60
SSSTGGICDS PHQILDGENC TLIDALLGDP QCDGFQNKKW DLFVERSKAY SNCYPYDVPD  120
YASLRSLVAS SGTLEFNNES FNWTGVTQNG TSSACKRRSN NSFFSRLNWL THLKFKYPAL  180
NVTMPNNEKF DKLYIWGVHH PGTDNDQISL YAQASGRITV STKRSQQTVI PNIGSRPRVR  240
DIPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HR                                                      372

SEQ ID NO: 16          moltype = AA  length = 370
FEATURE                Location/Qualifiers
source                 1..370
                       mol_type = protein
                       organism = Influenza virus A
SEQUENCE: 16
MNTQILVFAL VAIIPTNADK ICLGHHAVSN GTKVNTLTER GVEVVNATET VERTNVPRIC  60
SKGKRTVDLG QCGLLGTITG PPQCDQFLEF SADLIIERRE GSDVCYPGKF VNEEALRQIL  120
RESGGIDKET MGFTYSGIRT NGATSACRRS GSSFYAEMKW LLSNTDNAAF PQMTKSYKNT  180
RRDPALIVWG IHHSGSTTEQ TKLYGSGSKL ITVGSSNYQQ SFVPSPGARP QVNGQSGRID  240
FHWLILNPND TVTFSFNGAF IAPDRASFLR GKSMGIQSGV QVDANCEGDC YHSGGTIISN  300
LPFQNINSRA VGKCPRYVKQ ESLMLATGMK NVPELPKGRG LFGAIAGFIE NGWEGLIDGW  360
YGFRHQNAQG                                                         370

SEQ ID NO: 17          moltype = AA  length = 386
FEATURE                Location/Qualifiers
source                 1..386
                       mol_type = protein
                       organism = Influenza virus A
SEQUENCE: 17
MNTQILVFAL VAIIPTNADK ICLGHHAVSN GTKVNTLTER GVEVVNATET VERTNVPRIC  60
SKGKRTVDLG QCGLLGTITG PPQCDQFLEF SADLIIERRE GSDVCYPGKF VNEEALRQIL  120
RESGGIDKET MGFTYSGIRT NGATSACRRS GSSFYAEMKW LLSNTDNAAF PQMTKSYKNT  180
RKDPALIIWG IHHSGSTTEQ TKLYGSGNKL ITVGSSNYQQ SFVPSPGARP QVNGQSGRID  240
FHWLILNPND TVTFSFNGAF IAPDRASFLR GKSMGIQSGV QVDANCEGDC YHSGGTIISN  300
LPFQNINSRA VGKCPRYVKQ ESLLLATGMK NVPEIPKRRR RGLFGAIAGF IENGWEGLID  360
GWYGFRHQNA QGEGTAADYK STQSAI                                       386

SEQ ID NO: 18          moltype = AA  length = 388
FEATURE                Location/Qualifiers
source                 1..388
                       mol_type = protein
                       organism = Influenza virus A
SEQUENCE: 18
MNTQILVFAL VAIIPTNADK ICLGHHAVSN GTKVNTLTER GVEVVNATET VERTNVPRIC  60
SKGKRTVDLG QCGLLGTITG PPQCDQFLEF SADLIIERRE GSDVCYPGKF VNEEALRQIL  120
RESGGIDKEA MGFTYSGIRT NGTTSTCRRS GSSFYAEMKW LLSNTDNAAF PQMTKSYKNT  180
RKDPALIIWG IHHSGSTTEQ TKLYGSGNKL ITVGSSNYQQ SFVPSPGERP QVNGQSGRID  240
FHWLMLNPND TVTFSFNGAF IAPDRASFLR GKSMGIQSGV QVDANCEGDC YHSGGTIISN  300
LPFQNINSRA VGKCPRYVKQ ESLLLATGMK NVPEIPKGSR VRRGLFGAIA GFIENGWEGL  360
IDGWYGFRHQ NAQGEGTAAD YKSTQSAI                                     388

SEQ ID NO: 19          moltype = AA  length = 363
FEATURE                Location/Qualifiers
source                 1..363
                       mol_type = protein
```

```
                        organism = Influenza virus A
SEQUENCE: 19
MNTQILVFAL VAIIPTNADK ICLGHHAVSN GTKVNTLTER GVEVVNATET VERTNVPRIC  60
SKGKRTVDLG QCGLLGTITG PPQCDQFLEF SADLIIERRE GSDVCYPGKF INEEALRQIL  120
RESGGIDKET MGFTYSGIRT NGATSACRRS GSSFYAEMKW LLSNTDNAAF PQMTKSYKNT  180
RKDPALITWG IHHSGSTTEQ TKLYGSGNKL ITVGSSNYQQ SFVPSPGARP QVNGQSGRID  240
FHWLVLNPND TVTFSFNGAF IAPDRASFLR GKSMGIQSGV QVDANCEGDC YHSGGTIISN  300
LPFQNINSRA VGKCPRYVKQ ESLMLATGMK NVPEIPKGRG LFGAIAGFIE NGWEGLIDGW  360
YGF                                                               363

SEQ ID NO: 20           moltype = AA  length = 560
FEATURE                 Location/Qualifiers
source                  1..560
                        mol_type = protein
                        organism = Influenza virus A
SEQUENCE: 20
MNTQILVFAL IAIIPTNADK ICLGHHAVSN GTKVNTLTER GVEVVNATET VERTNIPRIC  60
SKGKRTVDLG QCGLLGTITG PPQCDQFLEF SADLIIERRE GSDVCYPGKF VNEEALRQIL  120
RESGGIDKEA MGFTYSGIRT DGATSACRRS GSSFYAEMKW LLSNTDDAAF PQMTKSYKNT  180
RKSPALIVWG IHHSVSTAEQ TKLYGSGNKL VTVGSSNYQQ SFVPSPGARP QVNGLSGRID  240
FHWLMLNPND TVTFSFNGAF IAPDRASFLR GKSMGIQSGV QVDANCEGDC YHSGGTIISN  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFN EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
VMGLVFICVK NGNMRCTICI                                             560

SEQ ID NO: 21           moltype = AA  length = 560
FEATURE                 Location/Qualifiers
source                  1..560
                        mol_type = protein
                        organism = Influenza virus A
SEQUENCE: 21
MNTQILVFAL IAIIPTNADK ICLGHHAVSN GTKVNTLTER GVEVVNATET VERTNIPRIC  60
SKGKRTVDLG QCGLLGTITG PPQCDQFLEF SADLIIERRE GSDVCYPGKF VNEEALRQIL  120
RESGGIDKEA MGFTYSGIRT NGATSACRRS GSSFYAEMKW LLSNTDNAAF PQMTKSYKNT  180
RKNPALIVWG IHHSGSTAEQ TKLYGSGNKL VTVGSSNYQQ SFAPSPGART QVNGQSGRID  240
FHWLMLNPND TVTFSFNGAF IAPDRASFLR GKSMGIQSGV QVDADCEGDC YHSGGTIISN  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFT EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
AMGLVFICVK NGNMRCTICI                                             560

SEQ ID NO: 22           moltype = AA  length = 554
FEATURE                 Location/Qualifiers
source                  1..554
                        mol_type = protein
                        organism = Influenza virus A
SEQUENCE: 22
MNTQILVFAL IAIIPTNADK ICLGHHAVSN GTKVNTLTER GVEVVNATET VERTNIPRIC  60
SKGKKTVDLG QCGLLGTITG PPQCDQFLEF SADLIIERRE GSDVCYPGKF VNEEALRQIL  120
RESGGIDKEA MGFTYSGIRA NGATSACRRS GSSFYAEMKW LLSNTDNAAF PQMTKSYKNT  180
RKSPALIVWG IHHSVSTAEQ TKLYGSGNKL VTVGSSNYQQ SFVPSPGARP QVNGLSGRID  240
FHWLMLNPND TVTFSFNGAF IAPDRASFLR GKSMGIQSGV QVDANCEGDC YHSGGTIISN  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFN EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
VMGLVFICVK NGNM                                                   554

SEQ ID NO: 23           moltype = AA  length = 560
FEATURE                 Location/Qualifiers
source                  1..560
                        mol_type = protein
                        organism = Influenza virus A
SEQUENCE: 23
MNTQILVFAL IAIIPTNADK ICLGHHAVSN GTKVNTLTER GVEVVNATET VERTNIPRIC  60
SKGKRTVDLG QCGLLGTITG PPQCDQFLEF SADLIIERRE GSDVCYPGKF VNEEALRQIL  120
RESGGIDKEA MGFTYSGIRA NGTTSACRRS GSSFYAEMKW LLSNTDNAAF PQMTKSYKNT  180
RKSPALIVWG IHHSVSTAEQ TKLYGSGNKL VTVGSSNYQQ SFVPSPGARP QVNGLSGRID  240
FHWLMLNPND TVTFSFNGAF IAPDRASFLR GKSMGIQSGV QVDANCEGDC YHSGGTIISS  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFN EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
VMGLVFICVK NGNMRCTICI                                             560

SEQ ID NO: 24           moltype = AA  length = 560
```

```
FEATURE                Location/Qualifiers
source                 1..560
                       mol_type = protein
                       organism = Influenza virus A
SEQUENCE: 24
MNTQILVFAL IAIIPTNADK ICLGHHAVSN GTKVNTLTER GVEVVNATET VERTNIPRIC  60
SKGKRTVDLG QCGLLGTITG PPQCDQFLEF SADLIIERRE GSDVCYPGKF VKEEALRQIL  120
RESGGIDKEA MGFTYSGIRT NGATSACRRS GSSFYAEMKW LLSNTDNAAF PQMTKSYKNT  180
RKSPALIVWG IHHSVSTAEQ TKLYGSGNKL VTVGSSNYQQ SFVPSPGARP QVNGLSGRID  240
FHWLMLNPND TVTFSFNGAF IAPDRASFLR GKSMGIQSGV QVDANCEGDC YHSGGTIISN  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFN EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
VMGLVFICVK NGNMRCTICI                                              560

SEQ ID NO: 25          moltype = AA  length = 560
FEATURE                Location/Qualifiers
source                 1..560
                       mol_type = protein
                       organism = Influenza virus A
SEQUENCE: 25
MNTQILVFAL IAIIPTNADK ICLGHHAVSN GTKVNTLTER GVEVVNATET VERTNIPRIC  60
SKGKRTVDLG QCGLLGTITG PPQCDQFLEF SADLIIERRE GSDVCYPGKF VNEEALRQIL  120
RESGGIDKEA MGFTYSGIRA NGATSACRRS GSSFYAEMKW LLSNTDNAAF PQMTKSYKNT  180
RKSPALIVWG IHHSVSTAEQ TKLYGSGNKL VTVGSSNYQQ SFVPSPGARP QVNGLSGRID  240
FHWLMLNPND TVTFSFNGAF IAPDRASFLR GKSMGIQSGV QVDANCEGDC YHSGGTIISS  300
LPFQNIDSRA VGKCPRYVKQ RSLLLATGMK NVPEIPKGRG LFGAIAGFIE NGWEGLIDGW  360
YGFRHQNAQG EGTAADYKST QSAIDQITGK LNRLIEKTNQ QFELIDNEFN EVEKQIGNVI  420
NWTRDSITEV WSYNAELLVA MENQHTIDLA DSEMDKLYER VKRQLRENAE EDGTGCFEIF  480
HKCDDDCMAS IRNNTYDHSK YREEAMQNRI QIDPVKLSSG YKDVILWFSF GASCFILLAI  540
VMGLVFICVK NGNMRCTICI                                              560

SEQ ID NO: 26          moltype = AA  length = 561
FEATURE                Location/Qualifiers
REGION                 1..561
                       note = Synthetic
source                 1..561
                       mol_type = protein
                       organism = synthetic construct
SEQUENCE: 26
MYKIVVIIAL LGAVKGLDKI CLGHHAVANG TIVKTLTNEQ EEVTNATETV ESTGINRLCM  60
KGRKHKDLGN CHPIGMLIGT PACDLHLTGM WDTLIERENA IAYCYPGATV NVEALRQKIM  120
ESGGINKIST GFTYGSSINS AGTTRACMRN GGNSFYAELK WLVSKSKGQN FPQTTNTYRN  180
TDTAEHLIMW GIHHPSSTQE KNDLYGTQSL SISVGSSTYR NNFVPVVGAR PQVNGQSGRI  240
DFHWTLVQPG DNITFSHNGG LIAPSRVSKL IGRGLGIQSD APIDNNCESK CFWRGGSINT  300
RLPFQNLSPR TVGQCPKYVN RRSLMLATGM RNVPELIQGR GLFGAIAGFL ENGWEGMVDG  360
WYGFRHQNAQ GTGQAADYKS TQAAIDQITG KLNRLVEKTN TEFESIESEF SEIEHQIGNV  420
INWTKDSITD IWTYQAELLV AMENQHTIDM ADSEMLNLYE RVRKQLRQNA EEDGKGCFEI  480
YHACDDSCME SIRNNTYDHS QYREEALLNR LNINPVTLSS GYKDIILWFS FGASCFVLLA  540
VVMGLFFFCL KNGNMRCTIC I                                            561

SEQ ID NO: 27          moltype = AA  length = 59
FEATURE                Location/Qualifiers
source                 1..59
                       mol_type = protein
                       organism = Influenza virus A
SEQUENCE: 27
MKTIIALSYI LCLVFAQKLP GNDNSTATLC LGHHAVPNGT IVKTITNDQI EVTNATELV   59

SEQ ID NO: 28          moltype = AA  length = 40
FEATURE                Location/Qualifiers
source                 1..40
                       mol_type = protein
                       organism = Influenza virus A
SEQUENCE: 28
PGNDNSTATL CLGHHAVPNG TIVKTITNDQ IEVTNATELV                        40

SEQ ID NO: 29          moltype = AA  length = 25
FEATURE                Location/Qualifiers
source                 1..25
                       mol_type = protein
                       organism = Influenza virus A
SEQUENCE: 29
AVPNGTIVKT ITNDQIEVTN ATELV                                        25

SEQ ID NO: 30          moltype = AA  length = 190
FEATURE                Location/Qualifiers
source                 1..190
```

```
                        mol_type = protein
                        organism = Influenza virus A
SEQUENCE: 30
LKLATGMRNV PEKQTRGIFG AIAGFIENGW EGMVDGWYGF RHQNSEGIGQ AADLKSTQAA  60
INQINGKLNR LIGKTNEKFH QIEKEFSEVE GRIQDLEKYV EDTKVDLWSY NAELLVALEN  120
QHTIDLTDSE MNKLFERTKK QLRENAEDMG NGCFKIYHKC DNACIGSIRN GTYDHDVYRD  180
EALNNRFQIK                                                         190

SEQ ID NO: 31           moltype = AA  length = 66
FEATURE                 Location/Qualifiers
source                  1..66
                        mol_type = protein
                        organism = Influenza virus A
SEQUENCE: 31
LKLATGMRNV PEKQTRGIFG AIAGFIENGW EGMVDGWYGF RHQNSEGIGQ AADLKSTQAA  60
INQING                                                             66

SEQ ID NO: 32           moltype = AA  length = 50
FEATURE                 Location/Qualifiers
source                  1..50
                        mol_type = protein
                        organism = Influenza virus A
SEQUENCE: 32
LKLATGMRNV PEKQTRGIFG AIAGFIENGW EGMVDGWYGF RHQNSEGIGQ             50

SEQ ID NO: 33           moltype = AA  length = 25
FEATURE                 Location/Qualifiers
source                  1..25
                        mol_type = protein
                        organism = Influenza virus A
SEQUENCE: 33
LKLATGMRNV PEKQTRGIFG AIAGF                                        25

SEQ ID NO: 34           moltype = AA  length = 7
FEATURE                 Location/Qualifiers
REGION                  1..7
                        note = Synthetic
source                  1..7
                        mol_type = protein
                        organism = synthetic construct
SEQUENCE: 34
VFPGCGV                                                            7

SEQ ID NO: 35           moltype = AA  length = 6
FEATURE                 Location/Qualifiers
REGION                  1..6
                        note = Synthetic
source                  1..6
                        mol_type = protein
                        organism = synthetic construct
SEQUENCE: 35
CFNGIC                                                             6

SEQ ID NO: 36           moltype = AA  length = 5
FEATURE                 Location/Qualifiers
REGION                  1..5
                        note = Synthetic
source                  1..5
                        mol_type = protein
                        organism = synthetic construct
SEQUENCE: 36
ALMAQ                                                              5

SEQ ID NO: 37           moltype = AA  length = 5
FEATURE                 Location/Qualifiers
REGION                  1..5
                        note = Synthetic
source                  1..5
                        mol_type = protein
                        organism = synthetic construct
SEQUENCE: 37
ELMEQ                                                              5

SEQ ID NO: 38           moltype = AA  length = 36
FEATURE                 Location/Qualifiers
REGION                  1..36
                        note = Synthetic
source                  1..36
                        mol_type = protein
```

```
                        organism = synthetic construct
SEQUENCE: 38
GKTNEKFHQI EKEFSEVEGR IQDLEKYVED TKVDLW                      36

SEQ ID NO: 39           moltype = AA  length = 4
FEATURE                 Location/Qualifiers
REGION                  1..4
                        note = Synthetic
source                  1..4
                        mol_type = protein
                        organism = synthetic construct
SEQUENCE: 39
GGPD                                                         4

SEQ ID NO: 40           moltype = AA  length = 49
FEATURE                 Location/Qualifiers
REGION                  1..49
                        note = Synthetic
source                  1..49
                        mol_type = protein
                        organism = synthetic construct
SEQUENCE: 40
DLKSTQAAIN QINGKLNRLI ALMAQGGPDS YNAELLVALE NQHTIDLTD        49

SEQ ID NO: 41           moltype = AA  length = 68
FEATURE                 Location/Qualifiers
REGION                  1..68
                        note = Synthetic
source                  1..68
                        mol_type = protein
                        organism = synthetic construct
SEQUENCE: 41
NSEGIGQAAD LKSTQAAINQ INGKLNRLIA LMAQGGPDSY NAELLVALEN QHTIDLTDSE  60
MNKLFERT                                                     68

SEQ ID NO: 42           moltype = AA  length = 88
FEATURE                 Location/Qualifiers
REGION                  1..88
                        note = Synthetic
source                  1..88
                        mol_type = protein
                        organism = synthetic construct
SEQUENCE: 42
NSEGIGQAAD LKSTQAAINQ INGKLNRLIA LMAQGGPDSY NAELLVALEN QHTIDLTDSE  60
MNKLFERTKK QLRENAEDMG NGCFKIYH                               88

SEQ ID NO: 43           moltype = AA  length = 163
FEATURE                 Location/Qualifiers
REGION                  1..163
                        note = Synthetic
source                  1..163
                        mol_type = protein
                        organism = synthetic construct
SEQUENCE: 43
LKLATGMRNV PEKQTRGIFG AIAGFIENGW EGMVDGWYGF RHQNSEGIGQ AADLKSTQAA  60
INQINGKLNR LIALMAQGGP DSYNAELLVA LENQHTIDLT DSEMNKLFER TKKQLRENAE  120
DMGNGCFKIY HKCDNACIGS IRNGTYDHDV YRDEALNNRF QIK              163

SEQ ID NO: 44           moltype = AA  length = 42
FEATURE                 Location/Qualifiers
REGION                  1..42
                        note = Synthetic
source                  1..42
                        mol_type = protein
                        organism = synthetic construct
SEQUENCE: 44
SYNAELLVAL ENQHTIDLTD SEMNKLFERT KKQLRENAED MG               42

SEQ ID NO: 45           moltype = AA  length = 62
FEATURE                 Location/Qualifiers
REGION                  1..62
                        note = Synthetic
source                  1..62
                        mol_type = protein
                        organism = synthetic construct
SEQUENCE: 45
SYNAELLVAL ENQHTIDLTD SEMNKLFERT KKQLRENAED MGNGCFKIYH KCDNACIGSI  60
RN                                                           62
```

```
SEQ ID NO: 46          moltype = AA  length = 82
FEATURE                Location/Qualifiers
REGION                 1..82
                       note = Synthetic
source                 1..82
                       mol_type = protein
                       organism = synthetic construct
SEQUENCE: 46
SYNAELLVAL ENQHTIDLTD SEMNKLFERT KKQLRENAED MGNGCFKIYH KCDNACIGSI  60
RNGTYDHDVY RDEALNNRFQ IK                                           82

SEQ ID NO: 47          moltype = AA  length = 396
FEATURE                Location/Qualifiers
REGION                 1..396
                       note = Synthetic
source                 1..396
                       mol_type = protein
                       organism = synthetic construct
SEQUENCE: 47
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                             396

SEQ ID NO: 48          moltype = AA  length = 395
FEATURE                Location/Qualifiers
REGION                 1..395
                       note = Synthetic
source                 1..395
                       mol_type = protein
                       organism = synthetic construct
SEQUENCE: 48
MKTIIALSYI LCLVFAQKLP GNDNSTATLC LGHHAVPNGT IVKTITNDQI EVTNATELCF  60
NGICLKLATG MRNVPEKQTR GIFGAIAGFI ENGWEGMVDG WYGFRHQNSE GIGQAADLKS  120
TQAAINQING MVNRVIALMA QGGPDAYLAE LLVALLNQHV IDLTDSEMRK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                              395

SEQ ID NO: 49          moltype = AA  length = 396
FEATURE                Location/Qualifiers
REGION                 1..396
                       note = Synthetic
source                 1..396
                       mol_type = protein
                       organism = synthetic construct
SEQUENCE: 49
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIELM EQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                             396

SEQ ID NO: 50          moltype = AA  length = 396
FEATURE                Location/Qualifiers
REGION                 1..396
                       note = Synthetic
source                 1..396
                       mol_type = protein
                       organism = synthetic construct
SEQUENCE: 50
MKTIIALSYI LCLVFAQKLP GNDNSTATLC LGHHAVPNCT IVKTITNDQI EVTNATELVF  60
PGCGVLKLAT GMRCVPEKQT RGIFGAIAGF IENGWEGMVD GWYGFRHQNS EGIGQAADLK  120
STQAAINQIN GMVNRVIELM EQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                             396

SEQ ID NO: 51          moltype = AA  length = 395
FEATURE                Location/Qualifiers
REGION                 1..395
                       note = Synthetic
```

```
source                 1..395
                       mol_type = protein
                       organism = synthetic construct
SEQUENCE: 51
MKTIIALSYI LCLVFAQKLP GNDNSTATLC LGHHAVPNGT IVKTITNDQI EVTNATELVF  60
PGCVLKLATG MRNVPEKQTR GIFGAIAGFI ENGWEGMVDG WYGFRHQNSE GIGQAADLKS  120
TQAAINQING MVNRVIALMA QGGPDCYLAE LLVALLNQHV IDLTDSEMRK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                            395

SEQ ID NO: 52          moltype = AA  length = 395
FEATURE                Location/Qualifiers
REGION                 1..395
                       note = Synthetic
source                 1..395
                       mol_type = protein
                       organism = synthetic construct
SEQUENCE: 52
MKTIIALSYI LCLVFAQKLP GNDNSTATLC LGHHAVPNGT IVKTITNDQI EVTNATELVF  60
PCGVLKLATG MRNVPEKQTR GIFGAIAGFI ENGWEGMVDG WYGFRHQNSE GIGQAADLKS  120
TQAAINQING MVNRVIALMA QGGPDCYLAE LLVALLNQHV IDLTDSEMRK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                            395

SEQ ID NO: 53          moltype = AA  length = 396
FEATURE                Location/Qualifiers
REGION                 1..396
                       note = Synthetic
source                 1..396
                       mol_type = protein
                       organism = synthetic construct
SEQUENCE: 53
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM EEGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 54          moltype = AA  length = 396
FEATURE                Location/Qualifiers
REGION                 1..396
                       note = Synthetic
source                 1..396
                       mol_type = protein
                       organism = synthetic construct
SEQUENCE: 54
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 55          moltype = AA  length = 396
FEATURE                Location/Qualifiers
REGION                 1..396
                       note = Synthetic
source                 1..396
                       mol_type = protein
                       organism = synthetic construct
SEQUENCE: 55
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMLNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 56          moltype = AA  length = 396
FEATURE                Location/Qualifiers
REGION                 1..396
```

```
                        note = Synthetic
source                  1..396
                        mol_type = protein
                        organism = synthetic construct
SEQUENCE: 56
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRLIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 57           moltype = AA  length = 396
FEATURE                 Location/Qualifiers
REGION                  1..396
                        note = Synthetic
source                  1..396
                        mol_type = protein
                        organism = synthetic construct
SEQUENCE: 57
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMLNRLIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 58           moltype = AA  length = 396
FEATURE                 Location/Qualifiers
REGION                  1..396
                        note = Synthetic
source                  1..396
                        mol_type = protein
                        organism = synthetic construct
SEQUENCE: 58
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GLVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 59           moltype = AA  length = 396
FEATURE                 Location/Qualifiers
REGION                  1..396
                        note = Synthetic
source                  1..396
                        mol_type = protein
                        organism = synthetic construct
SEQUENCE: 59
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIAWM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 60           moltype = AA  length = 396
FEATURE                 Location/Qualifiers
REGION                  1..396
                        note = Synthetic
source                  1..396
                        mol_type = protein
                        organism = synthetic construct
SEQUENCE: 60
MKTIIALSYI LCLVFAQKLP GNDNSTATLC LGHHAVPNGT IVKTITNDQI EVTNATELVW  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 61           moltype = AA  length = 396
FEATURE                 Location/Qualifiers
```

```
REGION                  1..396
                        note = Synthetic
source                  1..396
                        mol_type = protein
                        organism = synthetic construct
SEQUENCE: 61
MKTIIALSYI LCLVFAQKLP GNDNSTATLC LGHHAVPNGT IVKTICNDQI EVTNATELVF  60
PGCGVLKLAT GMRNVPEKQT RGIFGAIAGF IENGWEGMVD GWYGFRHQNS EGIGQAADLK  120
STQAAINCIN GMVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 62           moltype = AA  length = 396
FEATURE                 Location/Qualifiers
REGION                  1..396
                        note = Synthetic
source                  1..396
                        mol_type = protein
                        organism = synthetic construct
SEQUENCE: 62
MKTIIALSYI LCLVFAQKLP GNDNSTATLC LGHHAVPNGT IVKTITNDNI TVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 63           moltype = AA  length = 395
FEATURE                 Location/Qualifiers
REGION                  1..395
                        note = Synthetic
source                  1..395
                        mol_type = protein
                        organism = synthetic construct
SEQUENCE: 63
MKTIIALSYI LCLVFAQKLP GNDNSTATLC LGHHAVPNGT IVKTITNDQI EVTNATELVF  60
PCGVLKLATG MRNVPEKQTR GIFGAIAGFI ENGWEGMVDG WYGFRHQNSE GIGQAADLKS  120
TQAAINQING MVNRVIALMA QGGPDCYLAE LLVALLNQHV IDLTDSEMNK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                            395

SEQ ID NO: 64           moltype = AA  length = 395
FEATURE                 Location/Qualifiers
REGION                  1..395
                        note = Synthetic
source                  1..395
                        mol_type = protein
                        organism = synthetic construct
SEQUENCE: 64
MKTIIALSYI LCLVFAQKLP GNDNSTATLC LGHHAVPNGT IVKTITNDQI EVTNATELVF  60
PCGVLKLATG MRNVPEKQTR GIFGAIAGFI ENGWEGMVDG WYGFRHQNSE GIGQAADLKS  120
TQAAINQING MVNRVIALME EGGPDCYLAE LLVALLNQHV IDLTDSEMNK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                            395

SEQ ID NO: 65           moltype = AA  length = 395
FEATURE                 Location/Qualifiers
REGION                  1..395
                        note = Synthetic
source                  1..395
                        mol_type = protein
                        organism = synthetic construct
SEQUENCE: 65
MKTIIALSYI LCLVFAQKLP GNDNSTATLC LGHHAVPNGT IVKTITNDNI TVTNATELVF  60
PCGVLKLATG MRNVPEKQTR GIFGAIAGFI ENGWEGMVDG WYGFRHQNSE GIGQAADLKS  120
TQAAINQING MVNRVIALME EGGPDCYLAE LLVALLNQHV IDLTDSEMNK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                            395

SEQ ID NO: 66           moltype = AA  length = 396
```

```
FEATURE                 Location/Qualifiers
REGION                  1..396
                        note = Synthetic
source                  1..396
                        mol_type = protein
                        organism = synthetic construct
SEQUENCE: 66
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM EEGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 67           moltype = AA  length = 396
FEATURE                 Location/Qualifiers
REGION                  1..396
                        note = Synthetic
source                  1..396
                        mol_type = protein
                        organism = synthetic construct
SEQUENCE: 67
MKTIIALSYI LCLVFAQKLP GNDNSTATLC LGHHAVPNGT IVKTITNDNI TVTNATELVF  60
PGCGVLKLAT GMRNVPEKQT RGIFGAIAGF IENGWEGMVD GWYGFRHQNS EGIGQAADLK  120
STQAAINQIN GMVNRVIALM EEGGPDCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 68           moltype = AA  length = 396
FEATURE                 Location/Qualifiers
REGION                  1..396
                        note = Synthetic
source                  1..396
                        mol_type = protein
                        organism = synthetic construct
SEQUENCE: 68
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPNCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 69           moltype = AA  length = 396
FEATURE                 Location/Qualifiers
REGION                  1..396
                        note = Synthetic
source                  1..396
                        mol_type = protein
                        organism = synthetic construct
SEQUENCE: 69
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPTCYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 70           moltype = AA  length = 396
FEATURE                 Location/Qualifiers
REGION                  1..396
                        note = Synthetic
source                  1..396
                        mol_type = protein
                        organism = synthetic construct
SEQUENCE: 70
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPACYLA ELLVALLNQH VIDLTDSEMN KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396
```

```
SEQ ID NO: 71          moltype = AA  length = 396
FEATURE                Location/Qualifiers
REGION                 1..396
                       note = Synthetic
source                 1..396
                       mol_type = protein
                       organism = synthetic construct
SEQUENCE: 71
MKTIIALSYI LCLVFAQKLP GNDNSTATLC LGHHAVPNGT IVKTITNDQI EVTNATELVF  60
PNCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 72          moltype = AA  length = 396
FEATURE                Location/Qualifiers
REGION                 1..396
                       note = Synthetic
source                 1..396
                       mol_type = protein
                       organism = synthetic construct
SEQUENCE: 72
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGPPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 73          moltype = AA  length = 395
FEATURE                Location/Qualifiers
REGION                 1..395
                       note = Synthetic
source                 1..395
                       mol_type = protein
                       organism = synthetic construct
SEQUENCE: 73
MKTIIALSYI LCLVFAQKLP GNDNSTATLC LGHHAVPNGT IVKTITNDQI EVTNATELCF  60
NGICLKLATG MRNVPEKQTR GIFGAIAGFI ENGWEGMVDG WYGFRHQNSE GIGQAADLKS  120
TQAAINQING MVNRVIALMA QGPPDCYLAE LLVALLNQHV IDLTDSEMRK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                             395

SEQ ID NO: 74          moltype = AA  length = 395
FEATURE                Location/Qualifiers
REGION                 1..395
                       note = Synthetic
source                 1..395
                       mol_type = protein
                       organism = synthetic construct
SEQUENCE: 74
MKTIIALSYI LCLVFAQKLP GNDNSTATLC LGHHAVPNCT IVKTITNDQI EVTNATELCF  60
NGICLKLATG MRCVPEKQTR GIFGAIAGFI ENGWEGMVDG WYGFRHQNSE GIGQAADLKS  120
TQAAINQING MVNRVIELME QGGPDCYLAE LLVALLNQHV IDLTDSEMRK LFERTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                             395

SEQ ID NO: 75          moltype = AA  length = 396
FEATURE                Location/Qualifiers
REGION                 1..396
                       note = Synthetic
source                 1..396
                       mol_type = protein
                       organism = synthetic construct
SEQUENCE: 75
MKTIIALSYI FCLALAQDLP GNDNSTATLC LGHHAVPNGT LVKTITDDQI EVTNATELVF  60
PGCGVLKLAT GMRNVPEKQT RGLFGAIAGF IENGWEGMID GWYGFRHQNS EGTGQAADLK  120
STQAAIDQIN GMVNRVIALM AQGGPDCYLA ELLVALLNQH VIDLTDSEMR KLFEKTRRQL  180
RENAEDMGNG CFKIYHKCDN ACIESIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396
```

```
SEQ ID NO: 76          moltype = AA  length = 396
FEATURE                Location/Qualifiers
REGION                 1..396
                       note = Synthetic
source                 1..396
                       mol_type = protein
                       organism = synthetic construct
SEQUENCE: 76
MKTIIALSYI FCLVFAQNLP GNDNSTATLC LGHHAVPNGT LVKTITNDQI EVTNATELVF  60
PGCGVLKLAT GMRNVPEKQT RGIFGAIAGF IENGWEGMVD GWYGFRHQNS EGTGQAADLK  120
STQAAIDQIN GMVNRVIALM AQGGPDCYLA ELLVALLNQH VIDLTDSEMR KLFEKTRRQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                          396

SEQ ID NO: 77          moltype = AA  length = 396
FEATURE                Location/Qualifiers
REGION                 1..396
                       note = Synthetic
source                 1..396
                       mol_type = protein
                       organism = synthetic construct
SEQUENCE: 77
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGTGQAADLK  120
STQAAINQIN GMVNRVIALM AQGGPDCYLA ELLVALLNQH VIDLTDSEMR KLFERTKKQL  180
RENAEDMGNG CFKIYHKCDN ACIESIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                          396

SEQ ID NO: 78          moltype = AA  length = 396
FEATURE                Location/Qualifiers
REGION                 1..396
                       note = Synthetic
source                 1..396
                       mol_type = protein
                       organism = synthetic construct
SEQUENCE: 78
MKTIIALSYI LCLVFAQKLP GNDNSTATLC LGHHAVPNGT IVKTITNDRI EVTNATELVF  60
PGCGVLKLAT GMRNVPERQT RGIFGAIAGF IENGWEGMVD GWYGFRHQNS EGRGQAADLK  120
STQAAIDQIN GMVNRVIALM AQGGPDCYLA ELLVALLNQH VIDLTDSEMR KLFEKTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                          396

SEQ ID NO: 79          moltype = AA  length = 395
FEATURE                Location/Qualifiers
REGION                 1..395
                       note = Synthetic
source                 1..395
                       mol_type = protein
                       organism = synthetic construct
SEQUENCE: 79
MKTIIALSYI FCLALAQDLP GNDNSTATLC LGHHAVPNGT LVKTITDDQI EVTNATELVF  60
PGCVLKLATG MRNVPEKQTR GLFGAIAGFI ENGWEGMIDG WYGFRHQNSE GTGQAADLKS  120
TQAAIDQING MVNRVIALMA QGGPDCYLAE LLVALLNQHV IDLTDSEMRK LFEKTRRQLR  180
ENAEDMGNGC FKIYHKCDNA CIESIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                           395

SEQ ID NO: 80          moltype = AA  length = 395
FEATURE                Location/Qualifiers
REGION                 1..395
                       note = Synthetic
source                 1..395
                       mol_type = protein
                       organism = synthetic construct
SEQUENCE: 80
MKTIIALSYI FCLVFAQNLP GNDNSTATLC LGHHAVPNGT LVKTITNDQI EVTNATELVF  60
PGCVLKLATG MRNVPEKQTR GIFGAIAGFI ENGWEGMVDG WYGFRHQNSE GTGQAADLKS  120
TQAAIDQING MVNRVIALMA QGGPDCYLAE LLVALLNQHV IDLTDSEMRK LFEKTRRQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
```

```
KDILDKIELI GNENHGLYLA DQYVKGIAKS RKSGS                         395

SEQ ID NO: 81          moltype = AA  length = 395
FEATURE                Location/Qualifiers
REGION                 1..395
                       note = Synthetic
source                 1..395
                       mol_type = protein
                       organism = synthetic construct
SEQUENCE: 81
MKTIIALSYI LCLVFAQKLP GNDNSTATLC LGHHAVPNGT IVKTITNDQI EVTNATELVF  60
PGCVLKLATG MRNVPEKQTR GIFGAIAGFI ENGWEGMVDG WYGFRHQNSE GTGQAADLKS  120
TQAAINQING MVNRVIALMA QGGPDCYLAE LLVALLNQHV IDLTDSEMRK LFERTKKQLR  180
ENAEDMGNGC FKIYHKCDNA CIESIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                         395

SEQ ID NO: 82          moltype = AA  length = 395
FEATURE                Location/Qualifiers
REGION                 1..395
                       note = Synthetic
source                 1..395
                       mol_type = protein
                       organism = synthetic construct
SEQUENCE: 82
MKTIIALSYI LCLVFAQKLP GNDNSTATLC LGHHAVPNGT IVKTITNDRI EVTNATELVF  60
PGCVLKLATG MRNVPERQTR GIFGAIAGFI ENGWEGMVDG WYGFRHQNSE GRGQAADLKS  120
TQAAIDQING MVNRVIALMA QGGPDCYLAE LLVALLNQHV IDLTDSEMRK LFEKTKKQLR  180
ENAEDMGNGC FKIYHKCDNA CIGSIRNGTY DHDVYRDEAL NNRFQIKSGG DIIKLLNEQV  240
NKEMQSSNLY MSMSSWCYTH SLDGAGLFLF DHAAEEYEHA KKLIIFLNEN NVPVQLTSIS  300
APEHKFEGLT QIFQKAYEHE QHISESINNI VDHAIKSKDH ATFNFLQWYV AEQHEEEVLF  360
KDILDKIELI GNENHGLYLA DQYVKGIAKS RKSGS                         395

SEQ ID NO: 83          moltype = AA  length = 388
FEATURE                Location/Qualifiers
REGION                 1..388
                       note = Synthetic
source                 1..388
                       mol_type = protein
                       organism = synthetic construct
SEQUENCE: 83
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKAG PPGGMQIYEG  240
KLTAEGLRFG IVASRFNHAL VDRLVEGAID CIVRHGGREE DITLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                 388

SEQ ID NO: 84          moltype = AA  length = 388
FEATURE                Location/Qualifiers
REGION                 1..388
                       note = Synthetic
source                 1..388
                       mol_type = protein
                       organism = synthetic construct
SEQUENCE: 84
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM EEGGPDCYLA ELLVALLNQH VIDLTDSEMR KLFERTKKQL  180
RENAEDMGNG CFKIYHKCDN ACIGSIRNGT YDHDVYRDEA LNNRFQIKAG PPGGCQIYEG  240
KLTAEGLRFG IVASRFNHAL VDRLVEGAID CIVRHGGREE DCTLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                 388

SEQ ID NO: 85          moltype = AA  length = 388
FEATURE                Location/Qualifiers
REGION                 1..388
                       note = Synthetic
source                 1..388
                       mol_type = protein
                       organism = synthetic construct
SEQUENCE: 85
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM EEGGPDCYLA ELLVALLNQH VIDLTDSEMR KLFERTKKQL  180
RENAEDMGNG CFKIYHKCDN ACIGSIRNGT YDHDVYRDEA LNNRFQIKAG PPGGMQIYEG  240
KLTAEGLRFG IVASRFNHAL VDRLVEGAID CIVRHGGREE DITLVRVPGS WEIPVAAGEL  300
```

```
ARKEDIDAVI AIGVLIRGAT PHFDYIASEV SKGLADLSLE LRKPITFGVI TADTLEQAIE  360
RAGTKHGNKG WEAALSAIEM ANLFKSLR                                     388

SEQ ID NO: 86          moltype = AA  length = 388
FEATURE                Location/Qualifiers
REGION                 1..388
                       note = Synthetic
source                 1..388
                       mol_type = protein
                       organism = synthetic construct
SEQUENCE: 86
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM EEGGPDCYLA ELLVALLNQH VIDLTDSEMR KLFERTKKQL  180
RENAEDMGNG CFKIYHKCDN ACIGSIRNGT YDHDVYRDEA LNNRFQIKAG SGGGCQIYEG  240
KLTAEGLRFG IVASRFNHAL VDRLVEGAID CIVRHGGREE DCTLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                     388

SEQ ID NO: 87          moltype = AA  length = 388
FEATURE                Location/Qualifiers
REGION                 1..388
                       note = Synthetic
source                 1..388
                       mol_type = protein
                       organism = synthetic construct
SEQUENCE: 87
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKAG PPGGMQIYEG  240
KLTAEGLRFG IVASRFNHAL VDRLVEGAID CIVRHGGREE DITLVRVPGS WEIPVAAGEL  300
ARKEDIDAVI AIGVLIRGAT PHFDYIASEV SKGLANLALE LRKPITFGVI TADTLEQAIE  360
RAGTKHGNKG WEAALSAIEM ANLFKSLR                                     388

SEQ ID NO: 88          moltype = AA  length = 389
FEATURE                Location/Qualifiers
REGION                 1..389
                       note = Synthetic
source                 1..389
                       mol_type = protein
                       organism = synthetic construct
SEQUENCE: 88
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMN KLFERTKKQL  180
RENAEDMGNG CFKIYHKCDN ACIGSIRNGT YDHDVYRDEA LNNRFQIKAG PPPGGMQIYE  240
GKLTAEGLRF GIVASRFNHA LVDRLVEGAI DCIVRHGGRE EDITLVRVPG SWEIPVAAGE  300
LARKEDIDAV IAIGVLIRGA TPHFDYIASE VSKGLADLSL ELRKPITFGV ITADTLEQAI  360
ERAGTKHGNK GWEAALSAIE MANLFKSLR                                    389

SEQ ID NO: 89          moltype = AA  length = 388
FEATURE                Location/Qualifiers
REGION                 1..388
                       note = Synthetic
source                 1..388
                       mol_type = protein
                       organism = synthetic construct
SEQUENCE: 89
MKTIIALSYI LCLVFAQKLP GNDNSTATLC LGHHAVPNCT IVKTITNDQI EVTNATELVF  60
PGCGVLKLAT GMRCVPEKQT RGIFGAIAGF IENGWEGMVD GWYGFRHQNS EGIGQAADLK  120
STQAAINQIN GLVNRVIAWM EEGGPDCYLA ELLVALLNQH VIDLTDSEMN KLFERTKKQL  180
RENAEDMGNG CFKIYHKCDN ACIGSIRNGT YDHDVYRDEA LNNRFQIKAG PPGGMQIYEG  240
KLTAEGLRFG IVASRFNHAL VDRLVEGAID CIVRHGGREE DITLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                     388

SEQ ID NO: 90          moltype = AA  length = 281
FEATURE                Location/Qualifiers
REGION                 1..281
                       note = Synthetic
source                 1..281
                       mol_type = protein
                       organism = synthetic construct
SEQUENCE: 90
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKPG SGYIPEAPRD  240
```

```
GQAYVRKDGE WVLLSTFLGS GLNDIFEAQK IEWHEGHHHH H                     281

SEQ ID NO: 91           moltype = AA  length = 283
FEATURE                 Location/Qualifiers
REGION                  1..283
                        note = Synthetic
source                  1..283
                        mol_type = protein
                        organism = synthetic construct
SEQUENCE: 91
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKGG PGSGYIPEAP  240
RDGQAYVRKD GEWVLLSTFL GSGLNDIFEA QKIEWHEGHH HHH                   283

SEQ ID NO: 92           moltype = AA  length = 389
FEATURE                 Location/Qualifiers
REGION                  1..389
                        note = Synthetic
source                  1..389
                        mol_type = protein
                        organism = synthetic construct
SEQUENCE: 92
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DSGGDIIKLL NEQVNKEMQS  240
SNLYMSMSSW CYTHSLDGAG LFLFDHAAEE YEHAKKLIIF LNENNVPVQL TSISAPEHKF  300
EGLTQIFQKA YEHEQHISES INNIVDHAIK SKDHATFNFL QWYVAEQHEE EVLFKDILDK  360
IELIGNENHG LYLADQYVKG IAKSRKSGS                                   389

SEQ ID NO: 93           moltype = AA  length = 388
FEATURE                 Location/Qualifiers
REGION                  1..388
                        note = Synthetic
source                  1..388
                        mol_type = protein
                        organism = synthetic construct
SEQUENCE: 93
MNTQILVFAL IAIIPTNADK ICLGHHAVSN GTKVNTLTER GVEVVNATEL VFPGCVLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
ELIGNENHGL YLADQYVKGI AKSRKSGS                                    388

SEQ ID NO: 94           moltype = AA  length = 388
FEATURE                 Location/Qualifiers
REGION                  1..388
                        note = Synthetic
source                  1..388
                        mol_type = protein
                        organism = synthetic construct
SEQUENCE: 94
MNTQILVFAL IAIIPTNADK ICLGHHAVSN GTKVNTLTER GVEVVNATEL VFPCGVLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
ELIGNENHGL YLADQYVKGI AKSRKSGS                                    388

SEQ ID NO: 95           moltype = AA  length = 389
FEATURE                 Location/Qualifiers
REGION                  1..389
                        note = Synthetic
source                  1..389
                        mol_type = protein
                        organism = synthetic construct
SEQUENCE: 95
MNTQILVFAL IAIIPTNADK ICLGHHAVSN GTKVNTLTER GVEVVNATEL VFPNCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DSGGDIIKLL NEQVNKEMQS  240
SNLYMSMSSW CYTHSLDGAG LFLFDHAAEE YEHAKKLIIF LNENNVPVQL TSISAPEHKF  300
EGLTQIFQKA YEHEQHISES INNIVDHAIK SKDHATFNFL QWYVAEQHEE EVLFKDILDK  360
IELIGNENHG LYLADQYVKG IAKSRKSGS                                   389
```

```
SEQ ID NO: 96          moltype = AA  length = 389
FEATURE                Location/Qualifiers
REGION                 1..389
                       note = Synthetic
source                 1..389
                       mol_type = protein
                       organism = synthetic construct
SEQUENCE: 96
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGPPDC YLAELLVAML NQHVIDLADS EMDKLYERVK RQLRENAEED  180
GTGCFEIFHK CDDDCMASIR NNTYDHSKYR EEAMQNRIQI DSGGDIIKLL NEQVNKEMQS  240
SNLYMSMSSW CYTHSLDGAG LFLFDHAAEE YEHAKKLIIF LNENNVPVQL TSISAPEHKF  300
EGLTQIFQKA YEHEQHISES INNIVDHAIK SKDHATFNFL QWYVAEQHEE EVLFKDILDK  360
IELIGNENHG LYLADQYVKG IAKSRKSGS                                   389

SEQ ID NO: 97          moltype = AA  length = 389
FEATURE                Location/Qualifiers
REGION                 1..389
                       note = Synthetic
source                 1..389
                       mol_type = protein
                       organism = synthetic construct
SEQUENCE: 97
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMEEGGPDC YLAELLVAML NQHVIDLADS EMDKLYERVK RQLRENAEED  180
GTGCFEIFHK CDDDCMASIR NNTYDHSKYR EEAMQNRIQI DSGGDIIKLL NEQVNKEMQS  240
SNLYMSMSSW CYTHSLDGAG LFLFDHAAEE YEHAKKLIIF LNENNVPVQL TSISAPEHKF  300
EGLTQIFQKA YEHEQHISES INNIVDHAIK SKDHATFNFL QWYVAEQHEE EVLFKDILDK  360
IELIGNENHG LYLADQYVKG IAKSRKSGS                                   389

SEQ ID NO: 98          moltype = AA  length = 389
FEATURE                Location/Qualifiers
REGION                 1..389
                       note = Synthetic
source                 1..389
                       mol_type = protein
                       organism = synthetic construct
SEQUENCE: 98
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ELMEQGGPDC YLAELLVAML NQHVIDLADS EMDKLYERVK RQLRENAEED  180
GTGCFEIFHK CDDDCMASIR NNTYDHSKYR EEAMQNRIQI DSGGDIIKLL NEQVNKEMQS  240
SNLYMSMSSW CYTHSLDGAG LFLFDHAAEE YEHAKKLIIF LNENNVPVQL TSISAPEHKF  300
EGLTQIFQKA YEHEQHISES INNIVDHAIK SKDHATFNFL QWYVAEQHEE EVLFKDILDK  360
IELIGNENHG LYLADQYVKG IAKSRKSGS                                   389

SEQ ID NO: 99          moltype = AA  length = 388
FEATURE                Location/Qualifiers
REGION                 1..388
                       note = Synthetic
source                 1..388
                       mol_type = protein
                       organism = synthetic construct
SEQUENCE: 99
MNTQILVFAL IAIIPTNADK ICLGHHAVSN GTKVNTLTER GVEVVNATEL CFNGICLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
ELIGNENHGL YLADQYVKGI AKSRKSGS                                    388

SEQ ID NO: 100         moltype = AA  length = 388
FEATURE                Location/Qualifiers
REGION                 1..388
                       note = Synthetic
source                 1..388
                       mol_type = protein
                       organism = synthetic construct
SEQUENCE: 100
MNTQILVFAL IAIIPTNADK ICLGHHAVSN GTKVNTLTER GVEVVNATEL VFPCGVLKLA  60
TGMKNVPEIP KGRGLFGAIA GFIENGWEGL IDGWYGFRHQ NAQGEGTAAD YKSTQSAIDQ  120
ITGMVNRVIA LMAQGPPDCY LAELLVAMLN QHVIDLADSE MDKLYERVKR QLRENAEEDG  180
TGCFEIFHKC DDDCMASIRN NTYDHSKYRE EAMQNRIQID SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
```

```
ELIGNENHGL YLADQYVKGI AKSRKSGS                                 388

SEQ ID NO: 101         moltype = AA  length = 276
FEATURE                Location/Qualifiers
REGION                 1..276
                       note = Synthetic
source                 1..276
                       mol_type = protein
                       organism = synthetic construct
SEQUENCE: 101
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DGGPGSGYIP EAPRDGQAYV  240
RKDGEWVLLS TFLGSGLNDI FEAQKIEWHE GHHHHH                         276

SEQ ID NO: 102         moltype = AA  length = 275
FEATURE                Location/Qualifiers
REGION                 1..275
                       note = Synthetic
source                 1..275
                       mol_type = protein
                       organism = synthetic construct
SEQUENCE: 102
MNTQILVFAL IAIIPTNADK ICLGHHAVSN GTKVNTLTER GVEVVNATEL VFPGCVLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID GGPGSGYIPE APRDGQAYVR  240
KDGEWVLLST FLGSGLNDIF EAQKIEWHEG HHHHH                          275

SEQ ID NO: 103         moltype = AA  length = 388
FEATURE                Location/Qualifiers
REGION                 1..388
                       note = Synthetic
source                 1..388
                       mol_type = protein
                       organism = synthetic construct
SEQUENCE: 103
MYKIVVIIAL LGAVKGLDKI CLGHHAVANG TIVKTLTNEQ EEVTNATELV FPGCGVLMLA  60
TGMRNVPELI QGRGLFGAIA GFLENGWEGM VDGWYGFRHQ NAQGTGQAAD YKSTQAAIDQ  120
ITGMVNRVVA LMAQGGPDCY LAELLVAMLN QHVIDMADSE MRNLYERVRK QLRQNAEEDG  180
KGCFEIYHAC DDSCMESIRN NTYDHSQYRE EALLNRLNIN SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
ELIGNENHGL YLADQYVKGI AKSRKSGS                                 388

SEQ ID NO: 104         moltype = AA  length = 387
FEATURE                Location/Qualifiers
REGION                 1..387
                       note = Synthetic
source                 1..387
                       mol_type = protein
                       organism = synthetic construct
SEQUENCE: 104
MYKIVVIIAL LGAVKGLDKI CLGHHAVANG TIVKTLTNEQ EEVTNATELV FPGCVLMLAT  60
GMRNVPELIQ GRGLFGAIAG FLENGWEGMV DGWYGFRHQN AQGTGQAADY KSTQAAIDQI  120
TGMVNRVVAL MAQGGPDCYL AELLVAMLNQ HVIDMADSEM RNLYERVRKQ LRQNAEEDGK  180
GCFEIYHACD DSCMESIRNN TYDHSQYREE ALLNRLNINS GGDIIKLLNE QVNKEMQSSN  240
LYMSMSSWCY THSLDGAGLF LFDHAAEEYE HAKKLIIFLN ENNVPVQLTS ISAPEHKFEG  300
LTQIFQKAYE HEQHISESIN NIVDHAIKSK DHATFNFLQW YVAEQHEEEV LFKDILDKIE  360
LIGNENHGLY LADQYVKGIA KSRKSGS                                  387

SEQ ID NO: 105         moltype = AA  length = 387
FEATURE                Location/Qualifiers
REGION                 1..387
                       note = Synthetic
source                 1..387
                       mol_type = protein
                       organism = synthetic construct
SEQUENCE: 105
MYKIVVIIAL LGAVKGLDKI CLGHHAVANG TIVKTLTNEQ EEVTNATELV FPCGVLMLAT  60
GMRNVPELIQ GRGLFGAIAG FLENGWEGMV DGWYGFRHQN AQGTGQAADY KSTQAAIDQI  120
TGMVNRVVAL MAQGGPDCYL AELLVAMLNQ HVIDMADSEM RNLYERVRKQ LRQNAEEDGK  180
GCFEIYHACD DSCMESIRNN TYDHSQYREE ALLNRLNINS GGDIIKLLNE QVNKEMQSSN  240
LYMSMSSWCY THSLDGAGLF LFDHAAEEYE HAKKLIIFLN ENNVPVQLTS ISAPEHKFEG  300
LTQIFQKAYE HEQHISESIN NIVDHAIKSK DHATFNFLQW YVAEQHEEEV LFKDILDKIE  360
LIGNENHGLY LADQYVKGIA KSRKSGS                                  387

SEQ ID NO: 106         moltype = AA  length = 388
```

```
FEATURE                Location/Qualifiers
REGION                 1..388
                       note = Synthetic
source                 1..388
                       mol_type = protein
                       organism = synthetic construct
SEQUENCE: 106
MYKIVVIIAL LGAVKGLDKI CLGHHAVANG TIVKTLTNEQ EEVTNATELV FPGCGVLMLA  60
TGMRNVPELI QGRGLFGAIA GFLENGWEGM VDGWYGFRHQ NAQGTGQAAD YKSTQAAIDQ  120
ITGMVNRVVE LMEQGGPDCY LAELLVAMLN QHVIDMADSE MRNLYERVRK QLRQNAEEDG  180
KGCFEIYHAC DDSCMESIRN NTYDHSQYRE EALLNRLNIN SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
ELIGNENHGL YLADQYVKGI AKSRKSGS                                     388

SEQ ID NO: 107         moltype = AA  length = 388
FEATURE                Location/Qualifiers
REGION                 1..388
                       note = Synthetic
source                 1..388
                       mol_type = protein
                       organism = synthetic construct
SEQUENCE: 107
MYKIVVIIAL LGAVKGLDKI CLGHHAVANG TIVKTLTNEQ EEVTNATELV FPGCGVLMLA  60
TGMRNVPELI QGRGLFGAIA GFLENGWEGM VDGWYGFRHQ NAQGTGQAAD YKSTQAAIDQ  120
ITGMVNRVVA LMAQGPPDCY LAELLVAMLN QHVIDMADSE MRNLYERVRK QLRQNAEEDG  180
KGCFEIYHAC DDSCMESIRN NTYDHSQYRE EALLNRLNIN SGGDIIKLLN EQVNKEMQSS  240
NLYMSMSSWC YTHSLDGAGL FLFDHAAEEY EHAKKLIIFL NENNVPVQLT SISAPEHKFE  300
GLTQIFQKAY EHEQHISESI NNIVDHAIKS KDHATFNFLQ WYVAEQHEEE VLFKDILDKI  360
ELIGNENHGL YLADQYVKGI AKSRKSGS                                     388

SEQ ID NO: 108         moltype = AA  length = 387
FEATURE                Location/Qualifiers
REGION                 1..387
                       note = Synthetic
source                 1..387
                       mol_type = protein
                       organism = synthetic construct
SEQUENCE: 108
MYKIVVIIAL LGAVKGLDKI CLGHHAVANG TIVKTLTNEQ EEVTNATELC FNGICLMLAT  60
GMRNVPELIQ GRGLFGAIAG FLENGWEGMV DGWYGFRHQN AQGTGQAADY KSTQAAIDQI  120
TGMVNRVVAL MAQGGPDCYL AELLVAMLNQ HVIDMADSEM RNLYERVRKQ LRQNAEEDGK  180
GCFEIYHACD DSCMESIRNN TYDHSQYREE ALLNRLNINS GGDIIKLLNE QVNKEMQSSN  240
LYMSMSSWCY THSLDGAGLF LFDHAAEEYE HAKKLIIFLN ENNVPVQLTS ISAPEHKFEG  300
LTQIFQKAYE HEQHISESIN NIVDHAIKSK DHATFNFLQW YVAEQHEEEV LFKDILDKIE  360
LIGNENHGLY LADQYVKGIA KSRKSGS                                      387

SEQ ID NO: 109         moltype = AA  length = 275
FEATURE                Location/Qualifiers
REGION                 1..275
                       note = Synthetic
source                 1..275
                       mol_type = protein
                       organism = synthetic construct
SEQUENCE: 109
MKTIIALSYI FCLALAQDLP GNDNSTATLC LGHHAVPNGT LVKTITDDQI EVTNATELVF  60
PGCGVLKLAT GMRNVPEKQT RGLFGAIAGF IENGWEGMID GWYGFRHQNS EGTGQAADLK  120
STQAAIDQIN GMVNRVIALM AQGGPDCYLA ELLVALLNQH VIDLTDSEMR KLFEKTRRQL  180
RENAEDMGNG CFKIYHKCDN ACIESIRNGT YDHDVYRDEA LNNRFQIKGV ELKSGYKDWI  240
LWISFAISCF LLCVVLLGFI MWACQRGNIR CNICI                             275

SEQ ID NO: 110         moltype = AA  length = 275
FEATURE                Location/Qualifiers
REGION                 1..275
                       note = Synthetic
source                 1..275
                       mol_type = protein
                       organism = synthetic construct
SEQUENCE: 110
MKTIIALSYI FCLVFAQNLP GNDNSTATLC LGHHAVPNGT LVKTITNDQI EVTNATELVF  60
PGCGVLKLAT GMRNVPEKQT RGIFGAIAGF IENGWEGMVD GWYGFRHQNS EGTGQAADLK  120
STQAAIDQIN GMVNRVIALM AQGGPDCYLA ELLVALLNQH VIDLTDSEMR KLFEKTRRQL  180
RENAEDMGNG CFKIYHKCDN ACIGSIRNGT YDHDVYRDEA LNNRFQIKGV ELKSGYKDWI  240
LWISFAISCF LLCVVLLGFI MWACQKGNIR CNICI                             275

SEQ ID NO: 111         moltype = AA  length = 275
FEATURE                Location/Qualifiers
REGION                 1..275
                       note = Synthetic
```

```
source                  1..275
                        mol_type = protein
                        organism = synthetic construct
SEQUENCE: 111
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGTGQAADLK  120
STQAAINQIN GMVNRVIALM AQGGPDCYLA ELLVALLNQH VIDLTDSEMR KLFERTKKQL  180
RENAEDMGNG CFKIYHKCDN ACIESIRNGT YDHDVYRDEA LNNRFQIKGV ELKSGYKDWI  240
LWISFAISCF LLCVALLGFI MWACQKGNIR CNICI                             275

SEQ ID NO: 112          moltype = AA  length = 275
FEATURE                 Location/Qualifiers
REGION                  1..275
                        note = Synthetic
source                  1..275
                        mol_type = protein
                        organism = synthetic construct
SEQUENCE: 112
MKTIIALSYI LCLVFAQKLP GNDNSTATLC LGHHAVPNGT IVKTITNDRI EVTNATELVF  60
PGCGVLKLAT GMRNVPERQT RGIFGAIAGF IENGWEGMVD GWYGFRHQNS EGRGQAADLK  120
STQAAIDQIN GMVNRVIALM AQGGPDCYLA ELLVALLNQH VIDLTDSEMR KLFEKTKKQL  180
RENAEDMGNG CFKIYHKCDN ACIGSIRNGT YDHDVYRDEA LNNRFQIKGV ELKSGYKDWI  240
LWISFAISCF LLCVALLGFI MWACQKGNIR CNICI                             275

SEQ ID NO: 113          moltype = AA  length = 275
FEATURE                 Location/Qualifiers
REGION                  1..275
                        note = Synthetic
source                  1..275
                        mol_type = protein
                        organism = synthetic construct
SEQUENCE: 113
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIELM EQGGPDCYLA ELLVALLNQH VIDLTDSEMR KLFERTKKQL  180
RENAEDMGNG CFKIYHKCDN ACIGSIRNGT YDHDVYRDEA LNNRFQIKGV ELKSGYKDWI  240
LWISFAISCF LLCVALLGFI MWACQKGNIR CNICI                             275

SEQ ID NO: 114          moltype = AA  length = 274
FEATURE                 Location/Qualifiers
REGION                  1..274
                        note = Synthetic
source                  1..274
                        mol_type = protein
                        organism = synthetic construct
SEQUENCE: 114
MKTIIALSYI LCLVFAQKLP GNDNSTATLC LGHHAVPNGT IVKTITNDQI EVTNATELVF  60
PGCVLKLATG MRNVPEKQTR GIFGAIAGFI ENGWEGMVDG WYGFRHQNSE GIGQAADLKS  120
TQAAINQING MVNRVIALMA QGGPDCYLAE LLVALLNQHV IDLTDSEMRK LFERTKKQLR  180
ENAEDMGNGC FKIYHKCDNA CIGSIRNGTY DHDVYRDEAL NNRFQIKGVE LKSGYKDWIL  240
WISFAISCFL LCVALLGFIM WACQKGNIRC NICI                              274

SEQ ID NO: 115          moltype = AA  length = 274
FEATURE                 Location/Qualifiers
REGION                  1..274
                        note = Synthetic
source                  1..274
                        mol_type = protein
                        organism = synthetic construct
SEQUENCE: 115
MKTIIALSYI LCLVFAQKLP GNDNSTATLC LGHHAVPNGT IVKTITNDQI EVTNATELVF  60
PCGVLKLATG MRNVPEKQTR GIFGAIAGFI ENGWEGMVDG WYGFRHQNSE GIGQAADLKS  120
TQAAINQING MVNRVIALMA QGGPDCYLAE LLVALLNQHV IDLTDSEMRK LFERTKKQLR  180
ENAEDMGNGC FKIYHKCDNA CIGSIRNGTY DHDVYRDEAL NNRFQIKGVE LKSGYKDWIL  240
WISFAISCFL LCVALLGFIM WACQKGNIRC NICI                              274

SEQ ID NO: 116          moltype = AA  length = 274
FEATURE                 Location/Qualifiers
REGION                  1..274
                        note = Synthetic
source                  1..274
                        mol_type = protein
                        organism = synthetic construct
SEQUENCE: 116
MKTIIALSYI FCLALAQDLP GNDNSTATLC LGHHAVPNGT LVKTITDDQI EVTNATELVF  60
PGCVLKLATG MRNVPEKQTR GLFGAIAGFI ENGWEGMIDG WYGFRHQNSE GTGQAADLKS  120
TQAAIDQING MVNRVIALMA QGGPDCYLAE LLVALLNQHV IDLTDSEMRK LFEKTRRQLR  180
ENAEDMGNGC FKIYHKCDNA CIESIRNGTY DHDVYRDEAL NNRFQIKGVE LKSGYKDWIL  240
WISFAISCFL LCVVLLGFIM WACQRGNIRC NICI                              274
```

```
SEQ ID NO: 117         moltype = AA  length = 274
FEATURE                Location/Qualifiers
REGION                 1..274
                       note = Synthetic
source                 1..274
                       mol_type = protein
                       organism = synthetic construct
SEQUENCE: 117
MKTIIALSYI FCLVFAQNLP GNDNSTATLC LGHHAVPNGT LVKTITNDQI EVTNATELVF  60
PGCVLKLATG MRNVPEKQTR GIFGAIAGFI ENGWEGMVDG WYGFRHQNSE GTGQAADLKS  120
TQAAIDQING MVNRVIALMA QGGPDCYLAE LLVALLNQHV IDLTDSEMRK LFEKTRRQLR  180
ENAEDMGNGC FKIYHKCDNA CIGSIRNGTY DHDVYRDEAL NNRFQIKGVE LKSGYKDWIL  240
WISFAISCFL LCVVLLGFIM WACQKGNIRC NICI                            274

SEQ ID NO: 118         moltype = AA  length = 274
FEATURE                Location/Qualifiers
REGION                 1..274
                       note = Synthetic
source                 1..274
                       mol_type = protein
                       organism = synthetic construct
SEQUENCE: 118
MKTIIALSYI LCLVFAQKLP GNDNSTATLC LGHHAVPNGT IVKTITNDQI EVTNATELVF  60
PGCVLKLATG MRNVPEKQTR GIFGAIAGFI ENGWEGMVDG WYGFRHQNSE GTGQAADLKS  120
TQAAINQING MVNRVIALMA QGGPDCYLAE LLVALLNQHV IDLTDSEMRK LFERTKKQLR  180
ENAEDMGNGC FKIYHKCDNA CIESIRNGTY DHDVYRDEAL NNRFQIKGVE LKSGYKDWIL  240
WISFAISCFL LCVALLGFIM WACQKGNIRC NICI                            274

SEQ ID NO: 119         moltype = AA  length = 274
FEATURE                Location/Qualifiers
REGION                 1..274
                       note = Synthetic
source                 1..274
                       mol_type = protein
                       organism = synthetic construct
SEQUENCE: 119
MKTIIALSYI LCLVFAQKLP GNDNSTATLC LGHHAVPNGT IVKTITNDRI EVTNATELVF  60
PGCVLKLATG MRNVPERQTR GIFGAIAGFI ENGWEGMVDG WYGFRHQNSE GRGQAADLKS  120
TQAAIDQING MVNRVIALMA QGGPDCYLAE LLVALLNQHV IDLTDSEMRK LFEKTKKQLR  180
ENAEDMGNGC FKIYHKCDNA CIGSIRNGTY DHDVYRDEAL NNRFQIKGVE LKSGYKDWIL  240
WISFAISCFL LCVALLGFIM WACQKGNIRC NICI                            274

SEQ ID NO: 120         moltype = AA  length = 268
FEATURE                Location/Qualifiers
REGION                 1..268
                       note = Synthetic
source                 1..268
                       mol_type = protein
                       organism = synthetic construct
SEQUENCE: 120
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DPVKLSSGYK DVILWFSFGA  240
SCFILLAIVM GLVFICVKNG NMRCTICI                                   268

SEQ ID NO: 121         moltype = AA  length = 267
FEATURE                Location/Qualifiers
REGION                 1..267
                       note = Synthetic
source                 1..267
                       mol_type = protein
                       organism = synthetic construct
SEQUENCE: 121
MNTQILVFAL IAIIPTNADK ICLGHHAVSN GTKVNTLTER GVEVVNATEL VFPGCVLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID PVKLSSGYKD VILWFSFGAS  240
CFILLAIVMG LVFICVKNGN MRCTICI                                    267

SEQ ID NO: 122         moltype = AA  length = 267
FEATURE                Location/Qualifiers
REGION                 1..267
                       note = Synthetic
source                 1..267
                       mol_type = protein
                       organism = synthetic construct
SEQUENCE: 122
```

```
MNTQILVFAL IAIIPTNADK ICLGHHAVSN GTKVNTLTER GVEVVNATEL VFPCGVLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID PVKLSSGYKD VILWFSFGAS  240
CFILLAIVMG LVFICVKNGN MRCTICI                                      267

SEQ ID NO: 123         moltype = AA  length = 268
FEATURE                Location/Qualifiers
REGION                 1..268
                       note = Synthetic
source                 1..268
                       mol_type = protein
                       organism = synthetic construct
SEQUENCE: 123
MNTQILVFAL IAIIPTNADK ICLGHHAVSN GTKVNTLTER GVEVVNATEL VFPNCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DPVKLSSGYK DVILWFSFGA  240
SCFILLAIVM GLVFICVKNG NMRCTICI                                     268

SEQ ID NO: 124         moltype = AA  length = 268
FEATURE                Location/Qualifiers
REGION                 1..268
                       note = Synthetic
source                 1..268
                       mol_type = protein
                       organism = synthetic construct
SEQUENCE: 124
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DPVKLSSGYK DVILWFSFGA  240
SCFILLAIVM GLVFICVKNG NMRCTICI                                     268

SEQ ID NO: 125         moltype = AA  length = 268
FEATURE                Location/Qualifiers
REGION                 1..268
                       note = Synthetic
source                 1..268
                       mol_type = protein
                       organism = synthetic construct
SEQUENCE: 125
MNTQILVFAL IAIIPTNADK ICLGHHAVSN CTKVNTLTER GVEVVNATEL VFPGCGVLKL  60
ATGMKCVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMDKLYERVK RQLRENAEED  180
GTGCFEIFHK CDDDCMASIR NNTYDHSKYR EEAMQNRIQI DPVKLSSGYK DVILWFSFGA  240
SCFILLAIVM GLVFICVKNG NMRCTICI                                     268

SEQ ID NO: 126         moltype = AA  length = 268
FEATURE                Location/Qualifiers
REGION                 1..268
                       note = Synthetic
source                 1..268
                       mol_type = protein
                       organism = synthetic construct
SEQUENCE: 126
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGPPDC YLAELLVAML NQHVIDLADS EMDKLYERVK RQLRENAEED  180
GTGCFEIFHK CDDDCMASIR NNTYDHSKYR EEAMQNRIQI DPVKLSSGYK DVILWFSFGA  240
SCFILLAIVM GLVFICVKNG NMRCTICI                                     268

SEQ ID NO: 127         moltype = AA  length = 268
FEATURE                Location/Qualifiers
REGION                 1..268
                       note = Synthetic
source                 1..268
                       mol_type = protein
                       organism = synthetic construct
SEQUENCE: 127
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ELMEQGGPDC YLAELLVAML NQHVIDLADS EMDKLYERVK RQLRENAEED  180
GTGCFEIFHK CDDDCMASIR NNTYDHSKYR EEAMQNRIQI DPVKLSSGYK DVILWFSFGA  240
SCFILLAIVM GLVFICVKNG NMRCTICI                                     268

SEQ ID NO: 128         moltype = AA  length = 268
FEATURE                Location/Qualifiers
REGION                 1..268
```

```
                         note = Synthetic
source                   1..268
                         mol_type = protein
                         organism = synthetic construct
SEQUENCE: 128
MNTQILILAL VAIIPTNADK ICLGHHAVSN GAKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ALMAQGGPDC YLAELLVAML NQHVIDLADS EMNKLYERVR RQLRENAEED  180
GTGCFEIFHK CDDDCMASIR NNTYDHSKYR EEAIQNRIQI DPVKLSSGYK DVILWFSFGA  240
SCFILLAIAM GLVFICVKNG NMRCTICI                                     268

SEQ ID NO: 129           moltype = AA  length = 270
FEATURE                  Location/Qualifiers
REGION                   1..270
                         note = Synthetic
source                   1..270
                         mol_type = protein
                         organism = synthetic construct
SEQUENCE: 129
MNTQILVFAL VASIPTNADK ICLGHHAVSN GTKVNTLTER GVEVVNATEL VFPGCGVLKL  60
ATGMKNVPEI PKRRRRGLFG AIAGFIENGW EGLIDGWYGF RHQNAQGEGT AADYKSTQSA  120
IDQITGMVNR VIALMAQGGP DCYLAELLVA MLNQHVIDLA DSEMNKLYER VKRQLRENAE  180
EDGTGCFEIF HKCDDDCMAS IRNNTYDHSK YREEAIQNRI QIDPVKLSSG YKDVILWFSF  240
GASCFILLAI AMGLVFICVK NGNMRCTICI                                   270

SEQ ID NO: 130           moltype = AA  length = 275
FEATURE                  Location/Qualifiers
REGION                   1..275
                         note = Synthetic
source                   1..275
                         mol_type = protein
                         organism = synthetic construct
SEQUENCE: 130
MKTIIALSYI FCLALAQDLP GNDNSTATLC LGHHAVPNGT LVKTITDDQI EVTNATELVF  60
PGCGVLKLAT GMRNVPEKQT RGLFGAIAGF IENGWEGMID GWYGFRHQNS EGTGQAADLK  120
STQAAIDQIN GMVNRVIELM EQGGPDCYLA ELLVALLNQH VIDLTDSEMR KLFEKTRRQL  180
RENAEDMGNG CFKIYHKCDN ACIESIRNGT YDHDVYRDEA LNNRFQIKGV ELKSGYKDWI  240
LWISFAISCF LLCVVLLGFI MWACQRGNIR CNICI                             275

SEQ ID NO: 131           moltype = AA  length = 275
FEATURE                  Location/Qualifiers
REGION                   1..275
                         note = Synthetic
source                   1..275
                         mol_type = protein
                         organism = synthetic construct
SEQUENCE: 131
MKTIIALSYI FCLALAQDLP GNDNSTATLC LGHHAVPNCT LVKTITDDQI EVTNATELVF  60
PGCGVLKLAT GMRCVPEKQT RGLFGAIAGF IENGWEGMID GWYGFRHQNS EGTGQAADLK  120
STQAAIDQIN GMVNRVIELM EQGGPDCYLA ELLVALLNQH VIDLTDSEMR KLFEKTRRQL  180
RENAEDMGNG CFKIYHKCDN ACIESIRNGT YDHDVYRDEA LNNRFQIKGV ELKSGYKDWI  240
LWISFAISCF LLCVVLLGFI MWACQRGNIR CNICI                             275

SEQ ID NO: 132           moltype = AA  length = 396
FEATURE                  Location/Qualifiers
REGION                   1..396
                         note = Synthetic
source                   1..396
                         mol_type = protein
                         organism = synthetic construct
SEQUENCE: 132
MKTIIALSYI LCLVFAQKLP GNDNSTATLC LGHHAVPNGT IVKTITNDQI EVTHATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 133           moltype = AA  length = 379
FEATURE                  Location/Qualifiers
REGION                   1..379
                         note = Synthetic
source                   1..379
                         mol_type = protein
                         organism = synthetic construct
SEQUENCE: 133
MKTIIALSYI LCLVFAQKLP GNDNSTATLC LGHHAVPNGT IVKTITNDQI EVTNATELVF  60
PGCGVLKLAT GMRNGSGWEG MVDGWYGFRH QNSEGIGQAA DLKSTQAAIN QINGMVNRVI  120
```

```
ALMAQGGPDC YLAELLVALL NQHVIDLTDS EMRKLFERTK KQLRENAEDM GNGCFKIYHK  180
CDNACIGSIR NGTYDHDVYR DEALNNRFQI KSGGDIIKLL NEQVNKEMQS SNLYMSMSSW  240
CYTHSLDGAG LFLFDHAAEE YEHAKKLIIF LNENNVPVQL TSISAPEHKF EGLTQIFQKA  300
YEHEQHISES INNIVDHAIK SKDHATFNFL QWYVAEQHEE EVLFKDILDK IELIGNENHG  360
LYLADQYVKG IAKSRKSGS                                              379

SEQ ID NO: 134         moltype = AA  length = 379
FEATURE                Location/Qualifiers
REGION                 1..379
                       note = Synthetic
source                 1..379
                       mol_type = protein
                       organism = synthetic construct
SEQUENCE: 134
MKTIIALSYI LCLVFAQKLP GNDNSTATLC LGHHAVPNCT IVKTITNDQI EVTNATELVF  60
PGCGVLKLAT GMRCGSGWEG MVDGWYGFRH QNSEGIGQAA DLKSTQAAIN QINGMVNRVI  120
ELMEQGGPDC YLAELLVALL NQHVIDLTDS EMRKLFERTK KQLRENAEDM GNGCFKIYHK  180
CDNACIGSIR NGTYDHDVYR DEALNNRFQI KSGGDIIKLL NEQVNKEMQS SNLYMSMSSW  240
CYTHSLDGAG LFLFDHAAEE YEHAKKLIIF LNENNVPVQL TSISAPEHKF EGLTQIFQKA  300
YEHEQHISES INNIVDHAIK SKDHATFNFL QWYVAEQHEE EVLFKDILDK IELIGNENHG  360
LYLADQYVKG IAKSRKSGS                                              379

SEQ ID NO: 135         moltype = AA  length = 380
FEATURE                Location/Qualifiers
REGION                 1..380
                       note = Synthetic
source                 1..380
                       mol_type = protein
                       organism = synthetic construct
SEQUENCE: 135
MKTIIALSYI LCLVFAQKLP GNDNSTATLC LGHHAVPNGT IVKTITNDQI EVTNATELVF  60
PGCGVLKLAT GMRNGSGGWE GMVDGWYGFR HQNSEGIGQA ADLKSTQAAI NQINGMVNRV  120
IALMAQGGPD CYLAELLVAL LNQHVIDLTD SEMRKLFERT KKQLRENAED MGNGCFKIYH  180
KCDNACIGSI RNGTYDHDVY RDEALNNRFQ IKSGGDIIKL LNEQVNKEMQ SSNLYMSMSS  240
WCYTHSLDGA GLFLFDHAAE EYEHAKKLII FLNENNVPVQ LTSISAPEHK FEGLTQIFQK  300
AYEHEQHISE SINNIVDHAI KSKDHATFNF LQWYVAEQHE EEVLFKDILD KIELIGNENH  360
GLYLADQYVK GIAKSRKSGS                                             380

SEQ ID NO: 136         moltype = AA  length = 390
FEATURE                Location/Qualifiers
REGION                 1..390
                       note = Synthetic
source                 1..390
                       mol_type = protein
                       organism = synthetic construct
SEQUENCE: 136
MKTIIALSYI LCLVFAQKLP GNDNSTATLC LGHHAVPNGT IVKTITNDQI EVTNATELVF  60
PGCGVLKLAT GMRNGGIFGA IAGFIENGWE GMVDGWYGFR HQNSEGIGQA ADLKSTQAAI  120
NQINGMVNRV IALMAQGGPD CYLAELLVAL LNQHVIDLTD SEMRKLFERT KKQLRENAED  180
MGNGCFKIYH KCDNACIGSI RNGTYDHDVY RDEALNNRFQ IKSGGDIIKL LNEQVNKEMQ  240
SSNLYMSMSS WCYTHSLDGA GLFLFDHAAE EYEHAKKLII FLNENNVPVQ LTSISAPEHK  300
FEGLTQIFQK AYEHEQHISE SINNIVDHAI KSKDHATFNF LQWYVAEQHE EEVLFKDILD  360
KIELIGNENH GLYLADQYVK GIAKSRKSGS                                  390

SEQ ID NO: 137         moltype = AA  length = 390
FEATURE                Location/Qualifiers
REGION                 1..390
                       note = Synthetic
source                 1..390
                       mol_type = protein
                       organism = synthetic construct
SEQUENCE: 137
MKTIIALSYI LCLVFAQKLP GNDNSTATLC LGHHAVPNGT IVKTITNDQI EVTNATELVF  60
PGCGVLKLAT GMRGGGIFGA IAGFIENGWE GMVDGWYGFR HQNSEGIGQA ADLKSTQAAI  120
NQINGMVNRV IALMAQGGPD CYLAELLVAL LNQHVIDLTD SEMRKLFERT KKQLRENAED  180
MGNGCFKIYH KCDNACIGSI RNGTYDHDVY RDEALNNRFQ IKSGGDIIKL LNEQVNKEMQ  240
SSNLYMSMSS WCYTHSLDGA GLFLFDHAAE EYEHAKKLII FLNENNVPVQ LTSISAPEHK  300
FEGLTQIFQK AYEHEQHISE SINNIVDHAI KSKDHATFNF LQWYVAEQHE EEVLFKDILD  360
KIELIGNENH GLYLADQYVK GIAKSRKSGS                                  390

SEQ ID NO: 138         moltype = AA  length = 396
FEATURE                Location/Qualifiers
REGION                 1..396
                       note = Synthetic
source                 1..396
                       mol_type = protein
                       organism = synthetic construct
SEQUENCE: 138
MKTIIALSYI LCLVFAQKLP GNDNSTATLC LGHHAVPNGT IVKTITNDQI EVTNATNLTF  60
```

```
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 139          moltype = AA  length = 396
FEATURE                 Location/Qualifiers
REGION                  1..396
                        note = Synthetic
source                  1..396
                        mol_type = protein
                        organism = synthetic construct
SEQUENCE: 139
MKTIIALSYI LCLVFAQKLP GNDNSTATLC LGHHAVPNGT IVKTITNDQI EVTNATELNF  60
TGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 140          moltype = AA  length = 396
FEATURE                 Location/Qualifiers
REGION                  1..396
                        note = Synthetic
source                  1..396
                        mol_type = protein
                        organism = synthetic construct
SEQUENCE: 140
MKTIIALSYI LCLVFAQKLP GNDNSTATLC LGHHAVPNGT IVKTITNDQI EVTNATELVF  60
PNCTVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 141          moltype = AA  length = 396
FEATURE                 Location/Qualifiers
REGION                  1..396
                        note = Synthetic
source                  1..396
                        mol_type = protein
                        organism = synthetic construct
SEQUENCE: 141
MKTIIALSYI LCLVFAQKLP GNDNSTATLC LGHHAVPNGT IVKTITNDQI EVTNATELVF  60
PGCGNLTLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 142          moltype = AA  length = 396
FEATURE                 Location/Qualifiers
REGION                  1..396
                        note = Synthetic
source                  1..396
                        mol_type = protein
                        organism = synthetic construct
SEQUENCE: 142
MKTIIALSYI LCLVFAQKLP GNDNSTATLC LGHHAVPNGT IVKTITNDQI EVTNATELVF  60
PGCGVLNLTT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                            396

SEQ ID NO: 143          moltype = AA  length = 396
FEATURE                 Location/Qualifiers
REGION                  1..396
                        note = Synthetic
source                  1..396
                        mol_type = protein
                        organism = synthetic construct
SEQUENCE: 143
```

```
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPNCTLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 144          moltype = AA  length = 397
FEATURE                 Location/Qualifiers
REGION                  1..397
                        note = Synthetic
source                  1..397
                        mol_type = protein
                        organism = synthetic construct
SEQUENCE: 144
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM ANGTGPDCYL AELLVALLNQ HVIDLTDSEM RKLFERTKKQ  180
LRENAEDMGN GCFKIYHKCD NACIGSIRNG TYDHDVYRDE ALNNRFQIKS GGDIIKLLNE  240
QVNKEMQSSN LYMSMSSWCY THSLDGAGLF LFDHAAEEYE HAKKLIIFLN ENNVPVQLTS  300
ISAPEHKFEG LTQIFQKAYE HEQHISESIN NIVDHAIKSK DHATFNFLQW YVAEQHEEEV  360
LFKDILDKIE LIGNENHGLY LADQYVKGIA KSRKSGS                          397

SEQ ID NO: 145          moltype = AA  length = 396
FEATURE                 Location/Qualifiers
REGION                  1..396
                        note = Synthetic
source                  1..396
                        mol_type = protein
                        organism = synthetic construct
SEQUENCE: 145
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHNNT EGIGQAADLK  120
STQAAINQIN GMVNRVIALM AQGGPDCYLA ELLVALLNQH VIDLTDSEMR KLFERTKKQL  180
RENAEDMGNG CFKIYHKCDN ACIGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 146          moltype = AA  length = 396
FEATURE                 Location/Qualifiers
REGION                  1..396
                        note = Synthetic
source                  1..396
                        mol_type = protein
                        organism = synthetic construct
SEQUENCE: 146
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIALM AQGGPDCYLA ELLVALLNQH VIDLTDSEMR KLFERTKKQL  180
RENAEDMGNG CFKIYHKCDN NCTGSIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 147          moltype = AA  length = 388
FEATURE                 Location/Qualifiers
REGION                  1..388
                        note = Synthetic
source                  1..388
                        mol_type = protein
                        organism = synthetic construct
SEQUENCE: 147
MKTIIALSYI LCLVFAQKLP GNDNSTATLC LGHHAVPNGT IVKTITNDQI EVTNATELCF  60
NGICLKLATG MRNVPEKQTR GIFGAIAGFI ENGWEGMVDG WYGFRHQNSE GIGQAADLKS  120
TQAAINQING MVNRVIALMA QGGPDAYLAE LLVALLNQHV IDLTDSEMRK LFERTKKQLR  180
ENAEDMGNGC FKIYHKCDNA CIGSIRNGTY DHDVYRDEAL NNRFQIKAGP PPGGMQIYEG  240
KLTAEGLRFG IVASRFNHAL VDRLVEGAID CIVRHGGREE DITLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                    388

SEQ ID NO: 148          moltype = AA  length = 388
FEATURE                 Location/Qualifiers
REGION                  1..388
                        note = Synthetic
source                  1..388
                        mol_type = protein
                        organism = synthetic construct
```

```
SEQUENCE: 148
MKTIIALSYI LCLVFAQKLP GNDNSTATLC LGHHAVPNGT IVKTITNDQI EVTNATELCF  60
NGICLKLATG MRNVPEKQTR GIFGAIAGFI ENGWEGMVDG WYGFRHQNSE GIGQAADLKS  120
TQAAINQING MVNRVIELME QGGPDAYLAE LLVALLNQHV IDLTDSEMRK LFERTKKQLR  180
ENAEDMGNGC FKIYHKCDNA CIGSIRNGTY DHDVYRDEAL NNRFQIKAGP PPGGMQIYEG  240
KLTAEGLRFG IVASRFNHAL VDRLVEGAID CIVRHGGREE DITLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                    388

SEQ ID NO: 149         moltype = AA  length = 388
FEATURE                Location/Qualifiers
REGION                 1..388
                       note = Synthetic
source                 1..388
                       mol_type = protein
                       organism = synthetic construct
SEQUENCE: 149
MKTIIALSYI LCLVFAQKLP GNDNSTATLC LGHHAVPNCT IVKTITNDQI EVTNATELCF  60
NGICLKLATG MRCVPEKQTR GIFGAIAGFI ENGWEGMVDG WYGFRHQNSE GIGQAADLKS  120
TQAAINQING MVNRVIELME QGGPDAYLAE LLVALLNQHV IDLTDSEMRK LFERTKKQLR  180
ENAEDMGNGC FKIYHKCDNA CIGSIRNGTY DHDVYRDEAL NNRFQIKAGP PPGGMQIYEG  240
KLTAEGLRFG IVASRFNHAL VDRLVEGAID CIVRHGGREE DITLVRVPGS WEIPVAAGEL  300
ARKEDIDAVI AIGVLIRGAT PHFDYIASEV SKGLADLSLE LRKPITFGVI TADTLEQAIE  360
RAGTKHGNKG WEAALSAIEM ANLFKSLR                                    388

SEQ ID NO: 150         moltype = AA  length = 389
FEATURE                Location/Qualifiers
REGION                 1..389
                       note = Synthetic
source                 1..389
                       mol_type = protein
                       organism = synthetic construct
SEQUENCE: 150
MKTIIALSYI LCLVFAQKLP GNDNSTATLC LGHHAVPNGT IVKTITNDQI EVTNATELVF  60
PGCGVLKLAT GMRNVPEKQT RGIFGAIAGF IENGWEGMVD GWYGFRHQNS EGIGQAADLK  120
STQAAINQIN GMVNRVIELM EQGGPDCYLA ELLVALLNQH VIDLTDSEMR KLFERTKKQL  180
RENAEDMGNG CFKIYHKCDN ACIGSIRNGT YDHDVYRDEA LNNRFQIKAG PPPGGMQIYE  240
GKLTAEGLRF GIVASRFNHA LVDRLVEGAI DCIVRHGGRE EDITLVRVPG SWEIPVAAGE  300
LARKEDIDAV IAIGVLIRGA TPHFDYIASE VSKGLADLSL ELRKPITFGV ITADTLEQAI  360
ERAGTKHGNK GWEAALSAIE MANLFKSLR                                   389

SEQ ID NO: 151         moltype = AA  length = 389
FEATURE                Location/Qualifiers
REGION                 1..389
                       note = Synthetic
source                 1..389
                       mol_type = protein
                       organism = synthetic construct
SEQUENCE: 151
MKTIIALSYI LCLVFAQKLP GNDNSTATLC LGHHAVPNCT IVKTITNDQI EVTNATELVF  60
PGCGVLKLAT GMRCVPEKQT RGIFGAIAGF IENGWEGMVD GWYGFRHQNS EGIGQAADLK  120
STQAAINQIN GMVNRVIELM EQGGPDCYLA ELLVALLNQH VIDLTDSEMR KLFERTKKQL  180
RENAEDMGNG CFKIYHKCDN ACIGSIRNGT YDHDVYRDEA LNNRFQIKAG PPPGGMQIYE  240
GKLTAEGLRF GIVASRFNHA LVDRLVEGAI DCIVRHGGRE EDITLVRVPG SWEIPVAAGE  300
LARKEDIDAV IAIGVLIRGA TPHFDYIASE VSKGLADLSL ELRKPITFGV ITADTLEQAI  360
ERAGTKHGNK GWEAALSAIE MANLFKSLR                                   389

SEQ ID NO: 152         moltype = AA  length = 382
FEATURE                Location/Qualifiers
REGION                 1..382
                       note = Synthetic
source                 1..382
                       mol_type = protein
                       organism = synthetic construct
SEQUENCE: 152
MNTQILVFAL IAIIPTNADK ICLGHHAVSN CTKVNTLTER GVEVVNATEL VFPGCGVLKL  60
ATGMKCVPEI PKGRGLFGAI AGFIENGWEG LIDGWYGFRH QNAQGEGTAA DYKSTQSAID  120
QITGMVNRVI ELMEQGGPDC YLAELLVAML NQHVIDLADS EMDKLYERVK RQLRENAEED  180
GTGCFEIFHK CDDDCMASIR NNTYDHSKYR EEAMQNRIQI DAGPPPGGMQ IYEGKLTAEG  240
LRFGIVASRF NHALVDRLVE GAIDCIVRHG GREEDITLVR VPGSWEIPVA AGELARKEDI  300
DAVIAIGVLI RGATPHFDYI ASEVSKGLAD LSLELRKPIT FGVITADTLE QAIERAGTKH  360
GNKGWEAALS AIEMANLFKS LR                                          382

SEQ ID NO: 153         moltype = AA  length = 381
FEATURE                Location/Qualifiers
REGION                 1..381
                       note = Synthetic
source                 1..381
                       mol_type = protein
```

```
                         organism = synthetic construct
SEQUENCE: 153
MNTQILVFAL IAIIPTNADK ICLGHHAVSN GTKVNTLTER GVEVVNATEL CFNGICLKLA  60
TGMKNVPEIP KGRGLFGAIA GFIENGWEGL IDGWYGFRHQ NAQGEGTAAD YKSTQSAIDQ  120
ITGMVNRVIA LMAQGGPDCY LAELLVAMLN QHVIDLADSE MDKLYERVKR QLRENAEEDG  180
TGCFEIFHKC DDDCMASIRN NTYDHSKYRE EAMQNRIQID AGPPPGGMQI YEGKLTAEGL  240
RFGIVASRFN HALVDRLVEG AIDCIVRHGG REEDITLVRV PGSWEIPVAA GELARKEDID  300
AVIAIGVLIR GATPHFDYIA SEVSKGLADL SLELRKPITF GVITADTLEQ AIERAGTKHG  360
NKGWEAALSA IEMANLFKSL R                                            381

SEQ ID NO: 154           moltype = AA  length = 381
FEATURE                  Location/Qualifiers
REGION                   1..381
                         note = Synthetic
source                   1..381
                         mol_type = protein
                         organism = synthetic construct
SEQUENCE: 154
MNTQILVFAL IAIIPTNADK ICLGHHAVSN CTKVNTLTER GVEVVNATEL CFNGICLKLA  60
TGMKCVPEIP KGRGLFGAIA GFIENGWEGL IDGWYGFRHQ NAQGEGTAAD YKSTQSAIDQ  120
ITGMVNRVIE LMEQGGPDCY LAELLVAMLN QHVIDLADSE MDKLYERVKR QLRENAEEDG  180
TGCFEIFHKC DDDCMASIRN NTYDHSKYRE EAMQNRIQID AGPPPGGMQI YEGKLTAEGL  240
RFGIVASRFN HALVDRLVEG AIDCIVRHGG REEDITLVRV PGSWEIPVAA GELARKEDID  300
AVIAIGVLIR GATPHFDYIA SEVSKGLADL SLELRKPITF GVITADTLEQ AIERAGTKHG  360
NKGWEAALSA IEMANLFKSL R                                            381

SEQ ID NO: 155           moltype = AA  length = 381
FEATURE                  Location/Qualifiers
REGION                   1..381
                         note = Synthetic
source                   1..381
                         mol_type = protein
                         organism = synthetic construct
SEQUENCE: 155
MNTQILVFAL IAIIPTNADK ICLGHHAVSN GTKVNTLTER GVEVVNATEL VFPCGVLKLA  60
TGMKNVPEIP KGRGLFGAIA GFIENGWEGL IDGWYGFRHQ NAQGEGTAAD YKSTQSAIDQ  120
ITGMVNRVIE LMEQGGPDCY LAELLVAMLN QHVIDLADSE MDKLYERVKR QLRENAEEDG  180
TGCFEIFHKC DDDCMASIRN NTYDHSKYRE EAMQNRIQID AGPPPGGMQI YEGKLTAEGL  240
RFGIVASRFN HALVDRLVEG AIDCIVRHGG REEDITLVRV PGSWEIPVAA GELARKEDID  300
AVIAIGVLIR GATPHFDYIA SEVSKGLADL SLELRKPITF GVITADTLEQ AIERAGTKHG  360
NKGWEAALSA IEMANLFKSL R                                            381

SEQ ID NO: 156           moltype = AA  length = 382
FEATURE                  Location/Qualifiers
REGION                   1..382
                         note = Synthetic
source                   1..382
                         mol_type = protein
                         organism = synthetic construct
SEQUENCE: 156
MNTQILVFAL IAIIPTNADK ICLGHHAVSN GTKVNTLTER GVEVVNATEL VFPGCGVLKL  60
ATGMKNVPEI PKGRGLFGAI AGFIENGWEG LIDGWYGFRH QNAQGEGTAA DYKSTQSAID  120
QITGMVNRVI ELMEQGPPDC YLAELLVAML NQHVIDLADS EMDKLYERVK RQLRENAEED  180
GTGCFEIFHK CDDDCMASIR NNTYDHSKYR EEAMQNRIQI DAGPPPGGMQ IYEGKLTAEG  240
LRFGIVASRF NHALVDRLVE GAIDCIVRHG GREEDITLVR VPGSWEIPVA AGELARKEDI  300
DAVIAIGVLI RGATPHFDYI ASEVSKGLAD LSLELRKPIT FGVITADTLE QAIERAGTKH  360
GNKGWEAALS AIEMANLFKS LR                                           382

SEQ ID NO: 157           moltype = AA  length = 381
FEATURE                  Location/Qualifiers
REGION                   1..381
                         note = Synthetic
source                   1..381
                         mol_type = protein
                         organism = synthetic construct
SEQUENCE: 157
MNTQILVFAL IAIIPTNADK ICLGHHAVSN GTKVNTLTER GVEVVNATEL VFPCGVLKLA  60
TGMKNVPEIP KGRGLFGAIA GFIENGWEGL IDGWYGFRHQ NAQGEGTAAD YKSTQSAIDQ  120
ITGMVNRVIE LMEQGPPDCY LAELLVAMLN QHVIDLADSE MDKLYERVKR QLRENAEEDG  180
TGCFEIFHKC DDDCMASIRN NTYDHSKYRE EAMQNRIQID AGPPPGGMQI YEGKLTAEGL  240
RFGIVASRFN HALVDRLVEG AIDCIVRHGG REEDITLVRV PGSWEIPVAA GELARKEDID  300
AVIAIGVLIR GATPHFDYIA SEVSKGLADL SLELRKPITF GVITADTLEQ AIERAGTKHG  360
NKGWEAALSA IEMANLFKSL R                                            381

SEQ ID NO: 158           moltype = AA  length = 396
FEATURE                  Location/Qualifiers
REGION                   1..396
                         note = Synthetic
source                   1..396
```

-continued

```
                         mol_type = protein
                         organism = synthetic construct
SEQUENCE: 158
MKTIIALSYI FCLALAQDLP GNDNSTATLC LGHHAVPNGT LVKTITDDQI EVTNATELVF  60
PGCGVLKLAT GMRNVPEKQT RGLFGAIAGF IENGWEGMID GWYGFRHQNS EGTGQAADLK  120
STQAAIDQIN GMVNRVIELM EQGGPDCYLA ELLVALLNQH VIDLTDSEMR KLFEKTRRQL  180
RENAEDMGNG CFKIYHKCDN ACIESIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 159           moltype = AA  length = 396
FEATURE                  Location/Qualifiers
REGION                   1..396
                         note = Synthetic
source                   1..396
                         mol_type = protein
                         organism = synthetic construct
SEQUENCE: 159
MKTIIALSYI FCLALAQDLP GNDNSTATLC LGHHAVPNCT LVKTITDDQI EVTNATELVF  60
PGCGVLKLAT GMRCVPEKQT RGLFGAIAGF IENGWEGMID GWYGFRHQNS EGTGQAADLK  120
STQAAIDQIN GMVNRVIELM EQGGPDCYLA ELLVALLNQH VIDLTDSEMR KLFEKTRRQL  180
RENAEDMGNG CFKIYHKCDN ACIESIRNGT YDHDVYRDEA LNNRFQIKSG GDIIKLLNEQ  240
VNKEMQSSNL YMSMSSWCYT HSLDGAGLFL FDHAAEEYEH AKKLIIFLNE NNVPVQLTSI  300
SAPEHKFEGL TQIFQKAYEH EQHISESINN IVDHAIKSKD HATFNFLQWY VAEQHEEEVL  360
FKDILDKIEL IGNENHGLYL ADQYVKGIAK SRKSGS                           396

SEQ ID NO: 160           moltype =   length =
SEQUENCE: 160
000
```

STABILIZED GROUP 2 INFLUENZA HEMAGGLUTININ STEM REGION TRIMERS AND USES THEREOF

CROSS REFERENCE TO RELATED APPLICATIONS

This application is a continuation of U.S. patent application Ser. No. 17/742,201, filed on May 1, 2022, which is a continuation of U.S. patent application Ser. No. 16/329,592, filed on Feb. 28, 2019, now issued as U.S. Pat. No. 11,338,033, which is a U.S. National Stage of International Application No. PCT/US2017/049894, filed on Sep. 1, 2017, which was published in English under PCT Article 21(2), which in turn claims priority to U.S. Provisional Application No. 62/383,267, filed on Sep. 2, 2016. The contents of each of the above-listed applications are incorporated by reference in their entirety.

REFERENCE TO SEQUENCE LISTING

This application contains a Sequence Listing submitted as an XML file in the form of the file named "4239-104868-19_Sequence_Listing.xml" (237,568 bytes), which was created on Oct. 13, 2023, and which is incorporated by reference herein.

BACKGROUND

Protective immune responses induced by vaccination against influenza viruses are primarily directed to the viral HA protein, which is a glycoprotein on the surface of the virus responsible for interaction of the virus with host cell receptors. HA proteins on the virus surface are trimers of HA protein monomers that are enzymatically cleaved to yield amino-terminal HA1 and carboxyl-terminal HA2 polypeptides. The globular head consists exclusively of the major portion of the HA1 polypeptide, whereas the stem that anchors the HA protein into the viral lipid envelope is comprised of HA2 and part of HA1. The globular head of a HA protein includes two domains: the receptor binding domain (RBD), an ~148-amino acid residue domain that includes the sialic acid-binding site, and the vestigial esterase domain, a smaller ~75-amino acid residue region just below the RBD. The globular head includes several antigenic sites that include immunodominant epitopes. Examples include the Sa, Sb, $Ca_1$, $Ca_2$ and Cb antigenic sites (see, for example, Caton, et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, the HA stem is highly conserved and experiences little antigenic drift. Unfortunately, unlike the immunodominant head, the conserved HA stem is not very immunogenic. Furthermore, gene segments of the viral genome can undergo reassortment (antigenic shift) in host species, creating new viruses with altered antigenicity that are capable of becoming pandemics [Salomon, R. et al. *Cell* 136, 402-410 (2009)]. Until now, each year, influenza vaccine is updated to reflect the predicted HA and neuraminidase (NA) for upcoming circulating viruses.

Recently, an entirely new class of broadly neutralizing antibodies against influenza viruses was isolated that recognize the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)]. Unlike strain-specific antibodies, those antibodies are capable of neutralizing multiple antigenically distinct viruses, and hence inducing such antibodies has been a focus of next generation universal vaccine development [Nabel, G. J. et al. *Nat Med* 16, 1389-1391 (2010)]. However, robustly eliciting these antibodies with such heterologous neutralizing profile by vaccination has been difficult [Steel, J. et al. *MBio* 1, e0018 (2010); Wang, T. T. et al. *PLoS Pathog* 6, e1000796 (2010); Wei, C. J. et al. *Science* 329, 1060-1064 (2010)]. Removal of the immunodominant head region of HA (which contains competing epitopes) and stabilization of the resulting stem domain through genetic manipulation is one potential way to improve the elicitation of these broadly neutralizing stem antibodies.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs that often comprise HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded, trimeric HA spikes that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLoS One* 5, e9784 (2010)]. Moreover, the immunity induced by the VLPs is essentially the same as current vaccines, and thus, will not likely significantly improve both potency and breadth of vaccine-induced protective immunity In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009);

Meldrum, F. C. et al. *Science* 257, 522-523 (1992); Naitou, M. et al. U.S. Patent 2011/0038025 (2011); Yamashita, I. *Biochim Biophys Acta* 1800, 846-857 (2010)], including a potential vaccine platform for displaying exogenous epitope peptides [Carter, D. C. et al. U.S. Patent 2006/0251679 (2006); Li, C. Q. et al. *Industrial Biotechnol* 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

Previous work has shown that the stem regions of Group 1 hemagglutinin proteins could be modified to form to a stabilized HA stem protein, the conformation of which is very similar to the pre-fusion conformation of full-length, wild-type (wt) influenza hemagglutinin protein. Additionally, when such modified stabilized stem (SS) HA proteins were joined to a monomeric subunit protein, such as ferritin, the resulting fusion protein formed nanoparticles, the surfaces of which displayed trimers of the SS-HA protein. Moreover, such nanoparticles were able to elicit an immune response Group 1 influenza viruses, indicating that the SS-HA protein trimers displayed by the nanoparticles had conformation similar to that of wt influenza HA protein. Such constructs are disclosed in International Patent Application No. PCT/US2015/032695, the content of which are incorporated herein in their entirety by reference. However, the antibodies elicited by the aforementioned nanoparticles were more protective against Group 1 influenza viruses than they were against Group 2 influenza viruses.

Thus, there remains a need for an efficacious influenza vaccine that provides robust protection against Group 2 influenza viruses. Further, there also remains a need for an influenza vaccine that protects individuals from heterologous strains of influenza virus, including evolving seasonal and pandemic influenza virus strains of the future. The present invention meets this need by providing a novel nanoparticle-based vaccine consisting of a novel Group 2 HA stabilized stem (SS) lacking the variable immunodominant head region, fused to the surface of nanoparticles, resulting in an influenza vaccine that is easily manufactured, potent, and elicits antibodies that are broadly heterosubtypic protective.

SUMMARY OF THE INVENTION

Accordingly, this disclosure provides recombinant proteins comprising a Group 2 influenza hemagglutinin (HA) protein, wherein the amino acid sequence of the head region is replaced with a linker comprising less than 5 contiguous amino acids from the head region of an influenza HA protein. Following administration of these recombinant proteins to a mammal, these recombinant proteins elicit an immune response to a Group 2 influenza HA protein in the mammal.

The recombinant proteins may comprise a first amino acid sequence from the stem region of a Group 2 influenza virus hemagglutinin (HA) protein, and a second amino acid sequence from the stem region of a Group 2 influenza virus hemagglutinin (HA) protein, wherein the first and second amino acid sequences are covalently joined by the linker sequence, and wherein the first amino acid sequence comprises at least 20 contiguous amino acid residues from the amino acid sequence upstream of the amino-terminal end of the head region sequence, and wherein the second amino acid sequence comprises at least 20 contiguous amino acid residues from the amino acid sequence downstream of the carboxyl-terminal end of the head region sequence. In this recombinant protein construct, the first amino acid sequence may comprise at least 20 contiguous amino acids from the upstream polypeptide sequence immediately adjacent to the amino terminal end of the head region. Alternatively or additionally, the first amino acid sequence may comprise at least 20 contiguous amino acids from SEQ ID NO:27, SEQ ID NO: 28 or SEQ ID NO: 29. Alternatively or additionally, the second amino acid sequence may comprise at least 20 contiguous amino acids from the downstream polypeptide sequence immediately adjacent to the carboxyl-terminal end of the head region. Alternatively or additionally, the first amino acid sequence may comprise at least 20 contiguous amino acids from SEQ ID NO: 31, SEQ ID NO:32 or SEQ ID NO:33.

The recombinant proteins may comprise an amino-terminal end of helix C (i.e., the membrane distal end of helix C) that is joined to the head region sequence modified to contain a first cysteine amino acid, and a linker sequence comprising a second cysteine amino acid such that the first and second cysteine form a disulfide bond.

The recombinant proteins may comprise an inter-helix region (i.e., the amino acid sequence connecting the N-terminal end of helix C to the carboxyl-terminal end of helix A (i.e., the membrane distal end of helix A)) that is modified so that the three-dimensional structure of the recombinant HA stem protein approximates the three-dimensional structure of the HA stem region in a native Group 2 HA protein. The recombinant proteins may comprise an amino acid linker sequence that is less than eight amino acids in length, and replaces the inter-helix region.

The recombinant proteins may comprise a membrane distal end of helix A that is extended by the addition of amino acids.

The recombinant proteins may comprise a third amino acid linker that is joined to the carboxyl-terminus of the amino acid sequence forming helix A and forms a helix that extends the length of helix A. The distal end of helix C may be linked to the carboxyl end of the third linker by the linker peptide. The linker peptide is preferably less than eight amino acids in length.

These recombinant proteins may comprise one or more mutations that increase the stability of the protein. These stabilizing mutations are preferably located in the amino acid sequences forming at least one of helix A and helix C.

These recombinant proteins may be joined to a monomeric subunit from ferritin or lumazine synthase.

Exemplary recombinant proteins of this disclosure may comprise an amino acid sequence that is at least 80% identical, or at least 85% identical, or at least 90% identical, or at least 95% identical, or at least 97% identical, or at least 99% identical to an amino acid sequence selected from the group consisting of SEQ ID NOs: 47-159.

Exemplary recombinant proteins of this disclosure may comprise an amino acid sequence selected from the group consisting of SEQ ID NOs: 47-159.

This disclosure also provides a nanoparticle comprising at least one recombinant protein of this disclosure.

This disclosure also provides immunogenic compositions comprising at least one protein that comprises an amino acid sequence at least 95% identical to these recombinant proteins. These immunogenic compositions may comprise a protein comprising an amino acid sequence selected from the group consisting of SEQ ID NOs: SEQ ID NOs: 47-159. These immunogenic compositions may comprise a protein consisting of an amino acid sequence selected from the group consisting of SEQ ID NOs:47-159. Thus, this disclosure also provides vaccine compositions comprising these immunogenic compositions, and an adjuvant.

This disclosure also provides methods of preventing or reducing the pathological effects of an influenza virus infection in a human comprising administering to a human in need thereof an immunologically effective dose of a vaccine composition of this disclosure.

Also provided are nucleic acids encoding the recombinant proteins of this disclosure. Preferably, the nucleic acid is DNA. Also provided are vectors comprising these nucleic acids. Also provided are host cells comprising these vectors. These host cells may be bacterial cells, yeast cells, or mammalian cells. These host cells may be inactivated.

This disclosure also provides pharmaceutical compositions comprising the recombinant proteins of this disclosure Similarly, these compositions may be a vaccine comprising the recombinant proteins of this disclosure, in combination with a physiologically acceptable carrier.

This disclosure also provides methods of vaccination, comprising administering a prophylactically or therapeutically effective amount of a recombinant protein of this disclosure to a subject.

This disclosure also provides a method of treatment of an influenza-associated disease, comprising administering a prophylactically or therapeutically effective amount of a recombinant protein of this disclosure to a subject in need thereof. Preferably, the subject is a human.

BRIEF DESCRIPTION OF THE FIGURES

FIG. 1A is a ribbon diagram depicting the design of full length HA-ferritin nanoparticles. FIG. 1B is a ribbon diagram depicting the design of HA stem-ferritin nanoparticles stabilized by a HIV gp41 trimerization domain. Both designs are described in detail in patent application PCT/US12/56822, which is incorporated herein by reference. FIG. 1C is a ribbon diagram depicting the design of group 1 HA stabilized stem nanoparticles disclosed in PCT patent application No. PCT/US15/32695, which is incorporated herein by reference.

FIGS. 3A and 3B show mutations in H3N2 design 231 that enable the formation of group 2 HA stabilized stem nanoparticles. FIG. 3A is a ribbon diagram depicting a model of a group 2 H3N2 stabilized HA stem trimer based on PDB ID 2YP2. Regions of mutations in the helices are shown in dark gray. FIG. 3B shows the sequence of H3 design #231 (SEQ ID NO: 47; based on the HA stem of A/Denmark35/2005 H3N2, GenBank ABU92694). Mutations made to the sequence are boxed. For reference, the C-terminal SGG linker is bolded, the C-terminal ferritin is underlined and a Asn to Gln ferritin mutation to remove an N-linked glycan is bolded.

FIGS. 4A-4D show mutations in H3N2 design 231 in the loop that replaces the HA1 head. FIG. 4A shows a ribbon diagram depicting a model of a group 2 H3N2 stabilized HA stem trimer based on PDB ID 2YP2. The seven mutations in the loop that replaces the HA1 head region, and the additional cysteine in helix C that forms a disulfide with the aforementioned loop are indicated. All other mutations in the helix regions are shown in dark grey. FIG. 4B depicts the mutated loop (indicated as replacing the head region in FIG. 4A) with side chains represented by stick models. The sequence shown is VFPGCGV, residues 59-65 of SEQ ID NO: 47. FIG. 4C shows variants of the loop sequence. The sequences are TELVFPGCGVLKL (residues 56-68 of SEQ ID NO: 47), TELVFPGCVLKL (residues 56-67 of SEQ ID NO: 51), TELVFPCGVLKL (residues 56-67 of SEQ ID NO: 52), TELVFPNCGVLKL (residues 56-68 of SEQ ID NO: 71), and TELCFNGICLKL (residues 56-67 of SEQ ID NO: 48). FIG. 4D shows the sequence of H3 design #231 (SEQ ID NO: 47). The mutations in the head and helix regions, which are illustrated in FIGS. 4A-4C, are boxed. For reference, the C-terminal SGG linker is bolded, the C-terminal ferritin is underlined and a Asn to Gln ferritin mutation to remove an N-linked glycan is bolded.

FIGS. 5A-5C show mutations in H3N2, design 231, in the loop that connects HA2 helices A and C. FIG. 5A is a ribbon diagram depicting a model of a group 2 H3N2 stabilized HA stem trimer based on PDB ID 2YP2. The four residues that connect HA2 helices A and C are indicated. Mutations in the helices are in dark grey. FIG. 5B shows a close-up of the loop (indicated region in FIG. 5A) with side chains represented by stick models. The sequence shown is GGPD, residues 143-146 of SEQ ID NO: 47. FIG. 5C shows the sequence of H3 design #231 (SEQ ID NO: 47). The mutations in the helices, and the amino acids making up the short linker, which are illustrated in FIGS. 5A and 5B, are boxed. For reference, the C-terminal SGG linker is bolded, the C-terminal ferritin is underlined and a Asn to Gln ferritin mutation to remove an N-linked glycan is bolded.

FIGS. 6A-6C show mutations in H3N2, design 231, in the C-terminal extension of helix A. FIG. 6A shows a ribbon diagram depicting a model of a group 2 H3N2 stabilized HA stem trimer based on PDB ID 2YP2. The five-residue extension of helix A is indicated. Mutations in the helices are in dark grey. FIG. 6B shows a close-up of the helical extension (also indicated in FIG. 6A) with side chains represented by stick models. The sequence shown is ALMAQ, residues 138-142 of SEQ ID NO: 47. FIG. 6C shows the sequence of H3 design #231 (SEQ ID NO: 47). Mutations in the helices, and the acids making up the five residue extension, are boxed. For reference, the C-terminal SGG linker is bolded, the C-terminal ferritin is underlined and a Asn to Gln ferritin mutation to remove an N-linked glycan is bolded.

FIGS. 7A and 7B show cavity-filling mutations in H3N2 design 231. FIG. 7A shows a ribbon diagram depicting a model of a group 2 H3N2 stabilized HA stem trimer based on PDB ID 2YP2. The seven cavity-filling mutations are in dark grey with side chains represented by stick models. FIG. 7B shows the sequence of H3 design #231 (SEQ ID NO: 47). Mutations to the helices and head region are boxed. For reference, the C-terminal SGG linker is bolded, the C-terminal ferritin is underlined and a Asn to Gln ferritin mutation to remove an N-linked glycan is bolded.

FIG. 8A shows a gel filtration elution profile for H3-SS-np_231 with a single peak at the expected elution volume. The expression yield for H3-SS-np_231 from Expi293 cells after gel filtration was 7.7 mg/L. FIG. 8B shows negative stain electron microscopy 2D class averages of H3-SS-np_231 revealing the formation of particles with a visible arrangement of HA stems projecting from hollow spheres.

FIG. 9A lists the $EC_{50}$ values from a kinetic ELISA H3-SS-np_231 recognition assay by three HA stem antibodies. The values for the recognition of H1-SS-np are also shown as a control. In both cases the nanoparticle was immobilized on the plate. FIG. 9B shows biolayer interferometry (BLI, from Octet) binding curves for CT149 recognition of H3-SS-np_231 (upper panel) and BLI kinetic constants for HA stem antibodies CT149 and CR9114 (lower panel).

FIGS. 11A-11F show electron microscopy of H3-SS-np nanoparticles variants. Negative stain electron microscopy 2D class averages of H3-SS-np variants revealing the formation of particles with a visible arrangement of HA stems projecting from hollow spheres. Images for the H3-SS-np 231 particle (upper left panel) are shown as a positive control.

FIGS. 12A-12C show the kinetic ELISA curves for FI6 (FIG. 12A), CT149 (FIG. 12B), and CR8020 (FIG. 12C) recognition of H3-SS-np_231 variants 249, 256, 258, 262 and 264. FIG. 12D lists the $EC_{50}$ values from the curves in FIGS. 12A-12C shown.

FIGS. 13A and 13B show kinetic ELISA results for H3-SS-np variants 235-295. FIG. 13A lists ELISA titers showing recognition of designs 235-265 by broadly neutralizing HA stem antibodies FI6, CT149 and D25 (negative control). FIG. 13B lists ELISA titers showing recognition of designs 266-296 by D25 and CT149. Supernatants from HEK293T cells expressing design immunogens were plated and detected by above antibodies.

FIG. 17 shows the sequence for H3-SS #231 fused to the N-terminus of aquifex aeolicus lumazine synthase (LS) 60-mer icosahedral nanoparticles (SEQ ID NO: 83). Mutations for H3-SS-np_231 are boxed. The six residue linker connecting H3-SS #231 to LS and a single LS mutation (N102D) deleting an N-linked glycan in LS is bolded. The C-terminal LS is underlined.

FIGS. 19A and 19B show the ELISA curves for HA stem antibodies CT149 (FIG. 19A) and CR8020 (FIG. 19B) recognition of H3-SS-LS-np variants 01, 02, 03 and 04. The $EC_{50}$ values from the curves are shown below each plot.

FIG. 22A shows neutralization of A/Anhui/1/2013 (H7N9). FIG. 21B shows neutralization of A/Wisconsin/67/2005 (H3N2). Sera from mice immunized with empty ferritin nanoparticle, Hl-SS-np and H3-SS-np (#231) serve as controls. Geometric mean titers are shown by horizontal lines. Horizontal dotted lines indicate the baseline titer of 50.

FIG. 23 shows the sequence locations of the 25 mutations enable the formation of group 2 H7 HA stabilized stem nanoparticles. The sequence for H7-SS-np_16 (SEQ ID NO: 92; based on A/Anhui/1/2013 (H7N9) HA, GenBank accession YP_009118475.1) is shown with H3 #231 mutations boxed. New H7 mutations are indicated with asterisks (two residues mutated to match H3N2 HA). For reference, the C-terminal SGG linker is bolded, the C-terminal ferritin is underlined and a Asn to Gln ferritin mutation to remove an N-linked glycan is bolded.

FIGS. 26A-26D show kinetic ELISA results for variants of H7-SS-np. FIGS. 26A-26C show the kinetic ELISA curves for FI6 (FIG. 26A), CT149 (FIG. 26B) and CR8020 (FIG. 26C) recognition of H7-SS-np variants 16, 18, 20, 21, 23, 25, 26 and an H1-SS-np positive control. FIG. 26D lists the $EC_{50}$ values from the curves in FIGS. 26A-26C shown. ND, not determined.

(FIG. 27A: H7-SS-16; FIG. 27B: H7-SS-18; FIG. 27C: H7-SS-21; FIG. 27D: H7-SS-23; FIG. 27E: H7-SS-25; FIG. 27F: H7-SS-26) are shown with the kinetic constants listed to the right of each curve set. Nanoparticles were immobilized to the sensor tip by amine coupling and incubated in various concentrations of antibody Fabs.

FIG. 30A shows neutralization to A/Anhui/1/2013 (H7N9). FIG. 30B shows neutralization of A/Wisconsin/67/2005 (H3N2). Sera from mice immunized with empty ferritin nanoparticle, H1-SS-np and H3-SS-np (#231) serve as controls. Geometric mean titers are shown by horizontal lines. Horizontal dotted lines indicate the baseline titer of 50.

FIG. 31 shows the sequence of four different examples of protein constructs of the invention, based on the sequence of the influenza subtype 10 HA (H10) protein. Mutations made to the influenza HA sequences are boxed. For reference, the C-terminal SGG linker is bolded, and the C-terminal ferritin sequence is underlined.

FIGS. 36A-C. shows weight loss curves for BALB/c mice (n=10) immunized with empty nanoparticles (FIG. 36A), H10ssF_4 (FIG. 36B), or H10ssF_5 (FIG. 36C), and then challenged with a lethal dose of A/Philippines/1982 (H3N2) influenza. FIG. 36D. shows survival curves for the same mice as in A. Mice immunized with ferritin nanoparticle alone (empty np) serve as a negative control.

FIG. 37A. shows survival curves for H10ssF-immunized BALB/c mice (n=10) challenged with a lethal dose of A/Shanghai/2/2013-like (H7N9) influenza. Mice immunized with ferritin nanoparticle alone (empty np) serve as a negative control. FIG. 37B shows weight loss six days post challenge for the same mice as in FIG. 37A. FIGS. 37C-G show weight loss over 12 days post challenge for the same mice as in FIGS. 37A & 3B7.

FIG. 38 shows the sequence of four different examples of protein constructs of the invention, based on the sequence of the influenza subtype 3 HA (H3) protein. Mutations made to the influenza HA sequences are boxed. For reference, the C-terminal SGG linker is bolded, and the C-terminal ferritin sequence is underlined. Also, a Asn to Gln ferritin mutation that removes an N-linked glycan is boxed and bolded.

FIG. 39 shows the sequence of four different examples of protein constructs of the invention, based on the sequence of the influenza subtype 7 HA (H7) protein. Mutations made to the influenza HA sequences are boxed. For reference, the C-terminal SGG linker is bolded, and the C-terminal ferritin sequence is underlined. Also, a Asn to Gln ferritin mutation that removes an N-linked glycan is boxed and bolded.

FIG. 41 shows the sequence of HA portion of protein constructs that exhibited activity in the B-cell activation assay illustrated in FIGS. 40A-C. Mutations made to the influenza HA sequences are boxed.

DETAILED DESCRIPTION OF THE INVENTION

Figure 1A:
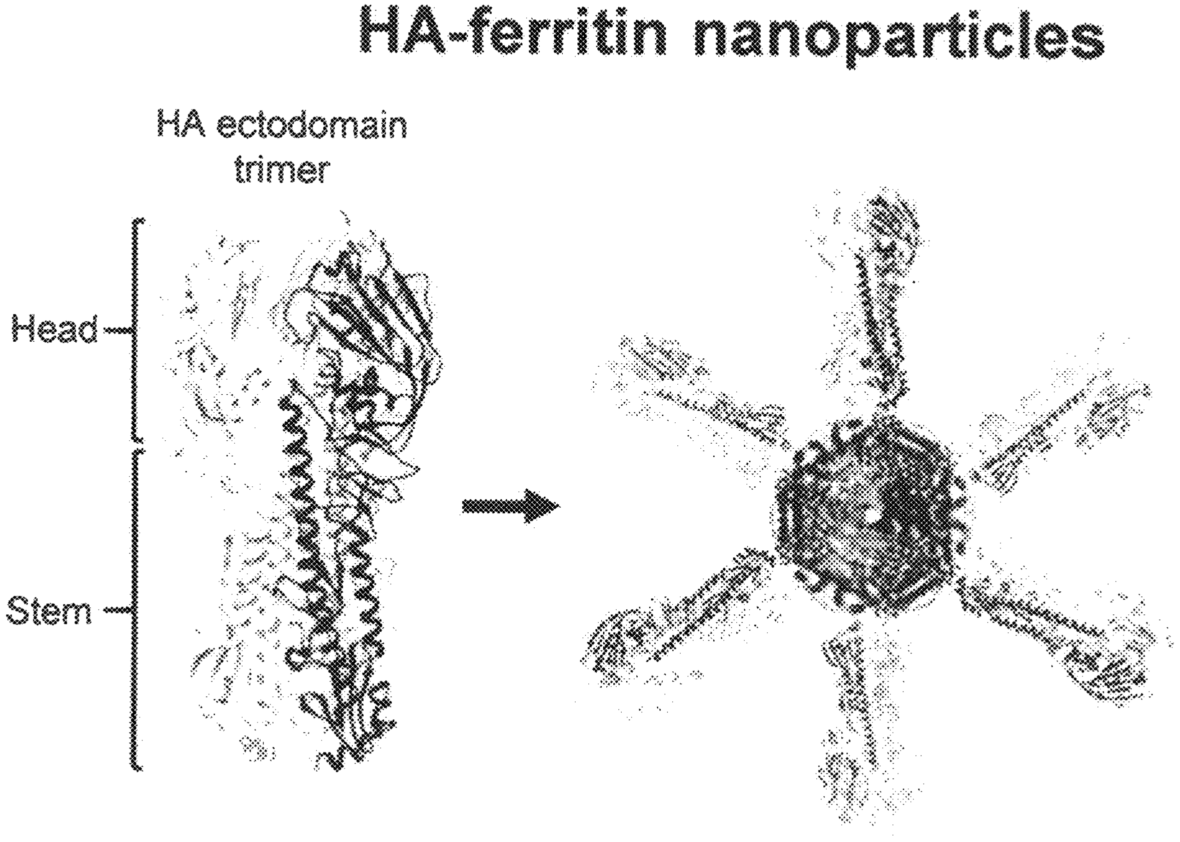
FIGS. 1A-1C provide a summary of prior art.
Figure 1B:
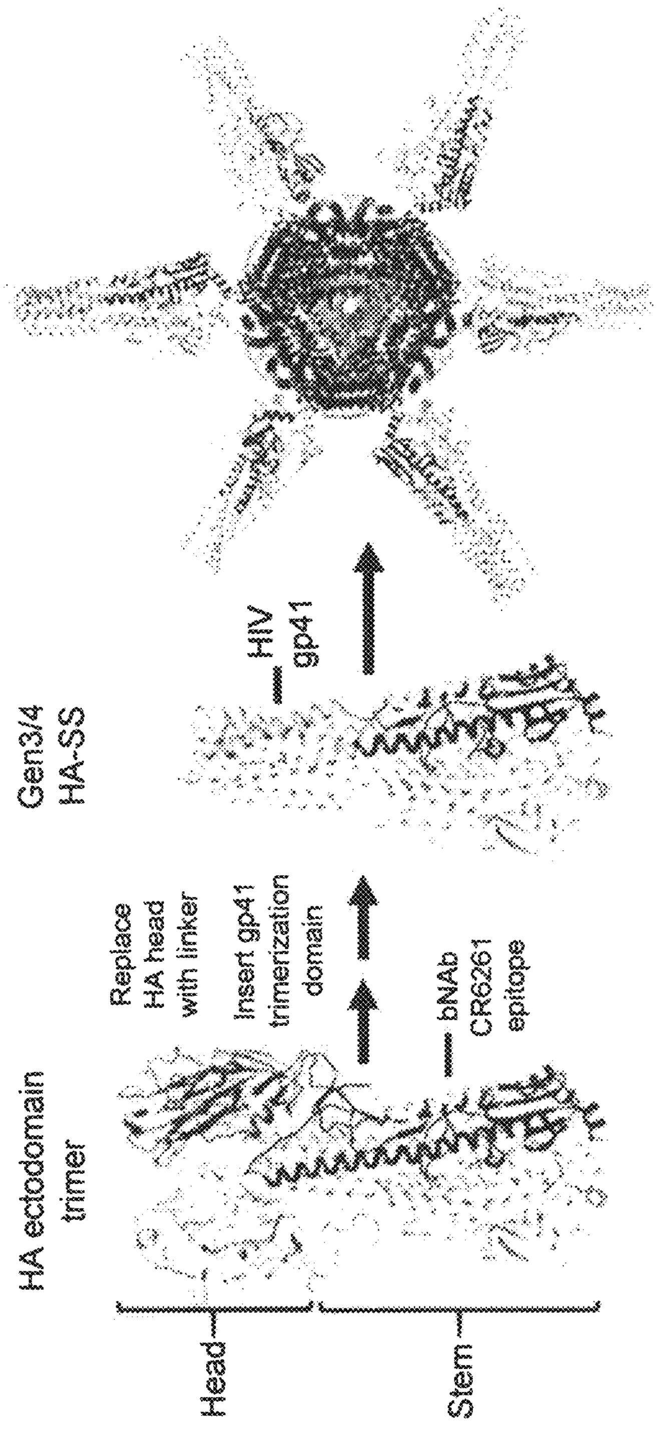
Figure 1C:
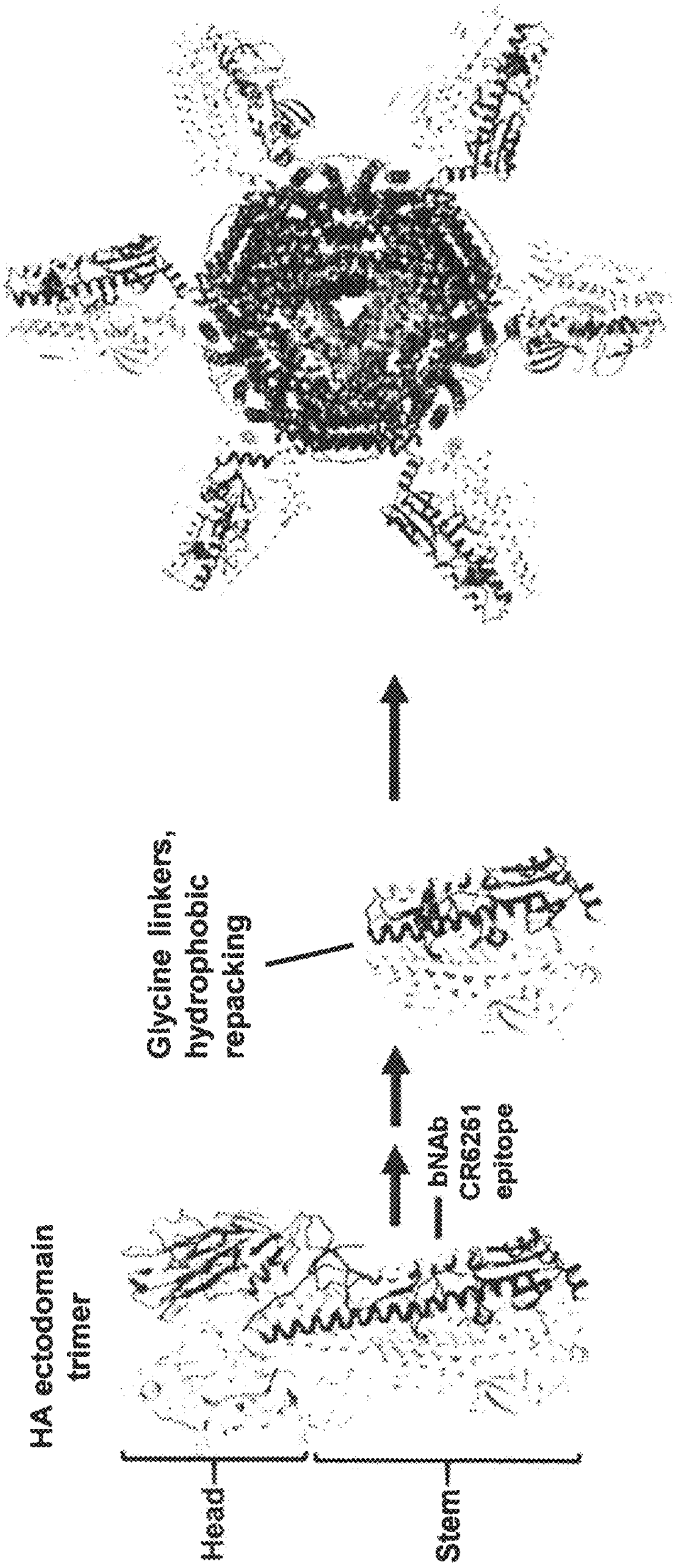
Figure 2:
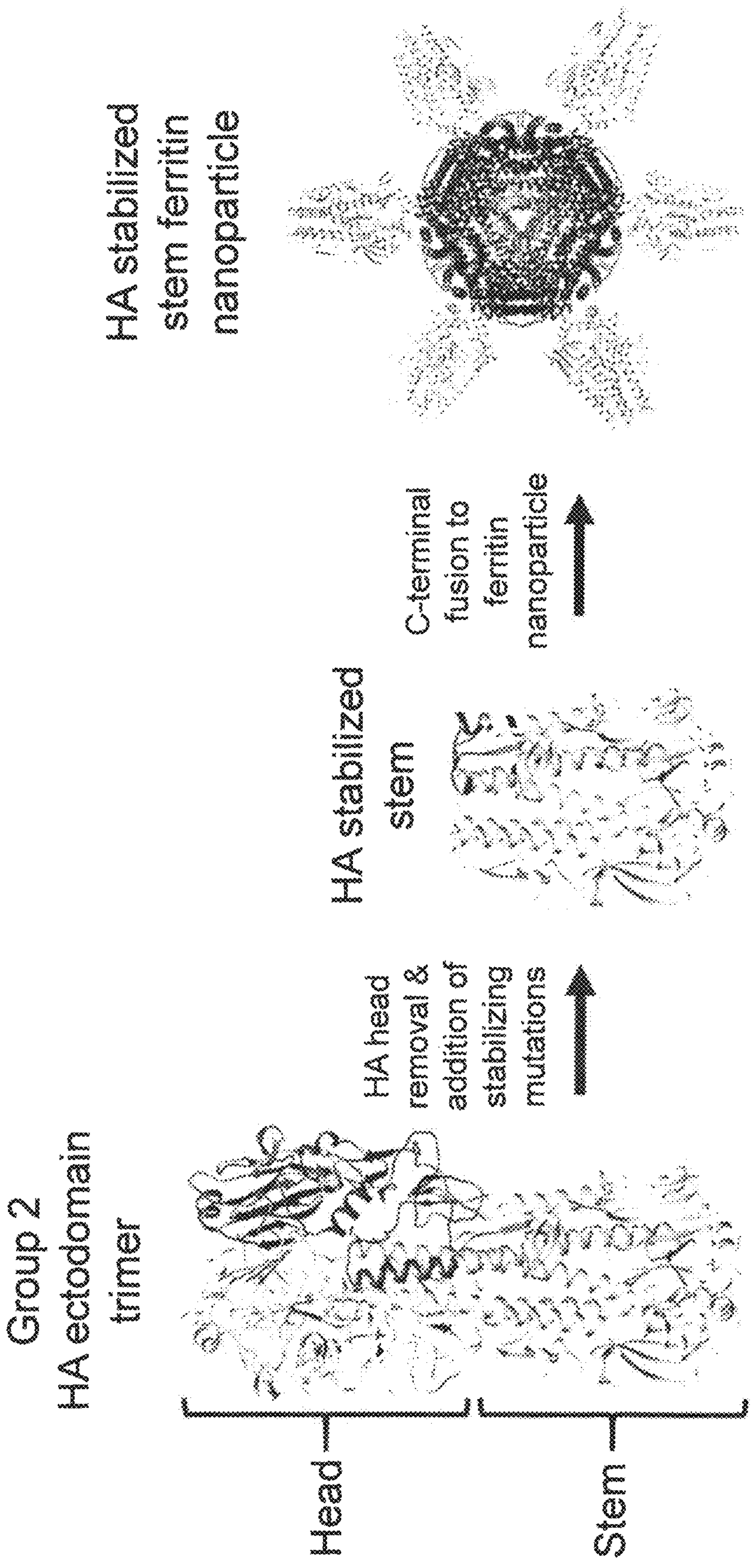
FIG. 2 depicts the creation of self-assembling group 2 HA stem nanoparticles. Ribbon diagrams depict (from left to right) the design of group 2 HA stabilized stem nanoparticles. The head region of one HA monomer is represented in dark gray. The stem region of that same monomer is shown in a medium grey. The other two monomers are shown in light gray.
Figure 8A:
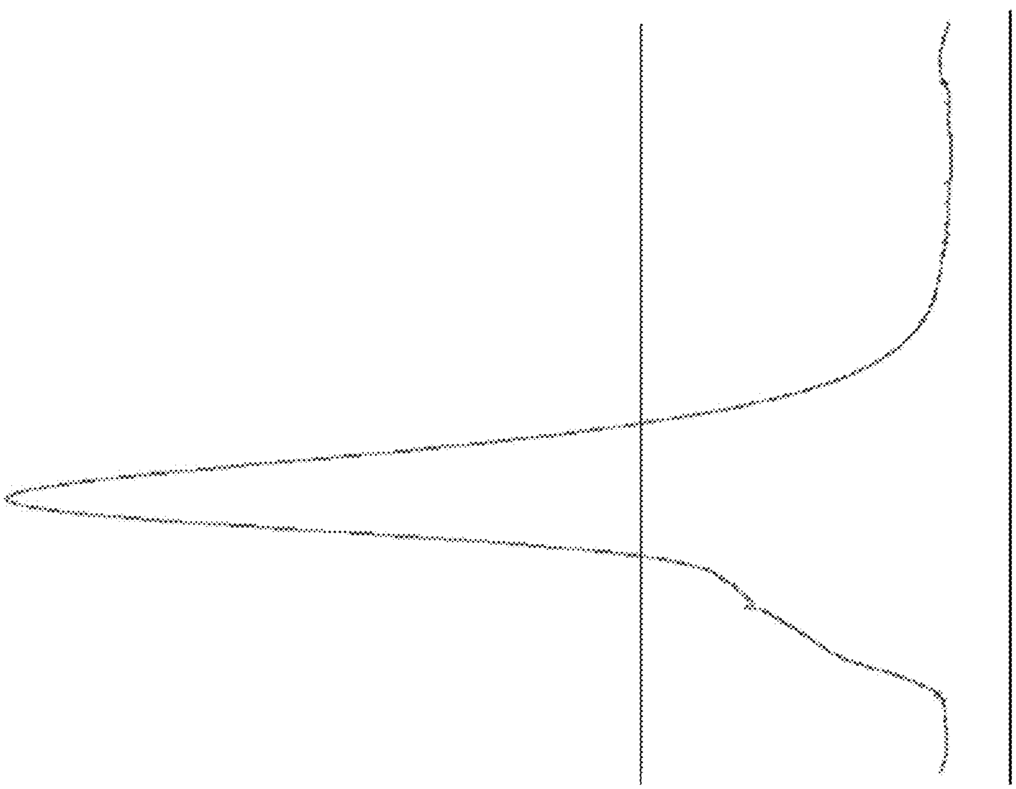
FIGS. 8A and 8B show the expression and characterization of H3 stabilized stem ferritin nanoparticle 231 (H3-SS-np_231).
Figure 8B:
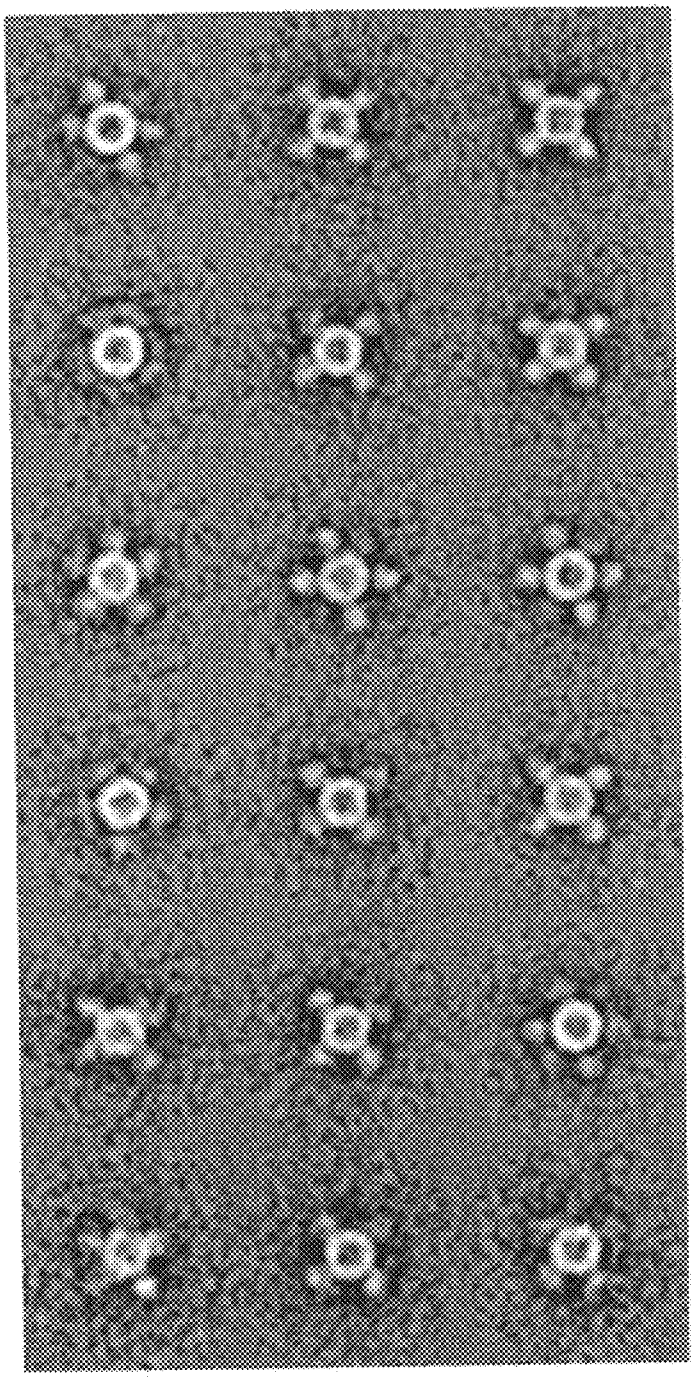
Figures 9A, 9B:
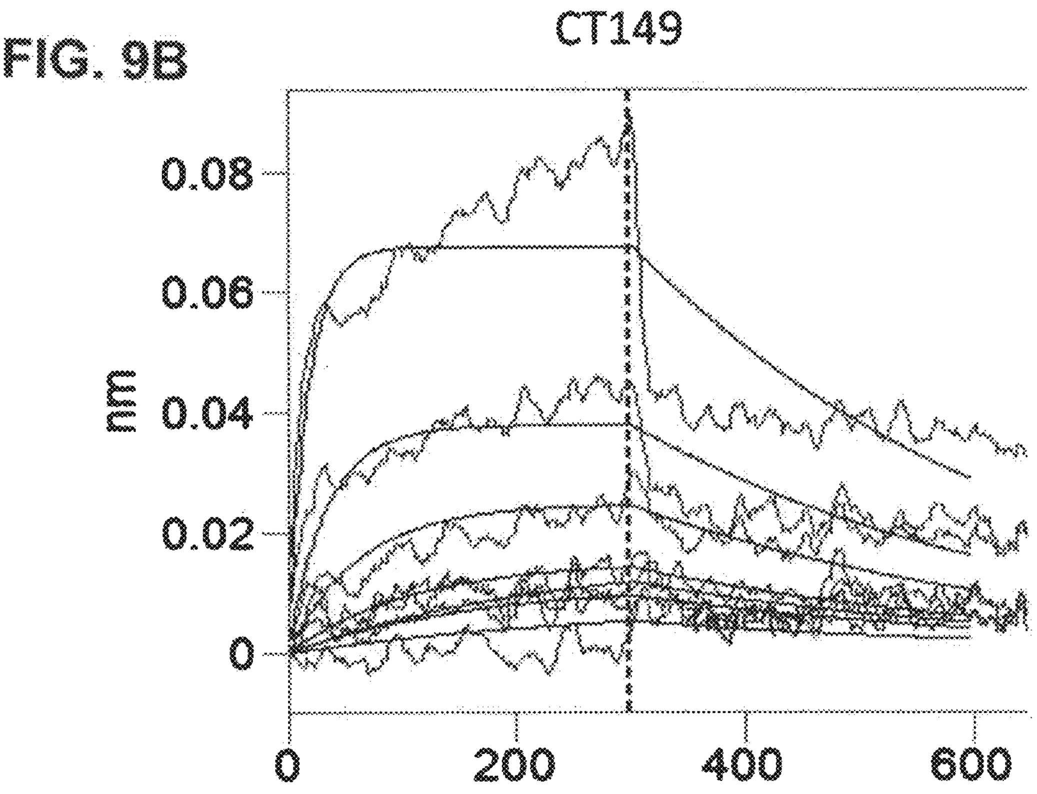
FIGS. 9A and 9B show HA stem antibody recognition of H3-SS-np_231.
Figure 10A:
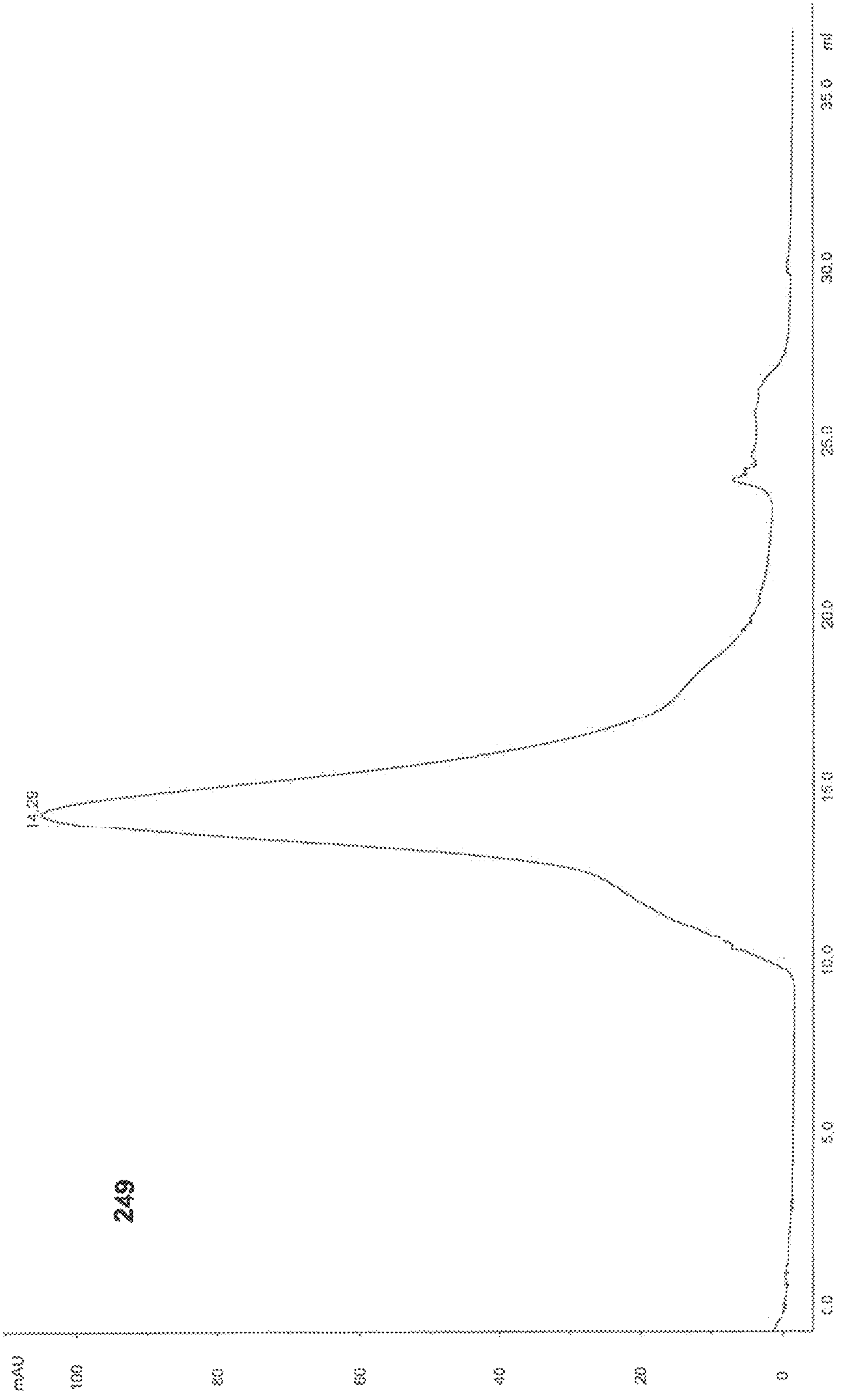
FIGS. 10A-10E show gel filtration profiles for five variants of H3-SS-np_231. Gel filtration Superose 6 10/30 profiles for H3-SS-np_231 variants, 249 (FIG. 10A), 256 (FIG. 10B), 258 (FIG. 10C), 262 (FIG. 10D) and 264 (FIG. 10E). In each case a single peak was eluted at a volume of approximately 14.5 mls. The final yields from Expi293 cells after gel filtration were 6-8 mg/L of culture.
Figure 10B:
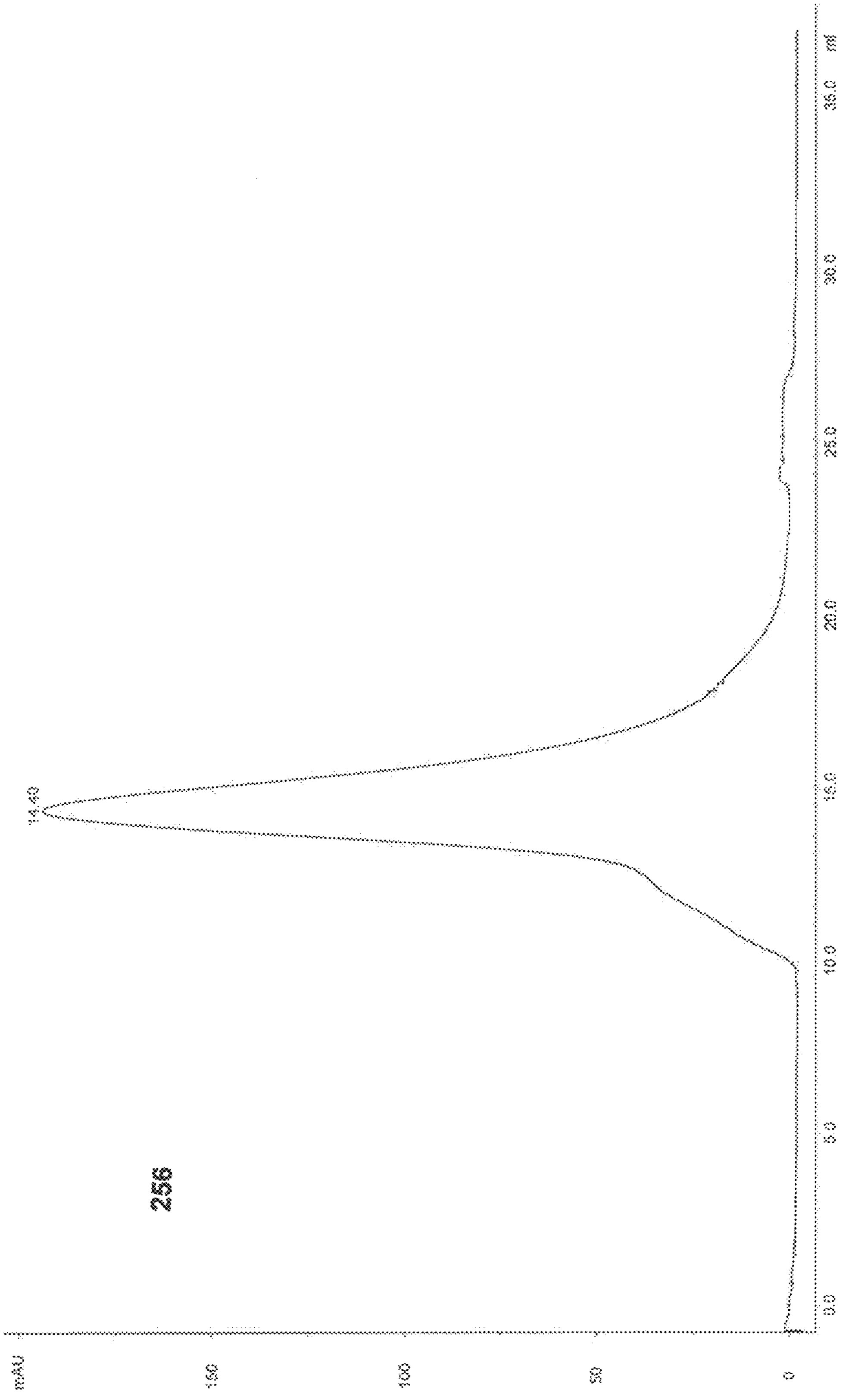
Figure 10C:
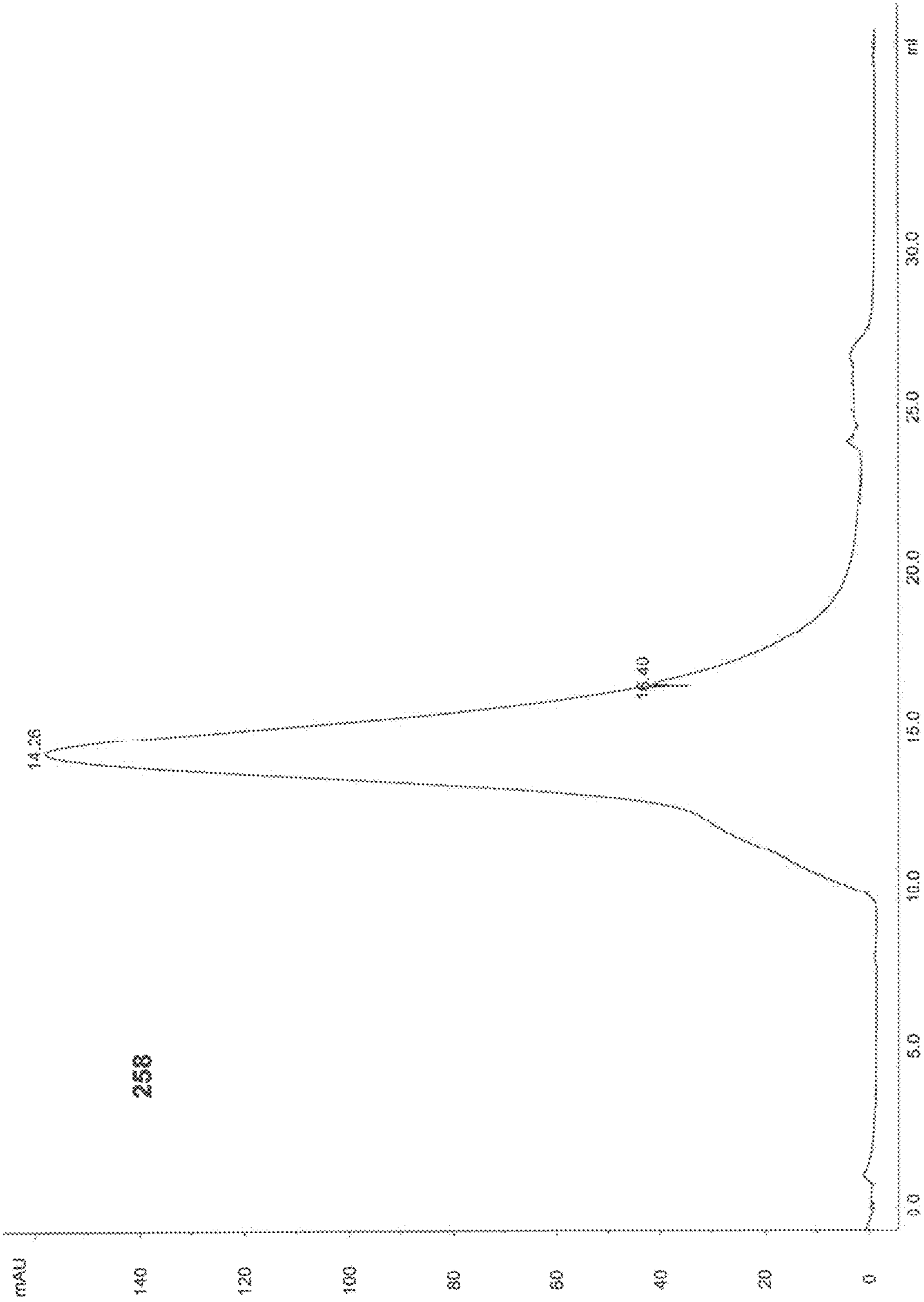
Figure 10D:
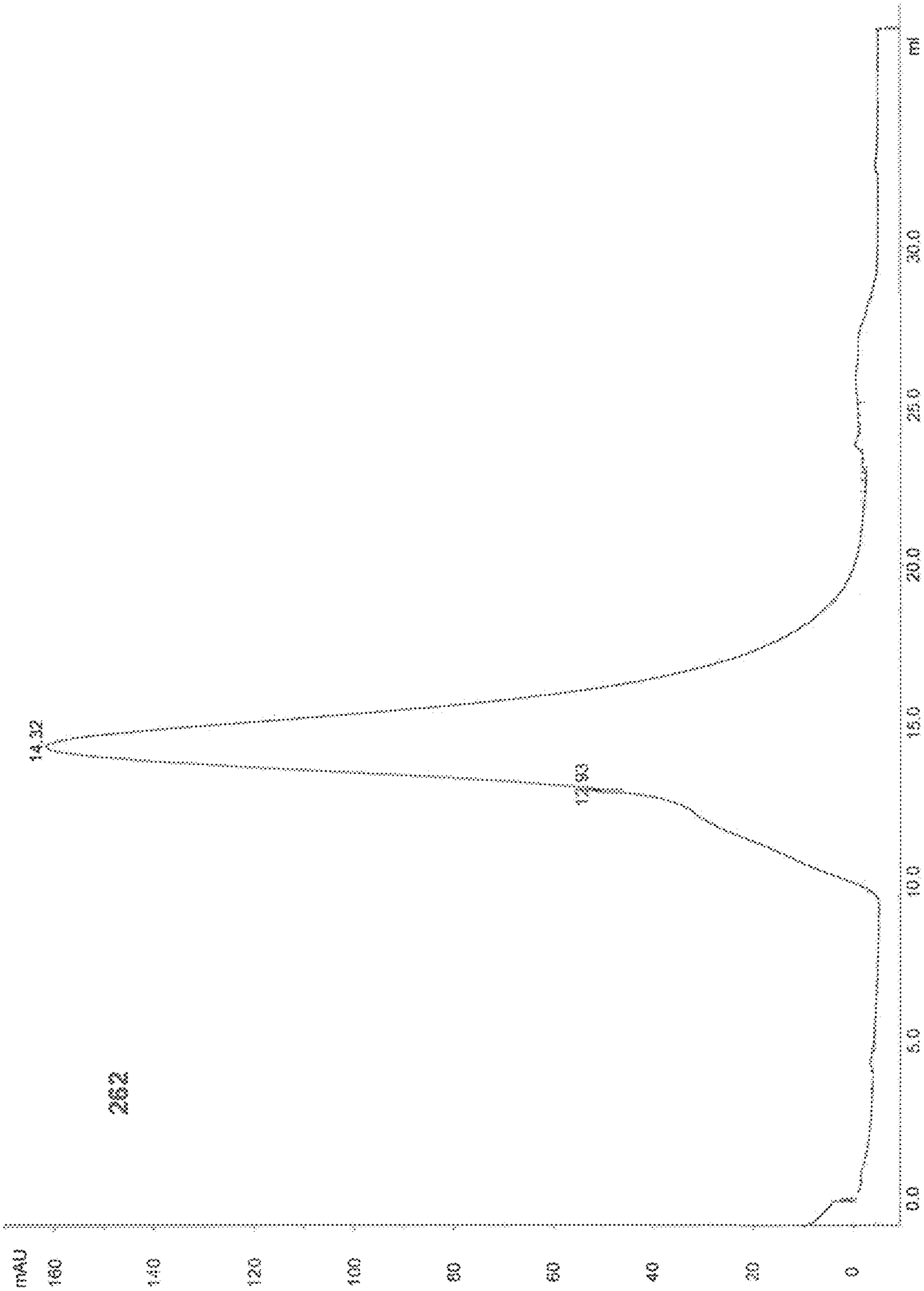
Figure 10E:
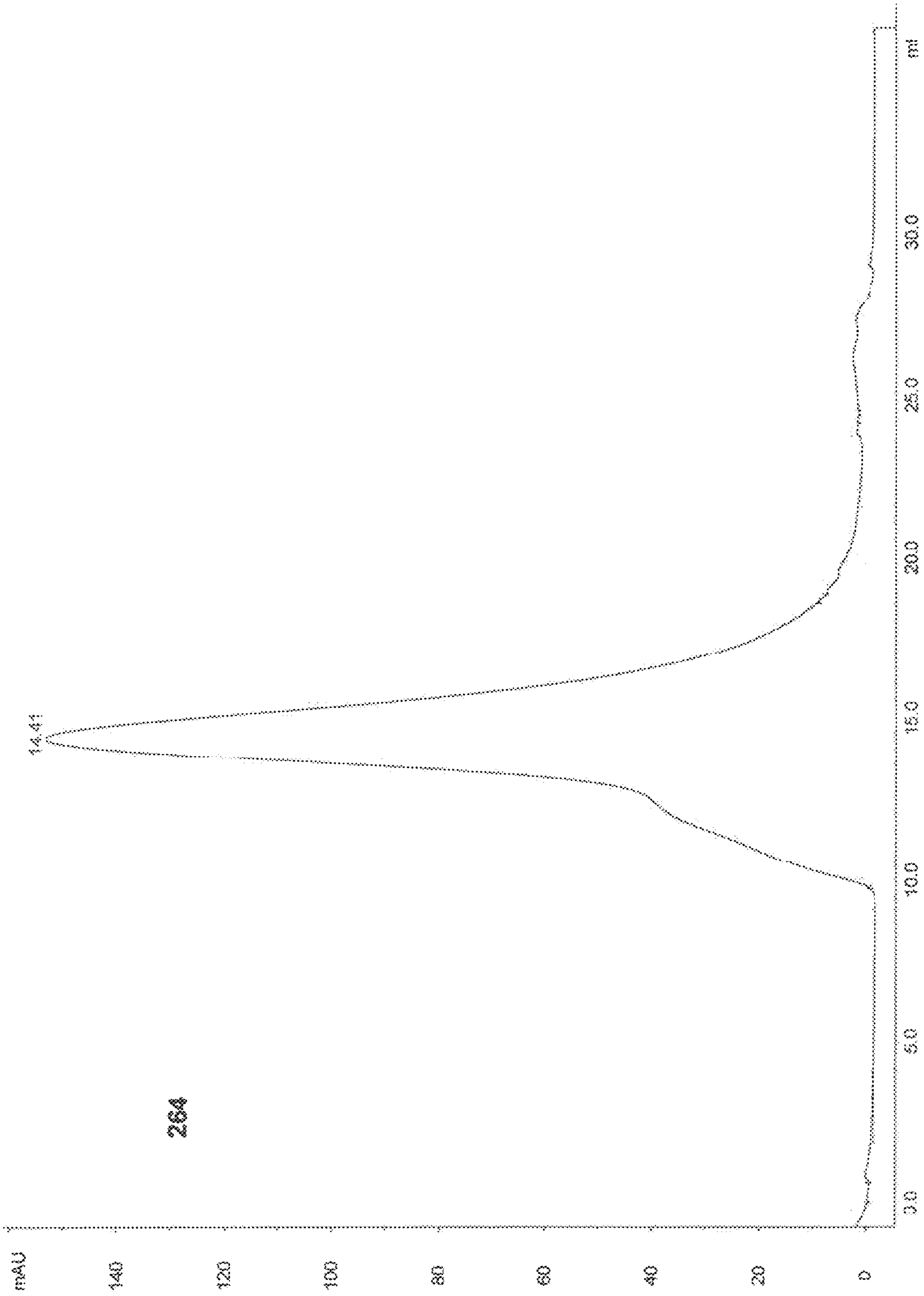
Figure 11A:
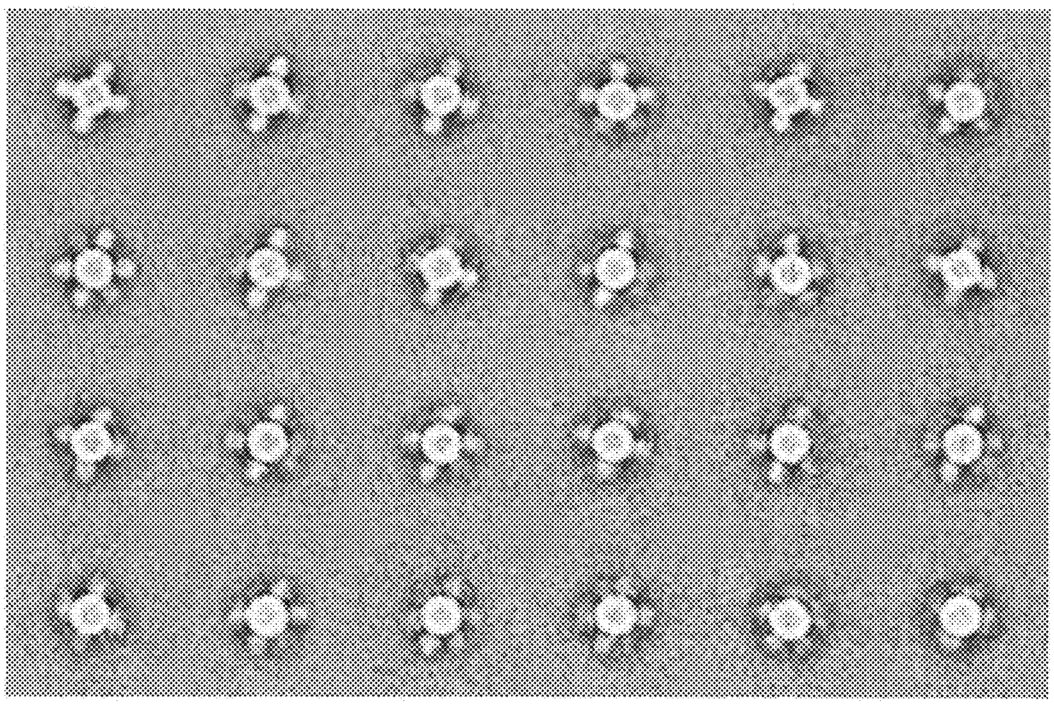
Figure 11B:
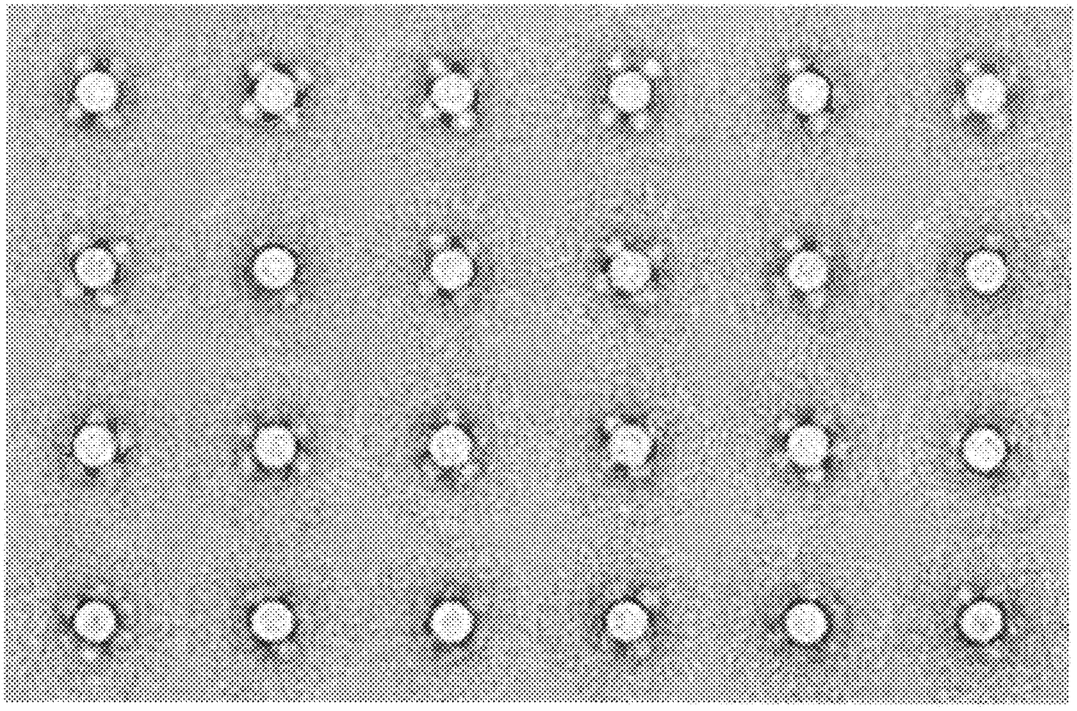
Figure 11C:
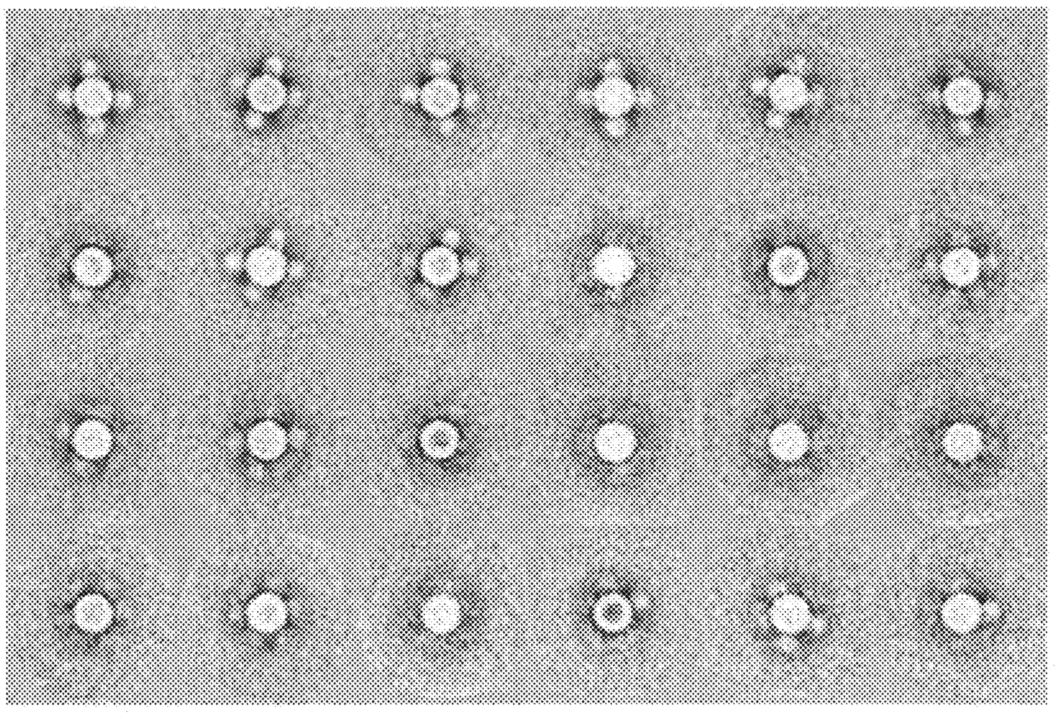
Figure 11D:
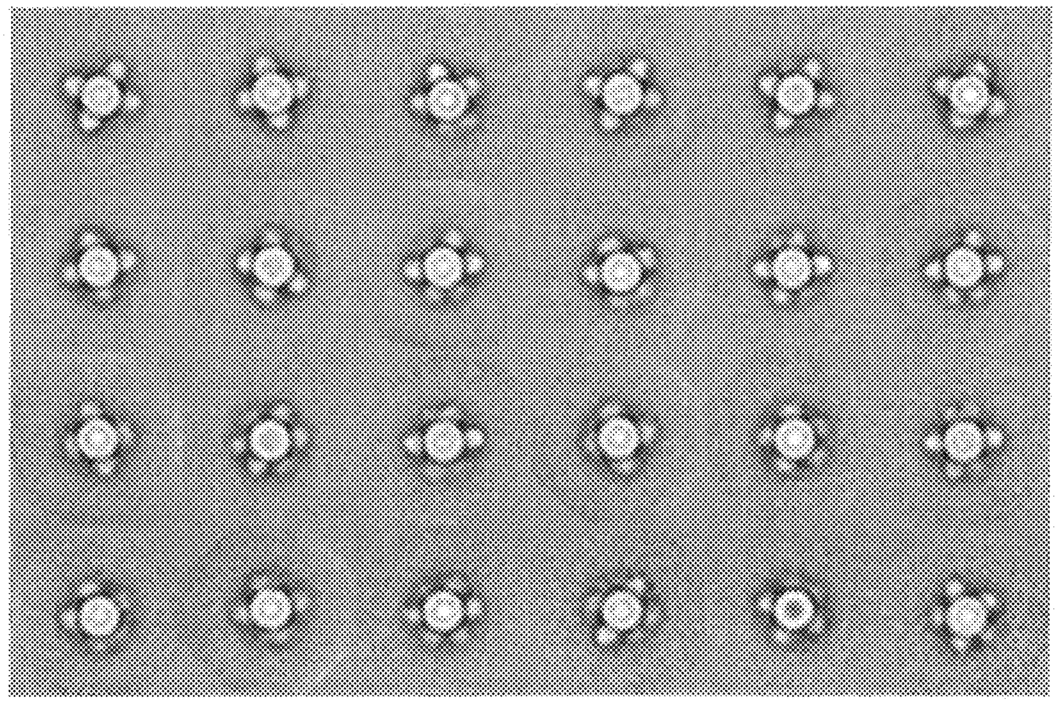
Figure 12A:
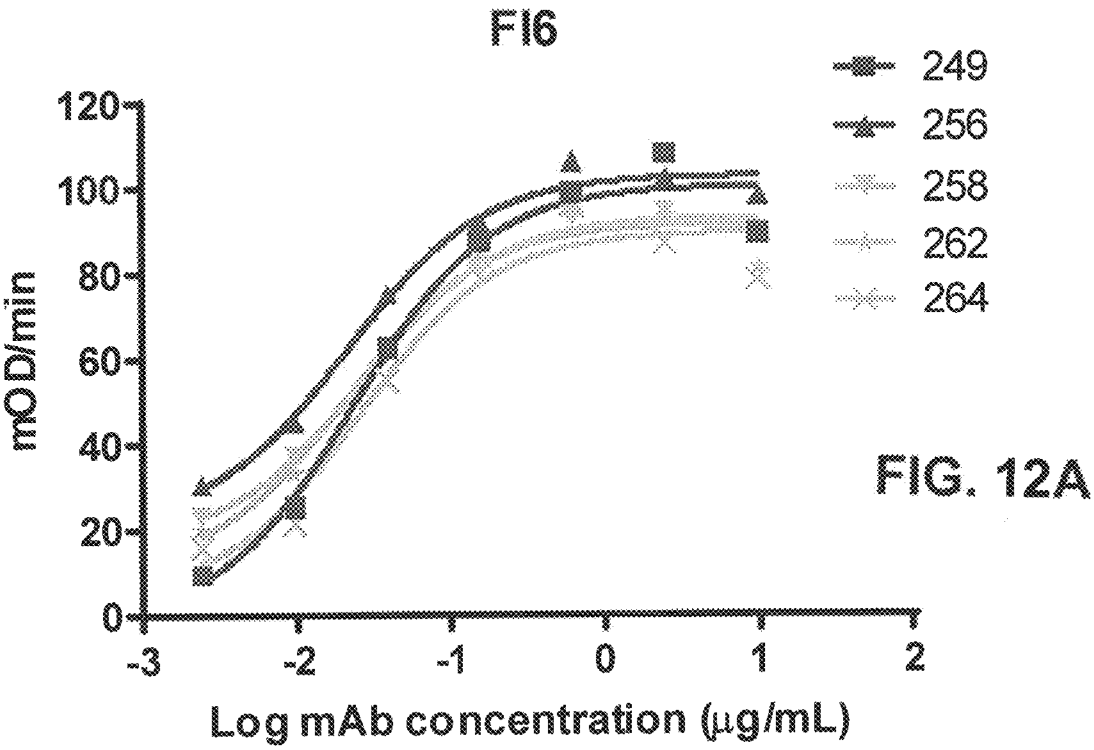
FIGS. 12A-12D show kinetic ELISA results for five variants of H3-SS-np_231.
Figure 12B:
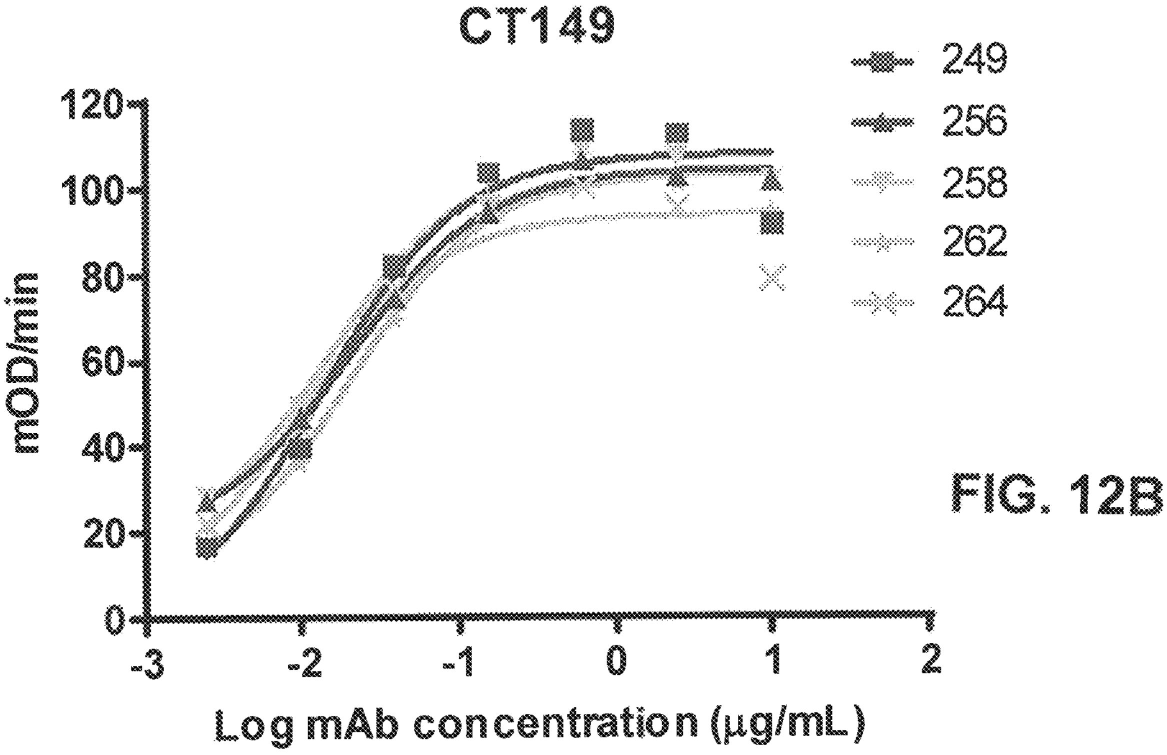
Figures 12C, 12D:
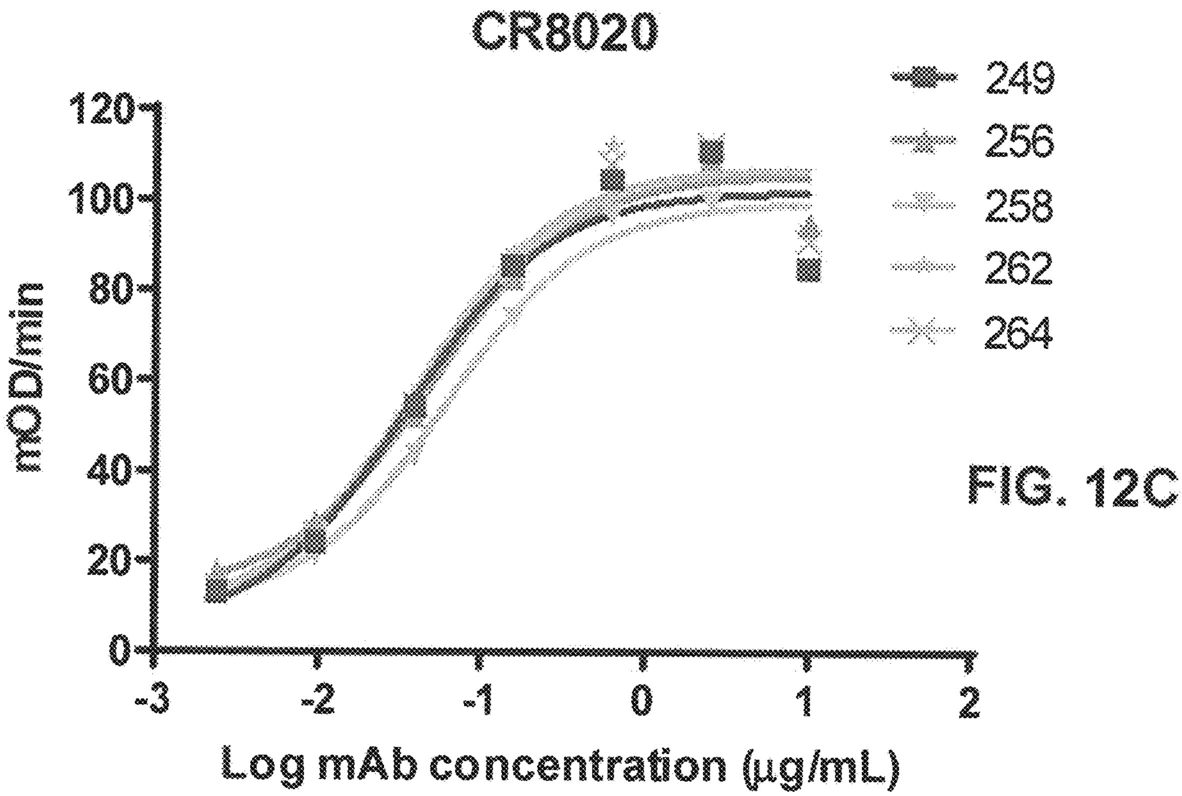
Figure 14:
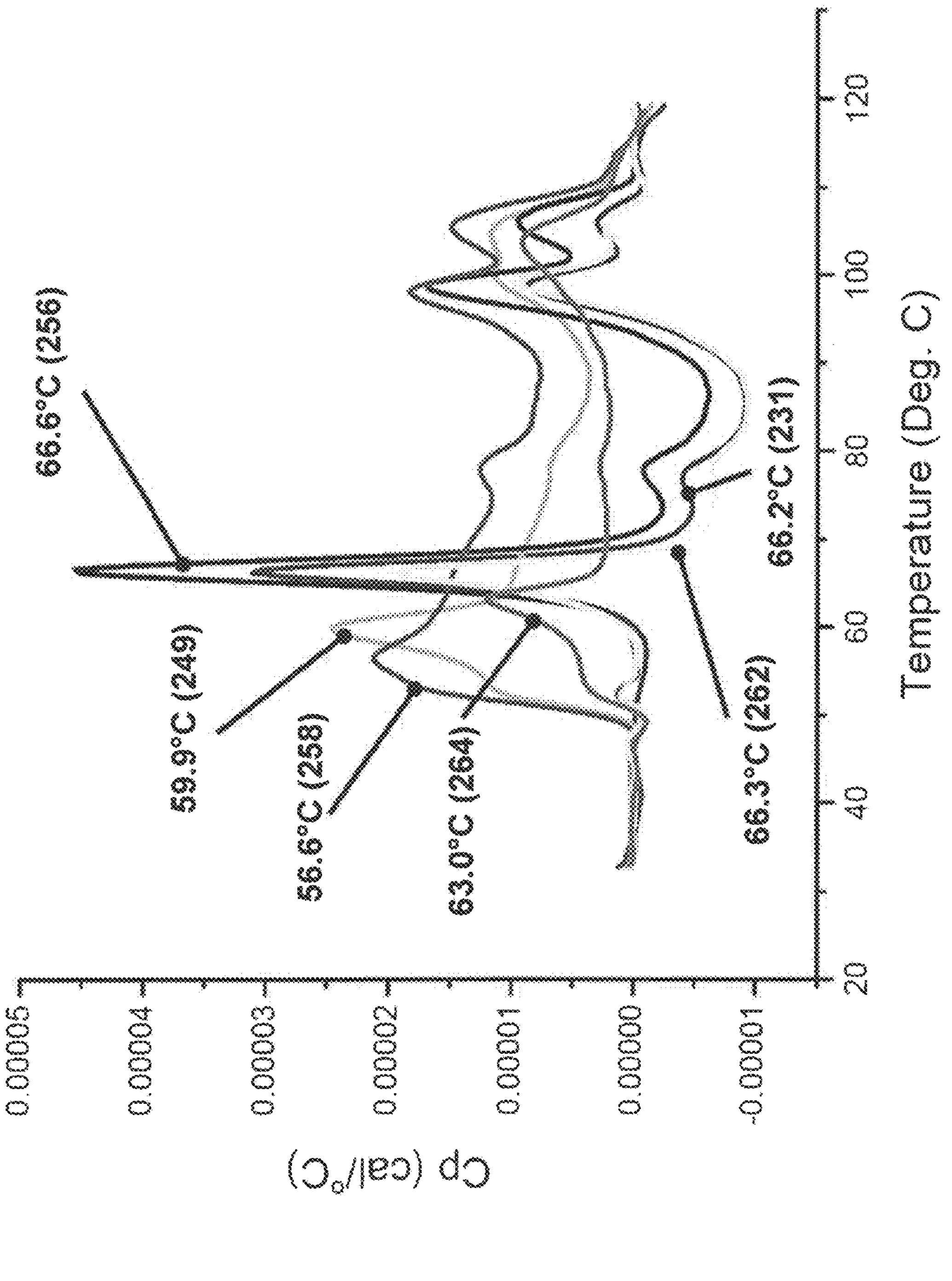
FIG. 14 shows dynamic scanning calorimetry (DSC) plots for H3-SS-np (#231) and five variants. Plots of heat capacity (Cp) versus temperature depicts melting transitions for each protein. The earliest melting points (TMs) for each design are noted. The design number is shown for each in parentheses. In this diagram, the Cp values on the Y-axis are shown with an arbitrary scale.
Figure 15A:
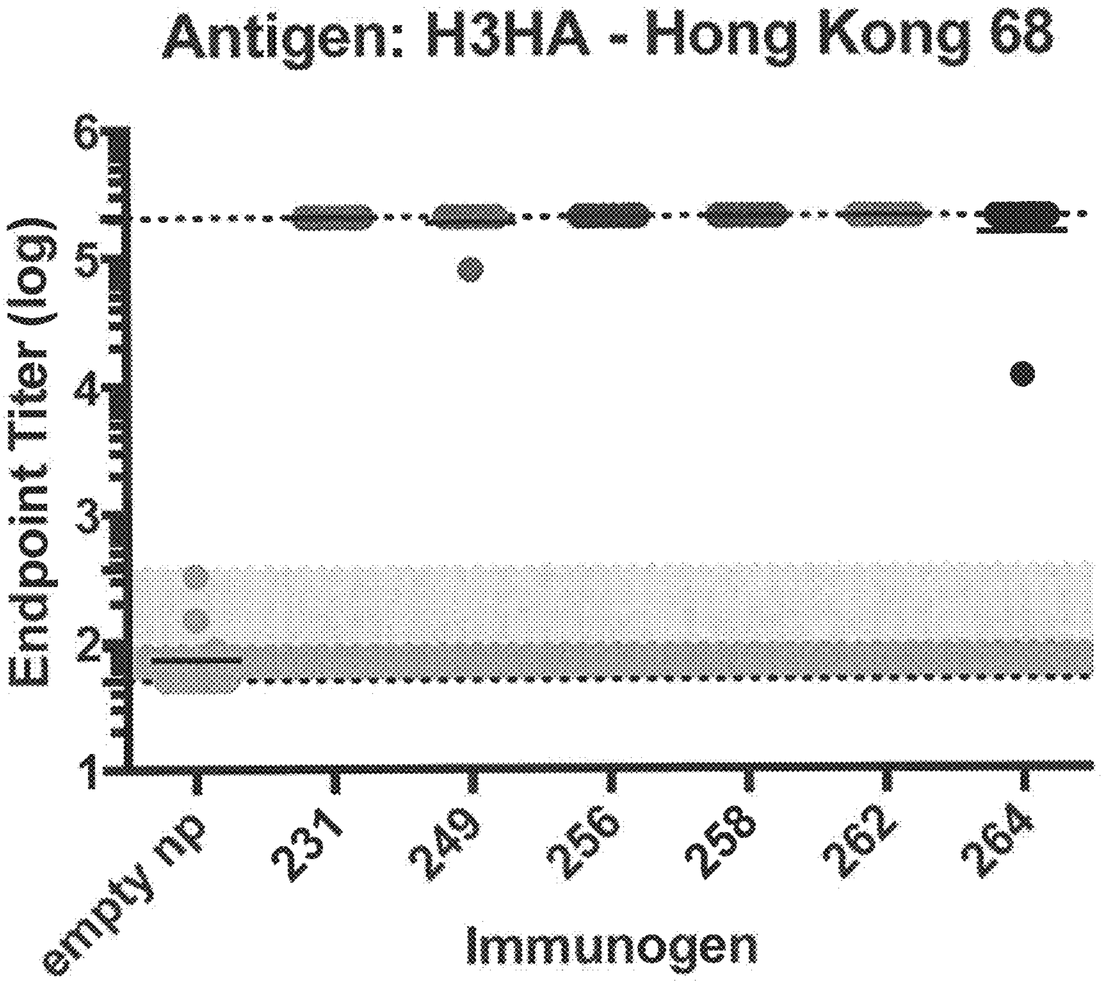
FIGS. 15A & 15B show immune responses of H3-SS-np-immunized mice to group 2 HAs. ELISA antibody endpoint titers of sera from BALB/c mice (n=10) immunized 3x with six different versions of SAS-adjuvanted H3-SS-np to plated A/Hong Kong/1/1968 (H3N2) HA (FIG. 15A) and A/Anhui/1/2013 (H7N9) (FIG. 15B). Sera from mice immunized with empty ferritin nanoparticle alone serves as a negative control. Geometric mean titers are shown by horizontal lines. Dark gray shading indicates the average titer for the negative control and light gray shading indicates the region up to four times the average titer of the negative control. Statistical analysis was performed using a two-tailed Student's t-test; *P<0.05, P<0.01, **P<0.0001.
Figure 15B:
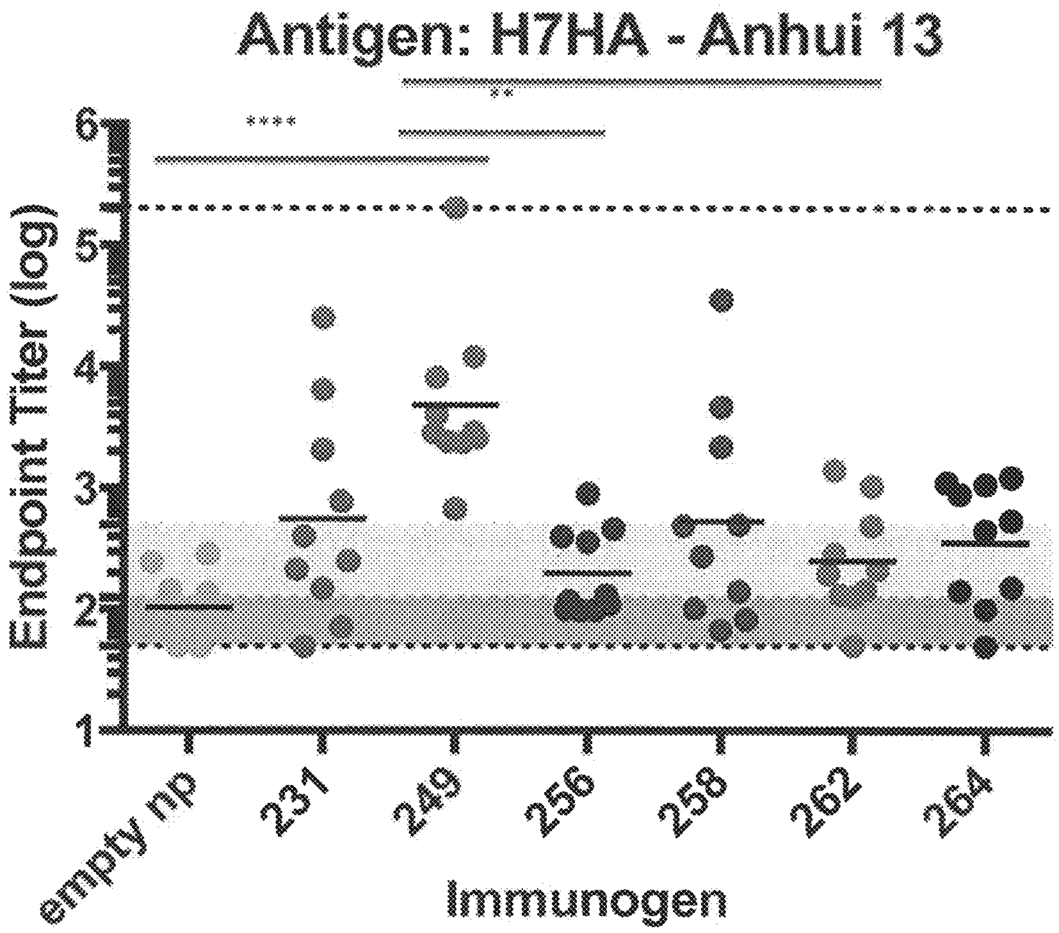
Figure 16A:
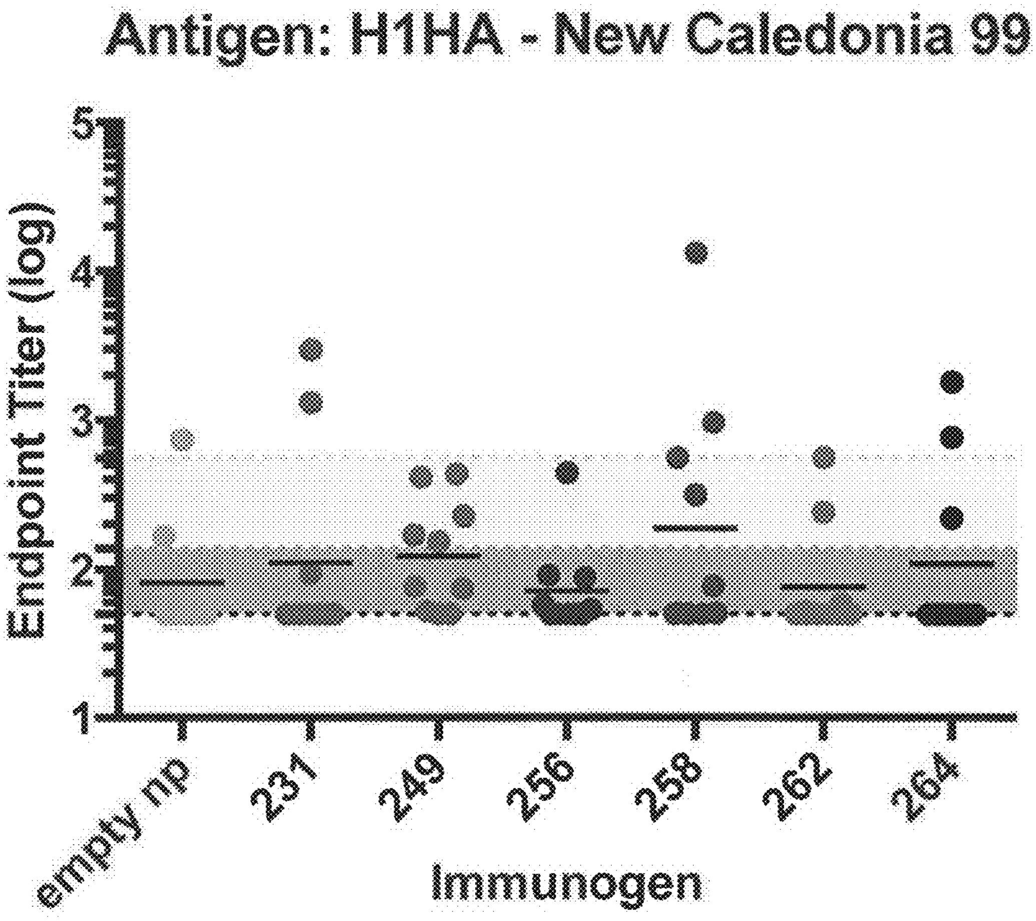
FIGS. 16A-16D show immune responses of H3-SS-np-immunized mice to group 1 HAs. ELISA antibody endpoint titers of sera from BALB/c mice (n=10) immunized 3× with six different versions of SAS-adjuvanted H3-SS-np to plated A/New Caledonia/20/1999 (H1N1) HA (FIG. 16A), A/Canada/720/2005 (H2N2) (FIG. 16B), A/Hong Kong/1074/1999 (H9N2) (FIG. 16C) and A/Vietnam/1203/2004 (H5N1) (FIG. 16D). Sera from mice immunized with empty ferritin nanoparticle alone serves as a negative control. Geometric mean titers are shown by horizontal lines. Dark gray shading indicates the average titer for the negative control and light gray shading indicates the region up to four times the average titer of the negative control.
Figure 16B:
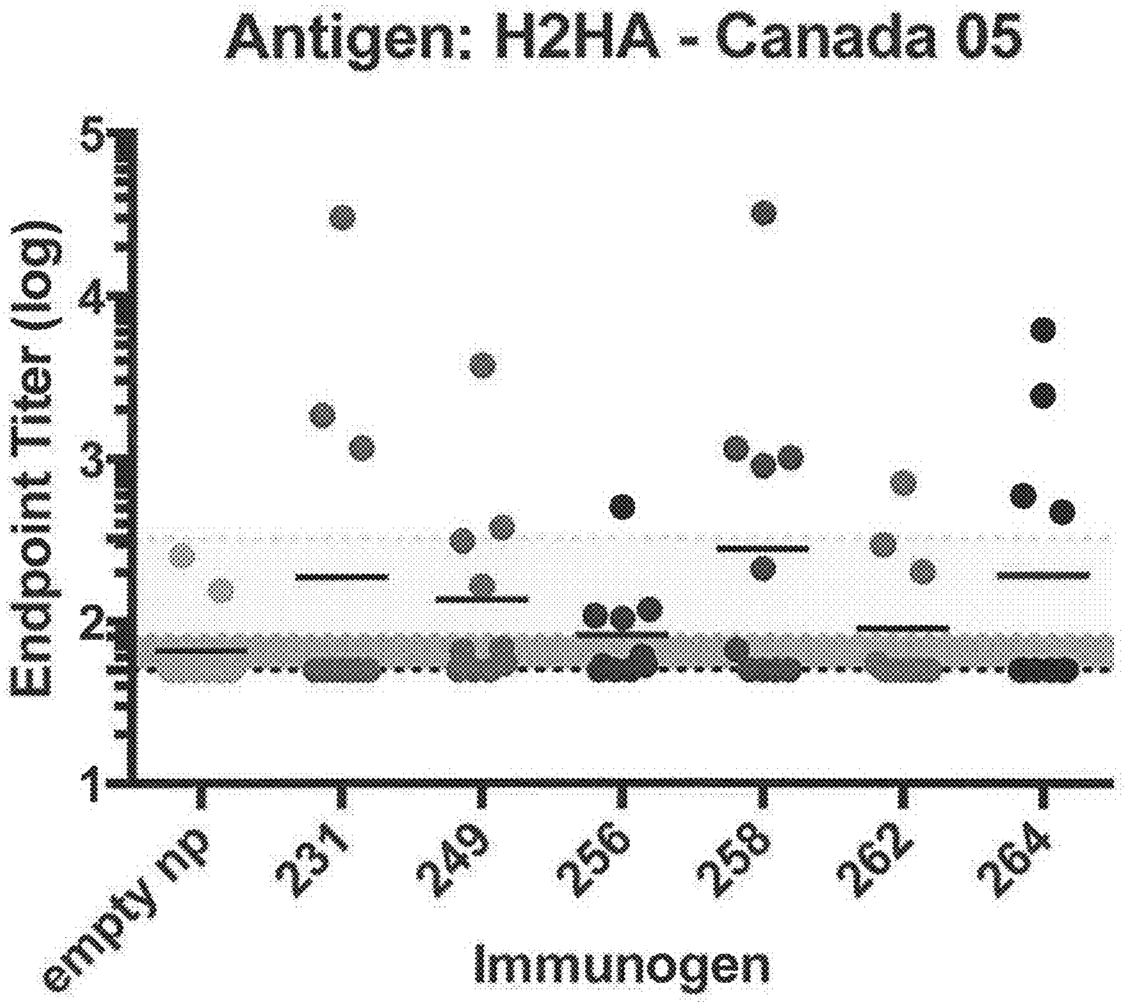
Figure 16C:
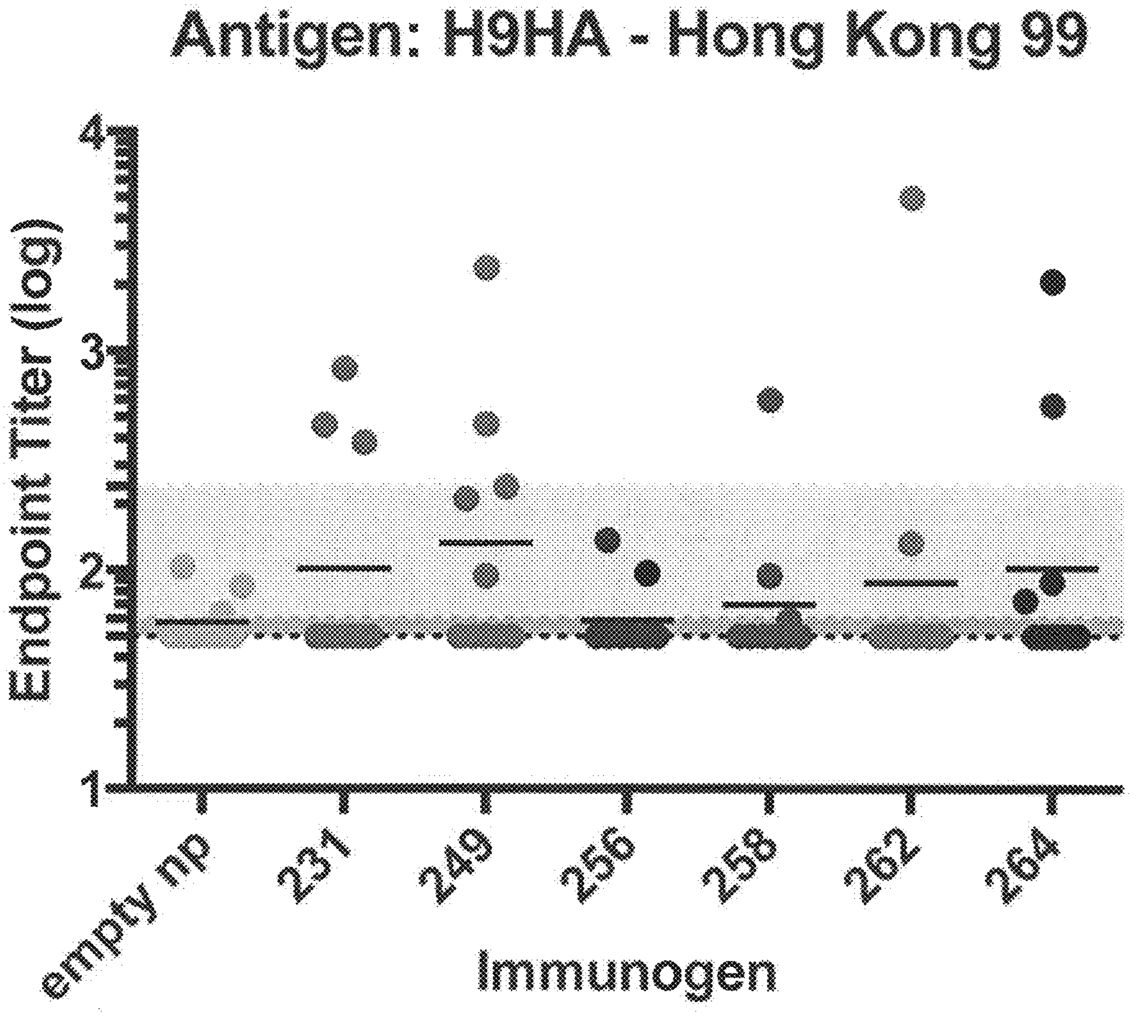
Figure 16D:
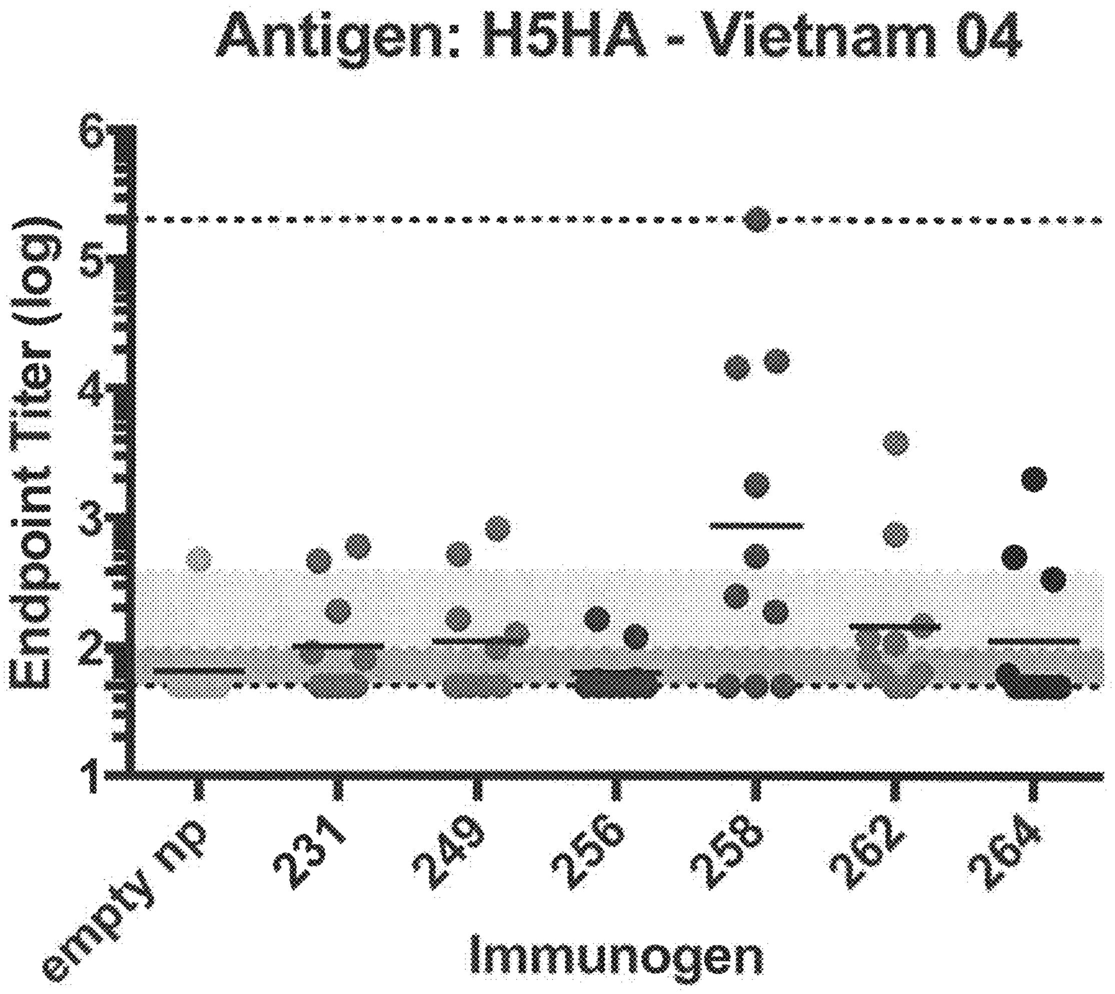
Figure 18A:
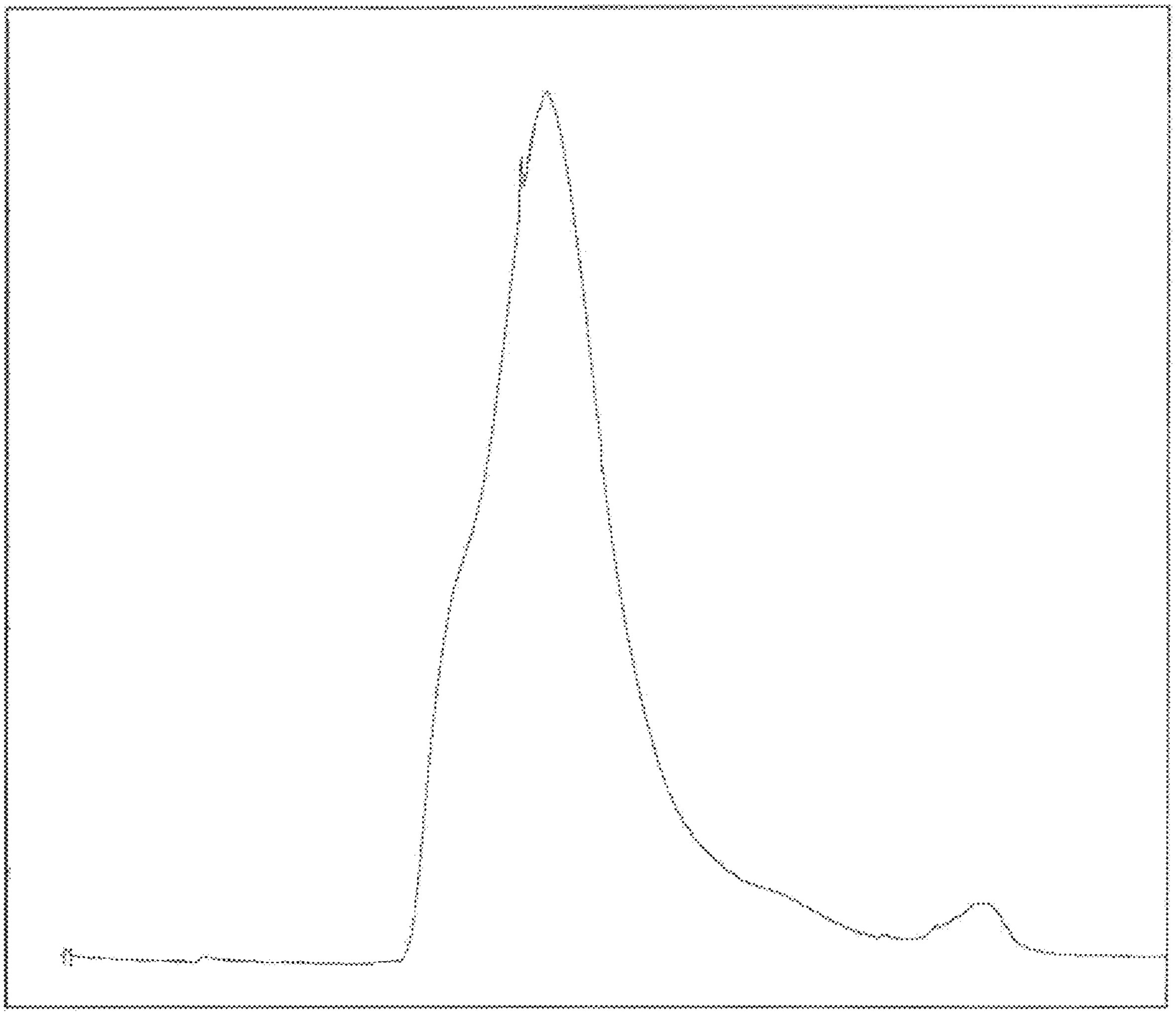
FIGS. 18A-18F are gel filtration profiles for six variants of H3-LS-np. A-F Gel filtration Superose 6 10/30 profiles for H3-SS-LS-np variants 01 (FIG. 18A), 02 (FIG. 18B), 03 (FIG. 18C), 04 (FIG. 18D), 06 (FIG. 18E) and 07 (FIG. 18F). In each case, except H3-SS-LS-04, a single peak was eluted. The final yields from Expi293 cells after gel filtration were 1-2 mg/L of culture.
Figure 18B:
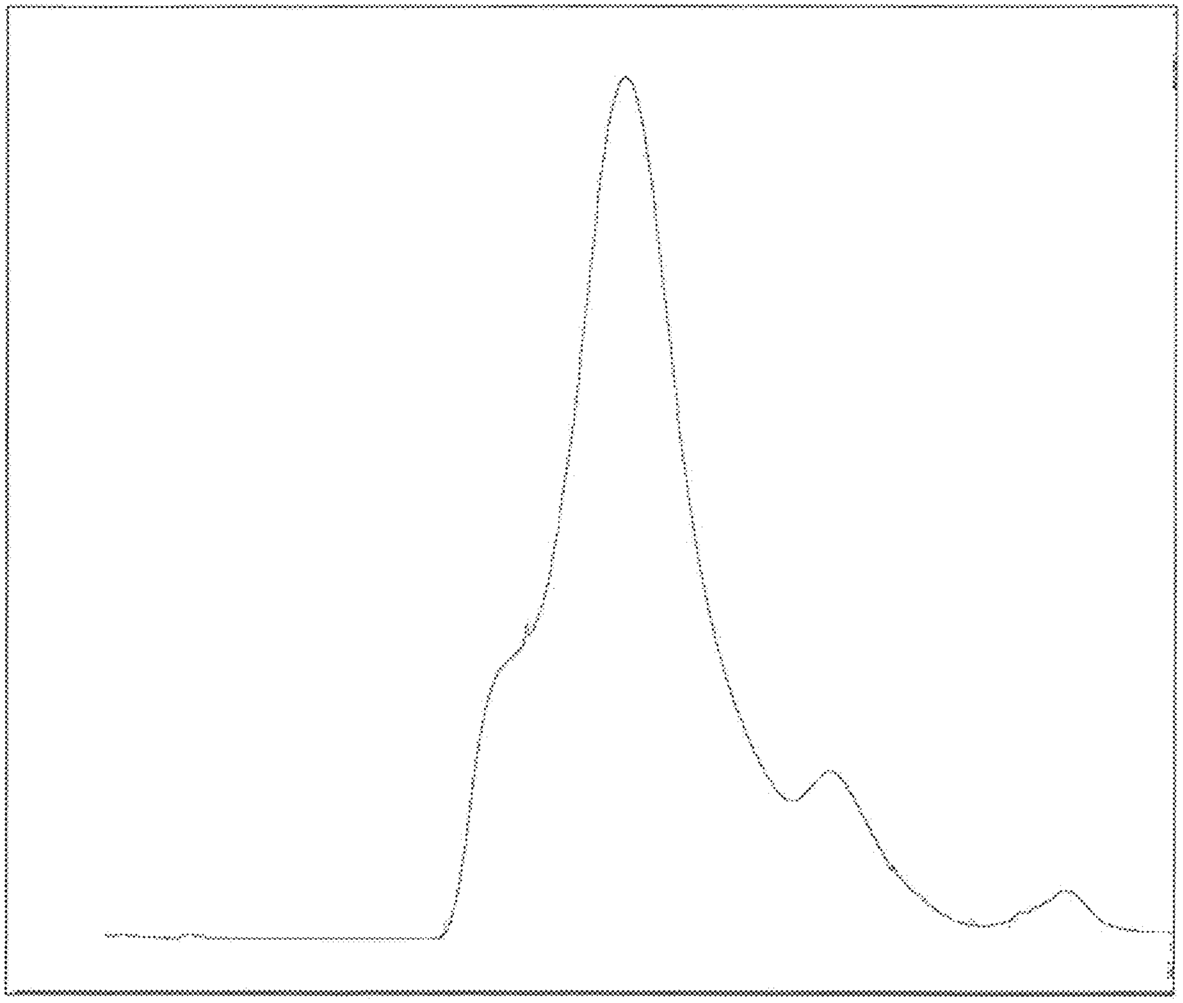
Figure 18C:
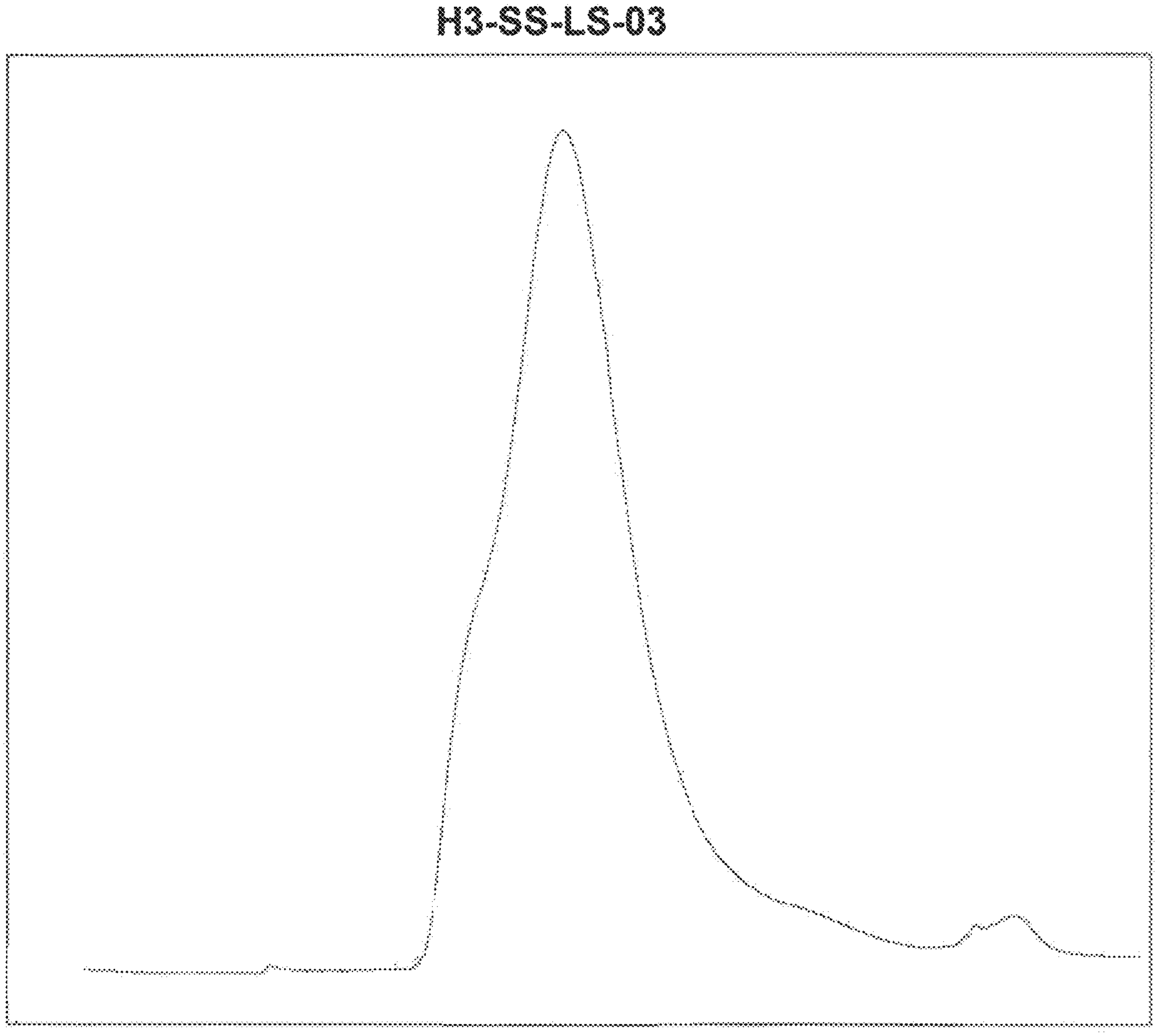
Figure 18D:
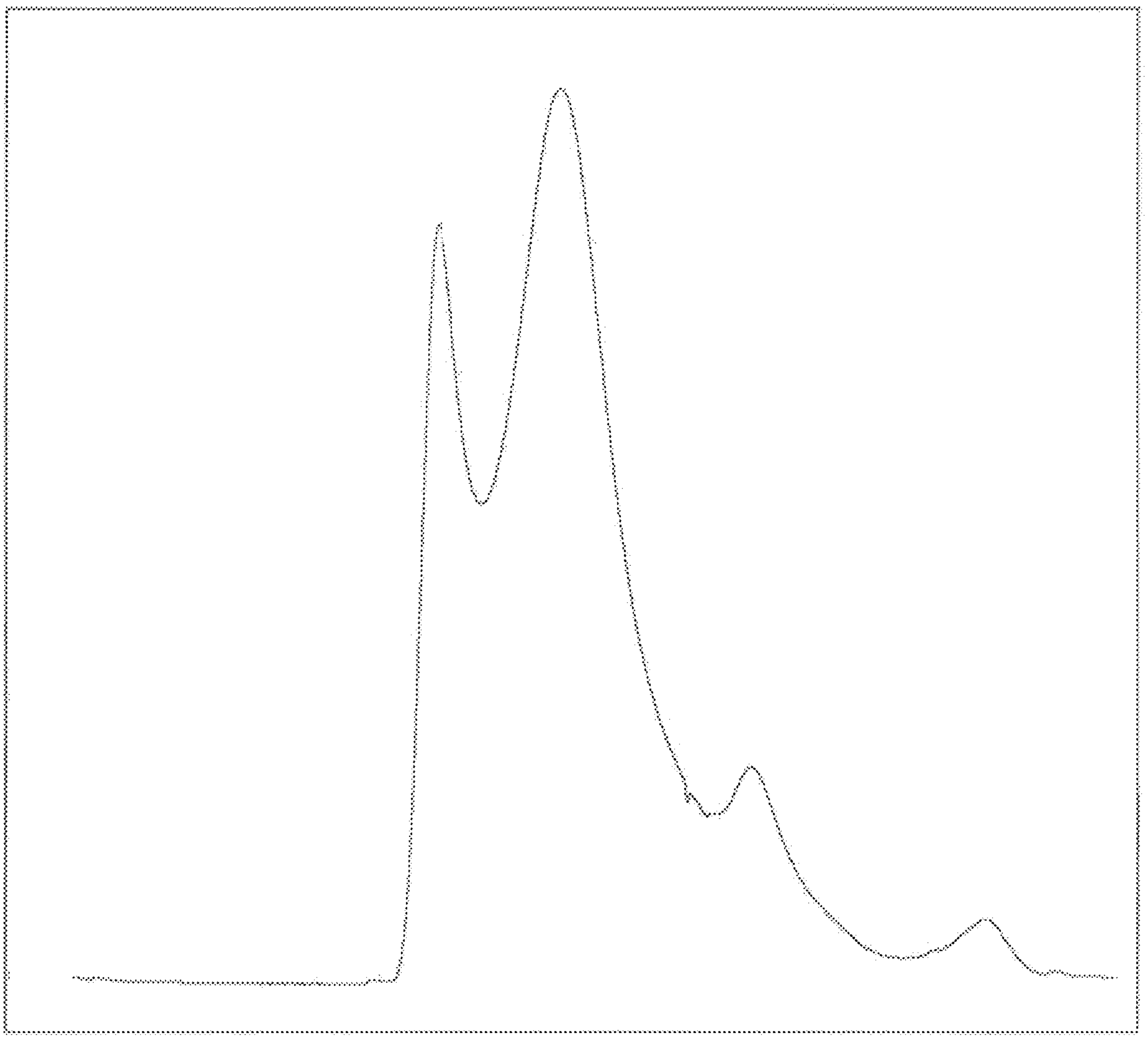
Figure 18E:
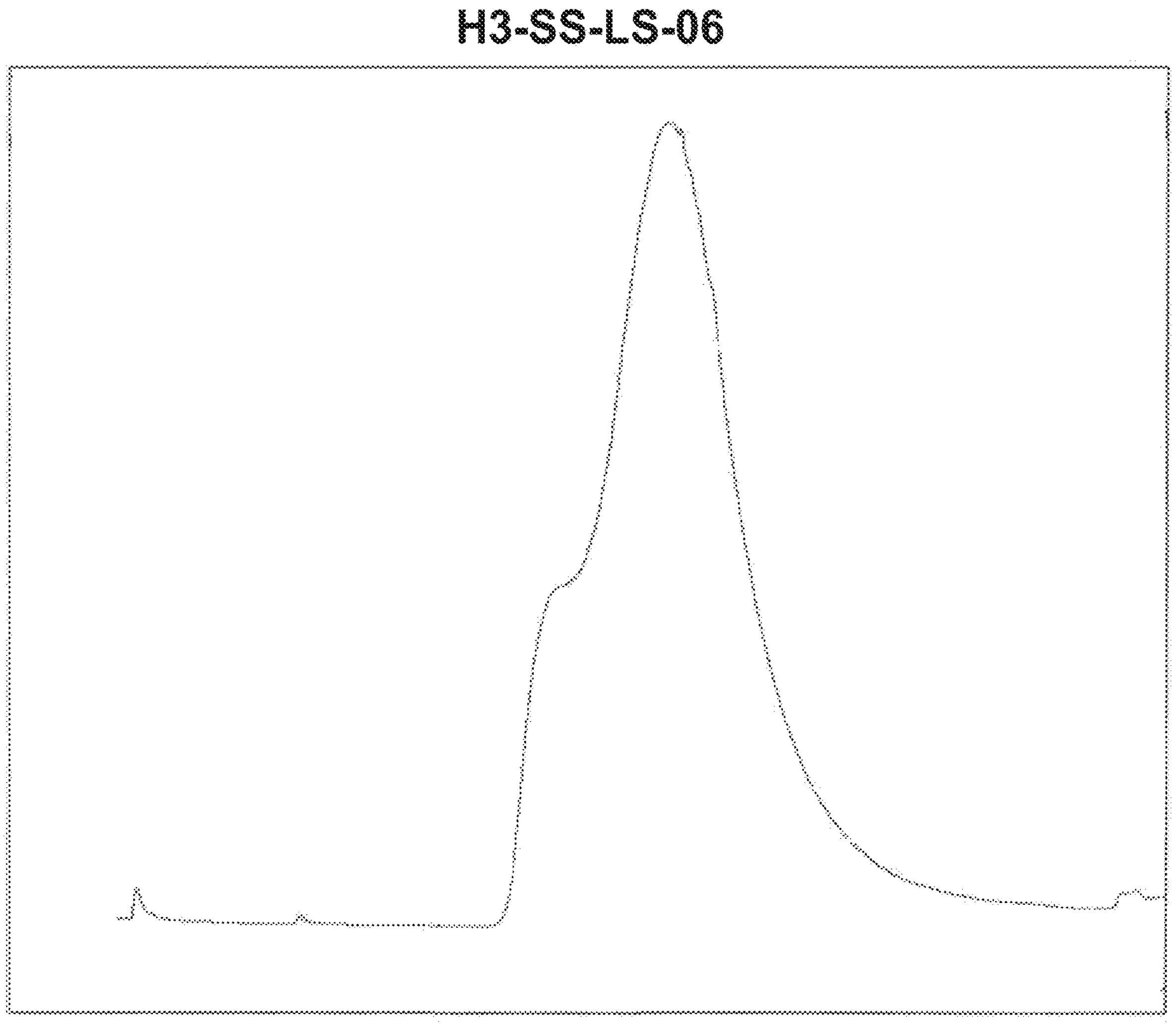
Figure 18F:
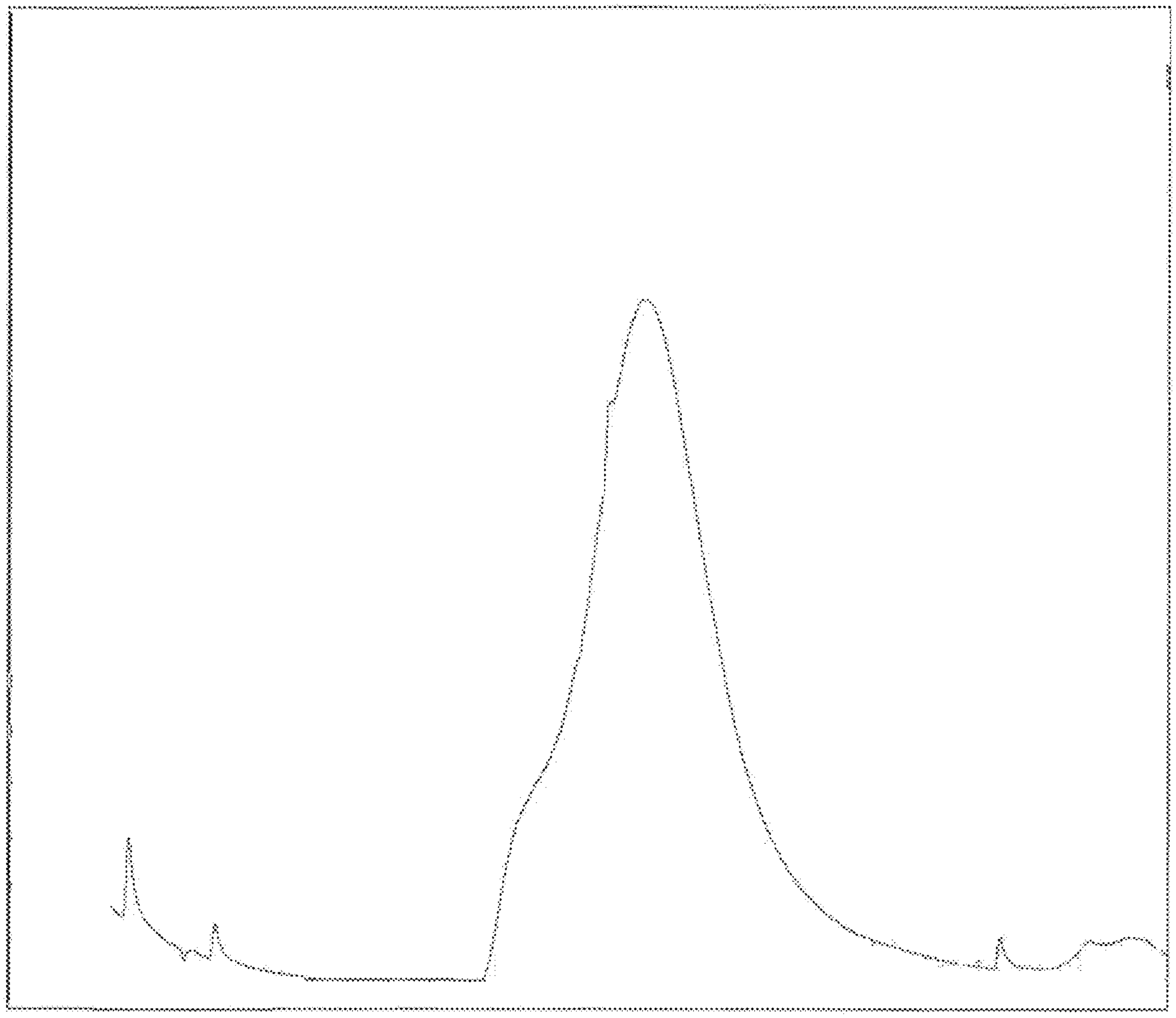
Figure 19A:
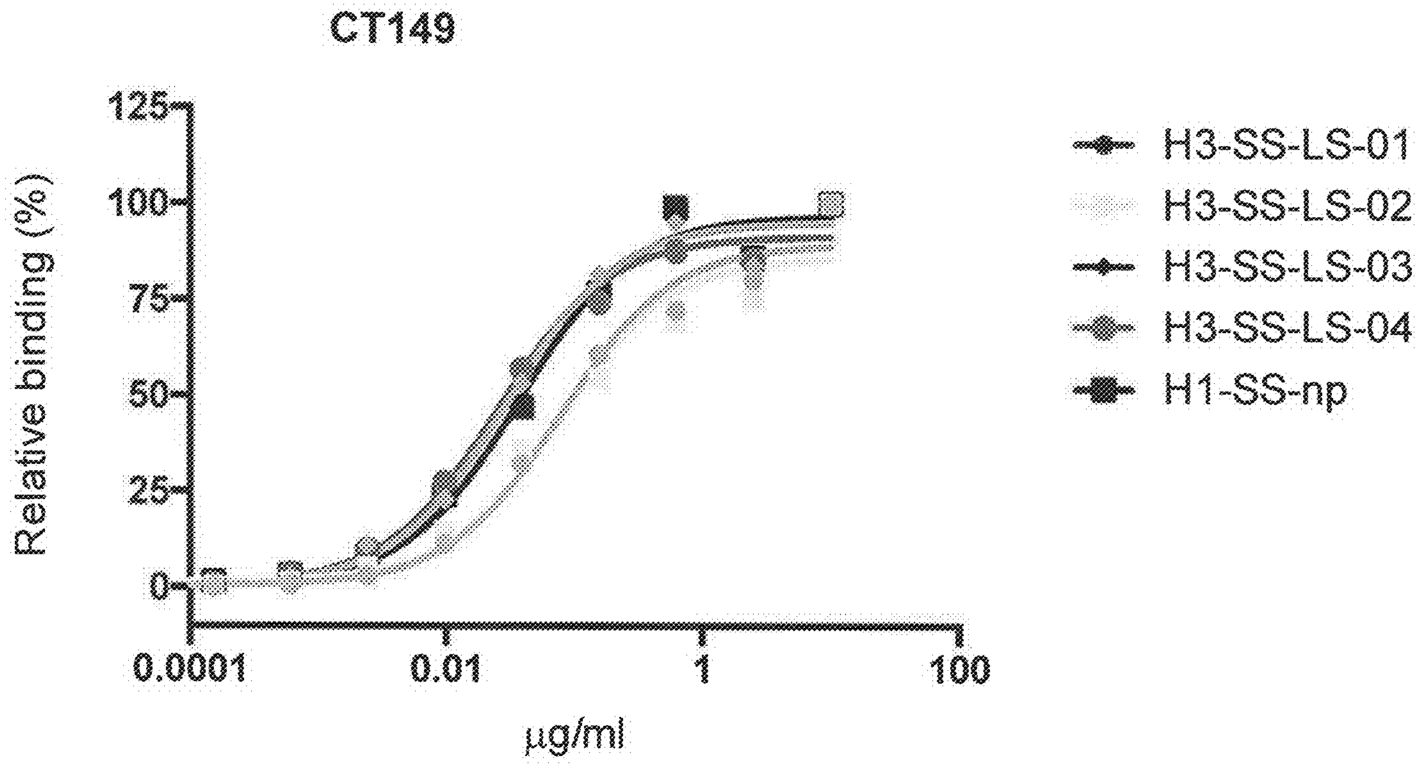
FIGS. 19A-19B show ELISA results for four variants of H3-LS-np.
Figure 19B:
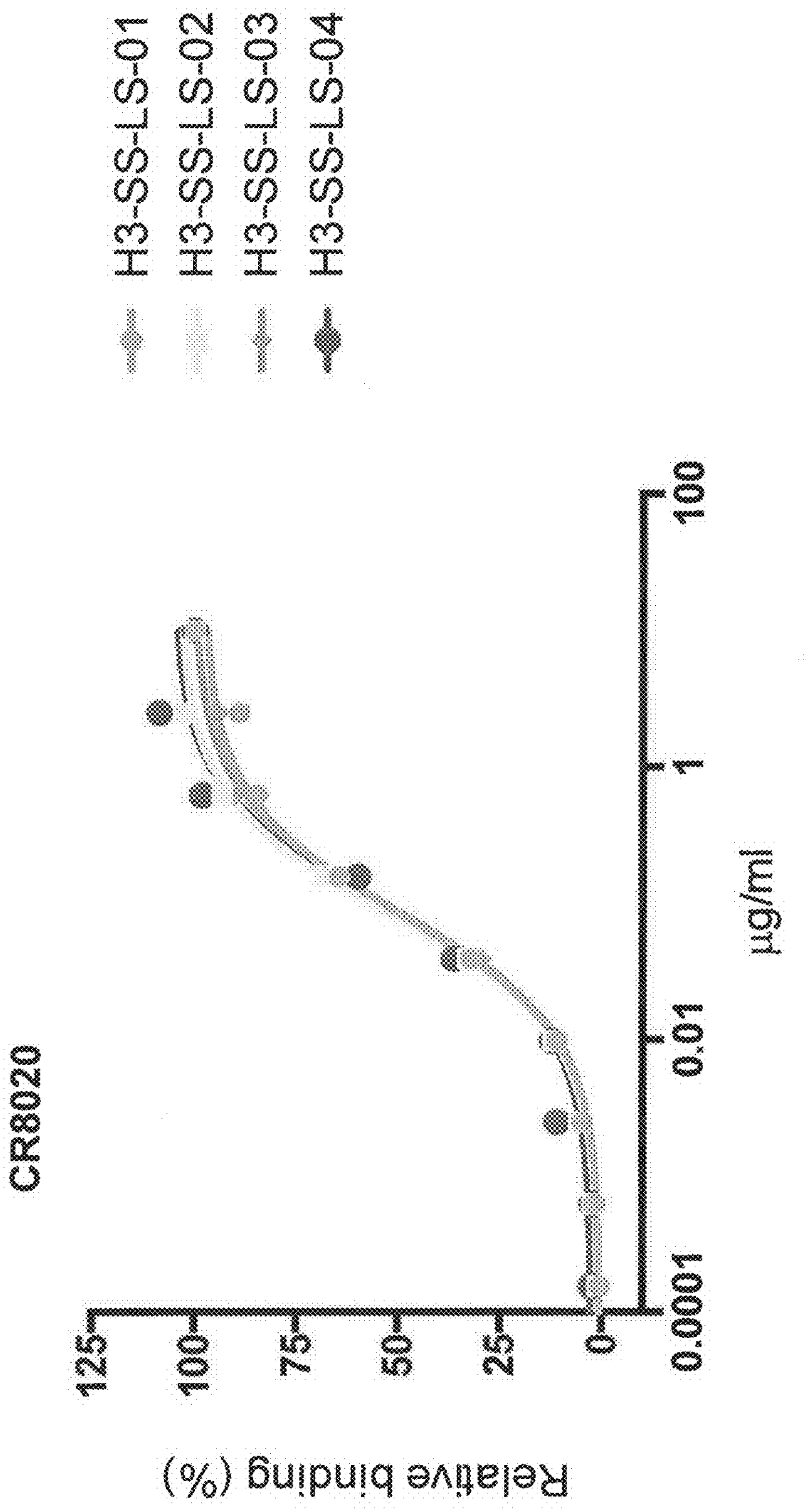
Figure 20:
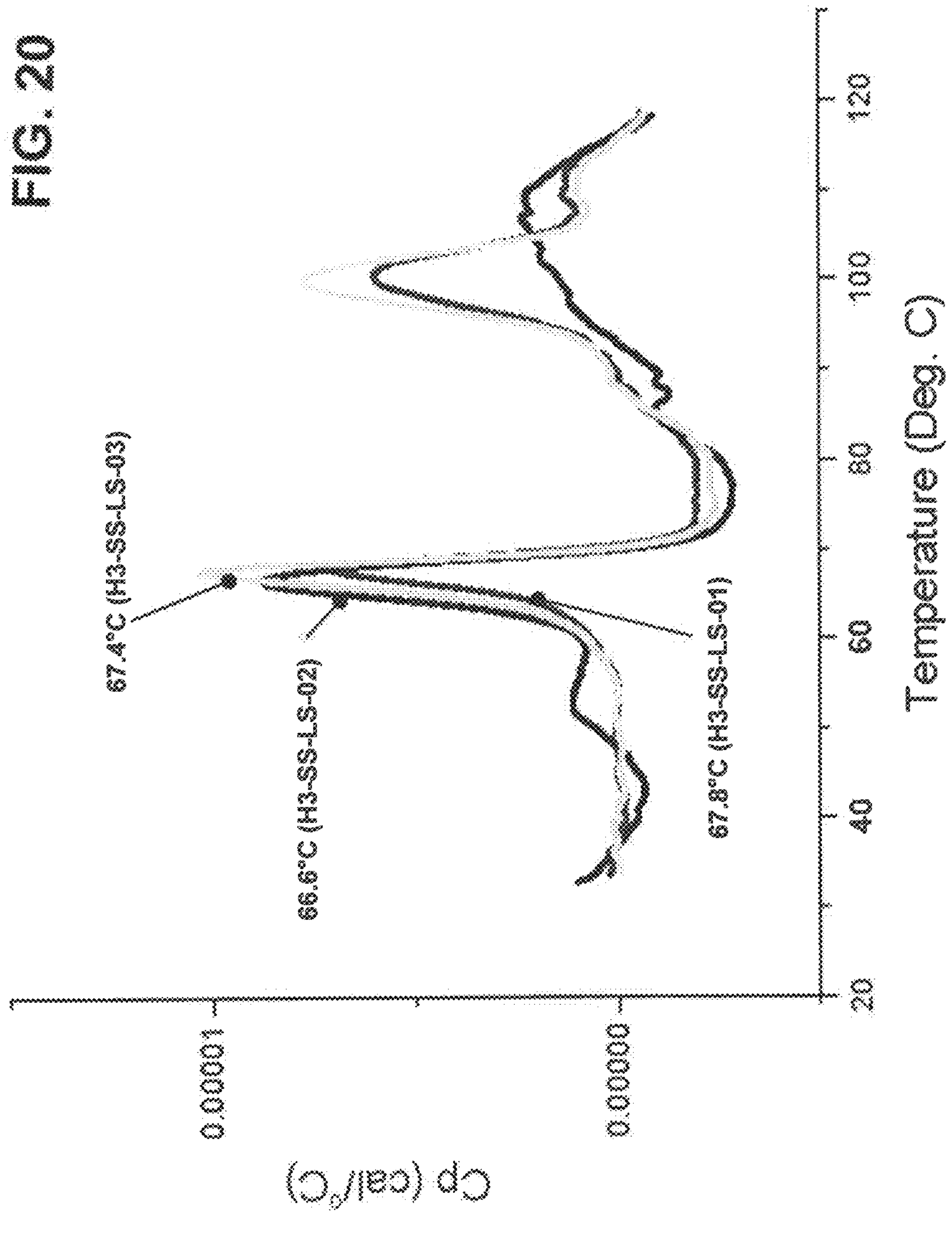
FIG. 20 is a dynamic scanning calorimetry (DSC) plot for three H3-SS-LS variants. Plots of heat capacity (Cp) versus temperature depicts melting transitions for each protein. The earliest melting points (TMs) for each design are noted and color-coded to match the associated curve. The design number is shown for each in parentheses. In this diagram, the Cp values on the Y-axis are shown with an arbitrary scale.
Figure 21A:
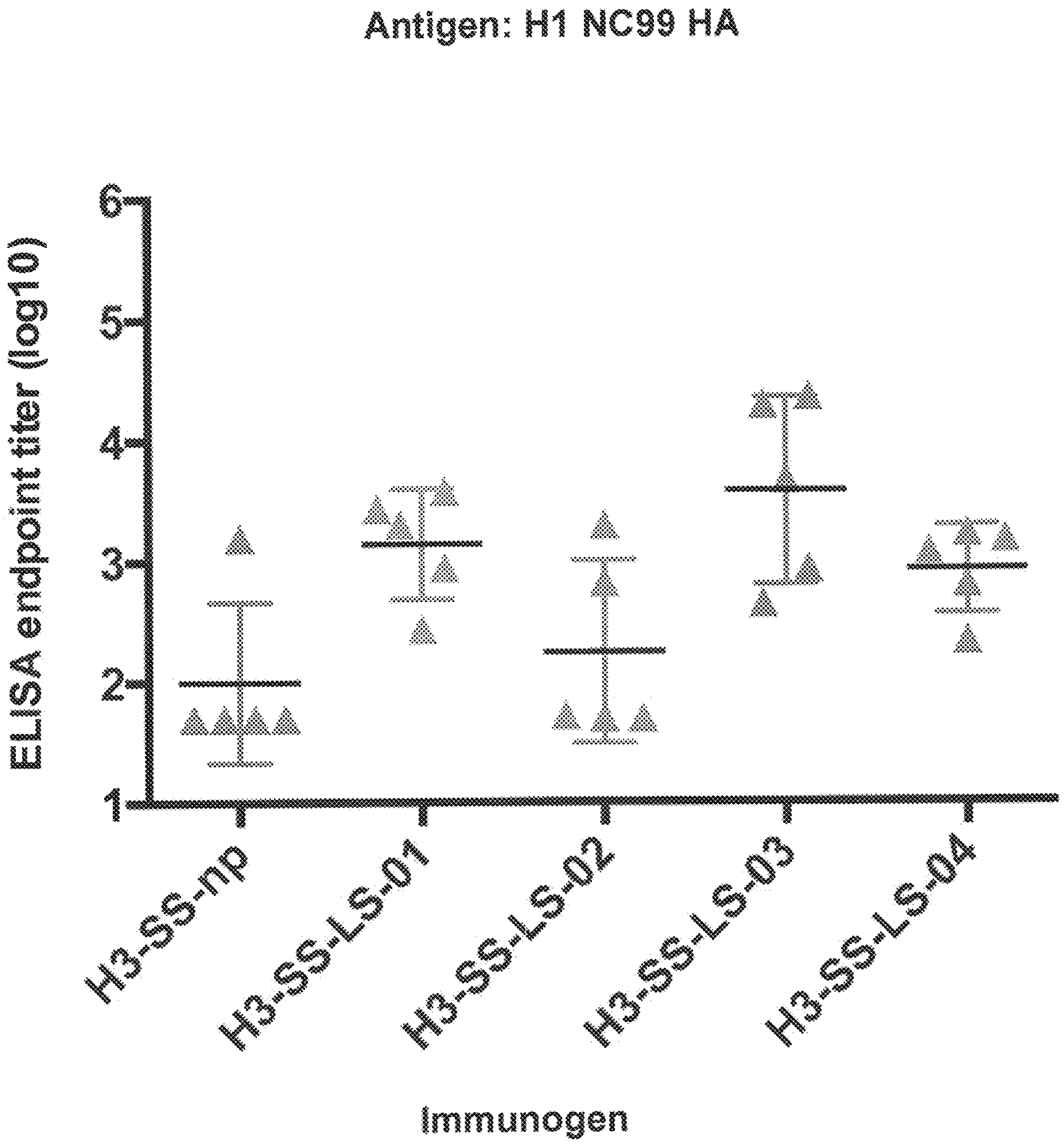
FIGS. 21A-21D show immune responses of H3-SS-LS-np-immunized mice to diverse HAs. ELISA antibody endpoint titers of sera from BALB/c mice (n=5) immunized 3× with four different versions of SAS-adjuvanted H3-SS-LS-np to plated A/New Caledonia/20/1999 (H1N1) HA (FIG. 21A), A/Vietnam/1203/2004 (H5N1) (FIG. 21B), A/Hong Kong/1/1968 (H3N2) (FIG. 21C) and A/Anhui/1/2013 (H7N9) (FIG. 21D). Sera from mice immunized with empty ferritin nanoparticle alone and H3-SS-np (#231) serve as a controls. Geometric mean titers are shown by horizontal lines.
Figure 21B:
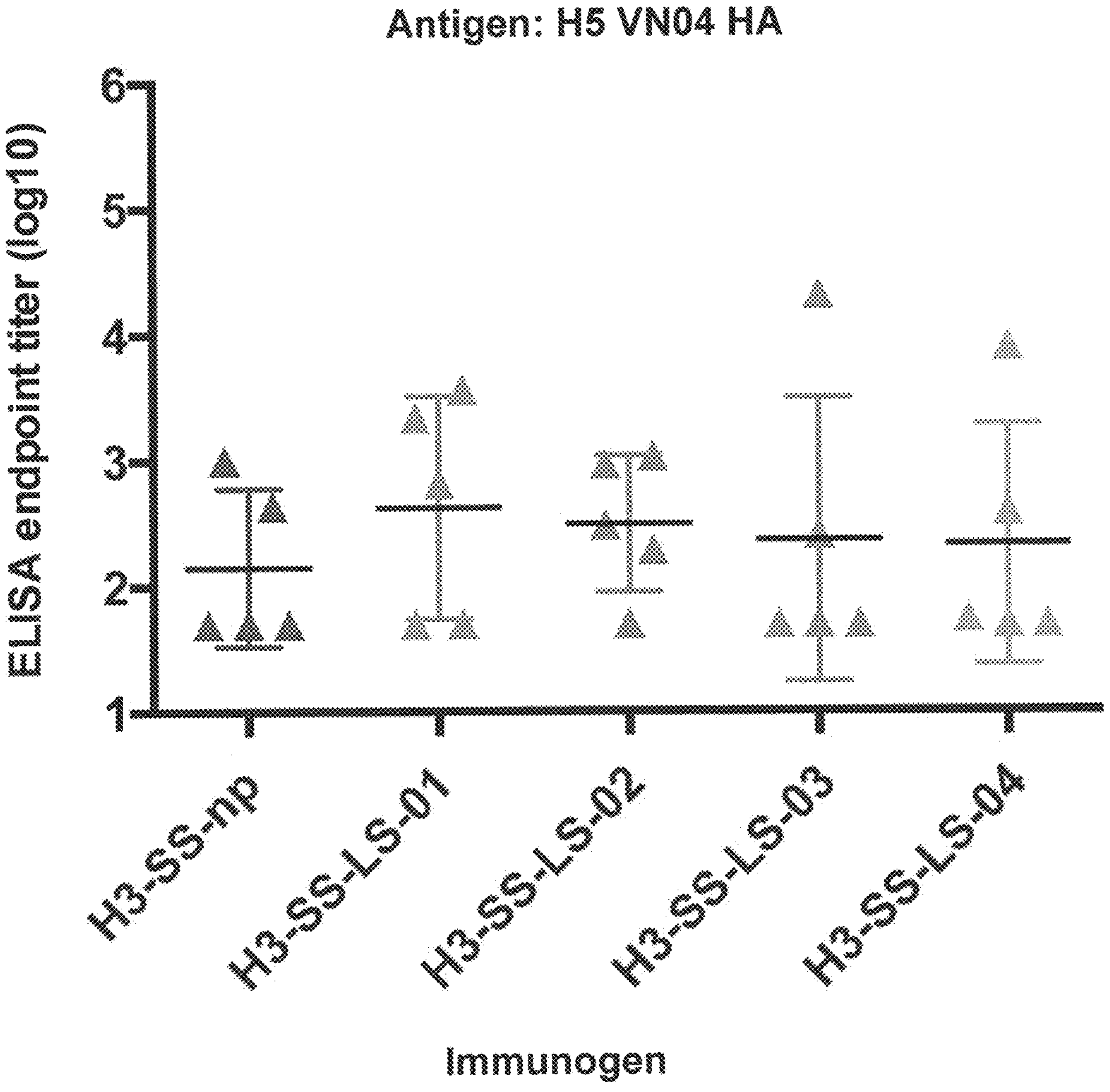
Figure 21C:
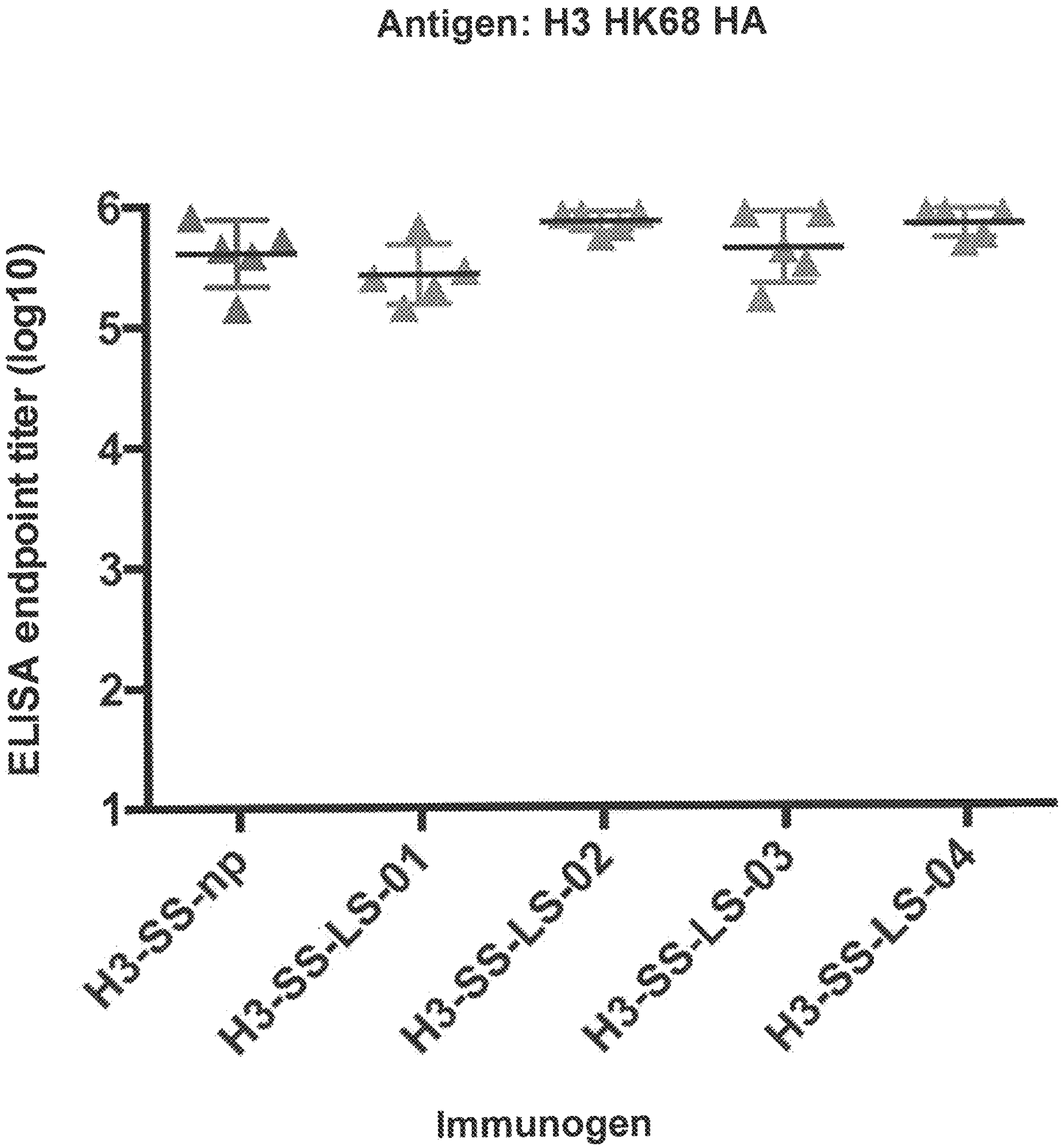
Figure 21D:
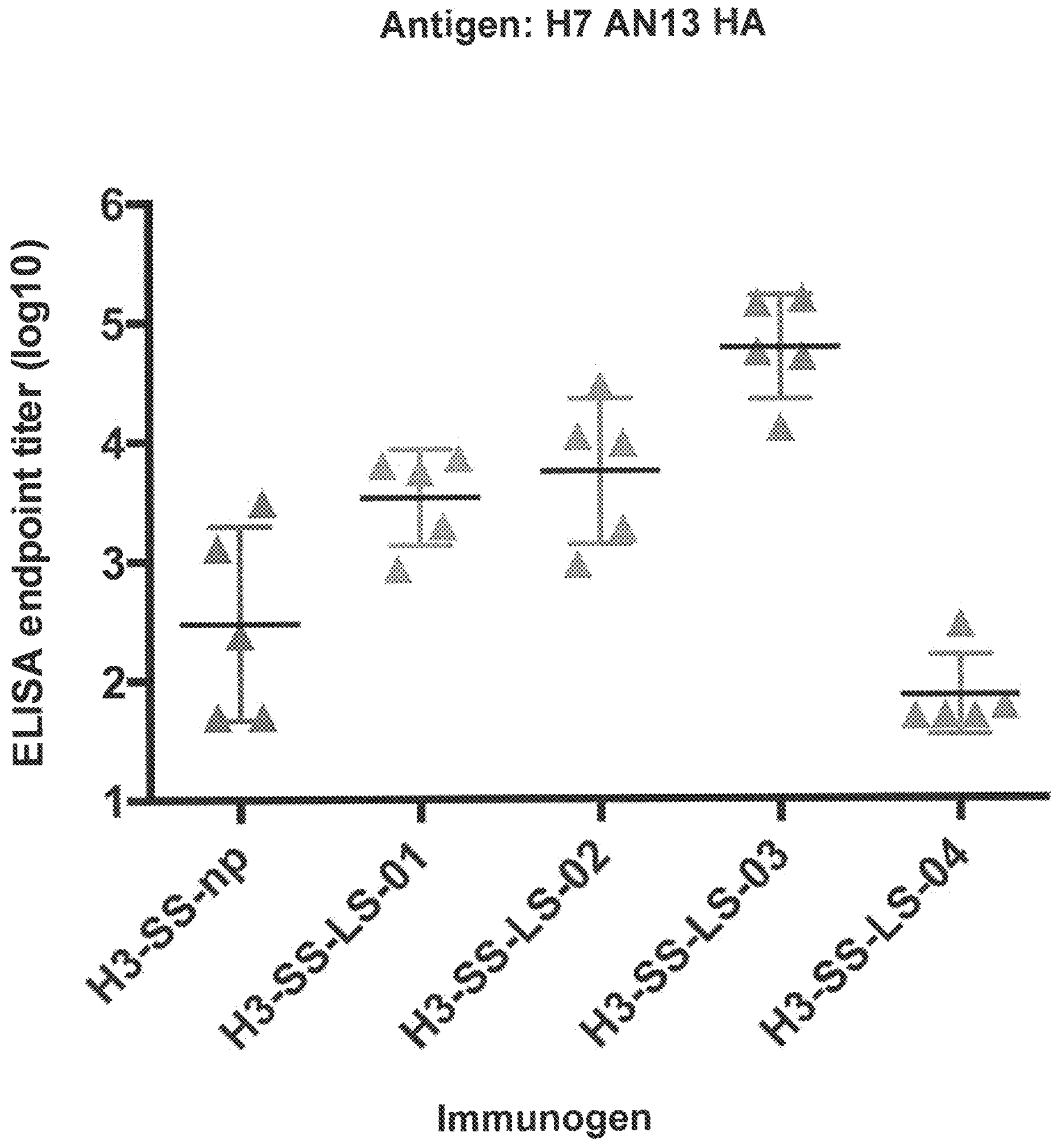
Figure 22A:
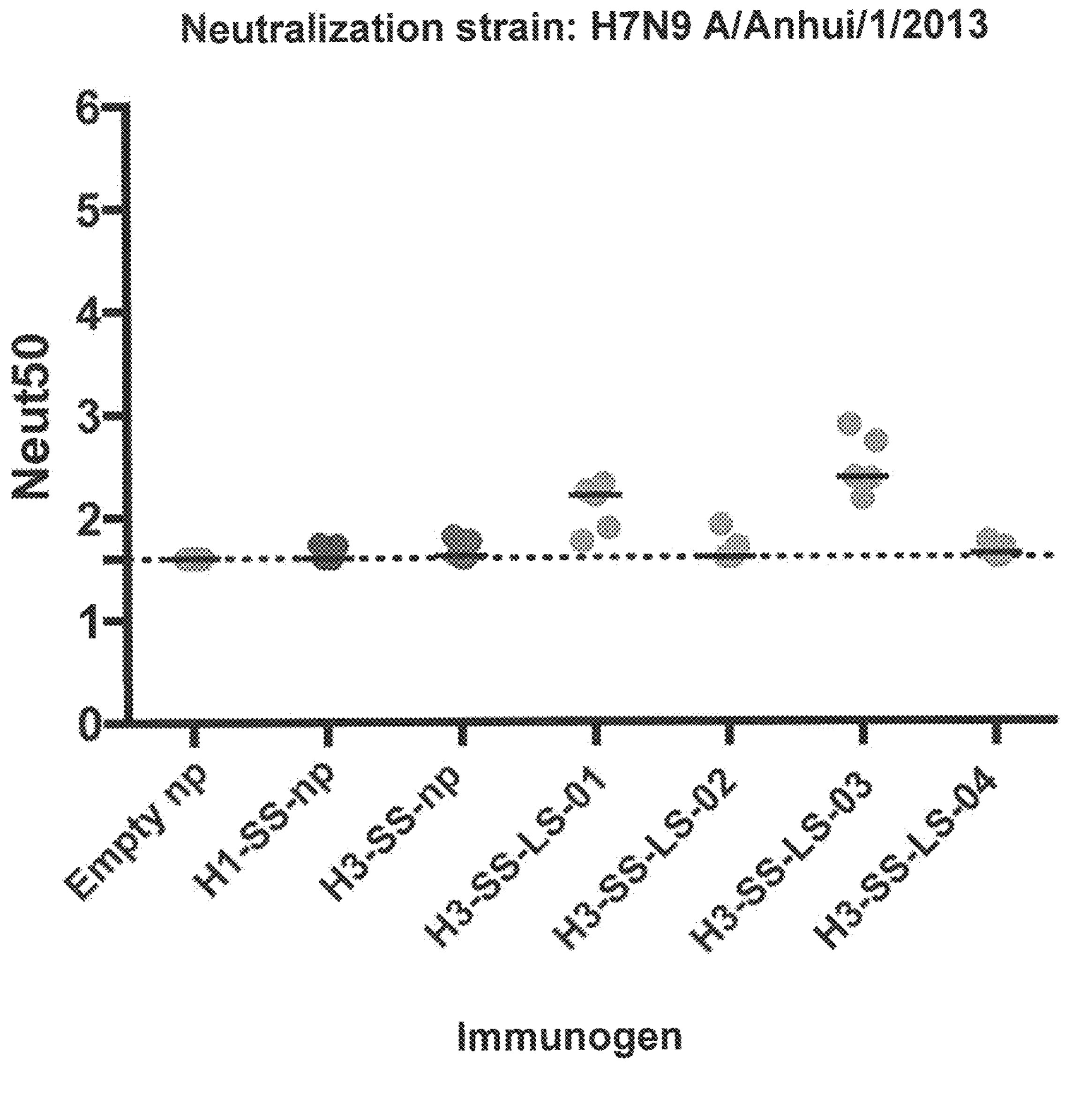
FIGS. 22A and 22B show neutralizing sera responses of H3-SS-LS-np-immunized mice to H3N2 and H7N9. Pseudovirus neutralization titers of sera from BALB/c mice (n=5) immunized 3× with four different versions of SAS-adjuvanted H3-SS-LS-np.
Figure 22B:
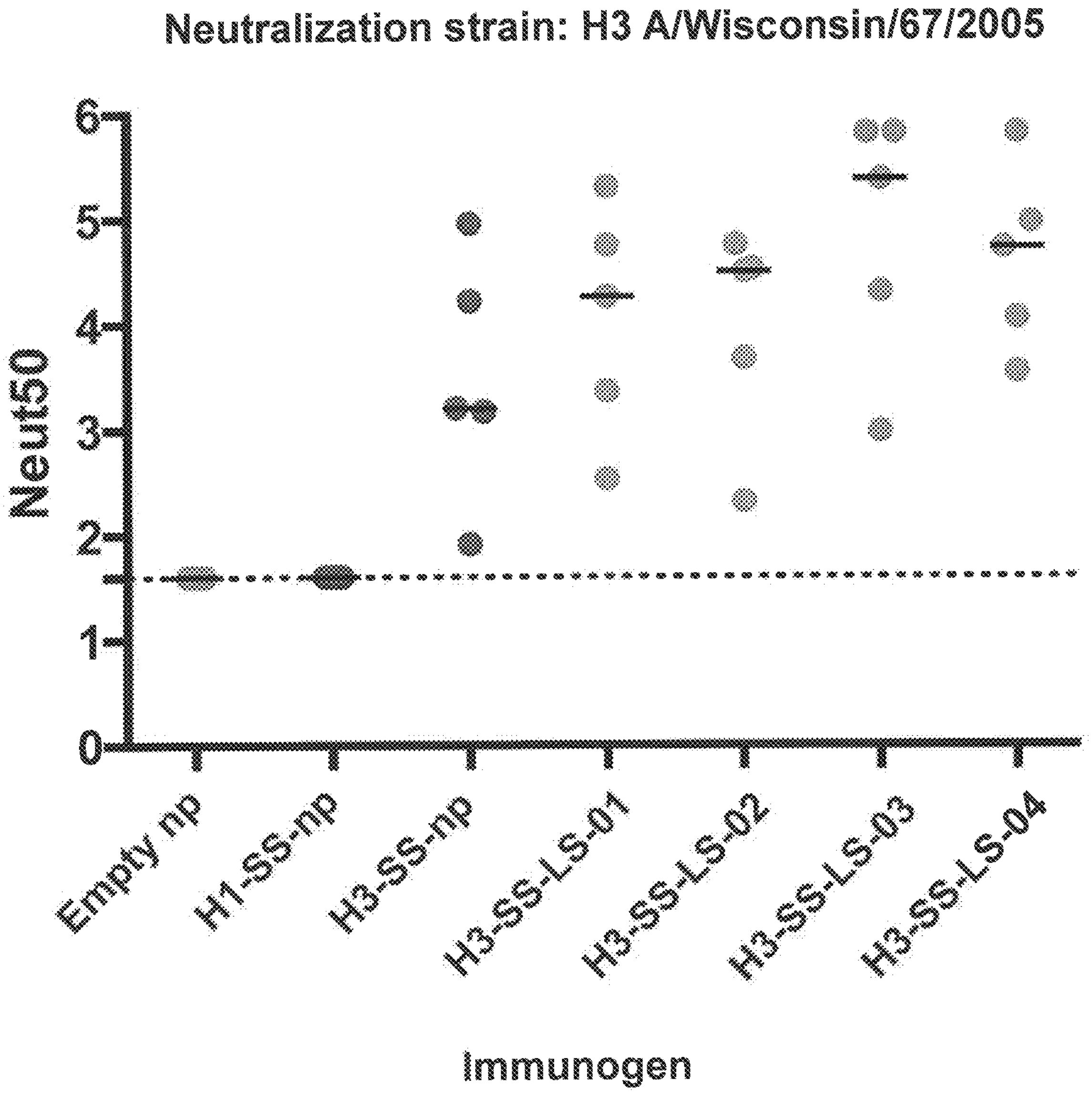
Figure 24A:
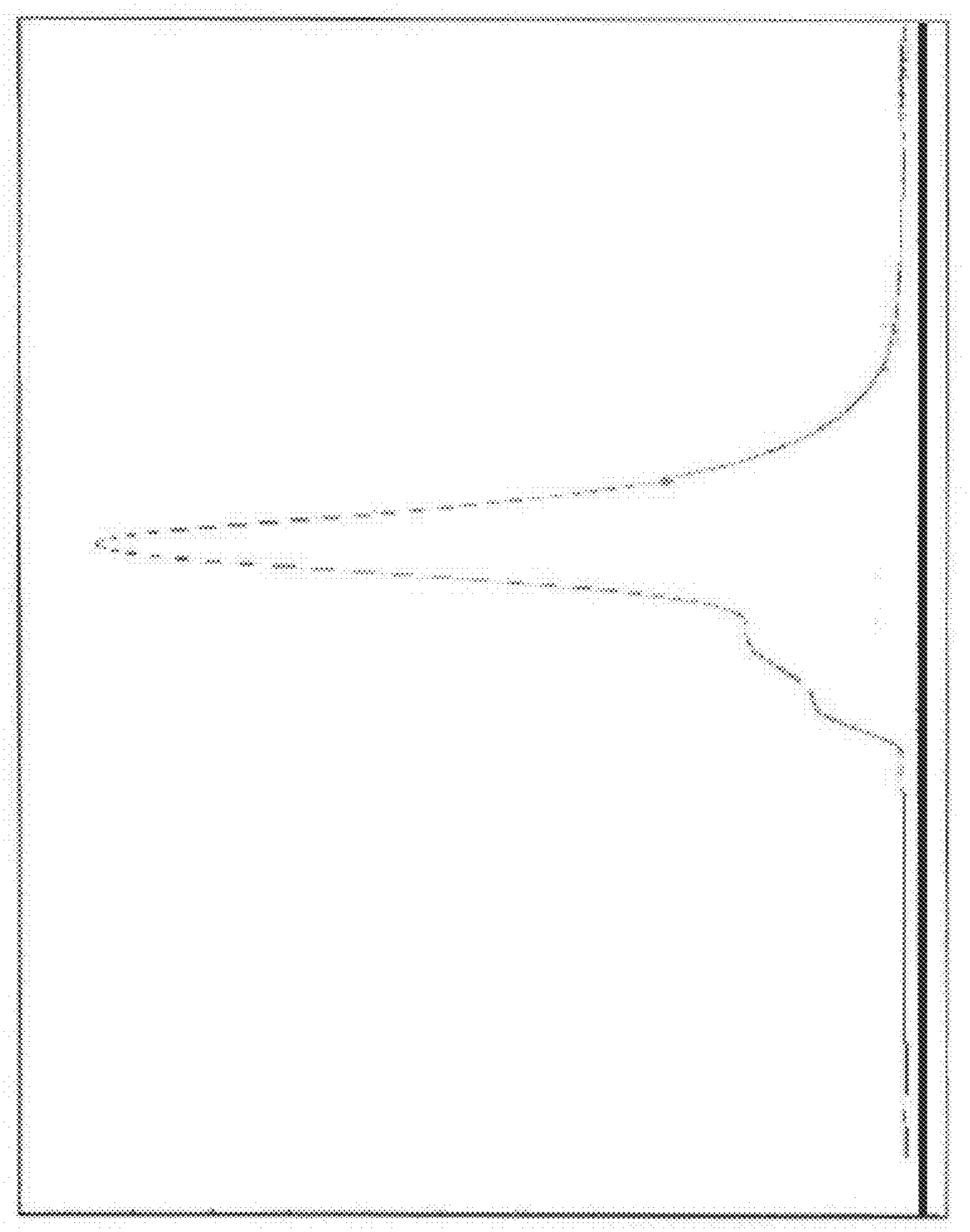
FIGS. 24A-24F show the purification of H7-SS-np variants. Gel filtration Superose 6 10/30 profiles for H7-SS-np variants 16 (FIG. 24A), 18 (FIG. 24B), 20 (FIG. 24C), 21 (FIG. 24D), 23 (FIG. 24E) and 26 (FIG. 24F) after GNA lectin affinity chromatography. The final yields from Expi293 cells after gel filtration were 5-10 mg/L of culture.
Figure 24B:
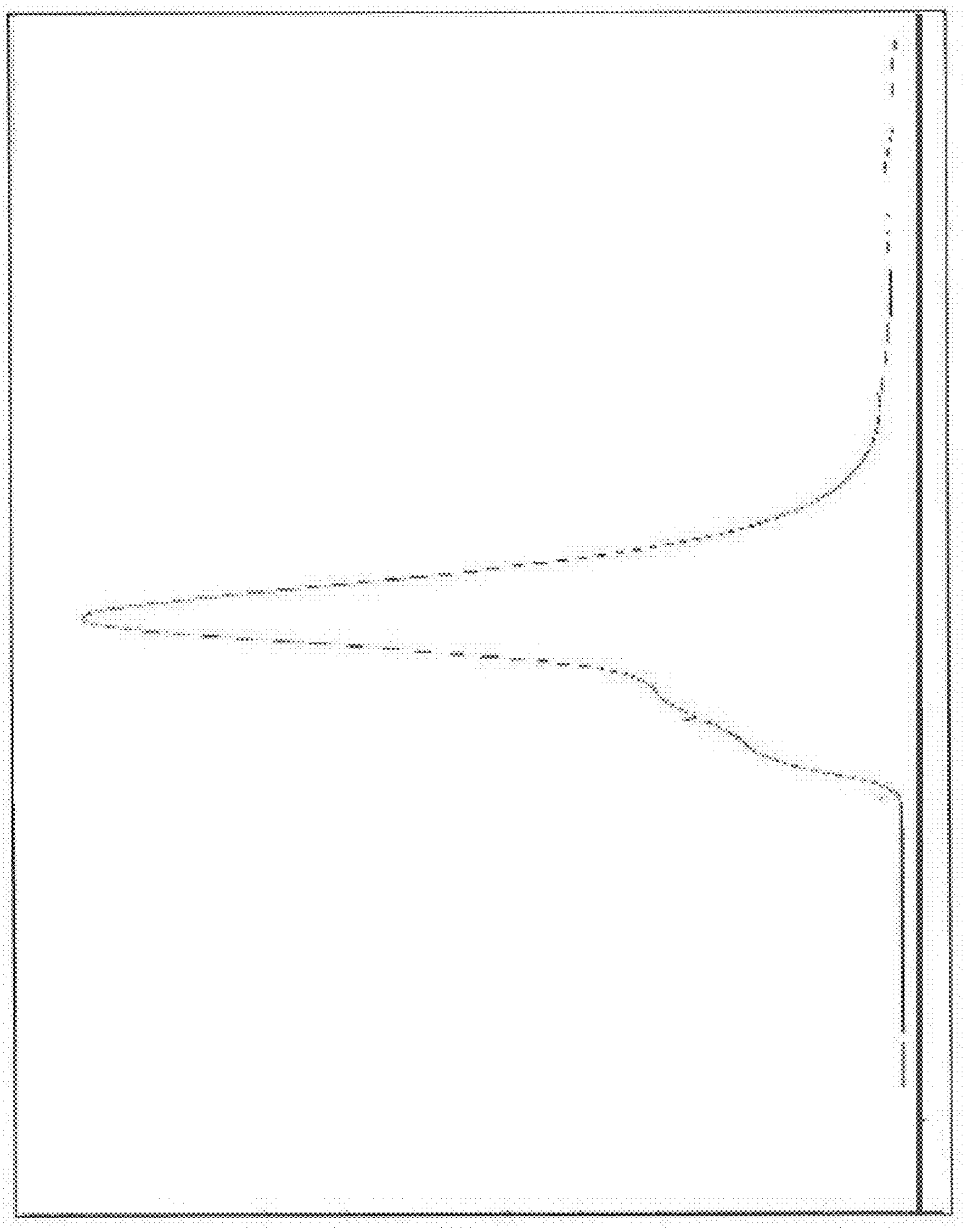
Figure 24C:
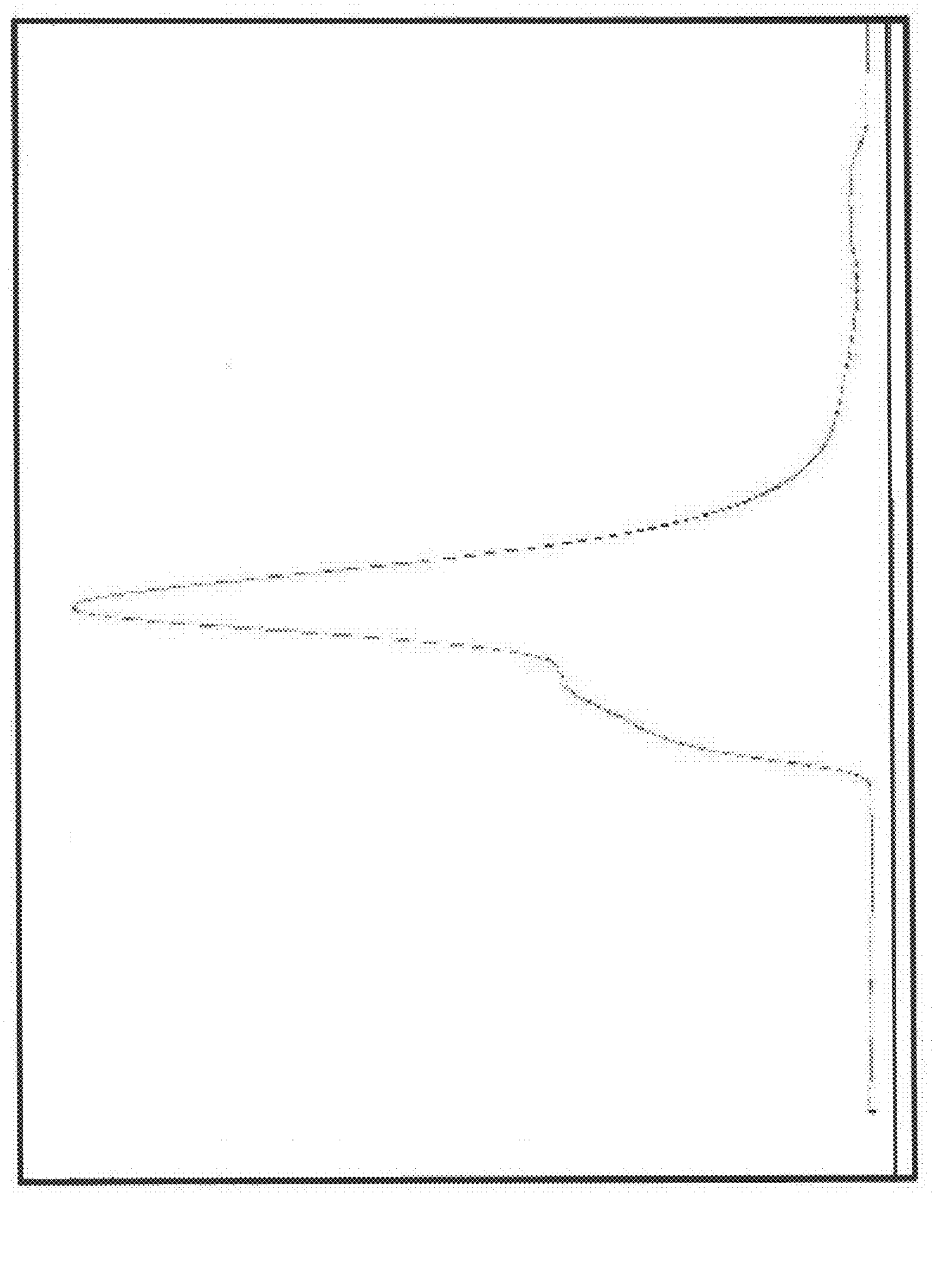
Figure 24D:
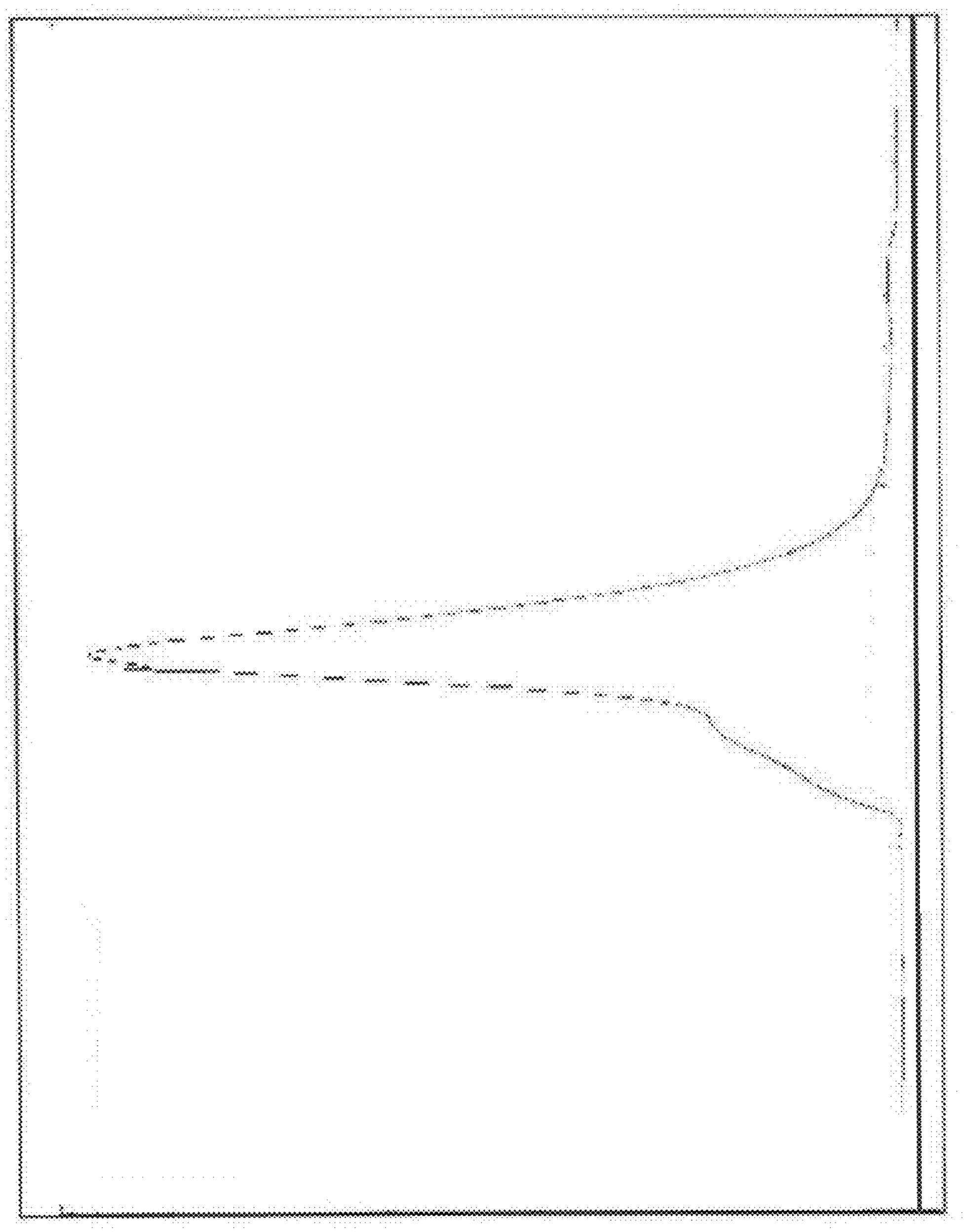
Figure 24E:
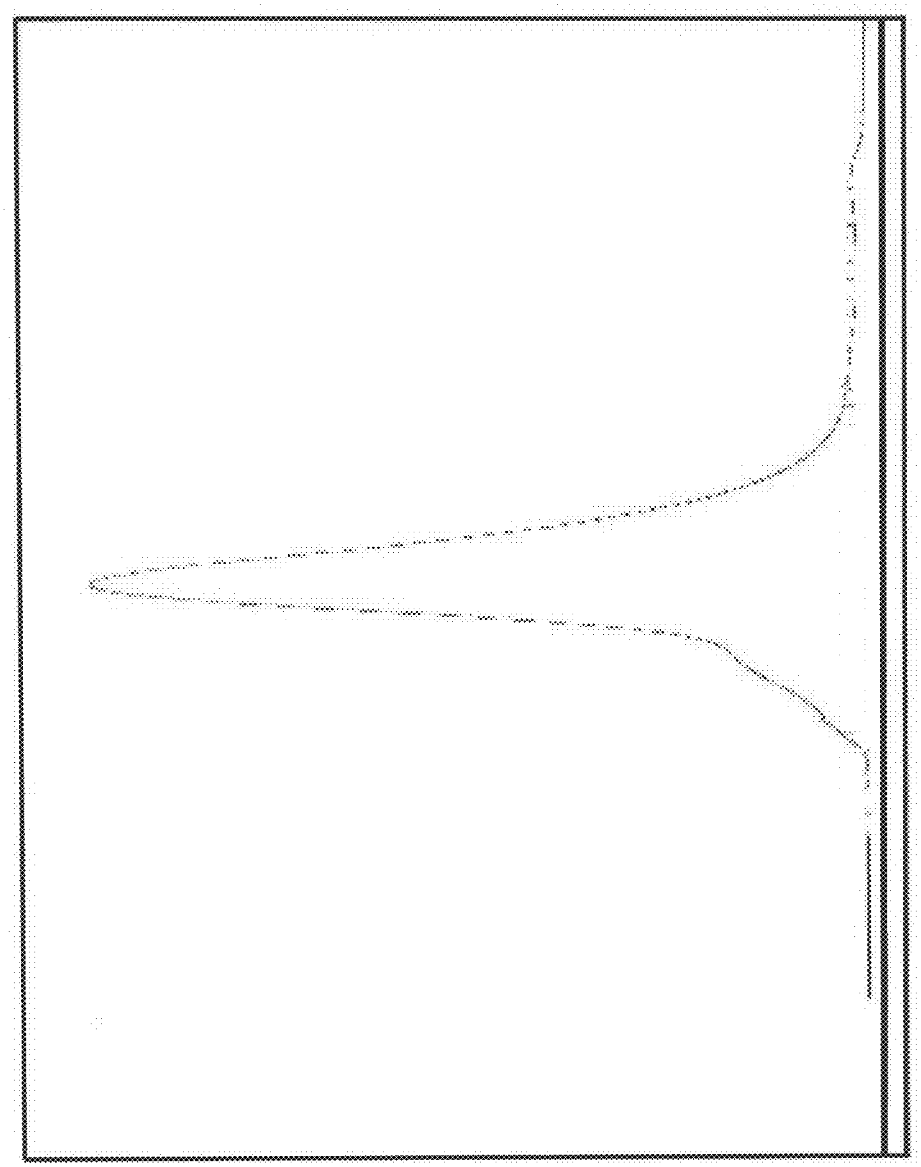
Figure 24F:
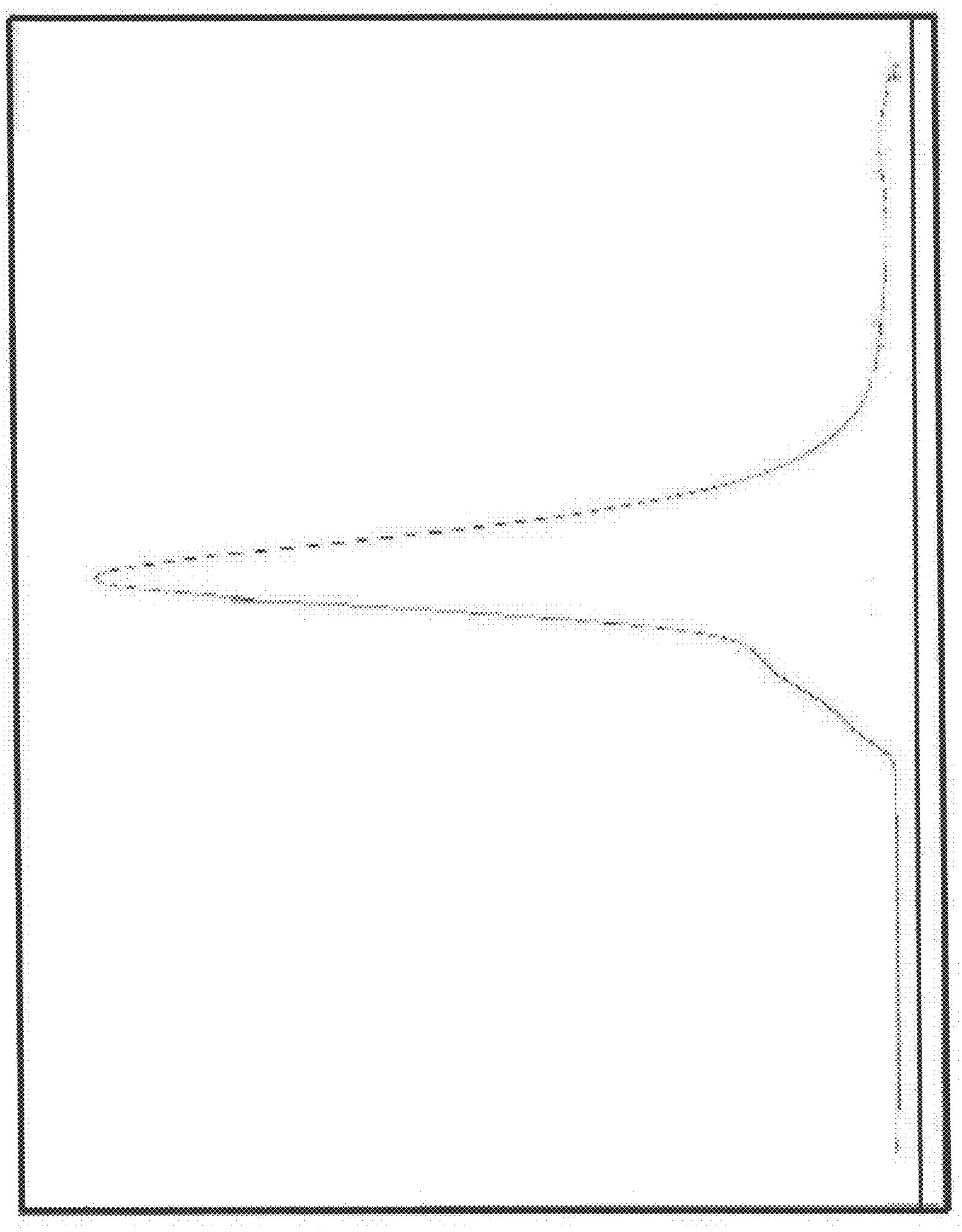
Figure 25A:
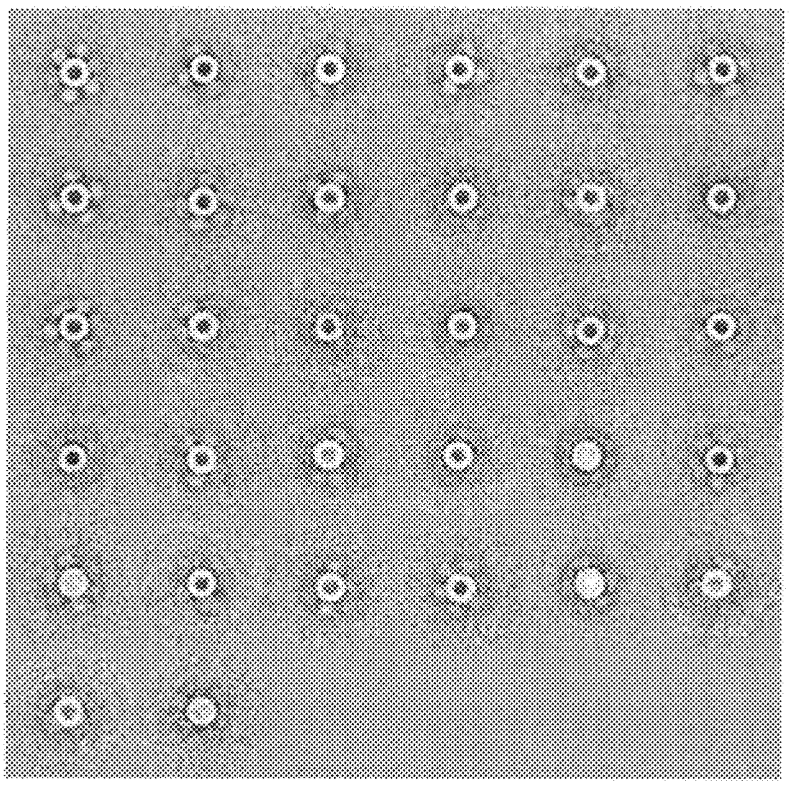
FIGS. 25A-25H show electron microscopy of H7-SS-np. Negative stain electron microscopy 2D class averages of H7-SS-np variants revealing the formation of particles with a visible arrangement of HA stems projecting from hollow spheres. Images for an H1-SS-np particle (upper left panel (FIG. 25A)) are shown as a positive control.
Figure 25B:
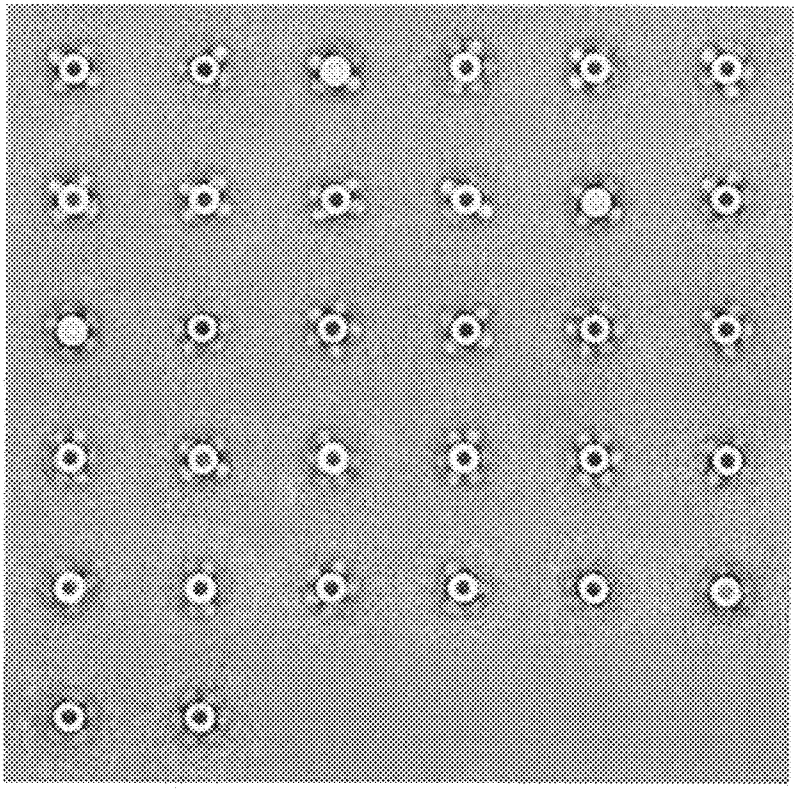
Figure 25C:
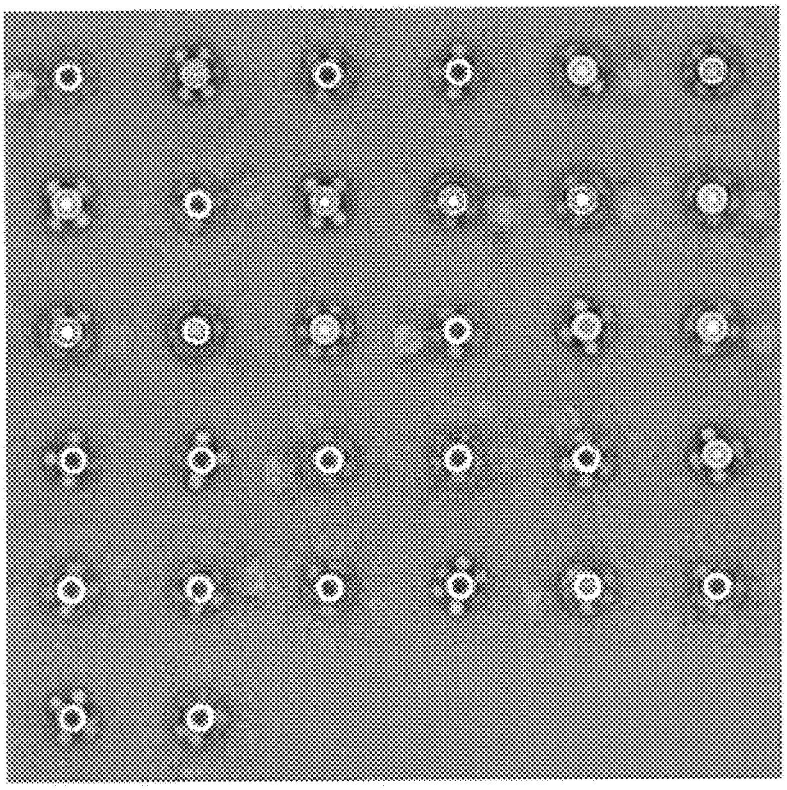
Figure 25D:
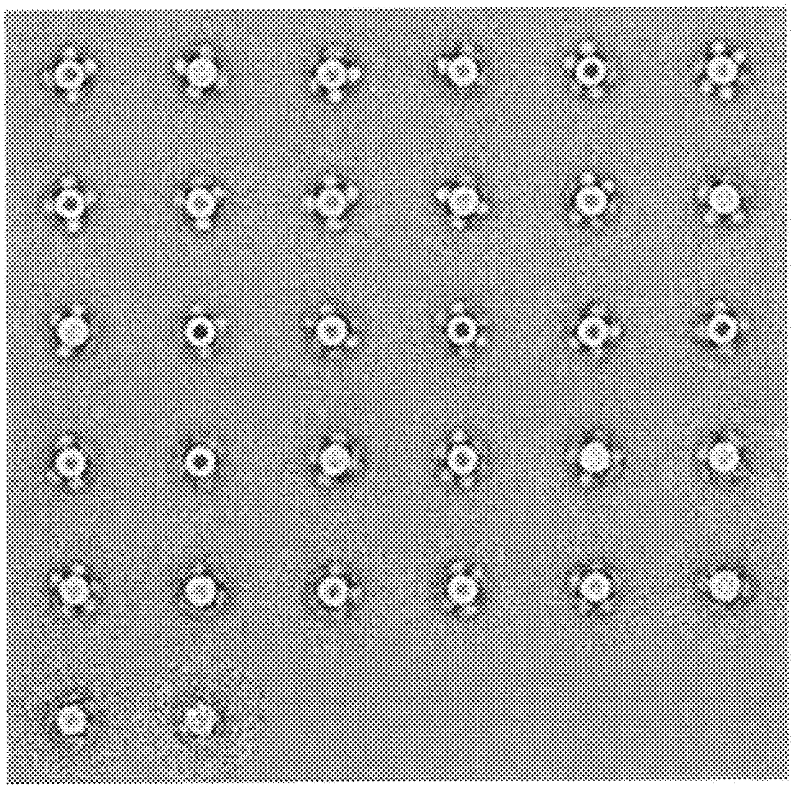
Figure 25E:
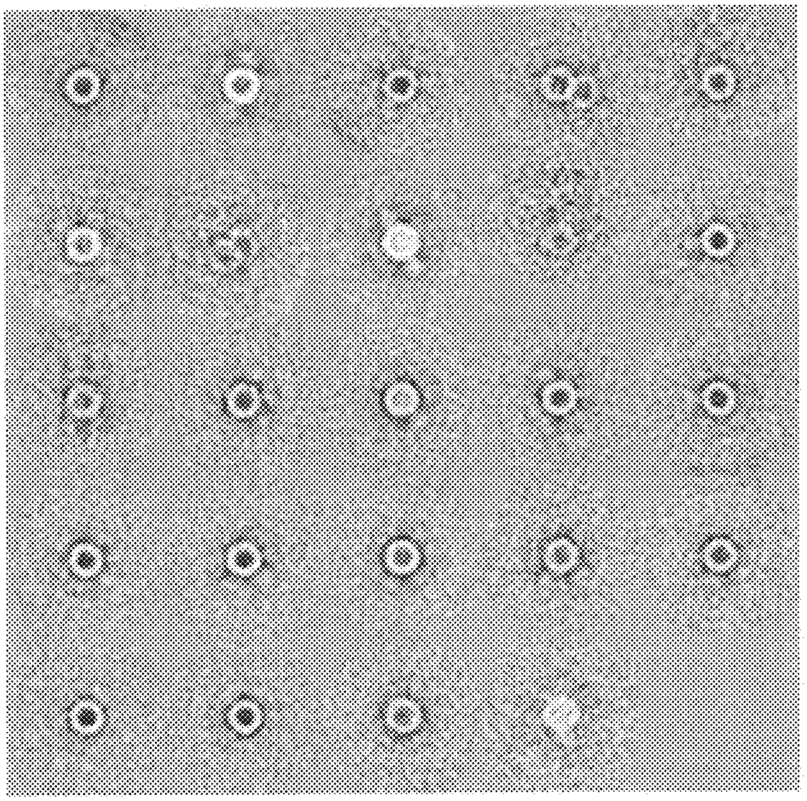
Figure 25F:
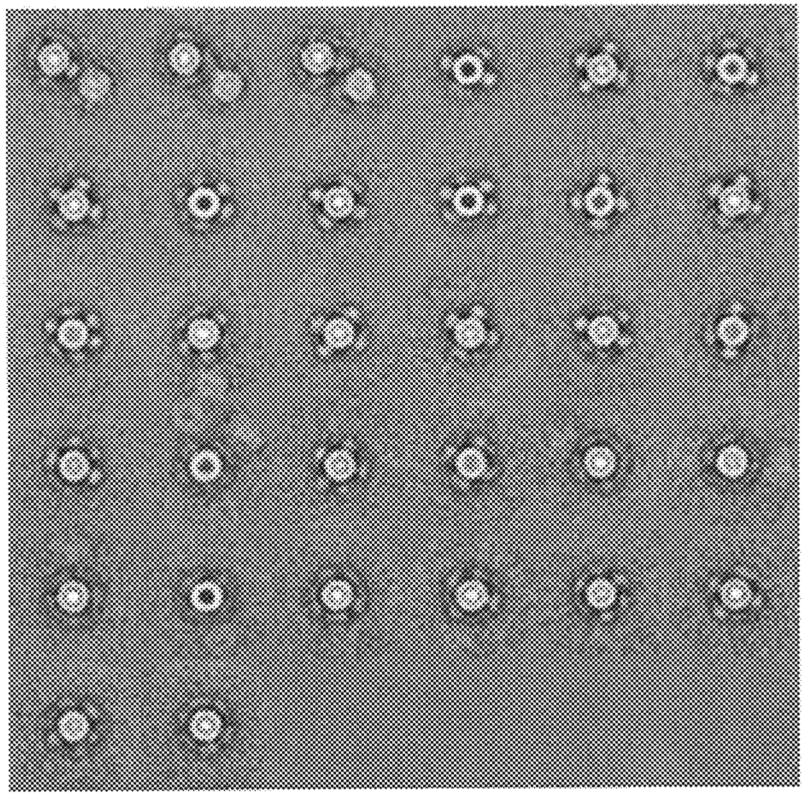
Figure 25G:
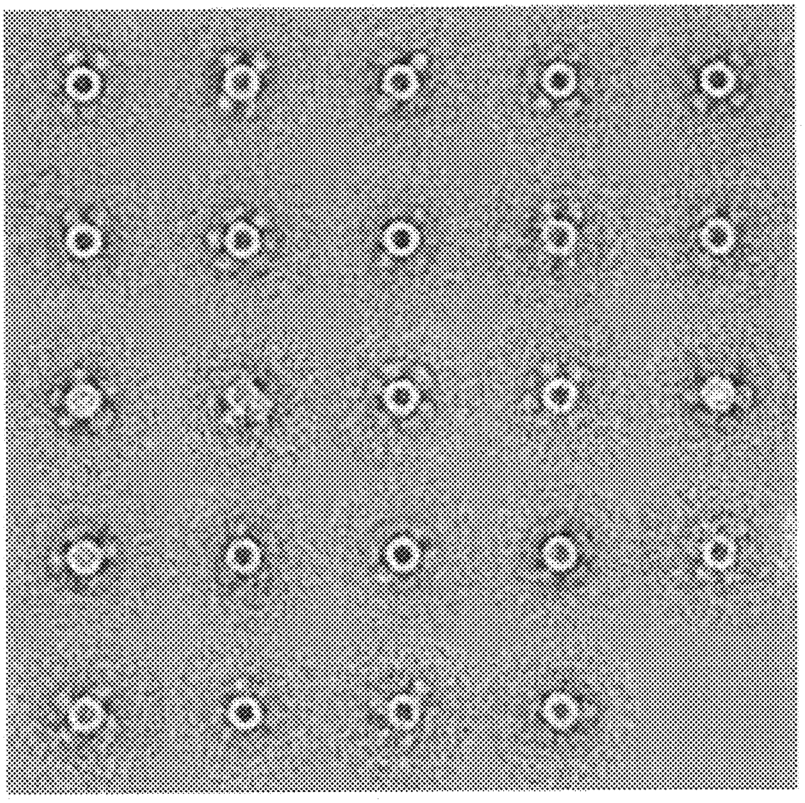
Figure 25H:
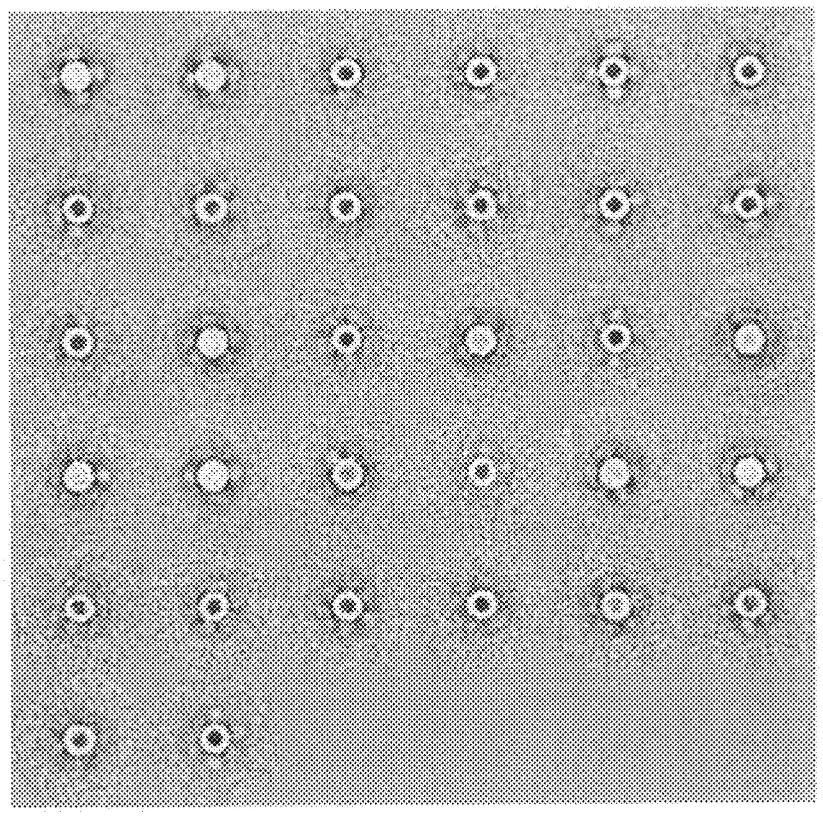
Figure 26A:
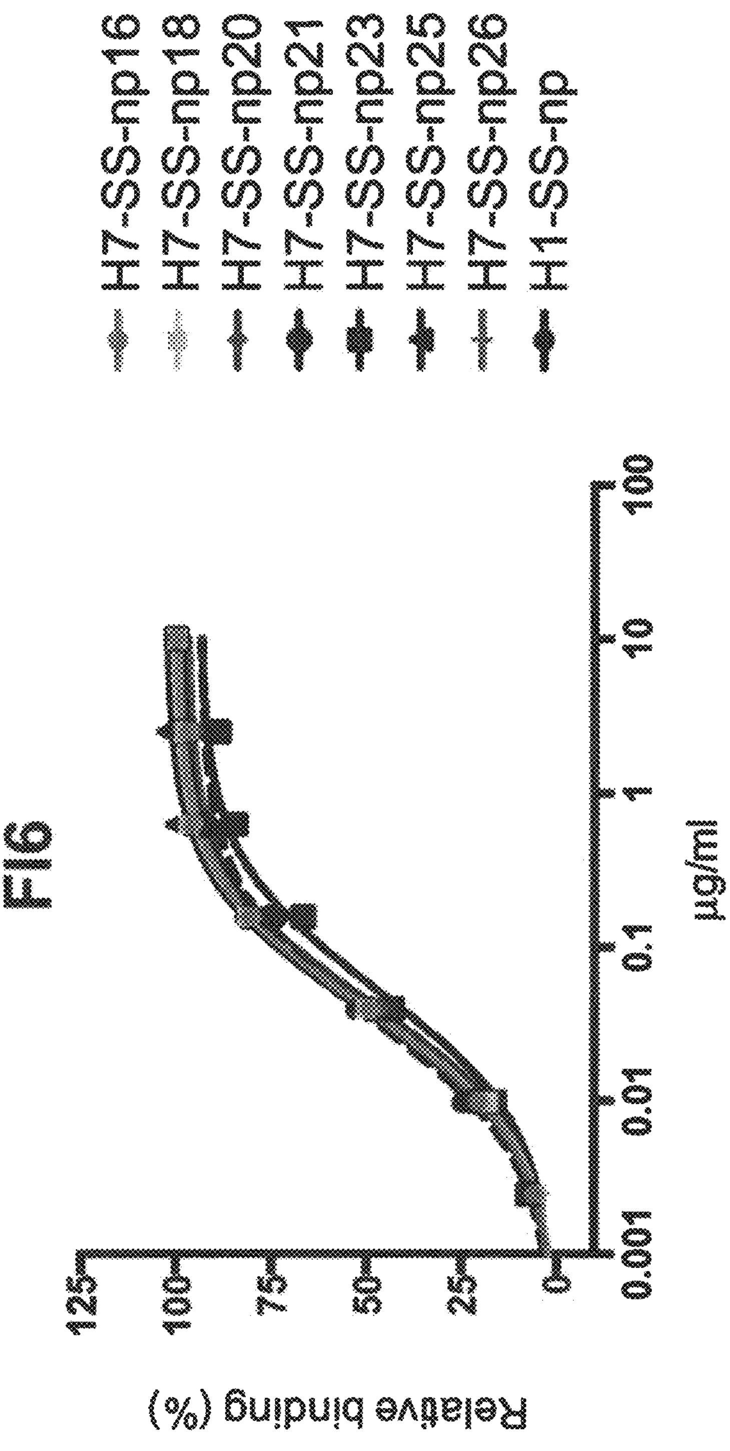
Figure 26B:
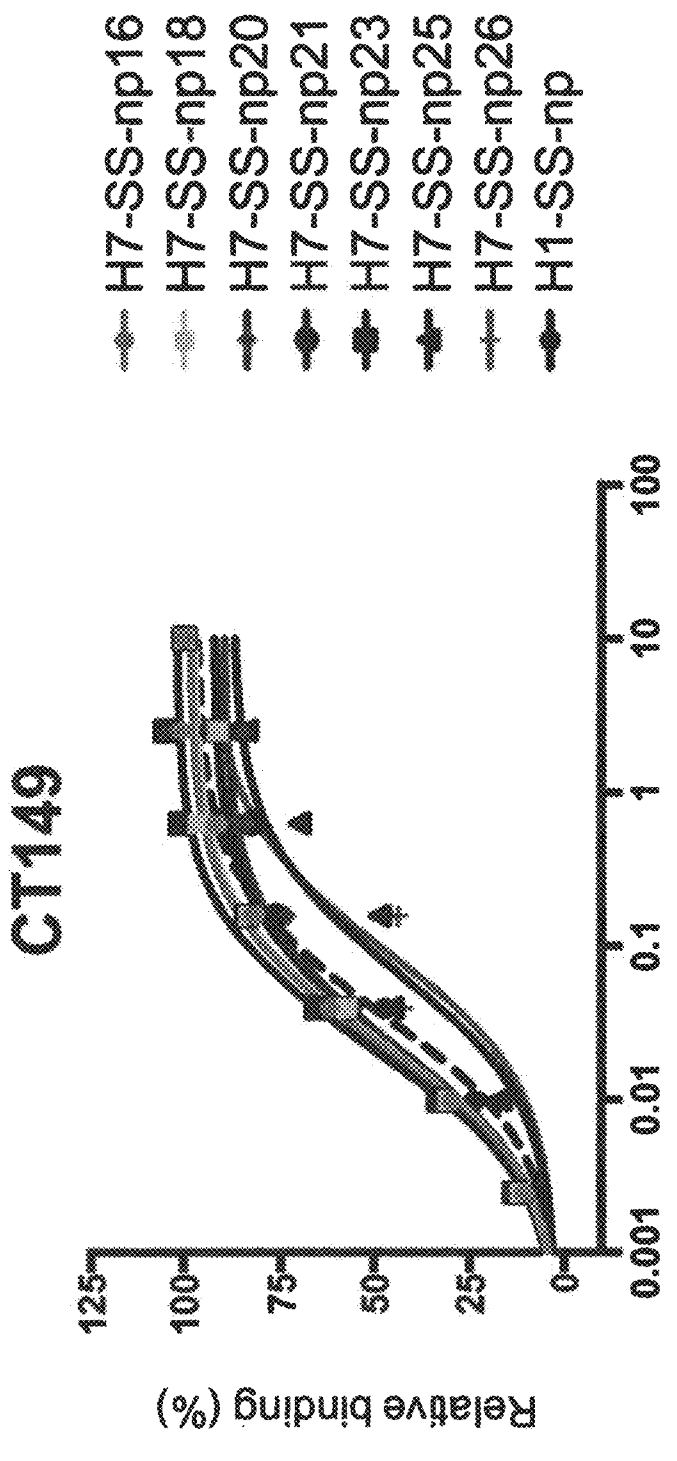
Figure 26C:
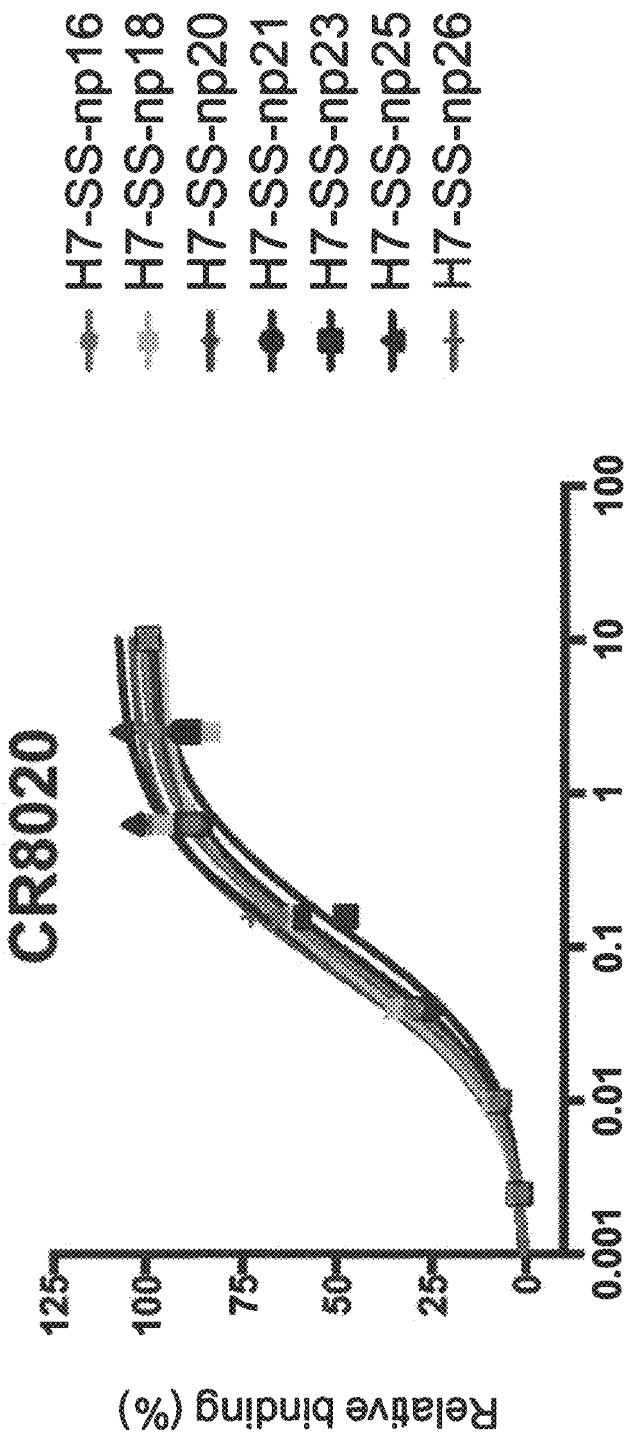
Figure 27A:
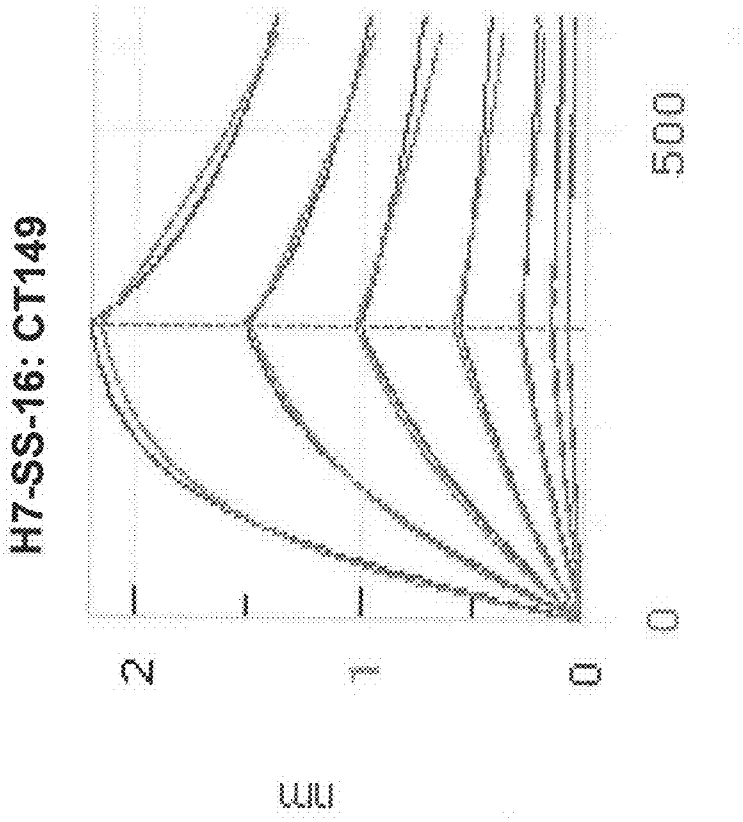
FIGS. 27A-27F show HA stem antibody recognition of H7-SS-np. Biolayer interferometry binding curves for CT149 recognition of six H7-SS-np variants
Figure 27B:
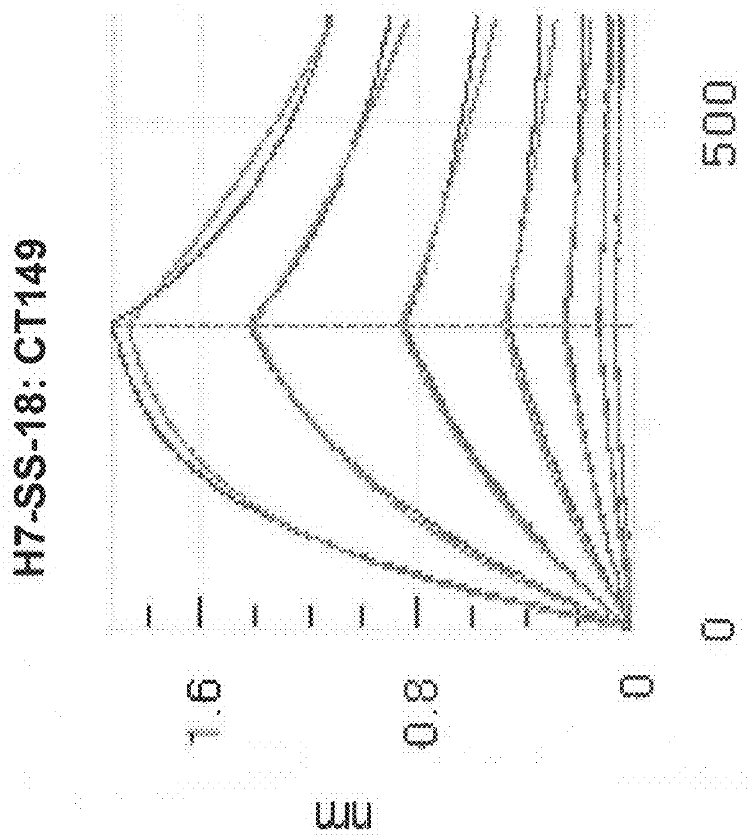
Figure 27C:
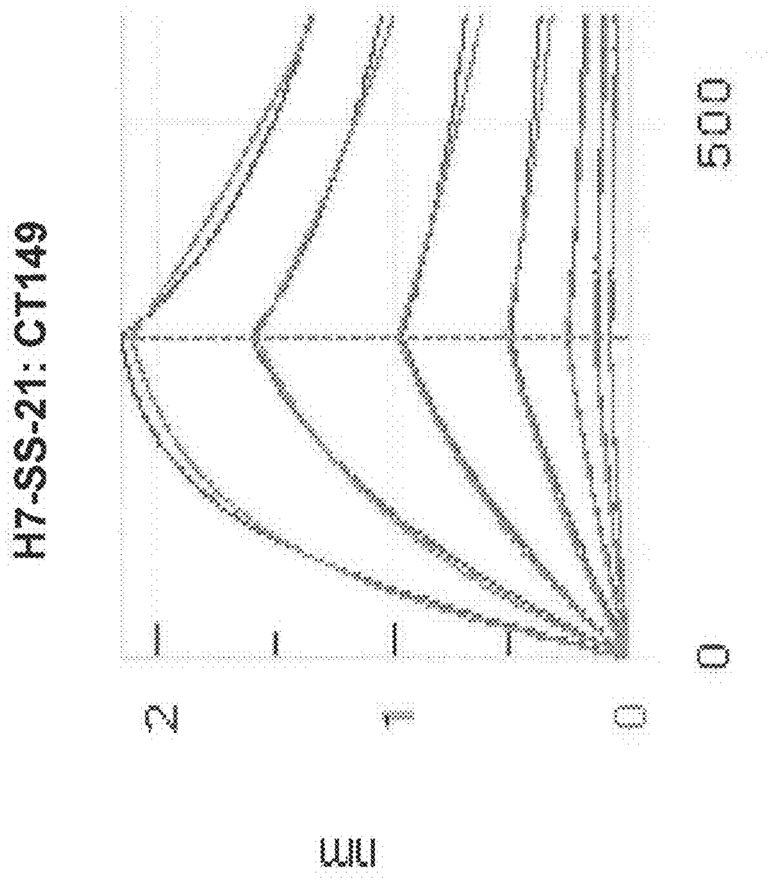
Figure 27D:
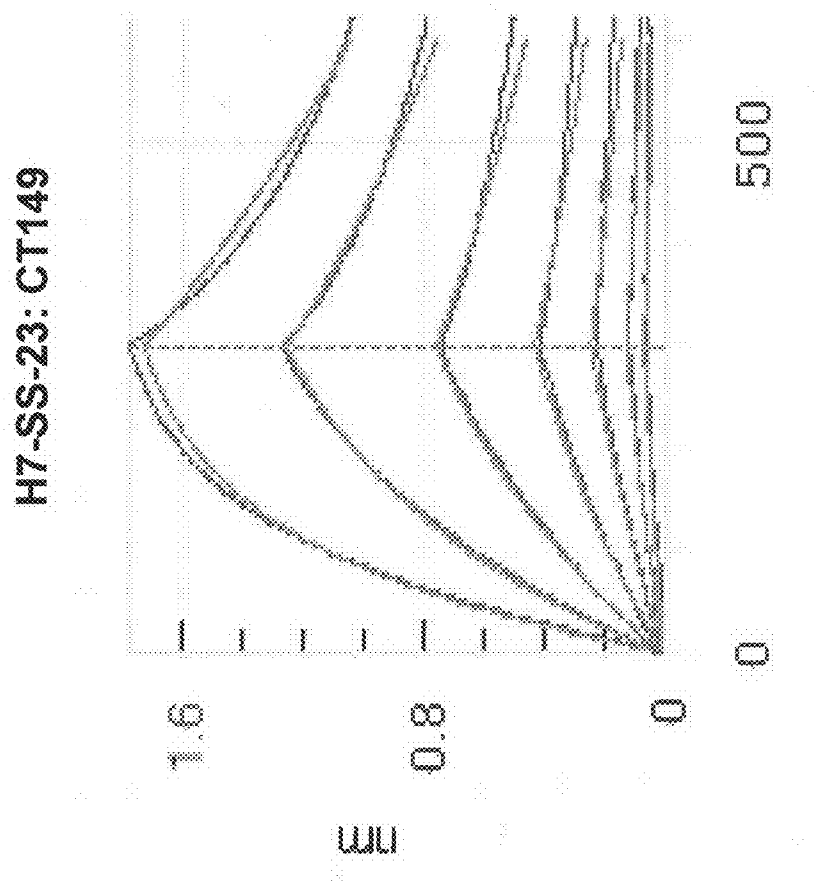
Figure 27E:
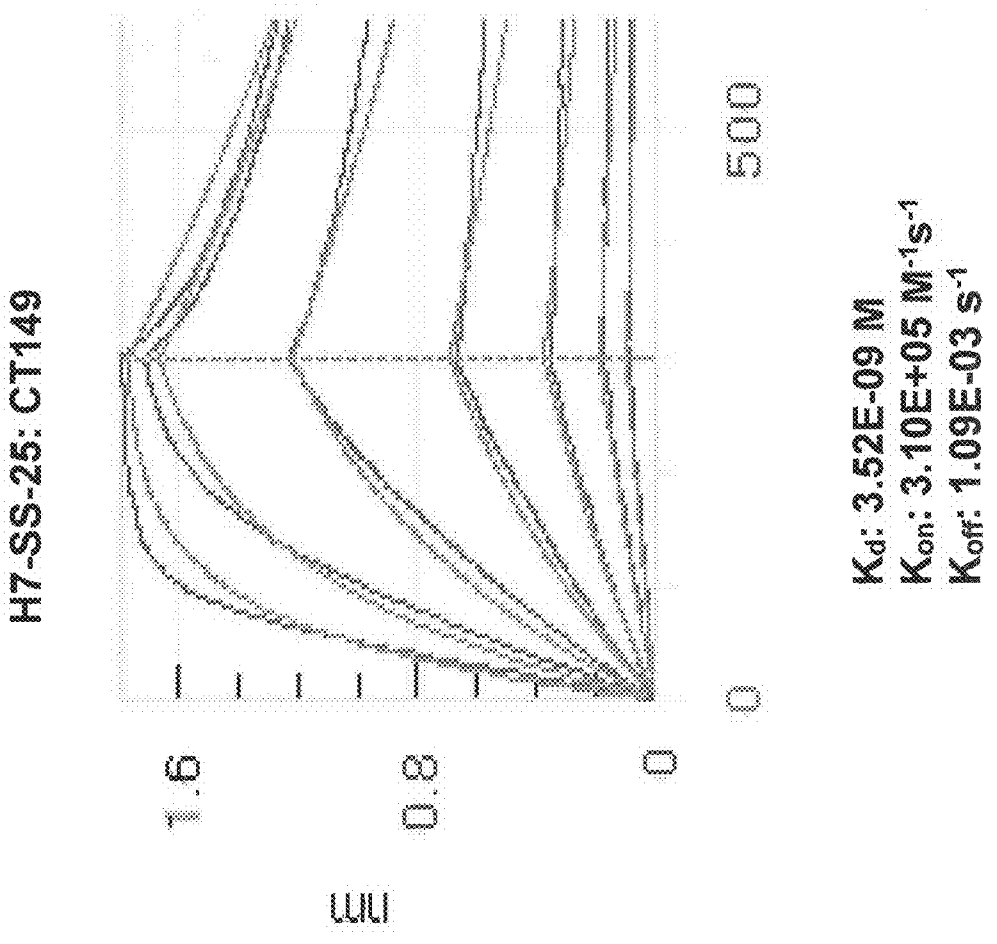
Figure 27F:
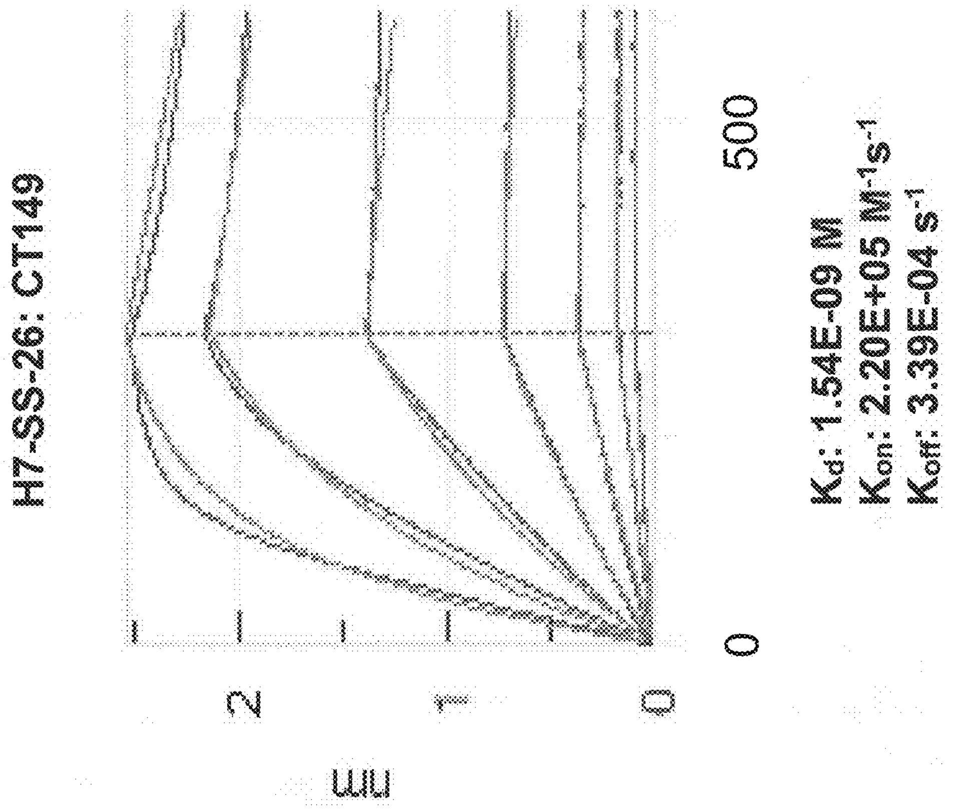
Figure 28:
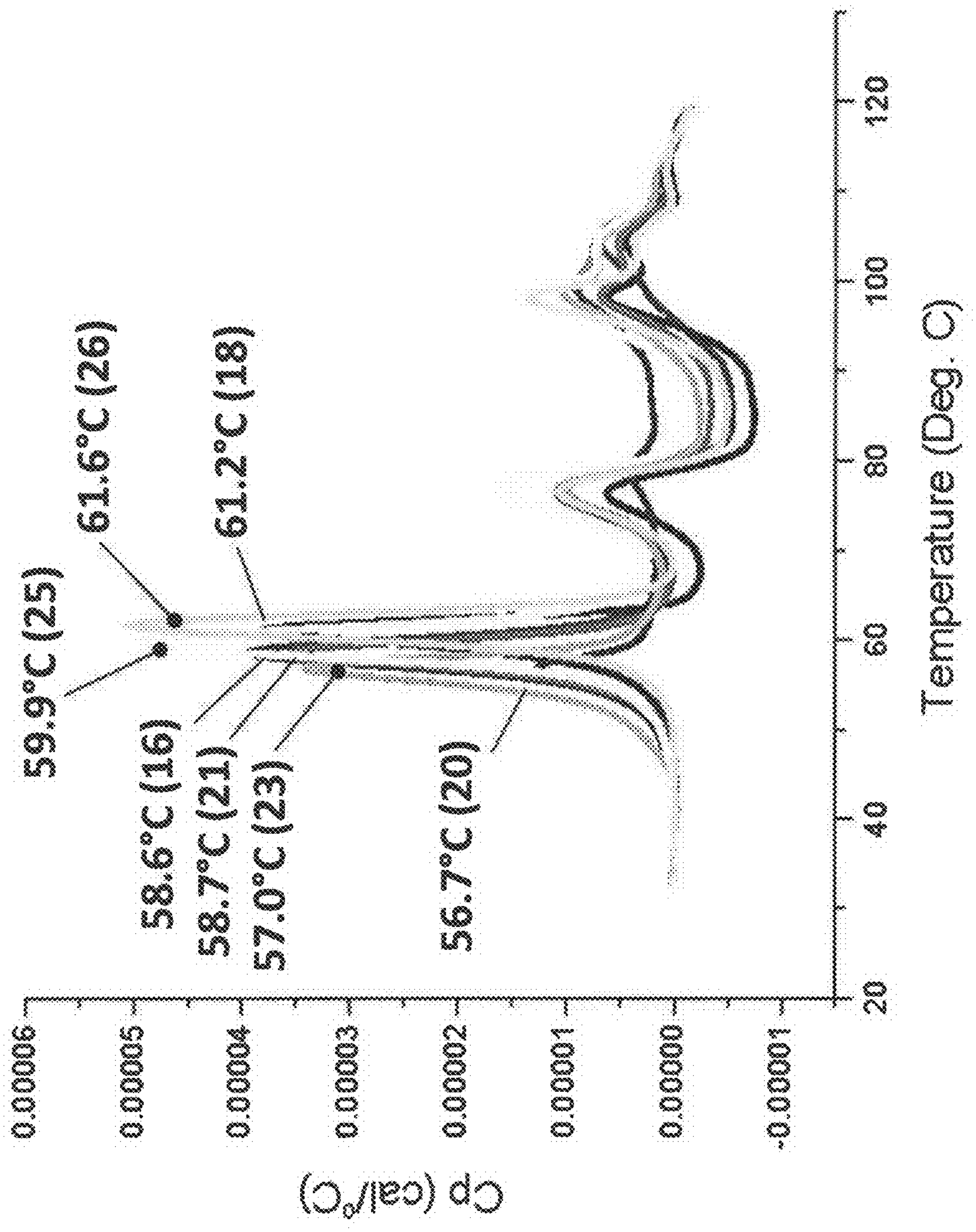
FIG. 28 shows dynamic scanning calorimetry (DSC) plots for seven H7-SS-np variants. Plots of heat capacity (Cp) versus temperature depicts melting transitions for each protein. The earliest melting points (TMs) for each protein are noted and color-coded to match the associated curve. The H7-SS-np design number is shown for each in parentheses. In this diagram, the Cp values on the Y-axis are shown with an arbitrary scale.
Figure 29A:
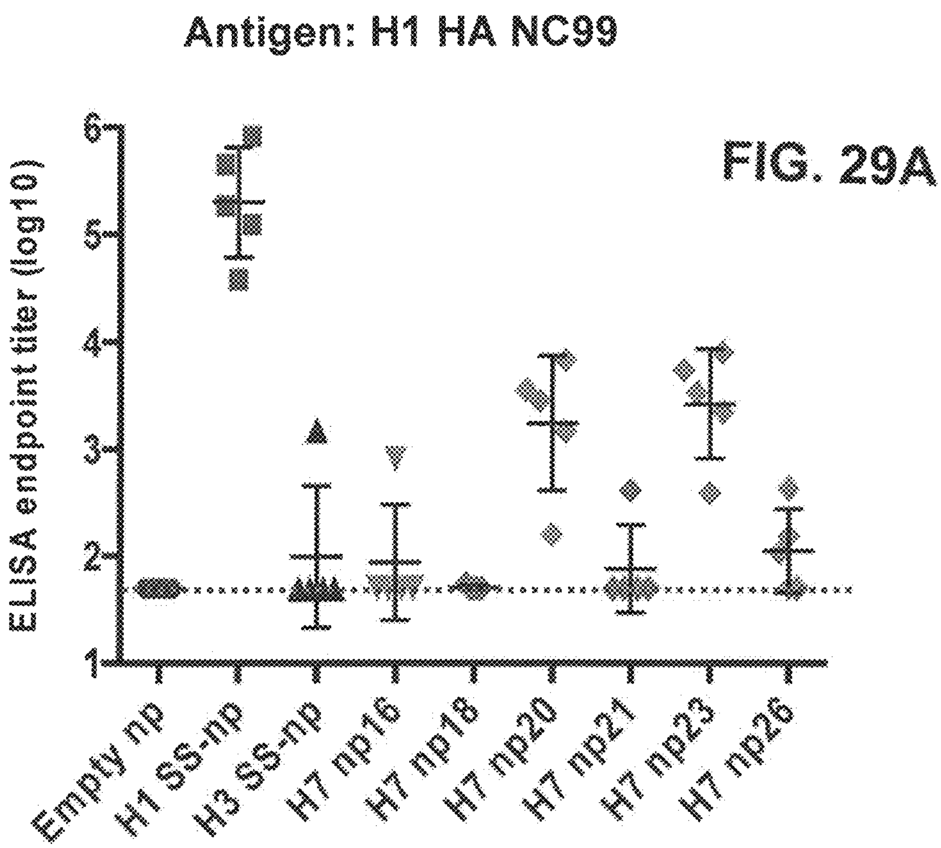
FIGS. 29A-29D show immune responses of H7-SS-np-immunized mice to diverse HAs. ELISA antibody endpoint titers of sera from BALB/c mice (n=5) immunized 3× with six different versions of SAS-adjuvanted H7-SS-np to plated A/New Caledonia/20/1999 (H1N1) HA (FIG. 29A), A/Vietnam/1203/2004 (H5N1) (FIG. 29B), A/Hong Kong/1/1968 (H3N2) (FIG. 29C) and A/Anhui/1/2013 (H7N9) (FIG. 29D). Sera from mice immunized with empty ferritin nanoparticle, H1-SS-np and H3-SS-np (#231) serve as controls. Geometric mean titers are shown by horizontal lines. Horizontal dotted lines indicate the baseline titer of 50.
Figure 29B:
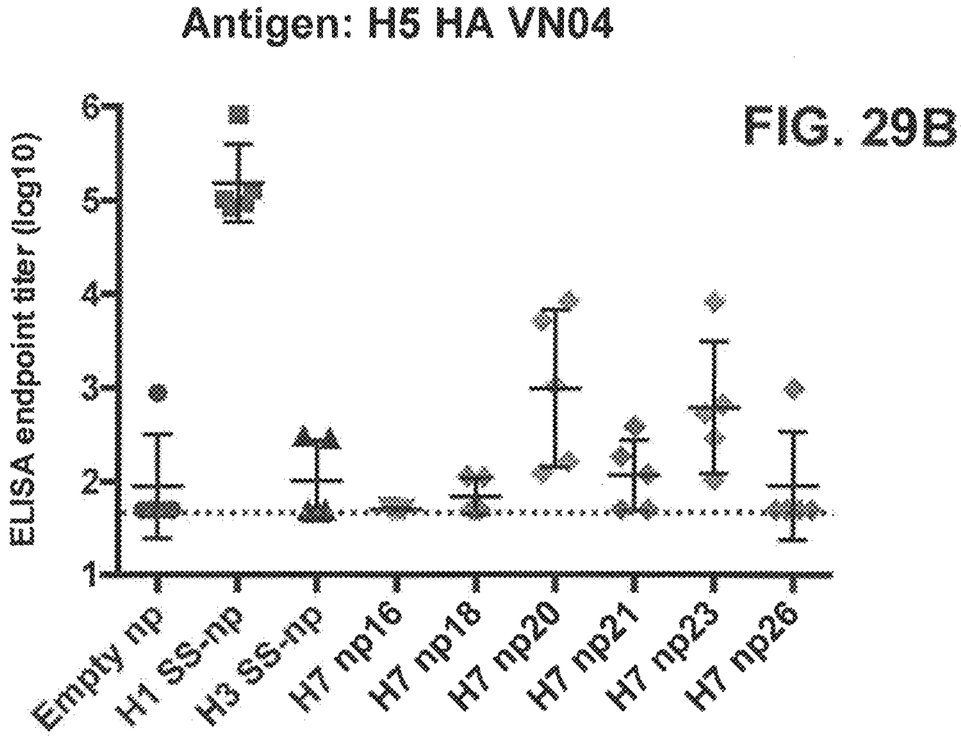
Figure 29C:
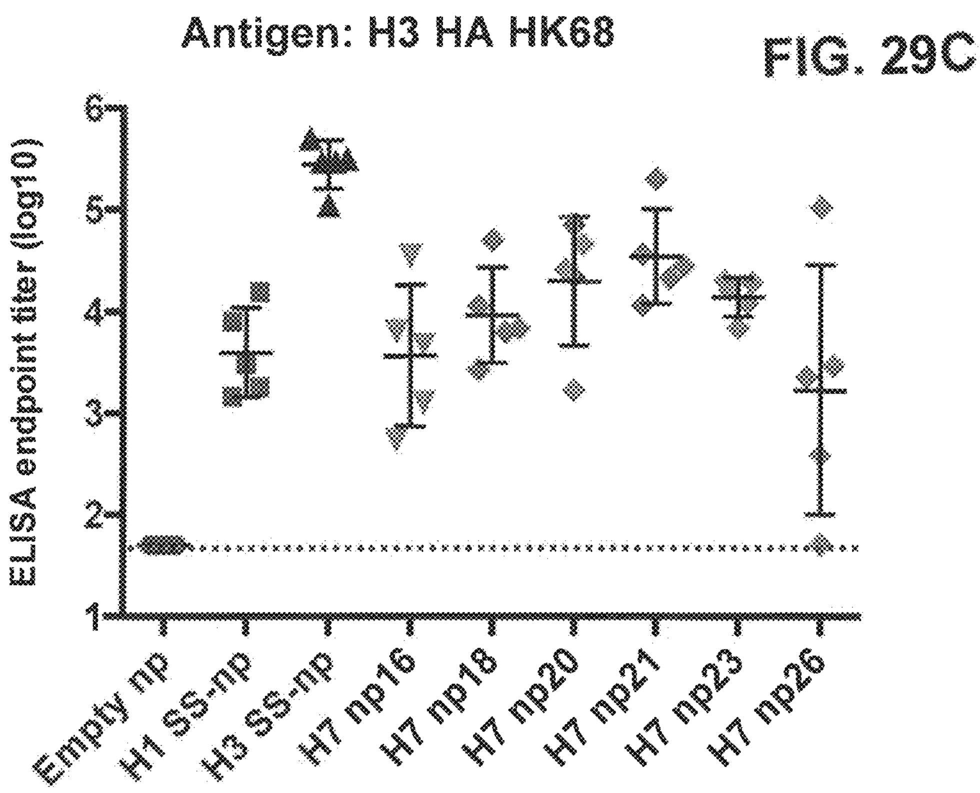
Figure 29D:
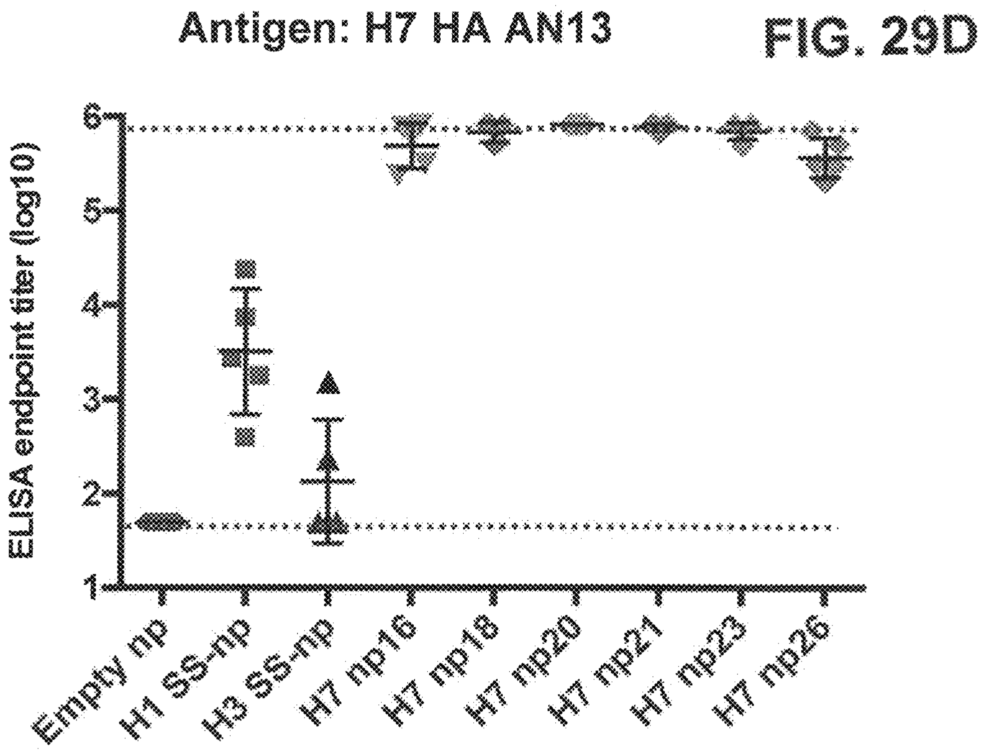
Figure 30B:
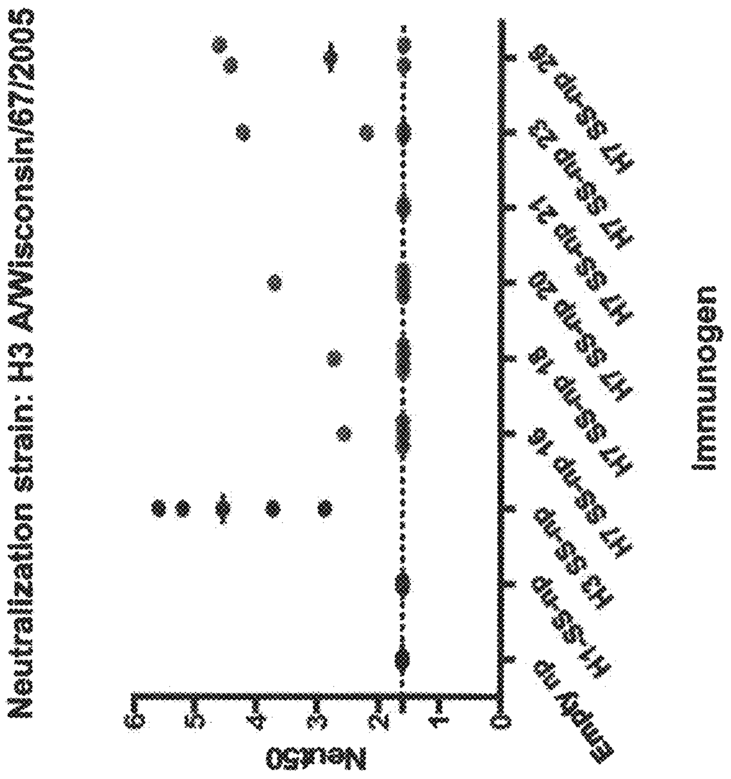
FIGS. 30A and 30B show neutralizing sera responses of H7-SS-np-immunized mice to H3N2 and H7N9. Pseudovirus neutralization titers of sera from BALB/c mice (n=5) immunized 3× with six different versions of SAS-adjuvanted H7-SS-np.
Figure 30A:
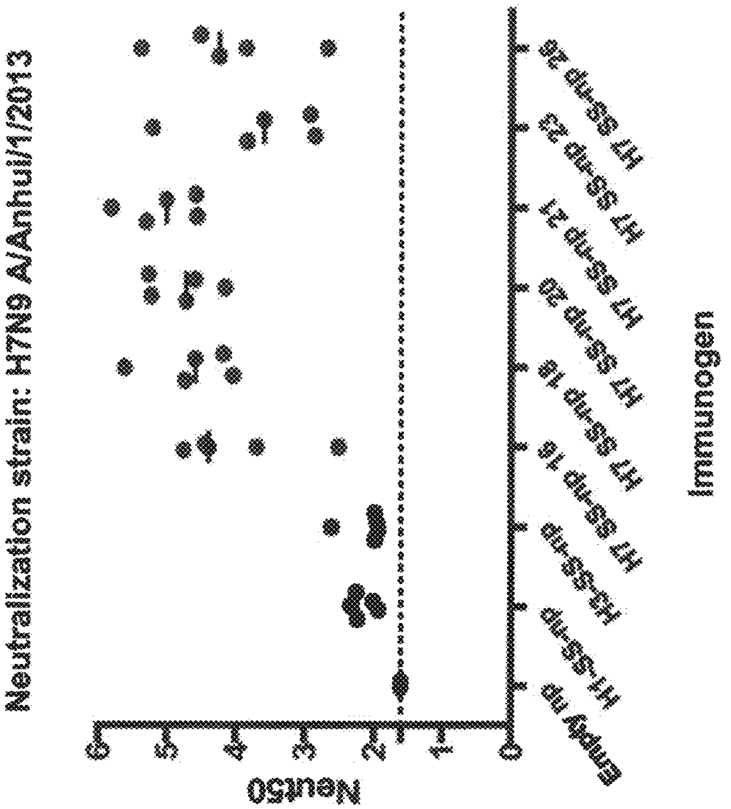
Figure 32A:
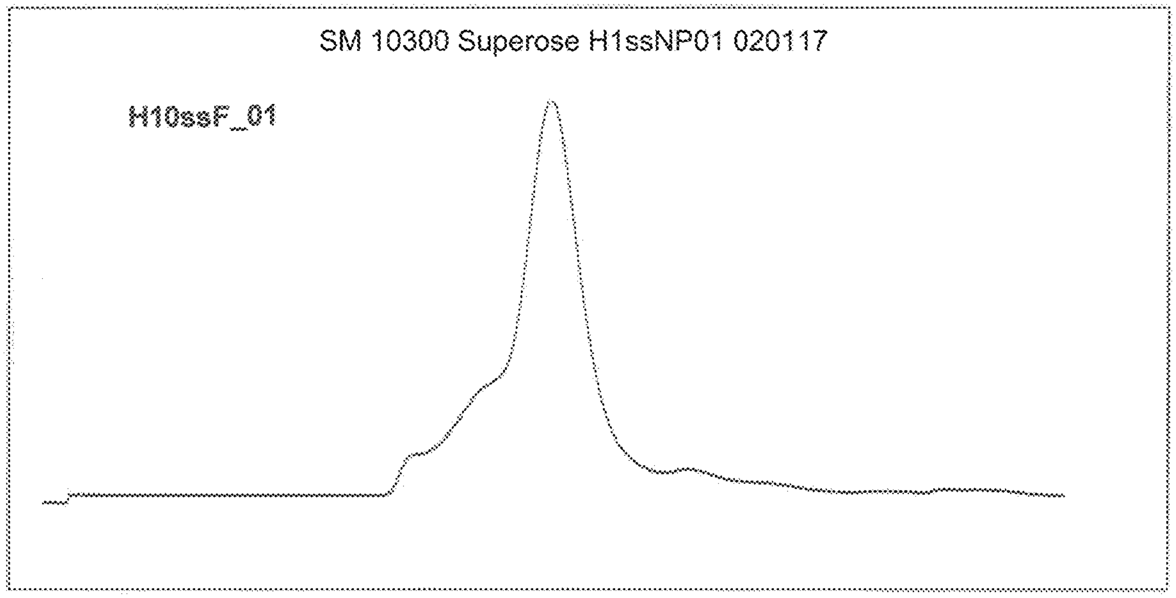
FIGS. 32A-32E show gel filtration Superdex 200 10/30 profiles for H10ssF variants 1 (FIG. 32A), 2 (FIG. 32B) 3 (FIG. 32C), 4 (FIG. 32D) and 5 (FIG. 32E). In each case a single peak was eluted at a volume of approximately 12.5 mls. The final yields from Expi293 cells after gel filtration were 6-8 mg/L of culture.
Figure 32B:
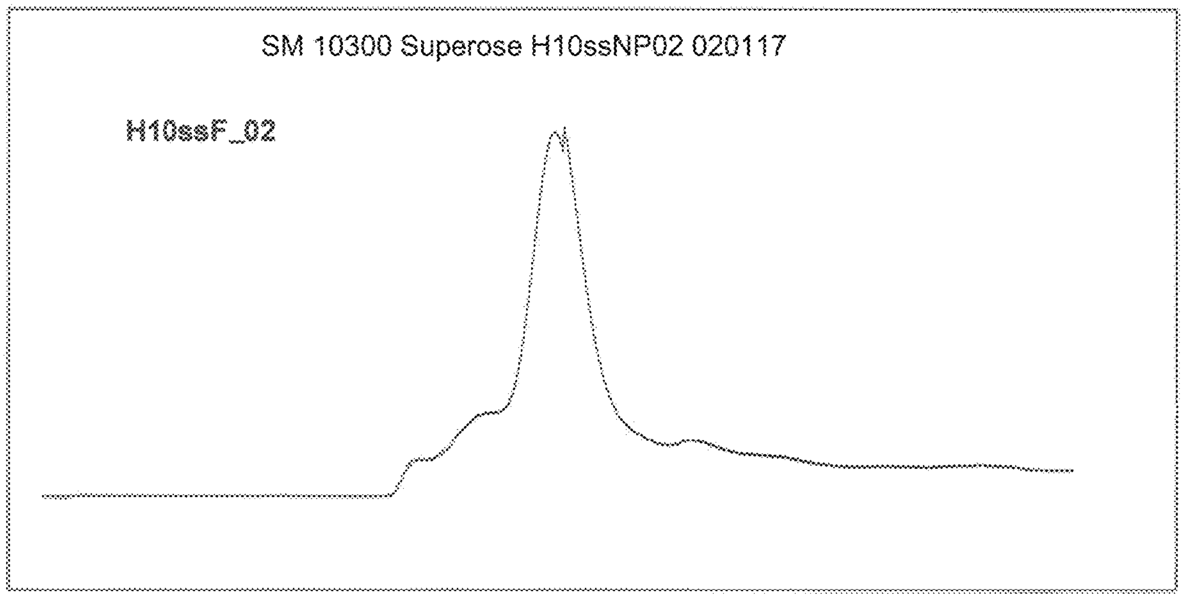
Figure 32C:
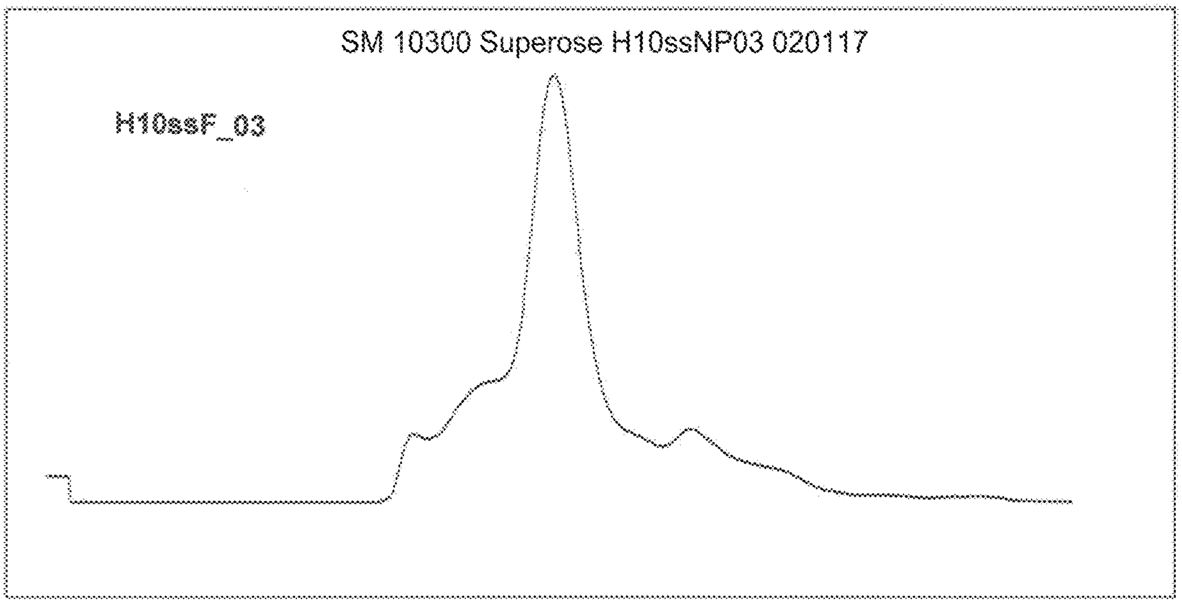
Figure 32D:
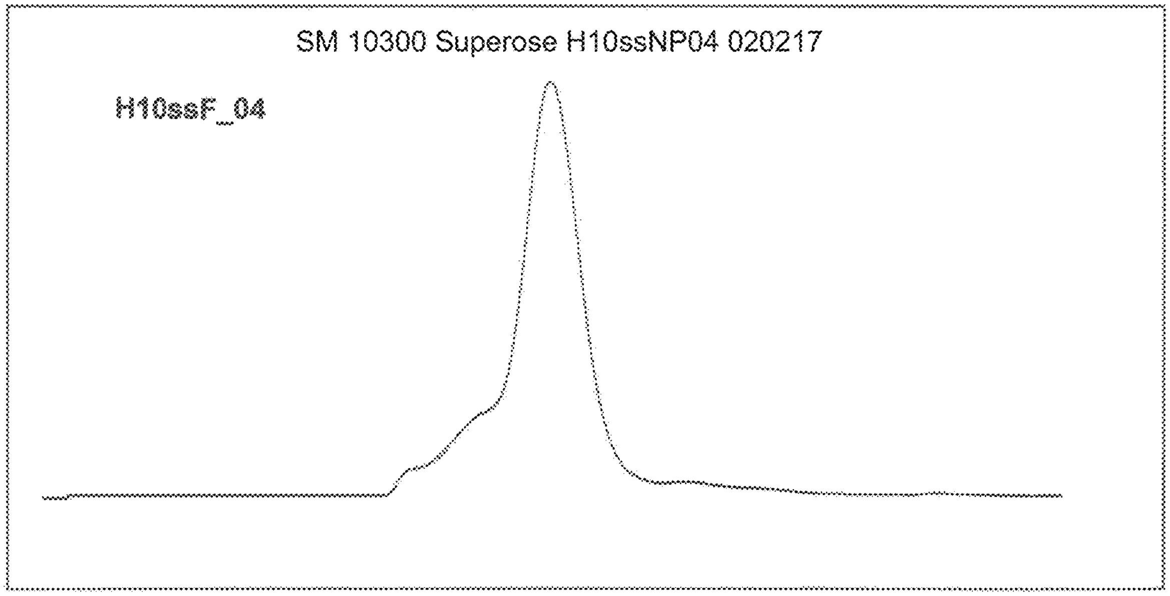
Figure 32E:
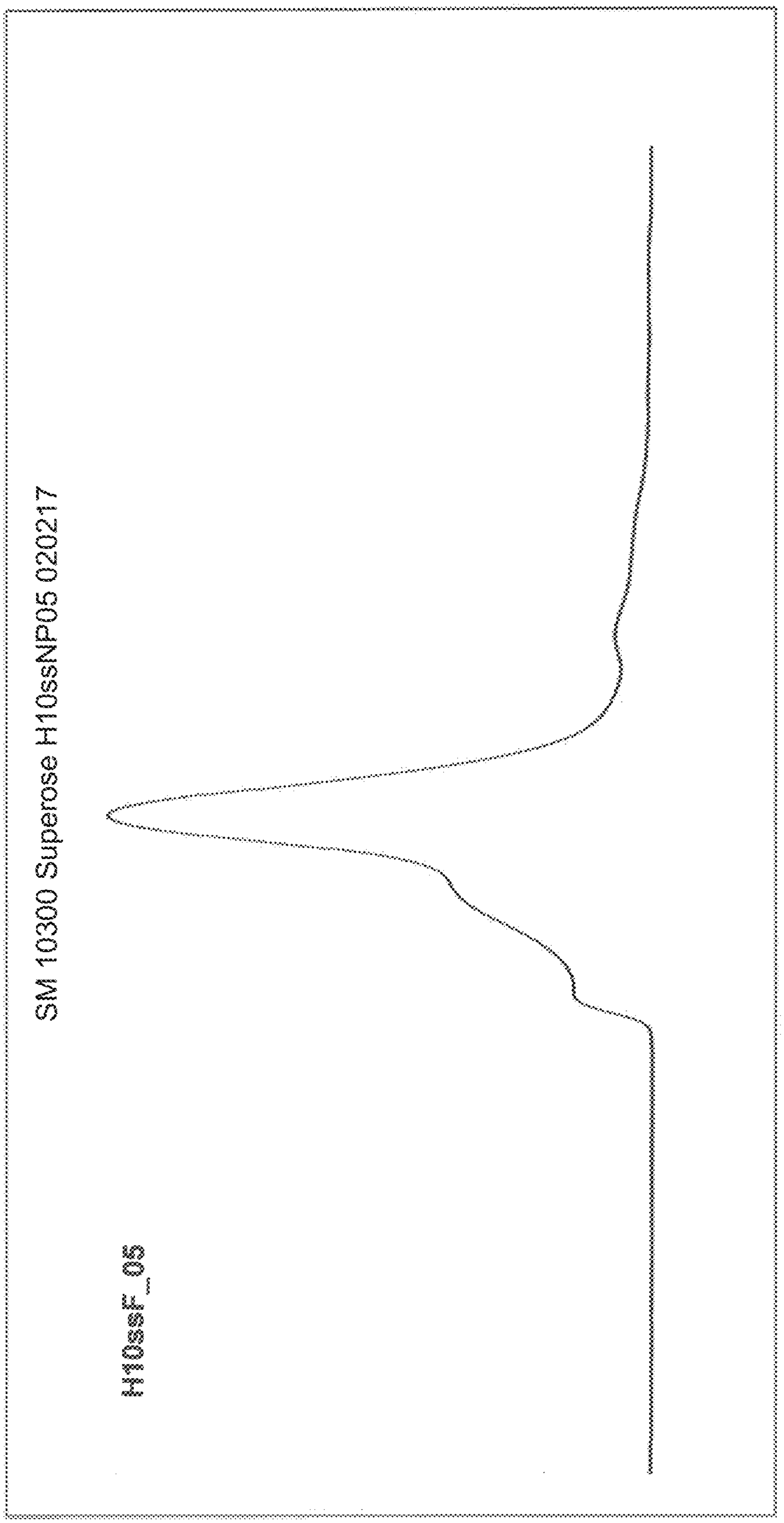
Figure 33A:
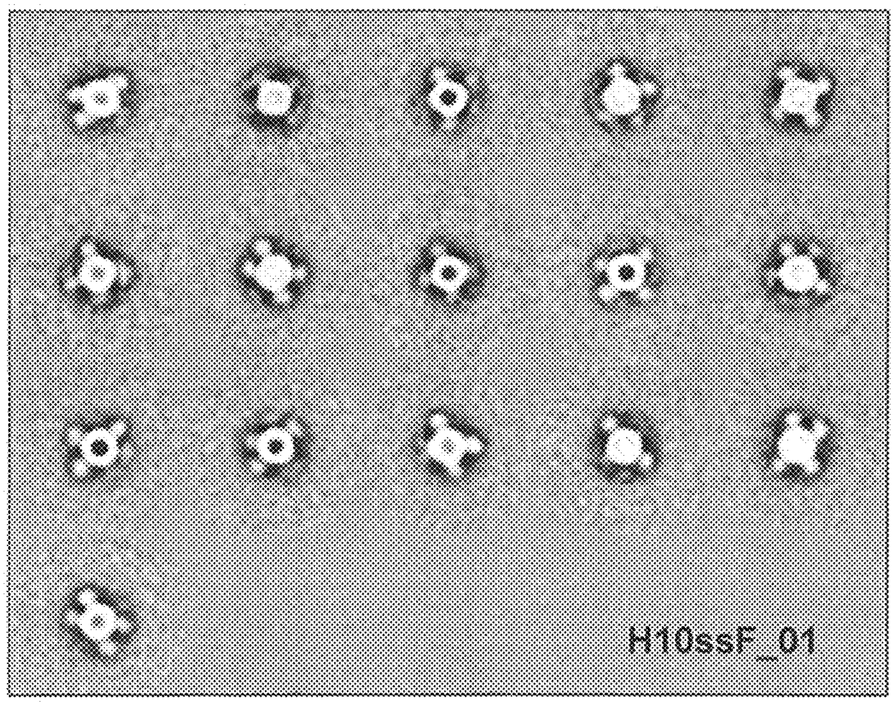
FIGS. 33A-33E. Electron microscopy of H10ssF nanoparticles variants. Negative stain electron microscopy 2D class averages of H10ssF variants revealing the formation of particles with a visible arrangement of HA stems projecting from hollow spheres.
Figure 33B:
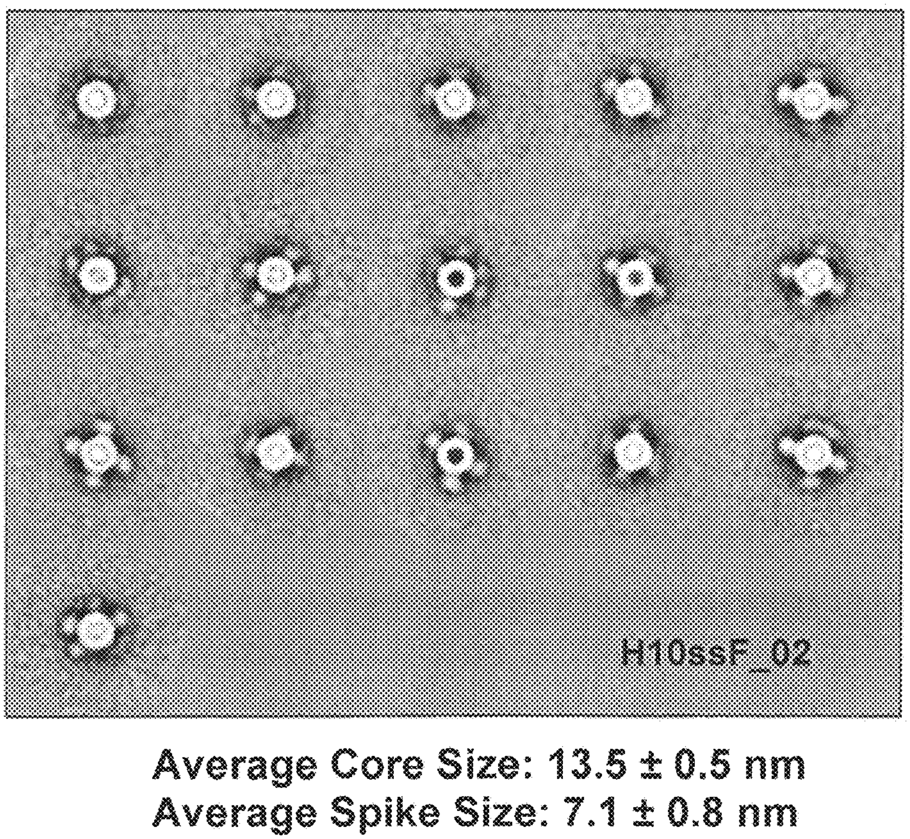
Figure 33C:
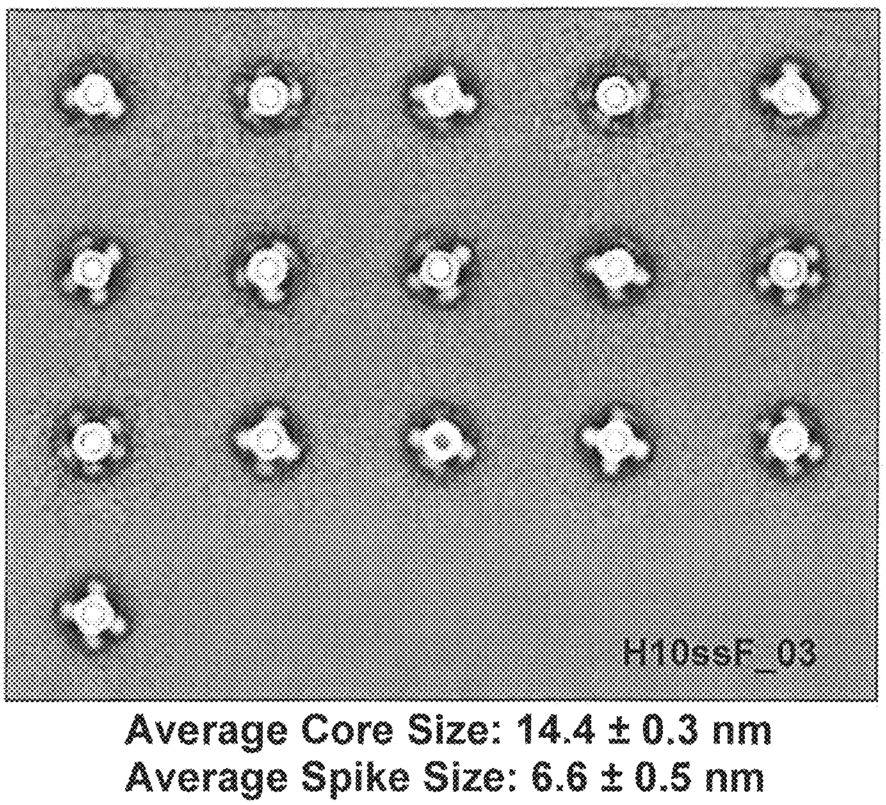
Figure 33D:
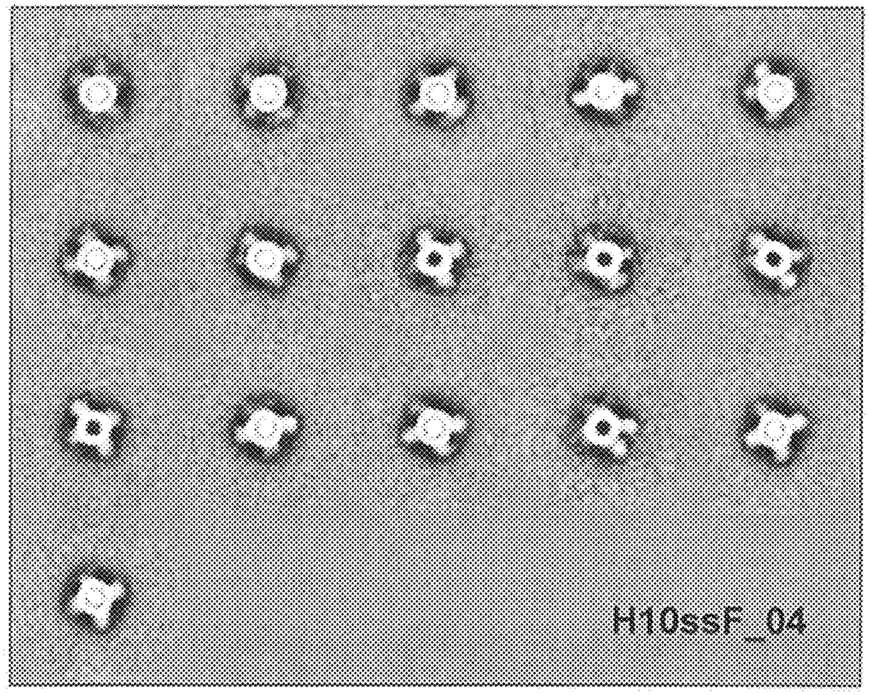
Figure 33E:
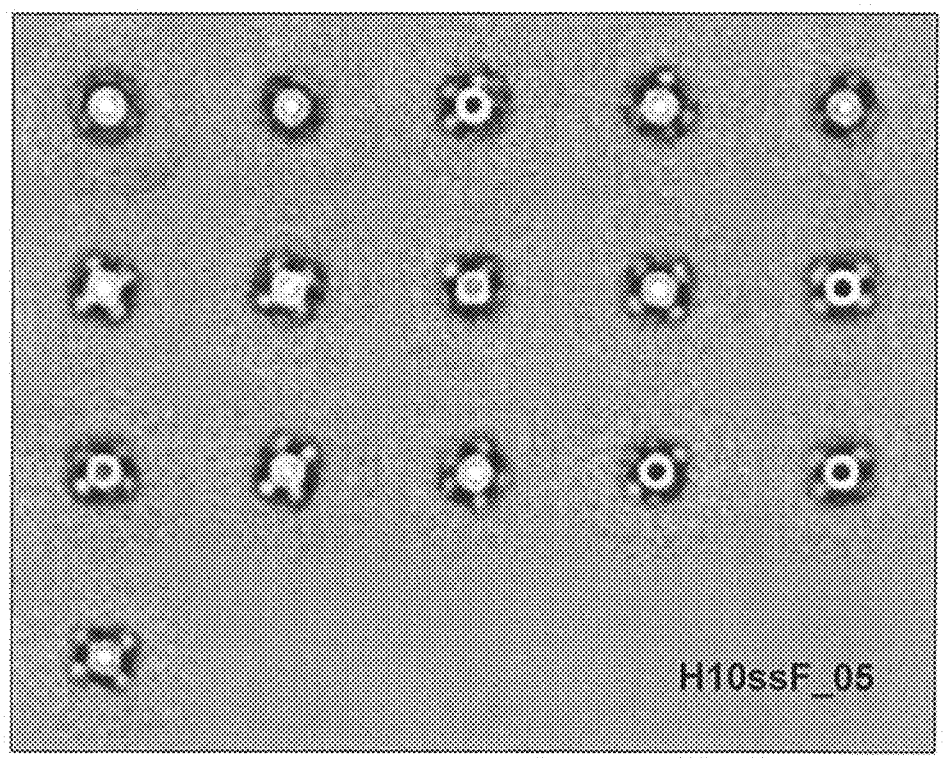
Figure 34A:
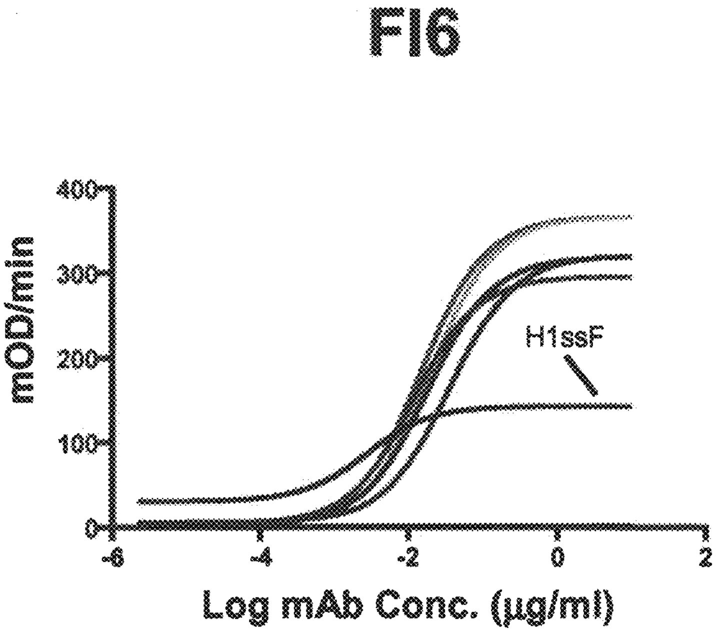
FIGS. 34A-34D show kinetic ELISA results for H10ssF variants 2-5. FIGs A-C. show ELISA curves. FIG D. shows IC50 values calculated from the curves. Supernatants from HEK293T cells expressing design immunogens were plated and detected by above antibodies
Figure 34B:
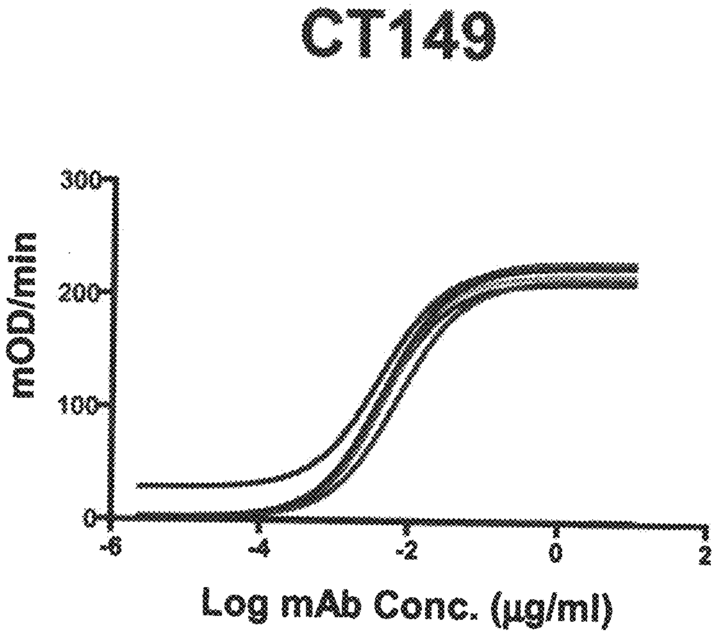
Figures 34C, 34D:
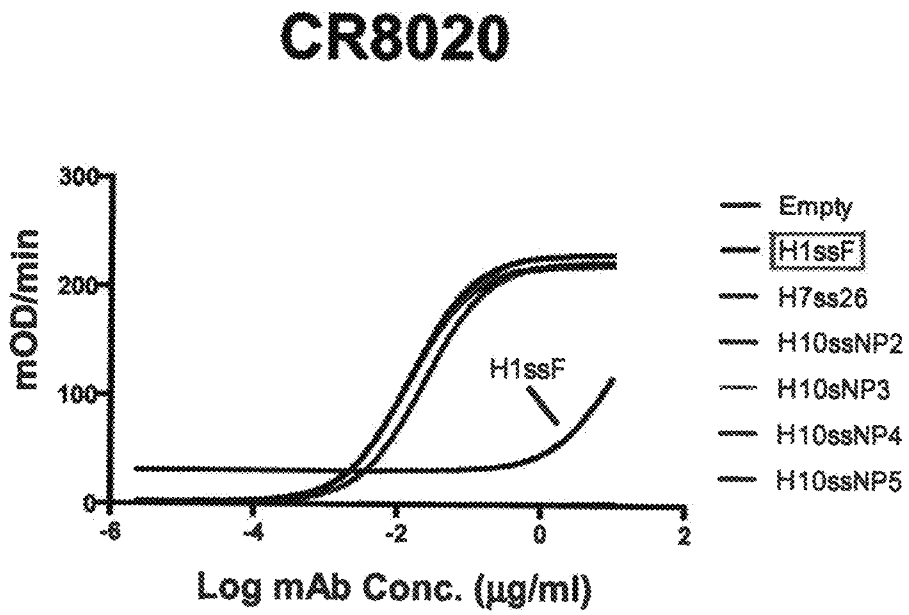

The present invention relates to a novel vaccine for influenza virus. More specifically, the present invention relates to novel, Group 2 influenza HA protein-based vaccines that elicit an immune response against the stem region of the HA protein from a broad range of influenza viruses. It also relates to self-assembling nanoparticles that display immunogenic portions of the pre-fusion conformation of the stem region from the Group 2 influenza HA protein on their surface. Such nanoparticles are useful for vaccinating individuals against influenza virus. Accordingly, the present invention also relates to protein constructs for producing such nanoparticles and nucleic acid molecules encoding such proteins. Additionally, the present invention relates to methods of producing nanoparticles of the present invention, and methods of using such nanoparticles to vaccinate individuals.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

For convenience, certain abbreviations can be used to refer to protein constructs, and portions thereof, of the invention. For example, HA can refer to influenza hemagglutinin protein, or a portion thereof. HA-SS refers to a stabilized stem region, or a portion of the stem region, from an influenza HA protein. Typically the HA portion of such a designation will refer to the subtype of the hemagglutinin protein. For example, a stabilized stem region from a subtype 3 hemagglutinin can be referred to as H3-SS. A protein construct comprising a HA-SS (e.g., H3-SS) joined to an influenza HA protein transmembrane domain can be referred to as HA-SS-TM (e.g., H3-SS-TM). A protein constructs comprising a HA-SS joined to a ferritin monomeric subunit can be referred to as HA-SS-np. Such a designation may also be followed by a number that indicates a particular construct containing specific alterations (e.g., H3-SS-np_231 (SEQ ID NO:47)). It should be noted that such a construct can also be referred to HAssF (e.g., H3ssF_231). In certain aspects of the invention, a HA-SS is joined to other monomeric subunits, such as, for example, lumazine synthase. Such a construct can be referred to by the designation HA-SS-LS (e.g., H3-SS_LS-01 (SEQ ID NO:83)) or HAssL (e.g., H3ssLS-01 (SEQ ID NO:83)).

In addition to the above, unless specifically defined otherwise, the following terms and phrases, which are common to the various embodiments disclosed herein, are defined as described below.

As used herein, a protein construct is a protein made by the hand of man, in which the amino acid sequence of a protein is modified so that the resulting modified protein comprises a sequence that is not found in nature. Protein constructs include protein in which two or more amino acid sequences have been covalently joined in a way not found in nature. The amino acid sequences being joined can be related or unrelated. As used herein, polypeptide sequences are unrelated, if their amino acid sequences are not normally found joined together via a covalent bond in their natural environment(s) (e.g., inside a cell). For example, the amino acid sequence of a ferritin monomeric subunit, and the amino acid sequence of a Group 2 influenza HA protein are not normally found joined together via a covalent bond. Thus, such sequences are considered unrelated.

Protein constructs can also comprise related amino acid sequences. For example, the structure of the influenza HA protein is such that the head region amino acid sequence is flanked on both ends by stem region amino acid sequences. Through genetic means, it is possible to create a modified version of an HA protein by removing amino acid residues from the middle of the head region, while maintaining a portion of the head region flanked by stem regions sequences. While the order of the sequences in the final molecule would remain the same, the spatial relationship between the amino acids would differ from the natural protein. Thus, such a molecule would be considered a protein construct. According to the present invention, protein constructs may also be referred to as fusion proteins.

Amino acid sequences in a protein construct can be joined directly to each other or they can be joined using a linker. A linker, linker sequence, linker peptide, and the like, is a short (e.g., 2-20) amino acid sequence used to connect two proteins having a desired characteristic (e.g., structure, epitope, immunogenicity, activity, etc.). A linker sequence typically does not have its own activity and is usually used to connect other parts of the protein construct, thereby allowing them to assume a desired conformation. Linker sequences are typically made from small amino acid residues and/or runs thereof, such as, for examples, serine, alanine and glycine, although the use of other amino acid residues is not excluded. For example, it may be desirable to include an amino acid that can form a covalent bond, such as a cysteine residue, in the linker sequence.

As used herein, the term immunogenic refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 93% identical, at least 94% identical, at least 95% identical, at least 96% identical, at least 97% identical, at least 98% identical or at least 99% identical. Methods of determining the percent identity between two amino acid or nucleic acid sequence are known in the art.

As used herein, an immune response to a vaccine, or nanoparticle, of the present invention is the development in a subject of a humoral and/or a cellular immune response to a Group 2 HA protein present in the vaccine. For purposes of the present invention, a "humoral immune response"

refers to an immune response mediated by antibody molecules, including secretory (IgA) or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a Group 2 HA protein present in the vaccine. These responses may serve to neutralize infectivity (e.g., antibody-dependent protection), and/or mediate antibody-complement, or antibody dependent cell cytotoxicity (ADCC) to provide protection to an immunized individual. Such responses can be determined using standard immunoassays and neutralization assays, well known in the art.

As used herein, the term antigenic, antigenicity, and the like, refers to a protein that is bound by an antibody or a group of antibodies Similarly, an antigenic portion of a protein is any portion that is recognized by an antibody or a group of antibodies. According to the present invention, recognition of a protein by an antibody means the antibody selectively binds to the protein. As used herein, the phrase selectively binds, selective binding, and the like, refer to the ability of an antibody to preferentially bind an HA protein as opposed to binding proteins unrelated to HA, or non-protein components in the sample or assay. An antibody that preferentially binds HA is one that binds HA but does not significantly bind other molecules or components that may be present in the sample or assay. Significant binding is considered, for example, binding of an anti-HA antibody to a non-HA molecule with an affinity or avidity great enough to interfere with the ability of the assay to detect and/or determine the level of anti-influenza antibodies, or HA protein, in the sample. Examples of other molecules and compounds that may be present in the sample, or the assay, include, but are not limited to, non-HA proteins, such as albumin, lipids and carbohydrates. According to the present invention, a non-HA protein is a protein having an amino acid sequence sharing less than 60% identity with the sequence of an influenza HA protein disclosed herein. In some embodiments, the antibody or antibodies provide broad heterosubtypic protection. In some embodiments, the antibody or antibodies are neutralizing As used herein, neutralizing antibodies are antibodies that prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane. According to the present invention, a neutralizing antibody is one that inhibits one or more such steps.

As used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group 2 influenza virus may neutralize a Group 1 virus. As an additional example, broadly neutralizing antibodies elicited against an HA protein from one sub-type or strain of virus, may neutralize another sub-type or strain of virus. For example, broadly neutralizing antibodies elicited against an HA protein from an H3 influenza virus may neutralize viruses from one or more sub-types selected from the group consisting of H1, H2, H4, H5, H6, H7, H8, H8, H10, H11, H12, H13, H14, H15, H16, H17 or H18.

According to the present invention all nomenclature used to classify influenza virus is that commonly used by those skilled in the art. Thus, a Type, or Group, of influenza virus refers to influenza Type A, influenza Type B or influenza type C. It is understood by those skilled in the art that the designation of a virus as a specific Type relates to sequence difference in the respective M1 (matrix) protein or NP (nucleoprotein). Type A influenza viruses are further divided into Group 1 and Group 2. These Groups are further divided into subtypes, which refers to classification of a virus based on the sequence of its HA protein. Examples of current commonly recognized subtypes are H1, H2, H3, H4, H5, H6, H7, H8, H8, H10, H11, H12, H13, H14, H15, H16, H17 or H18. Group 1 influenza subtypes are H1, H2, H5, H6, H8, H9, H11, H12, H13, H16, H17 and H18. Group 2 influenza subtypes are H3, H4, H7, H10, H14, and H15. Finally, the term strain refers to viruses within a subtype that differ from one another in that they have small, genetic variations in their genome.

As used herein, an influenza hemagglutinin protein, or HA protein, refers to a full-length influenza hemagglutinin protein or any portion thereof, that is useful for producing protein constructs and nanoparticles of the invention or that are capable of eliciting an immune response. Preferred HA proteins are those that are capable of forming a trimer. An epitope of a full-length influenza HA protein refers to a portion of such protein that can elicit an antibody response against the homologous influenza strain, i.e., a strain from which the HA is derived. In some embodiments, such an epitope can also elicit an antibody response against a heterologous influenza strain, i.e., a strain having an HA that is not identical to that of the HA of the immunogen. In some embodiments, the epitope elicits a broadly heterosubtypic protective response. In some embodiments, the epitope elicits neutralizing antibodies.

As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as the resulting variant protein retains the ability to elicit neutralizing or non-neutralizing antibodies against an influenza virus. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxyl terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein. In variants into which insertions have been made, the inserted amino acids may be referred to by referencing the amino acid residue after which the insertion was made. For example, an insertion of four amino acid residues after amino acid residue 402 could be referred to as 402a-402d. Moreover, if one of those inserted amino acids are later substituted with another amino acid, such a change can be referred to by reference to the letter position. For example, substitution of an inserted glycine (in the further position of the insert) with a threonine can be referred to as S402dT.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 1.

TABLE 1

Amino Acid Substitutions

| Original Amino Acid | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affect a protein activity" refers to a decrease in the activity of a protein by at least 10%, at least 20%, at least 30%, at least 40% or at least 50%. With regard to the present invention, such an activity may be measured, for example, as the ability of a protein to elicit protective antibodies against an influenza virus. Such activity may be measured by measuring the titer of such antibodies against influenza virus, the ability of such antibodies to protect against influenza infection or by measuring the number of types, subtypes or strains neutralized by the elicited antibodies. Methods of determining antibody titers, performing protection assays and performing virus neutralization assays are known to those skilled in the art. In addition to the activities described above, other activities that may be measured include the ability to agglutinate red blood cells and the binding affinity of the protein for a cell. Methods of measuring such activities are known to those skilled in the art.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

As used herein, a vaccinated subject is a subject that has been administered a vaccine that is intended to provide a protective effect against an influenza virus.

As used herein, the terms exposed, exposure, and the like, indicate the subject has come in contact with a person of animal that is known to be infected with an influenza virus.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

One embodiment of the present invention is a protein construct comprising a Group 2 influenza HA protein wherein the head region of the Group 2 influenza HA protein has been replaced with an amino acid sequence comprising less than 5 contiguous amino acid residues from the head region of an influenza HA protein. As used herein, a Group 2 HA protein, refers to a full-length influenza HA protein from a Group 2 influenza virus, or any portion/portions and/or variants thereof, that is/are useful for producing protein constructs and nanoparticles of the invention. Accordingly, the present invention is drawn to molecules that are capable of eliciting an immune response to the stem region of a Group 2 influenza HA protein. In some embodiments, the sequence of the HA protein construct has been further altered (i.e., mutated) to stabilize the stem region of the protein in a form that can be presented to the immune system. Examples of Group 2 influenza HA proteins useful for practicing the invention, and protein constructs made therefrom, are shown in Table 2, below.

TABLE 2

| PCT SEQ ID NO | Comments |
|---|---|
| | Monomeric Subunit Proteins |
| 1 | Amino acid sequence of ferritin monomeric subunit protein from *H. pylori*, MLSDIIKLLNEQVNKEMQSSNLYMSMSSWCYTHSLDGAGLFLFDHAAEE YEHAKKLIIFLNENNVPVQLTSISAPEHKFEGLTQIFQKAYEHEQHISESIN NIVDHAIKSKDHATFNFLQWYVAEQHEEEVLFKDILDKIELIGNENHGLY LADQYVKGIAKSRKSGS |
| 2 | amino acids 4-168 from SEQ ID NO: 2; Asn19 has been replaced with Gln, DIIKLLNEQVNKEMQSSNLYMSMSSWCYTHSLDGAGLFLFDHAAEEYEH AKKLIIFLNENNVPVQLTSISAPEHKFEGLTQIFQKAYEHEQHISESINNIVD HAIKSKDHATFNFLQWYVAEQHEEEVLFKDILDKIELIGNENHGLYLADQ YVKGIAKSRKSGS |

TABLE 2-continued

| PCT SEQ ID NO | Comments |
|---|---|
| 3 | Amino acid sequence of lumazine synthase from *aquifex aeolicus*, MQIYEGKLTAEGLRFGIVASRFNHALVDRLVEGAIDCIVRHGGREEDITL VRVPGSWEIPVAAGELARKEDIDAVIAIGVLIRGATPHFDYIASEVSKGLA DLSLELRKPITFGVITADTLEQAIERAGTKHGNKGWEAALSAIEMANLFK SLR |
| | FULL LENGTH HA |
| 4 | amino acid sequence of hemagglutinin protein from influenza A virus (A/Denmark/35/2005 (H3N2)); GenBank: ABU92694.1 |
| 5 | amino acid sequence of hemagglutinin protein from influenza A virus (A/Bangladesh/558/2012 (H3N2)); Accession: AJB43527.1 |
| 6 | amino acid sequence of hemagglutinin protein from influenza A virus (A/Sao Paulo/89403/2010 (H3N2)); Accession: AET10116.1 |
| 7 | amino acid sequence of hemagglutinin protein from influenza A virus (A/Bangladesh/541/2012 (H3N2)); Accession: AJB43525.1 |
| 8 | amino acid sequence of hemagglutinin protein from influenza A virus (A/Bangladesh/542/2012(H3N2)); Accession: AJB43524.1 |
| 9 | amino acid sequence of hemagglutinin protein from influenza A virus (A/Tocantins/979/2010 (H3N2)); Accession: AET10115.1 |
| 10 | amino acid sequence of hemagglutinin protein from influenza A virus (A/Tunisia/17332/2011 (H3N2)); Accession: AFV68725.1 |
| 11 | amino acid sequence of hemagglutinin protein from influenza A virus (A/Norway/88/2003 (H3N2)); Accession: ABR14669.1 |
| 12 | amino acid sequence of hemagglutinin protein from influenza A virus (A/Japan/AF2844/2012 (H3N2)); Accession: AFH57071.1 |
| 13 | amino acid sequence of hemagglutinin protein from influenza A virus (A/Texas/2977/2012(H3N2)); Accession: AFM45466.1 |
| 14 | amino acid sequence of hemagglutinin protein from influenza A virus (A/North Carolina/AF2716/2011 (H3N2)); Accession: ADY05375.1 |
| 15 | amino acid sequence of hemagglutinin protein from influenza A virus (A/Norway/70/2005 (H3N2)); Accession: ABI22080.1 |
| 16 | amino acid sequence of hemagglutinin protein from influenza A virus (A/duck/Chiba/24-203-44/2012 (H7N1)); Accession: BAN16716.1 |
| 17 | amino acid sequence of hemagglutinin protein from influenza A virus (A/chicken/Germany/2003 (H7N7)); Accession: CAG28959.1 |
| 18 | amino acid sequence of hemagglutinin protein from influenza A virus (A/chicken/Italy/444/1999 (H7N1)); Accession: CAG28956.1 |
| 19 | amino acid sequence of hemagglutinin protein from influenza A virus (A/mallard/Italy/4810-7/2004 (H7N7)); Accession: ABG57092.1 |
| 20 | amino acid sequence of hemagglutinin protein from influenza A virus (A/Anhui/DEWH72-03/2013 (H7N9)); Accession: AHZ39710.1 |
| 21 | amino acid sequence of hemagglutinin protein from influenza A virus (A/Shanghai/JS01/2013 (H7N9)); Accession: AGW82612.1 |
| 22 | amino acid sequence of hemagglutinin protein from influenza A virus (A/Guangdong/02/2013 (H791)); Accession: AHD25003.1 |
| 23 | amino acid sequence of hemagglutinin protein from influenza A virus (A/Shenzhen/SP44/2014 (H7N9)); Accession: AJJ91957.1 |
| 24 | amino acid sequence of hemagglutinin protein from influenza A virus (A/Beijing/3/2013 (H7N9)); Accession: AHM24224.1 |
| 25 | amino acid sequence of hemagglutinin protein from influenza A virus (A/Hong Kong/470129/2013 (H7N9)); Accession: AHF20528.1 |
| 26 | amino acid sequence of hemagglutinin protein from influenza A virus (A/Jiangxi/IPB13/2013(H10N8; Accession: AHK10761.1) |

TABLE 2-continued

| PCT SEQ ID NO | Comments |
|---|---|
| | Flanking Sequences |
| 27 | Amino acid sequence flanking amino-terminal end of head region from influenza virus A (Denmark/35/2005 (H3N2))-full (aa 1-59)<br>MKTIIALSYILCLVFAQKLPGNDNSTATLCLGHHAVPNGTIVKTITNDQIE<br>VTNATELV |
| 28 | Amino acid sequence flanking amino-terminal end of head region from influenza virus A (Denmark/35/2005 (H3N2))-partial (40 aa's)<br>PGNDNSTATLCLGHHAVPNGTIVKTITNDQIEVTNATELV |
| 29 | Amino acid sequence flanking amino-terminal end of head region from influenza virus A (Denmark/35/2005 (H3N2))-partial (25 aa's)<br>AVPNGTIVKTITNDQIEVTNATELV |
| 30 | Amino acid sequence of stem region flanking carboxyl-terminal end of head region from influenza virus A (Denmark/35/2005 (H3N2))<br>LKLATGMRNVPEKQTRGIFGAIAGFIENGWEGMVDGWYGFRHQNSEGIG<br>QAADLKSTQAAINQINGKLNRLIGKTNEKFHQIEKEFSEVEGRIQDLEKYV<br>EDTKVDLWSYNAELLVALENQHTIDLTDSEMNKLFERTKKQLRENAED<br>MGNGCFKIYHKCDNACIGSIRNGTYDHDVYRDEALNNRFQIK |
| 31 | Amino acid sequence of stem region flanking carboxyl-terminal end of head region from influenza virus A (Denmark/35/2005 (H3N2))-partial-66 aa's)<br>LKLATGMRNVPEKQTRGIFGAIAGFIENGWEGMVDGWYGFRHQNSEGIG<br>QAADLKSTQAAINQING |
| 32 | Amino acid sequence of stem region flanking carboxyl-terminal end of head region from influenza virus A (Denmark/35/2005 (H3N2))-partial-50 aa's)<br>LKLATGMRNVPEKQTRGIFGAIAGFIENGWEGMVDGWYGFRHQNSEGIG<br>Q |
| 33 | Amino acid sequence of stem region flanking carboxyl-terminal end of head region from influenza virus A (Denmark/35/2005 (H3N2))-partial-25 aa's)<br>LKLATGMRNVPEKQTRGIFGAIAGF |
| | Linker Sequences |
| 34 | VFPGCGV-head linker |
| 35 | CFNGIC-head linker |
| 36 | Helix A extension sequence-ALMAQ |
| 37 | Helix A extension sequence-ELMEQ |
| 38 | Inter-helix region-GKTNEKFHQIEKEFSEVEGRIQDLEKYVEDTKVDLW |
| 39 | Inter-helix linker-GGPD |
| | Head region carboxyl flank (inter-helix region replaced with linker) |
| 40 | DLKSTQAAI**N**QING**KL**NRLIALMAQGGPD**S**Y**N**AELLVAL**E**NQH**T**IDLTD |
| 41 | NSEG**I**GQAADLKSTQAAINQING**KL**NR**LI**ALMAQGGPD**S**Y**N**AELLVAL**E**<br>NQH**T**IDLTDSEM**N**KLFE**R**T |
| 42 | NSEG**I**GQAADLKSTQAAINQING**KL**NR**LI**ALMAQGGPD**S**Y**N**AELLVAL**E**<br>NQH**T**IDLTDSEM**N**KLFE**R**T**KK**QLRENAEDMGNGCFKIYH |
| 43 | LKLATGMRNVPE**K**QTRG**I**FGAIAGFIENGWEGMVDGWYGFRHQNSEG**I**<br>GQAADLKSTQAAI**N**QING**KL**NR**LI**ALMAQGGPD**S**Y**N**AELLVAL**E**NQH**T**I<br>DLTDSEM**N**KLFE**R**T**KK**QLRENAEDMGNGCFKIYHKCDNACI**G**SIRNGTY<br>DHDVYRDEALNNRFQIK |
| | Inter-helix carboxyl flank-goes all the way to end of stem; does not include TM domain |
| 44 | **S**Y**N**AELLVAL**E**NQH**T**IDLTDSEM**N**KLFE**R**T**KK**QLRENAEDMG |
| 45 | **S**Y**N**AELLVAL**E**NQH**T**IDLTDSEM**N**KLFE**R**T**KK**QLRENAEDMGNGCFKIY<br>HKCDNACI**G**SIRN |
| 46 | **S**Y**N**AELLVAL**E**NQH**T**IDLTDSEM**N**KLFE**R**T**KK**QLRENAEDMGNGCFKIY<br>HKCDNACI**G**SIRNGTYDHDVYRDEALNNRFQIK |

TABLE 2-continued

| PCT SEQ ID NO | Comments |
|---|---|
| | Protein Constructs With HA Joined to Monomeric Subunit |
| 47 | Amino acid sequence of H3-SS-np_231; (H3ssF_231) |
| 48 | Amino acid sequence of H3-SS-np_249; (H3ssF_249) |
| 49 | Amino acid sequence of H3-SS-np_256; (H3ssF_256) |
| 50 | Amino acid sequence of H3-SS-np_258; (H3ssF_258) |
| 51 | Amino acid sequence of H3-SS-np_262; (H3ssF_262) |
| 52 | Amino acid sequence of H3-SS-np_264; (H3ssF_264) |
| 53 | Amino acid sequence of H3-SS-np_265; (H3ssF_265) |
| 54 | Amino acid sequence of H3-SS-np_266; (H3ssF_266) |
| 55 | Amino acid sequence of H3-SS-np_267; (H3ssF_267) |
| 56 | Amino acid sequence of H3-SS-np_268; (H3ssF_268) |
| 57 | Amino acid sequence of H3-SS-np_269; (H3ssF_269) |
| 58 | Amino acid sequence of H3-SS-np_270; (H3ssF_270) |
| 59 | Amino acid sequence of H3-SS-np_271; (H3ssF_271) |
| 60 | Amino acid sequence of H3-SS-np_272; (H3ssF_272) |
| 61 | Amino acid sequence of H3-SS-np_279; (H3ssF_279) |
| 62 | Amino acid sequence of H3-SS-np_281; (H3ssF_281) |
| 63 | Amino acid sequence of H3-SS-np_287; (H3ssF_287) |
| 64 | Amino acid sequence of H3-SS-np_288; (H3ssF_288) |
| 65 | Amino acid sequence of H3-SS-np_289; (H3ssF_289) |
| 66 | Amino acid sequence of H3-SS-np_291; (H3ssF_291) |
| 67 | Amino acid sequence of H3-SS-np_292; (H3ssF_292) |
| 68 | Amino acid sequence of H3-SS-np_293; (H3ssF_293) |
| 69 | Amino acid sequence of H3-SS-np_294; (H3ssF_294) |
| 70 | Amino acid sequence of H3-SS-np_295; (H3ssF_295) |
| 71 | Amino acid sequence of H3-SS-np_296 (based on H7 #21); (H3ssF_296) |
| 72 | Amino acid sequence of H3-SS-np_297 (based on H7 #23); (H3ssF_297) |
| 73 | Amino acid sequence of H3-SS-np_298 (based on #249 and H7 #23); (H3ssF_298) |
| 74 | Amino acid sequence of H3-SS-np_299 (based on #249 and #258); (H3ssF_299) |
| 75 | Amino acid sequence of H3-SS-np_231_HK68; (H3ssF_231_HK68) |
| 76 | Amino acid sequence of H3-SS-np_231_BK79; (H3ssF_231_BK79) |
| 77 | Amino acid sequence of H3-SS-np_231 Wyo03; (H3ssF_231_Wyo03) |
| 78 | Amino acid sequence of H3-SS-np_231_Switz13; (H3ssF_231_Switz13) |
| 79 | Amino acid sequence of H3-SS-np_262_HK68; (H3ssF_262_HK68) |
| 80 | Amino acid sequence of H3-SS-np_262_BK79; (H3ssF_262_BK79) |
| 81 | Amino acid sequence of H3-SS-np_262_Wyo03 ; (H3ssF_262_Wyo03) |
| 82 | Amino acid sequence of H3-SS-np_262_Switz13; (H3ssF_262Switz13) |
| 83 | Amino acid sequence of H3-SS_LS-01 (based on #231, N298D, linker extension); (H3ssLS-01) |

TABLE 2-continued

| PCT SEQ ID NO | Comments |
|---|---|
| 84 | Amino acid sequence of H3-SS_LS-02 (based on #231, M197C, 1244C, N298D, linker extension, added glutamates); (H3ssLS-02) |
| 85 | Amino acid sequence of H3-SS_LS-03 (based on #231, N298D, linker extension, added glutamates); (H3ssLS-03) |
| 86 | Amino acid sequence of H3-SS_LS-04 (based on #231, M197, 1244C, N298D, linker extension, added glutamates); (H3ssLS-04) |
| 87 | Amino acid sequence of H3-SS_LS-05 (based on #266, S300A, linker extension); (H3ssLS-05) |
| 88 | Amino acid sequence of H3-SS_LS-06 (based on #266, N298D, linker extension); (H3ssLS-06) |
| 89 | Amino acid sequence of H3-SS_LS-07 (based on #274, N298D, linker extension); (H3ssLS-07) |
| 90 | Amino acid sequence of H3-SS-SA_01 |
| 91 | Amino acid sequence of H3-SS_SA_02 |
| 92 | Amino acid sequence of H7-SS-np_016 (based on H3 #231); (H7ssF_016) |
| 93 | Amino acid sequence of H7-SS-np_018 (based on H3 #262); (H7ssF_018) |
| 94 | Amino acid sequence of H7-SS-np_020 (based on H3 #264); (H7ss_F020) |
| 95 | Amino acid sequence of H7-SS-np_021 (based on a variation of H3 #231); (H7ssF_021) |
| 96 | Amino acid sequence of H7-SS-np_023(based on a variation of H3 #231); (H7ssF_023) |
| 97 | Amino acid sequence of H7-SS-np_025 (based on H3 #265); (H7ssF_025) |
| 98 | Amino acid sequence of H7-SS-np_026 (based on H3 #256); (H7ssF_026) |
| 99 | Amino acid sequence of H7-SS-np_027 (based on H3 #249); (H7ssF_027) |
| 100 | Amino acid sequence of H7-SS-np_028 (combine H7 #20 and #23); (H7ssF_028) |
| 101 | Amino acid sequence of H7-SS-SA_01 (from H7-SS-np #16); (H7ssSA_01) |
| 102 | Amino acid sequence of H7-SS-SA_02 (from H3-ss np #18); (H7ssSA_02) |
| 103 | Amino acid sequence of H10N8-SS-NP_01 (similar to H3 231, H7 16); (H10ssF_01) |
| 104 | Amino acid sequence of H10N8-SS-np_02 (similar to H3 262, H7 18); (H10ssF_02) |
| 105 | Amino acid sequence of H10N8-SS-np_03 (similar to H3 264, H7 20); (H10ssF_03) |
| 106 | Amino acid sequence of H10N8-SS-np_04 (similar to H3 256, H7 26); (H10ssF_04) |
| 107 | Amino acid sequence of H10N8-SS-np_05 (similar to H7 23); (H10ssF_05) |
| 108 | Amino acid sequence of H10N8-SS-np_06 (similar to H3 249, H7 27); (H10ssF_06) |
| | Protein Constructs With HA Joined to Transmembrane Domain |
| 109 | Amino acid sequence of H3-SS-TM_231_HK68 |
| 110 | Amino acid sequence of H3-SS-TM_231_BK79 |
| 111 | Amino acid sequence of H3-SS_TM_231_Wyo03 |
| 112 | Amino acid sequence of H3-SS-TM_231_Switz13 |
| 113 | Amino acid sequence of H3-SS-TM_256_Den05 |

TABLE 2-continued

| PCT SEQ ID NO | Comments |
|---|---|
| 114 | Amino acid sequence of H3-SS-TM_262_Den05 |
| 115 | Amino acid sequence of H3-SS-TM_264_Den05 |
| 116 | Amino acid sequence of H3-SS-TM_262_HK68 |
| 117 | Amino acid sequence of H3-SS-TM_262_BK79 |
| 118 | Amino acid sequence of H3-SS-TM_262_Wyo03 |
| 119 | Amino acid sequence of H3-SS-TM_262_Switz13 |
| 120 | Amino acid sequence of H7-SS-TM_016 |
| 121 | Amino acid sequence of H7-SS-TM_018 |
| 122 | Amino acid sequence of H7-SS-TM_020 |
| 123 | Amino acid sequence of H7-SS-TM_021 |
| 124 | Amino acid sequence of H7-SS-TM_023 |
| 125 | Amino acid sequence of H7-SS-TM_024 |
| 126 | Amino acid sequence of H7-SS-TM_025 |
| 127 | Amino acid sequence of H7-SS-TM_026 |
| 128 | Amino acid sequence of H7-SS_TM_027 (#16 with H7N7 A/England/268/1996) |
| 129 | Amino acid sequence of H7-SS_TM_028 (#16 with H7N7 A/Netherlands/219/2003) |
| 130 | Amino acid sequence of H3-SS-TM_256_HK68 |
| 131 | Amino acid sequence of H3-SS-TM_258_HK68 |
| | Protein Constructs With HA Joined to Monomeric Subunit |
| 132 | Amino acid sequence of H3-SS-np_300 (based on 231 with glycan at N38 removed); (H3ssF_300) |
| 133 | Amino acid sequence of H3-SS-np_301 (Delta cleavage loop; based on 231); (H3ssF_301) |
| 134 | Amino acid sequence of H3-SS-np_302 (Delta cleavage loop; based on 258); (H3ssF_302) |
| 135 | Amino acid sequence of H3-SS-np_303 (Delta cleavage loop; based on 231); (H3ssF_303) |
| 136 | Amino acid sequence of H3-SS-np_304 (Delta cleavage loop; based on 231); (H3ssF_304) |
| 137 | Amino acid sequence of H3-SS-np_305 (Delta cleavage loop; based on 231); (H3ssF_305) |
| 138 | Amino acid sequence of H3-SS-np_306 (Glycan addition; based on 231); (H3ssF_306) |
| 139 | Amino acid sequence of H3-SS-np_307 (Glycan addition; based on 231); (H3ssF_307) |
| 140 | Amino acid sequence of H3-SS-np_308 (Glycan addition; based on 231); (H3ssF_308) |
| 141 | Amino acid sequence of H3-SS-np_309 (Glycan addition; based on 231); (H3ssF_309) |
| 142 | Amino acid sequence of H3-SS-np_310 (Glycan addition; based on 231); (H3ssF_310) |
| 143 | Amino acid sequence of H3-SS-np_311 (Glycan addition; based on 231); (H3ssF_311) |
| 144 | Amino acid sequence of H3-SS-np_312 (Glycan addition; based on 231); (H3ssF_312) |

TABLE 2-continued

| PCT SEQ ID NO | Comments |
|---|---|
| 145 | Amino acid sequence of H3-SS-np_313 (Glycan addition; based on 231); (H3ssF_313) |
| 146 | Amino acid sequence of H3-SS-np_314 (Glycan addition; based on 231); (H3ssF_314) |
| 147 | Amino acid sequence of H3-SS-LS_08 (based on 249); (H3ssL_08) |
| 148 | Amino acid sequence of H3-SS-LS_09 (based on 249 + 256); (H3ssL_09) |
| 149 | Amino acid sequence of H3-SS-LS_10 (based on 249 + 258); (H3ssL_10) |
| 150 | Amino acid sequence of H3-SS-LS_11 (based on 256); (H3ssL_11) |
| 151 | Amino acid sequence of H3-SS-LS_12 (based on 258); (H3ssL_12) |
| 152 | Amino acid sequence of H7-SS-LS_01 (based on H3 258); (H7ssL_01) |
| 153 | Amino acid sequence of H7-SS-LS_02 (based on H3 249); (H7ssL_02) |
| 154 | Amino acid sequence of H7-SS-LS_03 (based on H3 249 & 258); (H7ssL_03) |
| 155 | Amino acid sequence of H7-SS-LS_04 (H7 20 + 26); (H7ssL_04) |
| 156 | Amino acid sequence of H7-SS-LS_05 (H7 23 + 26); (H7ssL05) |
| 157 | Amino acid sequence of H7-SS-LS_06 (H7 20 + 23 + 26); (H7ssL06) |
| 158 | Amino acid sequence of H3-SS-np_256_HK68; (H3ssF_256) |
| 159 | Amino acid sequence of H3-SS-np_258_HK68; (H3ssF_258) |

The influenza viruses, and the sequences there from, listed above are exemplary, and any other Group 2 influenza virus, and sequences and proteins therefrom can be used to practice the invention.

The trimeric HA protein on the surface of the virus comprises a globular head region and a stem, or stalk, region, which anchors the HA protein into the viral lipid envelope. The head region of influenza HA is formed exclusively from a major portion of the HA1 polypeptide, whereas the stalk region is made from segments of HA1 and HA2. According to the present invention, the head region consists of the amino acids of a Group 2 influenza HA protein corresponding to, approximately, amino acids 60-329 of the full-length HA protein of influenza A virus (A/Denmark/35/2005 (H3N2)) (SEQ ID NO:4). Similarly, as used herein, the stem region is formed from the amino acids of a Group 2 influenza HA protein corresponding to amino acids 1-59 and 330-519 of the full-length HA protein of influenza A virus (A/Denmark/35/2005 (H3N2)) (SEQ ID NO:4). As used herein, the term approximately, with regard to the head and stem regions means that the sequences cited above may vary in length by several (e.g., 1, 2, 3, 4, 5, 6, 7, 8, 9, or 10) amino acids without affecting the nature of the invention. Thus, for example, the head region may consist of amino acids 64-329, amino acids 60-326 or amino acids 62-327. Generally, the head and stem region will not vary from the locations recited above by more than ten amino acids. In certain aspects of the invention, the head region consists of the amino acid sequence between, and including, the amino acid residues corresponding to Cys68 and Cys321 of influenza A virus (A/Denmark/35/2005 (H3N2)) (SEQ ID NO:4). With regard to HA proteins, it is understood by those skilled in the art that HA proteins from different influenza viruses may have different lengths due to sequence differences (insertions, deletions) in the protein. Thus, reference to a corresponding region refers to a region of another protein that is identical, or nearly so (e.g., at least 90% identical, at least 95%, identical, at least 98% identical or at least 99% identical), in sequence, structure and/or function to the region being compared. For example, with regard to the stem region of an HA protein, the corresponding region in another HA protein may not have the same residue numbers, but will have a nearly identical sequence and will perform the same function. As an example, in the embodiment stated above, the head region of the HA protein from influenza virus A virus (A/Denmark/35/2005 (H3N2)) (SEQ ID NO:4) begins at amino acid 60. The corresponding amino acid at the beginning of the head region in A/New Caledonia/20/1999 (H1) is amino acid C60. To better clarify sequence comparisons between viruses, numbering systems are used by those in the field, which relate amino acid positions to a reference sequence. Thus, corresponding amino acid residues in HA proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the $100^{th}$ residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. While the H3 numbering system can be used to identify the location of amino acids, unless otherwise noted, the location of amino acid residues in HA proteins will be identified by general reference to the position of a corresponding amino acid from a sequence disclosed herein.

The inventors have also discovered that by combining specific sequences of the influenza virus HA protein with unrelated proteins, and nanoparticles made therefrom that are capable of presenting the HA protein to the immune system, immune responses to targeted regions of the HA protein can be elicited. Thus, one embodiment of the present invention is a protein construct comprising a Group 2 influenza virus HA protein joined to at least a portion of a monomeric subunit protein, wherein the head region of the Group 2 influenza virus HA protein has been replaced with an amino acid sequence comprising less than 5 contiguous amino acid residues from the head region of an influenza HA protein, and wherein the protein construct is capable of forming a nanoparticle.

By joining at least a portion of a Group 2 influenza HA protein to a monomeric subunit, protein constructs of the present invention are capable of assembling into nanoparticles expressing trimers of Group 2 influenza HA protein on their surface. Such trimers are in a pre-fusion form, and connection to the monomeric subunit, and expression on the nanoparticle stabilize the pre-fusion proteins in their trimeric form. Because of this, the HA protein is presented in a more native form, meaning certain surfaces of the stem polypeptides are not exposed, thereby reducing the risk that the stem polypeptides may induce an unfavorable antibody response.

In certain aspects, the at least a portion of a Group 2 influenza virus HA protein comprises at least one immunogenic portion from the stem region of a Group 2 influenza virus HA protein, wherein the protein construct elicits protective antibodies against an influenza virus. In certain aspects, the at least a portion of a Group 2 influenza virus HA protein comprises at least one immunogenic portion from the stem region of an HA protein selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein.

In certain aspects, the at least a portion of a Group 2 influenza virus HA protein comprises at least one immunogenic portion from the HA portion of a protein comprising an amino acid sequence at least 80%, at least 85% identical, at least 90% identical, at least 95% identical, at least 97% identical, or at least 99%, identical to a sequence selected from the group consisting of SEQ ID NO:4-SEQ ID NO:26. In certain aspects, the at least a portion of a Group 2 influenza virus HA protein comprises at least one immunogenic portion from the HA portion of a protein comprising an amino acid sequence selected from the group consisting of SEQ ID NO:4-SEQ ID NO:26. In certain aspects, the at least a portion of a Group 2 influenza virus HA protein comprises at least one immunogenic portion from the HA portion of a protein comprising an amino acid sequence at least 80% identical, at least 85% identical, at least 90% identical, at least 95% identical, at least 97% identical, or at least 99% identical to a sequence selected from the group consisting of SEQ ID NO: 47-SEQ ID NO:159. In certain aspects, the at least a portion of a Group 2 influenza virus HA protein comprises at least one immunogenic portion from the HA portion of a protein comprising an amino acid sequence at least 80% identical, at least 85% identical, at least 90% identical, at least 95% identical, at least 97% identical, or at least 99%, identical to a sequence selected from the group consisting of SEQ ID NO: 47-SEQ ID NO:159. In certain aspects, the at least a portion of a Group 2 influenze virus HA protein comprises at least one immunogenic portion from the HA portion of a protein comprising an amino acid sequence selected from the group consisting of SEQ ID NO:47-SEQ ID NO:159. In certain aspects, the at least a portion of a Group 2 influenza virus HA protein comprises at least one immunogenic portion from the HA portion of a protein comprising an amino acid sequence selected from the group consisting of SEQ ID NO:47-SEQ ID NO:159. In one embodiment protein constructs comprising immunogenic portions of a Group 2 influenza HA protein elicit the production of broadly protective antibodies against influenza virus.

Immunogenic portions of proteins can comprise epitopes, which are clusters of amino acid residues that are recognized by the immune system, thereby eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the protein) but which are in close special proximity in the finally folded protein. It is well understood by those skilled in the art that epitopes require a minimum of six amino acid residues in order to be recognized by the immune system. Thus, in certain aspects the immunogenic portion from a Group 2 influenza HA protein comprises at least one epitope. In one embodiment the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein having an amino acid sequence at least 80% identical, at least 85% identical, at least 90% identical, at least 95% identical, at least 97% identical, or at least 99% identical to an HA protein from an influenza virus selected from those listed in Table 2. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein from an influenza virus selected from those listed in Table 2, and variants thereof. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein comprising a sequence at least 80%, at least 85% identical, at least 90% identical, at least 95% identical, at least 97% identical, or at least 99%, identical to a sequence selected from the group consisting of SEQ ID NO:4-SEQ ID NO:26. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the stem region of a Group 2 influenza HA protein comprising a sequence selected from the group consisting of SEQ ID NO:4-SEQ ID NO:26. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the HA portion of a protein comprising a sequence at least 80%, at least 85% identical, at least 90% identical, at least 95% identical, at least 97% identical, or at least 99%, identical to a sequence selected from the group consisting of SEQ ID NO:47-SEQ ID NO:159. In certain aspects the at least a portion of a Group 2 influenza virus HA protein comprises at least 6 amino acids, at least 10 amino acids, at least 25 amino acids, at least 50 amino acids, at least 75 amino acids or at least 100 amino acids from the HA portion of a protein comprising a sequence selected from the group consisting of SEQ ID NO:47-SEQ ID NO:159.

In certain aspects of the invention, the amino acids are contiguous amino acids from the stem region of a Group 2 influenza virus HA protein. In certain aspects, protein constructs of the invention comprising at least 6 amino acids, at least 10 amino acids, at least 25 amino acids, at least 50 amino acids, at least 75 amino acids or at least 100 amino acids from the stem region of a Group 2 influenza virus HA protein elicit the production of broadly protective antibodies against influenza virus. In certain aspects of the invention, a protein construct comprises at least 6 amino acids, at least 10 amino acids, at least 25 amino acids, at least 50 amino acids, at least 75 amino acids or at least 100 amino acids from the stem region of a Group 2 influenza virus HA protein comprising an amino acid sequence at least 80% identical, at least 85% identical, at least 90% identical, at least 95% identical, at least 97% identical, or at least 99% identical to sequence selected from the group consisting of SEQ ID NO:4-SEQ ID NO:26. In certain aspects of the present invention, a protein construct comprises at least 6 amino acids, at least 10 amino acids, at least 25 amino acids, at least 50 amino acids, at least 75 amino acids or at least 100 amino acids from the stem region of a Group 2 influenza virus HA protein comprising an amino acid sequence selected from the group consisting of SEQ ID NO:4-SEQ ID NO:26. In certain aspects, the amino acids are non-contiguous, but are in close spatial proximity in the final protein.

While the present application exemplifies the use of stem region sequences from several exemplary Group 2 influenza virus HA proteins, the invention may also be practiced using stem regions from proteins comprising variations of the disclosed Group 2 influenza HA sequences. Thus, in certain aspects of the invention, the Group 2 influenza HA protein is from a virus selected from the Group 2 viruses listed in Table 2, and variants thereof. In certain aspects, the Group 2 influenza virus HA protein comprises an amino acid sequence at least 80%, at least 85%, at least 90%, at least 92%, at least 94%, at least 96%, at least 98% or at least 99% identical the stem region of a Group 2 influenza virus HA protein comprising an amino acid sequence selected from the group consisting of SEQ ID NO:4-SEQ ID NO:26. In certain aspects, the Group 2 influenza HA protein comprises an amino acid sequence selected from the group consisting of SEQ ID NO:4-SEQ ID NO:26.

In certain aspects of the invention, the head region sequence of the HA protein in the protein construct is replaced with a linker sequence. Any linker sequence may be used so long as the stem region sequences are able to adopt the desired conformation. While any amino acids may be used to make the linker sequence, in certain aspects of the invention the amino acids lack large or charged side chains. Preferred amino acids to use include, but are not limited to, cysteine, serine, glycine, alanine, valine and proline. In one embodiment, the linker is made from one or more amino acids selected from the group consisting of serine, glycine, cysteine, valine, proline and/or phenylalanine residues. In certain embodiments, it may be desirable to include an amino acid residue, the side chain of which is capable of forming a covalent bond, such as a disulfide bond, with another amino acid. One example of such an amino acid is cysteine. The length of the linker sequence may vary, but preferred embodiments use the shortest possible sequence in order to allow the stem sequences to form the desired structure. In certain aspects, the linker sequence is less than 12 amino acids in length. In one embodiment, the linker sequence is less than 10 amino acids in length. In one embodiment, the linker sequence is less than 5 amino acids in length. In preferred embodiments, the linker sequence lacks contiguous amino acid sequences from the head region of an HA protein. In certain aspects, the linker sequence comprises less than 5 contiguous amino acids from the head region of an HA protein. In certain aspects the head region sequence is replaced with an amino acid sequence comprising SEQ ID NO34, SEQ ID NO:35, or variants thereof.

The inventors have also discovered that the stability of protein constructs and nanoparticles of the invention can be improved by making further alterations to the Group 2 influenza virus HA protein of the disclosed protein constructs. For example, the inventors have discovered that extending the length of helix A improves the performance of protein constructs of the invention. Thus, one embodiment is a protein construct of the invention in which helix A has been extended by the addition of amino acids. One embodiment is a protein construct of the invention, wherein the protein construct comprises a Group 2 influenza virus HA protein joined to at least a portion of a monomeric subunit, wherein the head region of the Group 2 influenza virus HA protein has been replaced with an amino acid sequence comprising less than 5 contiguous amino acid residues from the head region of an influenza HA protein, and wherein the carboxy-terminal end of helix A (i.e., the portion that links to the amino end of helix C) has been extended by the addition of amino acid residues. It should be appreciated that because the goal is to extend the helix, the sequence of amino acids added to the carboxy-terminal end of helix A should preferably form a helix. In certain aspects of the invention, the length of helix A is extended by adding an amino acid sequence comprising SEQ ID NOs:36 or 37, or helix-forming variants thereof, to the carboxyl-end of helix A. In certain aspects of the invention, the length of helix A is extended by adding a sequence comprising, or consisting of, $X_1LMX_2Q$ (SEQ ID NO: 160), or helix-forming variants thereof, to the carboxyl-end of helix A, wherein the amino acids at positions $X_1$ and $X_2$ are acidic amino acids. It should be noted that $X_1$ and $X_2$ can, but need not, be the same amino acid residue. In certain aspects, the residues at the first and fourth position of such a linker are selected from the group consisting of glutamine, glutamic acid, asparagine, aspartic acid, glycine, and proline. In one embodiment, helix A is extended by adding an amino acid sequence consisting of SEQ ID NOs:36 or 37, or helix-forming variants thereof, to the carboxyl-end of helix A. In certain aspects of the invention, the length of helix A is extended by adding a sequence comprising ALMAQ (SEQ ID NO: 36) or ELMEQ (SEQ ID NO: 37), or helix-forming variants thereof, to the carboxyl-end of helix A. In certain aspects of the invention, the length of helix A is extended by adding a sequence consisting of ALMAQ (SEQ ID NO: 36) or ELMEQ (SEQ ID NO: 37), or helix-forming variants thereof, to the carboxyl-end of helix A.

In addition to extension of helix A, the inventors have discovered that modification of the amino acid sequence joining the carboxyl-end of helix A to the amino-end of helix C (herein referred to as the inter-helix region or inter-helix loop, one example of which is represented by SEQ ID NO:38), improves the stability and performance of protein constructs and nanoparticles of the invention. More particularly, the inventors have found that shortening the length of the inter-helix region improves the stability and performance of protein constructs and nanoparticles of the invention. Thus, in certain aspects of the invention, the amino acid sequence joining the carboxyl-end of helix A to the amino-end of helix C in a protein construct of the invention is modified to improve the stability of a protein construct of the invention. It should be appreciated that improving the stability of a protein construct of the invention means stabilizing the three-dimensional structure of a protein construct of the invention, and in particular the stem-region of a protein construct of the invention, such that it approximates the three-dimensional structure of the stem region of a native Group 2 influenza HA protein, and is able to elicit an immune response to a Group 2 influenza virus. Thus, in certain aspects of the invention, the inter-helix region of a protein construct of the invention is shortened. Such shortening can be achieved by removing amino acids from the existing inter-helix region, or by replacing amino acids of the inter-helix region with a linker sequence. In certain aspects, the inter-helix region of a protein construct of the invention is shortened to less than 6 amino acids. In certain aspects, amino acids of the inter-helix region are replaced with a linker sequence. In certain aspects of the invention, amino acids of an inter-helix region corresponding to the inter-helix region of an influenza virus A (Denmark/35/2005 (H3N2)) HA protein (SEQ ID NO:4) are replaced with a linker sequence. In certain aspects of the invention, amino acids of an inter-helix region corresponding to amino acids 402-437 of an influenza virus A (Denmark/35/2005(H3N2)) HA protein (SEQ ID NO:4) are replaced with a linker sequence. In certain aspects of the invention, an inter-helix region comprising amino acids 402-437 of SEQ ID NO:4 is replaced with a linker sequence. In certain aspects of the invention, an inter-helix region corresponding to a region of influenza virus A (Denmark/35/2005(H3N2)) HA protein (SEQ ID NO:4) represented by SEQ ID NO:38 is replaced with a linker sequence. In certain aspects of the invention, an inter-helix region of the Group 2 influenza virus HA protein comprising an amino acid sequence at least 90%, at least 97%, at least 99% identical to SEQ ID NO: 38, is replaced with a linker sequence. In one embodiment, a region of the Group 2 influenza virus HA protein comprising SEQ ID NO: 38, is replaced with a linker sequence. In certain aspects of the invention, a region of the Group 2 influenza virus HA protein consisting of SEQ ID NO: 38, is replaced with a linker sequence. In certain aspects of the invention, the inter-helix region is replaced with a linker sequence comprising GGPD (SEQ ID NO:39). In certain aspects of the invention, an inter-helix region corresponding to amino acids 402-437 of SEQ ID NO:4 is replaced with a linker sequence having the physical spatial, and/or chemical properties of a peptide consisting of GGPD (SEQ ID NO:39). In certain aspects of the invention, an inter-helix region corresponding to amino acids 402-437 of SEQ ID NO:4 is replaced with a linker sequence having the propensity to form a helix. In certain aspects of the invention, an inter-helix region corresponding to amino acids 402-437 of SEQ ID NO:4 is replaced with a linker sequence comprising GGPD (SEQ ID NO:39), or conservative variants thereof. In certain aspects of the invention, the inter-helix region is replaced with a linker sequence consisting of GGPD (SEQ ID NO:39).

As has been previously described, protein constructs of the invention can contain one, several or all of the mutations and sequence alterations described herein. Thus, for example, a protein construct in which helix A has been extended, as described supra, can also have the inter-helix region shortened or replaced with a linker sequence, as described supra. Thus, one aspect of the invention is a protein construct comprising a Group 2 influenza virus HA protein joined to at least a portion of a monomeric subunit protein, wherein the head region of the Group 2 influenza virus HA protein has been replaced with an amino acid sequence comprising less than 5 contiguous amino acid residues from the head region of an influenza HA protein, wherein the inter-helix region has been shortened or replaced with a linker sequence, and wherein the protein construct is capable of forming a nanoparticle. Methods of replacing the HA protein head region, and methods of shortening or replacing the inter-helix region are disclosed herein. It should be understood that in embodiments in which the carboxyl end of helix A has been extended by the addition of amino acids, the inter-helix region would be replaced with a linker that joins the amino-terminal end of helix C with the carboxyl-terminal end of the extension sequence of helix A.

The inventors have further discovered that the stability of protein constructs of the invention can be improved by making site-specific mutations in the sequence of the Group 2 influenza virus stem region. In particular, mutations that form ionic bonds, salt bridges, of that increase hydrophobic packing, and the like, can strengthen the stability of protein constructs and nanoparticles of the invention. Thus, in certain aspects of the invention, a protein construct of the invention comprises one or more mutations that forms or strengthens an ionic interaction, or a salt bridge, or that increases hydrophobic packing. Any type of mutation that has the desired effect of increasing the stability of a protein construct of the invention can be made, although substitution mutations are preferred. In certain aspects of the invention, a mutation is made in the Group 2 influenza virus HA protein at an amino acid location corresponding to a location in SEQ ID NO:4 selected from the group consisting of K396, L397, L400, 5438, N440, E448, T452 and N461. In one embodiment, the amino acid corresponding to K396 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to K396 in the influenza virus A (Denmark/35/2005(H3N2) HA protein (SEQ ID NO:4) is changed to a methionine or a leucine. In one embodiment, the amino acid corresponding to L397 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to L397 in the influenza virus A (Denmark/35/2005(H3N2) HA protein (SEQ ID NO:4) is changed to a valine. In certain aspects of the invention, the amino acid corresponding to L400 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to L400 in the influenza virus A (Denmark/35/2005(H3N2) HA protein (SEQ ID NO:4) is changed to a valine. In certain aspects of the invention, the amino acid corresponding to 5438 in the influenza virus A (Denmark/35/2005(H3N2) HA protein (SEQ ID NO:4) is changed to an amino acid residue selected from the group consisting of asparagine, glutamine, serine, threonine, and cysteine. In certain aspects of the invention, the amino acid corresponding to 5438 in the influenza virus A (Denmark/35/2005(H3N2) HA protein (SEQ ID NO:4) is changed to a cysteine. In certain aspects of the invention, the amino acid corresponding to N440 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to N440 in the influenza virus A (Denmark/35/2005(H3N2) HA protein (SEQ ID NO:4) is changed to a leucine. In certain aspects of the invention, the amino acid corresponding to E448 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to E448 in the influenza virus A (Denmark/35/2005(H3N2) HA protein (SEQ ID NO:4) is changed to a leucine. In certain aspects of the invention, the amino acid corresponding to T452 in the influenza virus A (Denmark/35/2005(H3N2) HA protein (SEQ ID NO:4) is changed to an amino acid residue selected from the group consisting of methionine, leucine, isoleucine, alanine and valine. In certain aspects of the invention, the amino acid corresponding to T452 in the influenza virus A (Denmark/35/2005(H3N2) HA protein (SEQ ID NO:4) is changed to a valine. In certain aspects of the invention, the amino acid corresponding to N461 in the influenza virus A (Denmark/35/2005(H3N2) HA protein (SEQ ID NO:4) is changed to an amino acid residue selected from the group consisting of histidine, lysine, glutamic acid, aspartic acid, and arginine. In certain aspects of the invention, the amino acid corresponding to N461 in the influenza virus A (Denmark/35/2005(H3N2) HA protein (SEQ ID NO:4) is changed to an amino acid residue selected from the group consisting of histidine, lysine, and arginine. In certain aspects of the invention, the amino acid corresponding to N461 in the influenza virus A (Denmark/35/2005(H3N2) HA protein (SEQ ID NO:4) is changed to an arginine.

Additional mutations that may stabilize protein constructs of the invention include a mutation at an amino acid location corresponding to a location in SEQ ID NO:4 selected from the group consisting of G39, T46, N54, T58, L331, N338, and Q392. It should be understood that mutations at such locations can include those in which the amino acid being inserted is similar in properties to those suggested herein.

In certain aspects of the invention, the amino acid corresponding to G39 in the influenza virus A (Denmark/35/2005 (H3N2) HA protein (SEQ ID NO:4) is changed to an amino acid residue selected from the group consisting of cysteine, serine, threonine, proline, asparagine, and glutamine In certain aspects of the invention, the amino acid corresponding to G39 in the influenza virus A (Denmark/35/2005 (H3N2) HA protein (SEQ ID NO:4) is changed to a cysteine.

In certain aspects of the invention, the amino acid corresponding to T46 in the influenza virus A (Denmark/35/2005 (H3N2) HA protein (SEQ ID NO:4) is changed to an amino acid residue selected from the group consisting of cysteine, serine, threonine, proline, asparagine, and glutamine. In certain aspects of the invention, the amino acid corresponding to T46 in the influenza virus A (Denmark/35/2005 (H3N2) HA protein (SEQ ID NO:4) is changed to a cysteine.

In certain aspects of the invention, the amino acid corresponding to N54 in the influenza virus A (Denmark/35/2005 (H3N2) HA protein (SEQ ID NO:4) is changed to an amino acid residue selected from the group consisting of histidine, arginine and lysine. In certain aspects of the invention, the amino acid corresponding to N54 in the influenza virus A (Denmark/35/2005(H3N2) HA protein (SEQ ID NO:4) is changed to a histidine.

In certain aspects of the invention, the amino acid corresponding to T58 in the influenza virus A (Denmark/35/2005 (H3N2) HA protein (SEQ ID NO:4) is changed to an amino acid residue selected from the group consisting of methionine, leucine, isoleucine, alanine and valine. In certain aspects of the invention, the amino acid corresponding to T58 in the influenza virus A (Denmark/35/2005(H3N2) HA protein (SEQ ID NO:4) is changed to a leucine.

In certain aspects of the invention, the amino acid corresponding to L331 in the influenza virus A (Denmark/35/2005(H3N2) HA protein (SEQ ID NO:4) is changed to an amino acid residue selected from the group consisting of histidine, arginine and lysine. In certain aspects of the invention, the amino acid corresponding to L331 in the influenza virus A (Denmark/35/2005(H3N2) HA protein (SEQ ID NO:4) is changed to a lysine.

In certain aspects of the invention, the amino acid corresponding to N338 in the influenza virus A (Denmark/35/2005(H3N2) HA protein (SEQ ID NO:4) is changed to an amino acid residue selected from the group consisting of cysteine, serine, proline, asparagine, glutamine, and threonine. In certain aspects of the invention, the amino acid corresponding to N338 in the influenza virus A (Denmark/35/2005(H3N2) HA protein (SEQ ID NO:4) is changed to a cysteine.

In certain aspects of the invention, the amino acid corresponding to Q392 in the influenza virus A (Denmark/35/2005(H3N2) HA protein (SEQ ID NO:4) is changed to an amino acid residue selected from the group consisting of cysteine, serine, proline, asparagine, glutamine, and threonine. In certain aspects of the invention, the amino acid corresponding to Q392 in the influenza virus A (Denmark/35/2005(H3N2) HA protein (SEQ ID NO:4) is changed to a cysteine.

In addition to the above, the inventors have discovered that mutations adding glycan linkage sites can be beneficial. Thus, in certain aspects of the invention, the protein construct comprise one or more mutations, or one or more pairs of mutations, selected from the group consisting of Q49N/E51T (mutation to add a group 1 glycan), E56N/V59T (mutations in head linker and adjacent residue), V59N/P61T (mutations in head linker), G62N/G64T (mutations in head linker), V329N/L331T (mutations in head linker and adjacent residue), L331N/L333T, D437N/Y439T (mutations in interhelix linker and adjacent residue), Q432N/G434T (inserted G) (mutations in interhelix linker and adjacent residue), Q372N/S374T, and A492N/I494T.

In addition, in certain aspects of the invention, the loop corresponding to amino acids 339-357 in the influenza virus A (Denmark/35/2005(H3N2) HA protein (SEQ ID NO:4) can be replaced with a glycine linker.

As has been previously described, protein constructs of the invention can contain one, several or all of the mutations and sequence alterations described herein. Thus, for example, a protein construct in which helix A has been extended, as described herein, can also have the inter-helix region shortened or replaced with a linker sequence, as described herein, and can also contain one or more of the site-specific mutations described herein. Thus, one aspect of the invention is a protein construct comprising a Group 2 influenza virus HA protein joined to at least a portion of a monomeric subunit protein, wherein the head region of the Group 2 influenza virus HA protein has been replaced with an amino acid sequence comprising less than 5 contiguous amino acid residues from the head region of an influenza HA protein, wherein the inter-helix region has been shortened or replaced with a linker sequence, wherein the HA portion of the protein construct comprises one or more site-specific mutation at a location corresponding to a location in SEQ ID NO:4 selected from the group consisting of K396, L397, L400, 5438, N440, E448, T452, N461, G39, T46, N54, T58, L331, N338, and D437, and wherein the protein construct is capable of forming a nanoparticle. Such constructs may also comprise one or more mutations, or one or more pairs of mutations, selected from the group consisting of Q49N/E51T, E56N/V59T (mutations in head linker and adjacent residue), V59N/P61T (mutations in head linker), G62N/G64T (mutations in head linker), V329N/L331T (mutations in head linker and adjacent residue), L331N/L333T, D437N/Y439T (mutations in interhelix linker and adjacent residue), Q432N/G434T (inserted G) (mutations in interhelix linker and adjacent residue), Q372N/S374T, and A492N/I494T. Methods of replacing the HA protein head region, extending helix A, shortening or replacing the inter-helix region, and suitable site-specific mutations have been disclosed herein. It should be understood that in embodiments in which the carboxyl end of helix A has been extended by the addition of amino acids, the inter-helix region would be replaced with a linker that joins the amino-terminal end of helix C with the carboxyl-terminal end of the extension sequence of helix A.

Heretofore has been described specific aspects of a protein construct of the invention, useful for producing nanoparticle vaccines. To aid in clarifying the invention, the inventors will now describe various aspects in alternative and greater detail. It should be understood that any aspects of the invention described below also apply to embodiments and aspects of protein constructs already described herein.

Protein constructs of the present invention can be made using recombinant technology to link together various portions of Group 3 influenza HA proteins, and make sequences alterations thereto. Recombinant technology can also be used to add appropriate linkers and monomeric subunits. In this way, protein constructs can be produced that comprise specific sequences necessary to produce protein constructs and consequently, nanoparticle vaccines of the invention. Thus, one embodiment of the present invention is a protein construct (also referred to herein as a fusion protein) comprising a first amino acid sequence from the stem region of a Group 2 influenza virus HA protein and a second amino acid sequence from the stem region of a Group 2 influenza virus HA protein, the first and second amino acid sequences being covalently linked by a linker sequence, wherein the first amino acid sequence comprises at least 20 contiguous amino acid residues from the amino acid sequence upstream of the amino-terminal end of the head region sequence;

wherein the second amino acid sequence comprises at least 20 contiguous amino acid residues from the amino acid sequence downstream of the carboxyl-terminal end of the head region sequence; and, wherein the first or second amino acid sequence is joined to at least a portion of a monomeric subunit domain such that the protein construct is capable of forming a nanoparticle.

In certain aspects of the invention, the first amino acid sequence is from the stem region of a Group 2 influenza virus HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the first amino acid sequence is from the stem region of an HA protein from a Group 2 virus listed in Table 2. In certain aspects of the invention, the first amino acid sequence is from the stem region of a Group 2 influenza HA protein, wherein the HA protein comprises an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the first amino acid sequence is from the stem region of a Group 2 influenza HA protein, wherein the HA protein comprises a sequence selected from the group consisting of SEQ ID NO:4-SEQ ID NO:26 and SEQ ID NO:47-SEQ ID NO:159.

In certain aspects of the invention, the second amino acid sequence is from the stem region of a Group 2 influenza HA protein from a virus selected from the group consisting of an influenza H3 virus, an influenza H4 virus, an H7 influenza virus, an H10 influenza virus, an H14 influenza virus, and an H15 influenza virus. In certain aspects of the invention, the second amino acid sequence is from the stem region of an HA protein from a Group 2 virus listed in Table 2. In certain aspects of the invention, the second amino acid sequence is from the stem region of a Group 2 influenza virus HA protein, wherein the HA protein comprises an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the second amino acid sequence is from the stem region of a Group 2 influenza virus HA protein comprising a sequence selected from the group consisting of SEQ ID NO:4-SEQ ID NO:26 and SEQ ID NO:47-SEQ ID NO:159.

As noted above, the first amino acid sequence comprises at least 20 contiguous amino acid residues from the amino acid sequence upstream of the amino-terminal end of the head region sequence. According to the present invention, the term upstream refers to the entirety of the amino acid sequence linked to the amino-terminal end of the first amino acid residue of the head region. Preferred upstream sequences are those that are immediately adjacent to the head region sequence. In certain aspects of the invention, the amino-terminal end of the head region is located at the amino acid residue corresponding to Q60 of the HA protein of influenza A (Denmark/35/2005 (H3N2)) HA protein (SEQ ID NO:4) In certain aspects of the invention, the first amino acid sequence comprises at least 20 contiguous amino acid residues from the region of a Group 2 influenza virus HA protein corresponding to amino acid residues 1-59 of the HA protein of influenza A Denmark/35/2005 (H3N2)) represented by SEQ ID NO:4. In certain aspects of the invention, the first amino acid sequence comprises at least 20 contiguous amino acid residues from a sequence at least 85%, at least 90%, at least 95% or at least 97% identical to a sequence selected from the group consisting of SEQ ID NO:27, SEQ ID NO:28 and SEQ ID NO:29. In certain aspects of the invention, the first amino acid sequence comprises at least 20 contiguous amino acid residues from a sequence selected from the group consisting of SEQ ID NO:27, SEQ ID NO:28 and SEQ ID NO:29.

In certain aspects of the invention, the first amino acid sequence comprises at least 40 contiguous amino acid residues from the amino acid region of an HA protein corresponding to amino acid residues 1-59 of influenza A Denmark/35/2005 (H3N2)) HA protein (SEQ ID NO:4). In certain aspects of the invention, the first amino acid sequence comprises at least 40 contiguous amino acid residues from a sequence at least 85%, at least 90%, at least 95% or at least 97% identical to SEQ ID NO:27 or SEQ ID NO:28. In certain aspects of the invention, the first amino acid sequence comprises at least 40 contiguous amino acid residues from SEQ ID NO:27 or SEQ ID NO:28.

In certain aspects of the invention, the first amino acid sequence comprises a sequence at least 85%, at least 90%, at least 95% or at least 97% identical to SEQ ID NO:27. In one embodiment, the first amino acid sequence comprises SEQ ID NO:27.

As noted above, the second amino acid sequence comprises at least 20 contiguous amino acid residues from the amino acid sequence downstream of the carboxyl-terminal end of the head region sequence. According to the present invention, the term downstream refers to the entirety of the amino acid sequence linked to the carboxyl-terminal amino acid residue of the head region. Preferred upstream sequences are those that are immediately adjacent to the head region sequence. In certain aspects of the invention, the carboxyl-terminal end of the head region is located at the amino acid position corresponding to T329 of the HA protein of influenza A (Denmark/35/2005(H3N2)) HA protein represented by SEQ ID NO:4. Thus, in certain aspects of the invention, the second amino acid sequence comprises at least 20 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 20 contiguous amino acids from a region of a Group 2 influenza HA protein comprising amino acid residues 330-519 of influenza A (Denmark/35/2005(H3N2)) (SEQ ID NO:4). In one embodiment, the second amino acid sequence comprises at least 20 contiguous amino acid residues from a sequence at least 85%, at least 90%, at least 95% or at least 97% identical to a sequence selected from the group consisting of SEQ ID NO:30, SEQ ID NO:31, SEQ ID NO:32 and SEQ ID NO:33. In one embodiment, the second amino acid sequence comprises at least 20 contiguous amino acid residues from a sequence selected from the group consisting of SEQ ID NO:30, SEQ ID NO:31, SEQ ID NO:32 and SEQ ID NO:33.

In certain aspects of the invention, the second amino acid sequence comprises at least 40 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 40 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40 contiguous amino acid residues from a sequence at least 85%, at least 90%, at least 95% or at least 97% identical to a sequence selected from the group consisting of SEQ ID NO:30, SEQ ID NO:31, and SEQ ID NO:32. In certain aspects of the invention, the second amino acid sequence comprises at least 20 contiguous amino acid residues from a sequence selected from the group consisting of SEQ ID NO:30, SEQ ID NO:31, and SEQ ID NO:32.

In certain aspects of the invention, the second amino acid sequence comprises an amino acid sequence at least 85%, at least 90%, at least 95% or at least 97% identical to SEQ ID NO:36. In one embodiment, the second amino acid sequence comprises SEQ ID NO:36.

In certain aspects of the invention, the second amino acid sequence comprises at least 60, at least 72, at least 75, at least 100, at least 150, at least 175, or at least 190 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 60, at least 72, at least 75, at least 100, at least 150, at least 175, or at least 190 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40, at least 60, at least 72, at least 75, at least 100, at least 150, at least 175, or at least 190 contiguous amino acid residues from a sequence at least 85%, at least 90%, at least 95% or at least 97% identical to SEQ ID NO:30. In one embodiment, the second amino acid sequence comprises at least 40, at least 60, at least 72, at least 75, at least 100, at least 150, at least 175, or at least 190 contiguous amino acid residues from SEQ ID NO:30.

As noted above, the first and second amino acid sequences of the protein construct can be joined by a linker sequence. Any linker sequence can be used as long as the linker sequence has less than five contiguous amino acid residues from the head region of an HA protein and so long as the first and second amino acids are able to form the desired conformation. In one embodiment, the linker sequence is less than 10 amino acids, less than 7 amino acids or less than 5 amino acids in length. In one embodiment, the linker sequence comprises glycine and serine. In one embodiment, the linker sequence joins the carboxyl-terminal end of the first amino acid sequence to the amino-terminal end of the second amino acid sequence. In certain aspects of the invention, the linker sequence joins the carboxyl-terminal end of the second amino acid sequence to the amino-terminal end of the first amino acid sequence. In certain aspects of the invention, the linker sequence is similar in chemical and special properties to a peptide consisting of SEQ ID NO:34 or SEQ ID NO:35. In certain aspects of the invention, the linker comprises SEQ ID NO:34 or SEQ ID NO:35, or conservative variants thereof. In one embodiment, the linker comprises SEQ ID NO:34 or SEQ ID NO:35. In certain aspects of the invention, the linker consists of SEQ ID NO:34 or SEQ ID NO:35.

In certain aspects of the invention, the second amino acid sequence comprises an amino acid sequence from a Group 2 influenza virus HA protein, corresponding to amino acids 330-519 of influenza A (Denmark/35/2005 (H3N2)) HA protein (SEQ ID NO:4), wherein the region corresponding to the inter-helix region of the HA protein (SEQ ID NO:4) is replaced with a linker peptide. In certain aspects of the invention, the inter-helix region of the influenza A (Denmark/35/2005 (H3N2)) HA protein (SEQ ID NO:4) consists essentially of amino acids 402-437 of SEQ ID NO:4. Thus, in certain aspects of the invention, the second amino acid sequence comprises an amino acid sequence from a Group 2 influenza virus HA protein, corresponding to amino acids 330-519 of influenza A (Denmark/35/2005 (H3N2)) HA protein (SEQ ID NO:4), wherein the region corresponding to amino acids 402-437 of SEQ ID NO:4 is replaced with a linker peptide. In certain aspects of the invention, the second amino acid sequence comprises an amino acid sequence at least 80% identical, at least 85% identical, at least 90% identical, at least 95% identical, at least 97% identical or at least 99% identical to SEQ ID NO:30, wherein the region corresponding to the inter-helix region (i.e., amino acids 402-437 of SEQ ID NO:4), is replaced with a linker peptide. In certain aspects of the invention, the second amino acid sequence comprises SEQ ID NO:30, wherein the region corresponding to the inter-helix region (i.e., amino acids 402-437 of SEQ ID NO:4), is replaced with a linker peptide. In certain aspects of the invention, the second amino acid sequence comprises SEQ ID NO:30, wherein amino acids 73-108 of SEQ ID NO:30 are replaced with a linker peptide. Any linker sequence can be used as the linker peptide in the second amino acid sequence, as long as the protein construct is able to form the desired conformation. In certain aspects of the invention, the linker peptide is less than 10 amino acids, less than 7 amino acids or less than 5 amino acids in length. In one embodiment, the linker peptide is four amino acids in length. In certain aspects of the invention, the linker sequence comprises one or more amino acids selected from the group consisting of glycine, serine, proline and aspartic acid. In certain aspects of the invention, the linker peptide comprises an amino acid sequence having chemical and spatial properties similar to a peptide consisting of SEQ ID NO:39. In certain aspects of the invention, the linker peptide comprises SEQ ID NO:39, or conservative variants thereof. In certain aspects of the invention, the linker peptide comprises SEQ ID NO:38. In certain aspects of the invention, the linker peptide consists of SEQ ID NO:39.

In certain aspects of the invention, the second amino acid sequence comprises a sequence at least 80% identical, at least 85% identical, at least 90% identical, at least 95% identical, at least 97% identical or at least 99% identical to a sequence selected from the group consisting of SEQ ID NO:40, SEQ ID NO:41, SEQ ID NO:42 and SEQ ID NO:43. In certain aspects of the invention, the second amino acid sequence comprises a sequence selected from the group consisting of SEQ ID NO:40, SEQ ID NO:41, SEQ ID NO:42, and SEQ ID NO:43.

One embodiment of the present invention is a protein construct (also referred to as a fusion protein) comprising a first amino acid sequence from the stem region of a Group 2 influenza virus HA protein, a second amino acid sequence from the stem region of a Group 2 influenza virus HA protein, and a third amino acid sequence from the stem region of a Group 2 influenza virus HA protein;

- wherein the first amino acid sequence comprises at least 20 contiguous amino acid residues from the amino acid sequence upstream of the amino-terminal end of the head region sequence of an influenza A virus HA protein, or an amino acid sequence at least 85% identical, at least 90% identical, at least 95% identical, at least 97% identical, or at least 99% identical, to at least 40 contiguous amino acids from the amino acid sequence upstream of the amino-terminal end of the head region sequence of an influenza A virus HA protein;
- wherein the second amino acid sequence comprises at least 20 contiguous amino acid residues from the amino acid sequence that connects the carboxyl-terminal end of the head region sequence to the inter-helix region of an influenza A virus HA protein, or an amino acid sequence at least 85% identical, at least 90% identical, at least 95% identical, at least 97% identical, or at least 99% identical, to at least 40 contiguous amino acid residues from the amino acid sequence that connects the carboxyl-terminal end of the head region sequence to the inter-helix region of an influenza A virus HA protein;
- wherein the third amino acid sequence comprises at least 20 contiguous amino acid residues from the amino acid sequence that connects the carboxyl-terminal end of the inter-helix region to the transmembrane domain (TM) of an influenza A virus HA protein, or an amino acid sequence at least 85% identical, at least 90% identical, at least 95% identical, at least 97% identical, or at least 99% identical, to at least 40 contiguous amino acid residues from the amino acid sequence that connects the carboxyl-terminal end of the inter-helix region to the transmembrane domain of an influenza A virus HA protein;
- wherein the first and second amino acid sequences are joined by a linker sequence; wherein the second and third amino acid sequences are joined by a linker peptide; and,
- wherein the first or third amino acid sequence is joined to at least a portion of a monomeric subunit domain such that the protein construct is capable of forming a nanoparticle.

In certain aspects of the invention, the first amino acid sequence is from a Group 2 influenza HA protein. In one embodiment, the first amino acid sequence is from a Group 2 influenza HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the first amino acid sequence is from a Group 2 influenza HA protein from a Group 2 virus listed in Table 2. In certain aspects of the invention, the first amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-159. In certain aspects of the invention, the first amino acid sequence is from the stem region of a Group 2 influenza HA protein comprising a sequence selected from the group consisting of SEQ ID NO:4-SEQ ID NO:26 and SEQ ID NO:47-159.

In certain aspects of the invention, the first amino acid sequence comprises at least 20 contiguous amino acid residues from the region of a Group 2 influenza virus HA protein corresponding to amino acid residues 1-59 of the HA protein of influenza A Denmark/35/2005 (H3N2)). In certain aspects of the invention, the first amino acid sequence comprises at least 20 contiguous amino acid residues from a sequence at least 85%, at least 90%, at least 95% or at least 97% identical to a sequence selected from the group consisting of SEQ ID NO:27, SEQ ID NO:28 and SEQ ID NO:29. In certain aspects of the invention, the first amino acid sequence comprises at least 20 contiguous amino acid residues from a sequence selected from the group consisting of SEQ ID NO:27, SEQ ID NO:28 and SEQ ID NO:29.

In certain aspects of the invention, the first amino acid sequence comprises at least 40 contiguous amino acid residues from the amino acid region of an HA protein corresponding to amino acid residues 1-59 of influenza A Denmark/35/2005 (H3N2)). In certain aspects of the invention, the first amino acid sequence comprises at least 40 contiguous amino acid residues from a sequence at least 85%, at least 90%, at least 95% or at least 97% identical to SEQ ID NO:27 and SEQ ID NO:28. In certain aspects of the invention, the first amino acid sequence comprises at least 40 contiguous amino acid residues from SEQ ID NO:27 and SEQ ID NO:28.

In certain aspects of the invention, the first amino acid sequence comprises a sequence corresponding to amino acid residues 1-59 of influenza A Denmark/35/2005 (H3N2)) HA protein (SEQ ID NO:4). In certain aspects of the invention, the first amino acid sequence comprises a sequence at least 85%, at least 90%, at least 95% or at least 97% identical to SEQ ID NO:27. In certain aspects of the invention, the first amino acid sequence comprises SEQ ID NO:27. In certain aspects of the invention, the first amino acid sequence consists of SEQ ID NO:27.

In certain aspects of the invention, the second amino acid sequence is from a Group 2 influenza HA protein. In certain aspects of the invention, the second amino acid sequence is from a Group 2 influenza HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the second amino acid sequence is from a Group 2 influenza HA protein from a Group 2 virus listed in Table 2. In certain aspects of the invention, the second amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-159. In certain aspects of the invention, the second amino acid sequence is from the stem region of a Group 2 influenza HA protein comprising a sequence selected from the group consisting of SEQ ID NO:4-SEQ ID NO:26 and SEQ ID NO:47-159.

In certain aspects of the invention, the second amino acid sequence comprises at least 20 contiguous amino acids from a region of a Group 2 influenza HA protein corresponding to amino acid residues 330-401 of influenza A (Denmark/35/2005(H3N2)) (SEQ ID NO:4). In certain aspects of the invention, the second amino acid sequence comprises at least 20 contiguous amino acid residues from a sequence at least 85%, at least 90%, at least 95% or at least 97% identical to a sequence selected from the group consisting of SEQ ID NO:30, SEQ ID NO:31, SEQ ID NO:32 and SEQ ID NO:33. In certain aspects of the invention, the second amino acid sequence comprises at least 20 contiguous amino acid residues from a sequence selected from the group consisting of SEQ ID NO:30, SEQ ID NO:31, SEQ ID NO:32 and SEQ ID NO:33. In certain aspects of the invention, the second amino acid sequence comprises at least 40 contiguous amino acid residues from a sequence at least 85%, at least 90%, at least 95% or at least 97% identical to a sequence selected from the group consisting of SEQ ID NO:30, SEQ ID NO:31, and SEQ ID NO:32. In certain aspects of the invention, the second amino acid sequence comprises at least 40 contiguous amino acid residues from a sequence selected from the group consisting of SEQ ID NO:30, SEQ ID NO:31, and SEQ ID NO:32.

In certain aspects of the invention, the second amino acid sequence comprises an amino acid sequence at least 85%, at least 90%, at least 95% or at least 97% identical to SEQ ID NO:31. In certain aspects of the invention, the second amino acid sequence comprises SEQ ID NO:31.

In certain aspects of the invention, the second amino acid sequence comprises at least 60, or at least 72, contiguous amino acids from the amino acid sequence of a Group 2 influenza HA protein, that is immediately downstream of the carboxyl-terminal end of the head region sequence of the HA protein. In certain aspects of the invention, the second amino acid sequence comprises at least 60, or at least 72 contiguous amino acids from the amino acid region of a Group 2 influenza virus HA protein, that corresponds to amino acid residues 330-401 of an influenza A (Denmark/35/2005 (H3N2)) HA protein (SEQ ID NO:4).

The first and second amino acid sequences are connected by a linker sequence. In certain aspects of the invention, the linker sequence is less than 10 amino acids, less than 7 amino acids or less than 5 amino acids in length. In certain aspects of the invention, the linker sequence comprises glycine and serine. In certain aspects of the invention, the linker sequence joins the carboxyl-terminal end of the first amino acid sequence to the amino-terminal end of the second amino acid sequence. In certain aspects of the invention, the linker sequence joins the carboxyl-terminal end of the second amino acid sequence to the amino-terminal end of the first amino acid sequence. In certain aspects of the invention, the linker sequence is similar in chemical and special properties to a peptide consisting of SEQ ID NO:34 or SEQ ID NO:35. In certain aspects of the invention, the linker comprises SEQ ID NO:34 or SEQ ID NO:35, or conservative variants thereof. In one embodiment, the linker comprises SEQ ID NO:34 or SEQ ID NO:35. In certain aspects of the invention, the linker consists of SEQ ID NO:34 or SEQ ID NO:35.

In certain aspects of the invention, the third amino acid sequence is from a Group 2 influenza HA protein. In certain aspects of the invention, the third amino acid sequence is from a Group 2 influenza HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the third amino acid sequence is from a Group 2 influenza HA protein from a Group 2 virus listed in Table 2. In certain aspects of the invention, the third amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-159. In certain aspects of the invention, the third amino acid sequence is from the stem region of a Group 2 influenza HA protein comprising a sequence selected from the group consisting of SEQ ID NO:4-SEQ ID NO:26, and SEQ ID NO:47-159.

In certain aspects of the invention, the third amino acid sequence comprises at least 20 contiguous amino acids from a region of a Group 2 influenza HA protein corresponding to amino acid residues 438-519 of influenza A (Denmark/35/2005(H3N2)) HA protein (SEQ ID NO:4). In certain aspects of the invention, the second amino acid sequence comprises at least 20 contiguous amino acid residues from a sequence at least 85%, at least 90%, at least 95% or at least 97% identical to a sequence selected from the group consisting of SEQ ID NO:44, SEQ ID NO:45 and SEQ ID NO:46. In certain aspects of the invention, the third amino acid sequence comprises at least 20 contiguous amino acid residues from a sequence selected from the group consisting of SEQ ID NO:44, SEQ ID NO:45 and SEQ ID NO:46. In certain aspects of the invention, the third amino acid sequence comprises at least 40 contiguous amino acid residues from a sequence at least 85%, at least 90%, at least 95% or at least 97% identical to a sequence selected from the group consisting of SEQ ID NO:44, SEQ ID NO:45 and SEQ ID NO:46. In certain aspects of the invention, the third amino acid sequence comprises at least 40 contiguous amino acid residues from a sequence selected from the group consisting of SEQ ID NO:44, SEQ ID NO:45, and SEQ ID NO:46.

In certain aspects of the invention, the third amino acid sequence comprises an amino acid sequence at least 85%, at least 90% at least 95% or at least 97% identical to a sequence selected from the group consisting of SEQ ID NO:44, SEQ ID NO:45 and SEQ ID NO:46. In certain aspects of the invention, the third amino acid sequence comprises an amino acid sequence selected from the group consisting of SEQ ID NO:44, SEQ ID NO:45, and SEQ ID NO:46.

In certain aspects of the invention, the third amino acid sequence comprises at least 60, or at least 75, contiguous amino acids from the amino acid sequence of a Group 2 influenza HA protein, that is immediately downstream of the carboxyl-terminal end of the inter-helix region sequence of a Group 2 influenza A (Denmark/35/2005 (H3N2)) HA protein. In certain aspects of the invention, the second amino acid sequence comprises at least 60, or at least 75 contiguous amino acids from the amino acid region of a Group 2 influenza virus HA protein, that corresponds to amino acid residues 438-519 of an influenza A (Denmark/35/2005 (H3N2)) HA protein (SEQ ID NO:4).

The linker peptide can comprise any sequence of amino acids, as long as the protein construct is able to form the desired conformation. In certain aspects of the invention, the linker peptide is less than 10 amino acids, less than 7 amino acids or less than 5 amino acids in length. In certain aspects of the invention, the linker peptide is four amino acids in length. In certain aspects of the invention, the linker sequence comprises an amino acid selected from the group consisting of glycine, serine, proline and aspartic acid. In certain aspects of the invention, the linker peptide comprises SEQ ID NO:39. In certain aspects of the invention, the linker peptide consists of SEQ ID NO:39.

As has been discussed, mutations to various locations in protein constructs of the invention can stabilize the three-dimensional structure of the protein constructs and/or nanoparticles comprising the construct. Thus, in certain aspects of the invention, the first amino acid sequence comprises at least one mutation at an amino acid location corresponding to a location in SEQ ID NO:4 selected from the group consisting of G39, T46, and T58. In certain aspects of the invention, the first amino acid sequence comprises at least one mutation selected from the group consisting of G39C, T46C, and N54H, T58L (numbering based on the sequence of the influenza A (Denmark/35/2005) (H3N2)) HA protein).

In certain aspects of the invention, the second amino acid sequence comprises at least one mutation at an amino acid location corresponding to a location in SEQ ID NO:4 selected from the group consisting of L331, N338, Q392, K396, L397 and L400. In certain aspects of the invention, the first amino acid sequence comprises at least one mutation selected from the group consisting of L331K, N338C, Q392C, and L400V (numbering based on the sequence of the influenza A (Denmark/35/2005) (H3N2)) HA protein).

In certain aspects of the invention, the third amino acid sequence comprises at least one mutation at an amino acid location corresponding to a location in SEQ ID NO:4 selected from the group consisting of S438, N440, E448, T452, and N461. In certain aspects of the invention, the first amino acid sequence comprises at least one mutation selected from the group consisting of S438C, N440L, E448L, T452V, and N461R(numbering based on the sequence of the influenza A (Denmark/35/2005) (H3N2)) HA protein).

As noted above, protein constructs of the invention can be joined to at least a portion of a monomeric subunit protein such that the protein construct is capable of forming a nanoparticle. In certain aspects of the invention, the at least a portion of the monomeric subunit protein is joined to the third amino acid sequence. In a preferred embodiment, the at least a portion of the monomeric subunit protein is joined to the carboxyl end of the third amino acid sequence. In certain aspects of the invention, the portion comprises at least 50, at least 100 or at least 150 amino acids from a monomeric subunit. In certain aspects of the invention, the monomeric subunit is ferritin. In certain aspects of the invention, the monomeric subunit is lumazine synthase. In certain aspects of the invention, the portion comprises at least 50, at least 100 or at least 150 amino acids from SEQ ID NO:1, SEQ ID NO:2 or SEQ ID NO:3. In certain aspects of the invention, the monomeric subunit comprises a sequence at least 85% identical, at least 90% identical or at least 95% identical to SEQ ID NO:1, SEQ ID NO:2 or SEQ ID NO:3. In certain aspects of the invention, the monomeric subunit comprises a sequence selected from the group consisting of SEQ ID NO:1, SEQ ID NO:2 and SEQ ID NO:3.

While the modifications made to the Group 2 influenza virus HA proteins disclosed herein have been described as separate embodiments, it should be appreciated that all such modification may be contained in a single protein construct. For example, a protein construct could be made in which a first amino acid sequence is joined by a linker to a second amino acid sequence, wherein the second amino acid sequence comprises an amino acid sequence from the region downstream of the carboxyl-terminal end of the head region of a group 2 influenza HA protein, but in which the inter-helix region corresponding to amino acids 402-437 of the Group 2 influenza A (Denmark/35/2005) (H3N2)) HA protein has been replaced with a linker peptide, and wherein one or more mutations have been introduced into the second amino acid sequence at a location corresponding to a location selected from the group consisting of L331, N338, K396, L397, L400, S438, N440, E448, T452, and N461, of the Group 2 influenza A (Denmark/35/2005) (H3N2)) HA protein, in order to increase the strength of the interaction between these amino acid residues in the folded protein.

While the protein constructs described heretofore can be used to produce nanoparticles capable of generating an immune response against one or more influenza viruses, in some embodiments, it may be useful to engineer further mutations into the amino acid sequences of proteins of the present invention. For example, it may be useful to alter sites such as enzyme recognition sites or glycosylation sites in the monomeric subunit protein, the trimerization domain, or linker sequences, in order to give the protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in certain aspects of the invention, potential N-linked glycosylation sites in the amino acid sequences from the monomeric ferritin subunit are mutated so that the mutated ferritin subunit sequences are no longer glycosylated at the mutated site. One such sequence of a mutated monomeric ferritin subunit is represented by SEQ ID NO:2. Further description of useful mutations are disclosed in International Application No. PCT/US2015/032695.

In some instances, it may be desirable to block the production of an immune response against certain amino acid sequences in the protein construct. This may be done by adding a glycosylation site near the site to be blocked such that the glycans sterically hinder the ability of the immune system to reach the blocked site. Thus, in certain aspects of the invention, the sequence of the protein construct has been altered to include one or more glycosylation sites. Examples of such sites include, but are not limited to, Asn-X-Ser, Asn-X-Thr and Asn-X-Cys. In some instances, the glycosylation site can be introduced into a linker sequence. Further examples of useful sites at which to introduce glycosylation sites include, but are not limited to, locations in Group 2 influenza HA proteins corresponding to amino acids 45-47, or amino acids 370-372 of the HA protein of influenza A New Caledonia/20/1999 (H1). Methods of introducing glycosylation sites are known to those skilled in the art.

Proteins and protein constructs of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can affect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In certain aspects of the invention, a vector can be a cytomegalovirus (CMV), retrovirus, adenovirus, adeno-associated virus, herpes virus, vaccinia virus, poliovirus, sindbis virus, or any other DNA or RNA virus vector. In certain aspects of the invention, a vector can be a pseudotyped lentiviral or retroviral vector. In certain aspects of the invention, a vector can be a DNA plasmid. In certain aspects of the invention, a vector can be a DNA plasmid comprising viral components and plasmid components to enable nucleic acid molecule delivery and expression. Methods for the construction of nucleic acid constructs of the present disclosure are well known. See, for example, *Molecular Cloning: A Laboratory Manual,* 3rd edition, Sambrook et al. 2001 Cold Spring Harbor Laboratory Press, and *Current Protocols in Molecular Biology,* Ausubel et al. eds., John Wiley & Sons, 1994. In certain aspects of the invention, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes a protein construct of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In certain aspects of the invention, a nucleic acid molecule can be genetically engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is known. It is to be appreciated that a nucleic acid construct can comprise one nucleic acid molecule or more than one nucleic acid molecule. It is also to be appreciated that a nucleic acid molecule can encode one protein or more than one protein.

In certain aspects of the invention the nucleic acid molecule of the invention encodes a protein construct of the invention. In certain aspects of the invention, a nucleic acid molecule encodes a protein at least 80% identical, at least 85% identical, at least 90% identical, at least 95% identical, at least 97% identical, at least 99% identical to a protein construct listed in Table 2. In certain aspects of the invention, a nucleic acid molecule encodes a protein comprising an amino acid sequence at least 80% identical, at least 85% identical, at least 90% identical, at least 95% identical, at least 97% identical, at least 99% identical to a sequence selected from the group consisting of SEQ ID NO:47-159.

Also encompassed by the present invention are expression systems for producing protein constructs of the present invention. In certain aspects of the invention, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the protein constructs of the present invention can be accomplished using any suitable conventional recombinant technology currently known in the field. For example, production of a nucleic acid molecule encoding a fusion protein can be carried out in E. coli using a nucleic acid molecule encoding a suitable monomeric subunit protein, such as the helicobacter pylori ferritin monomeric subunit, and fusing it to a nucleic acid molecule encoding a suitable influenza protein disclosed herein. The construct may then be transformed into protein expression cells, grown to suitable size, and induced to produce the fusion protein.

As has been described, because protein constructs of the present invention comprise a monomeric subunit protein, they can self-assemble. According to the present invention, the supramolecule resulting from such self-assembly is referred to as an HA expressing, monomeric subunit-based nanoparticle. For ease of discussion, the HA expressing, monomeric subunit-based nanoparticle will simply be referred to as a, or the, nanoparticle (np). Nanoparticles of the present invention have similar structural characteristics as the nanoparticles of the monomeric protein from which they are made. For example, with regard to ferritin, a ferritin-based nanoparticle contains 24 subunits and has 432 symmetry. In the case of nanoparticles of the present invention, the subunits are the protein constructs comprising a monomeric subunit (e.g., ferritin, lumazine synthase, etc.) joined to a Group 2 influenza virus HA protein. Such nanoparticles display at least a portion of the Group 2 influenza virus HA protein on their surface as HA trimers. In such a construction, the HA trimer is accessible to the immune system and thus can elicit an immune response. Thus, one embodiment of the invention is a nanoparticle comprising any protein construct disclosed or described herein. One embodiment of the present invention is a nanoparticle comprising a protein construct of the present invention, wherein the protein construct comprises amino acids from the stem region of a Group 2 influenza virus HA protein joined to a monomeric subunit protein. In certain aspects of the invention, the nanoparticle displays the Group 2 influenza virus HA protein on its surface as a HA trimer. In certain aspects of the invention, the Group 2 influenza virus HA protein is capable of eliciting protective antibodies to an influenza virus.

One embodiment of the invention is a nanoparticle comprising a protein construct of the invention. In certain aspects of the invention, the protein construct comprises a Group 2 influenza HA protein wherein the head region of the Group 2 influenza HA protein has been replaced with an amino acid sequence comprising less than 5 contiguous amino acid residues from the head region of an influenza HA protein. In certain aspects of the invention, the HA protein of the protein construct has also been altered by extending the length of helix A. In certain aspects of the invention, the HA protein of the protein construct has also been altered by shortening the inter-helix region or replacing the inter-helix region with a linker sequence. In certain aspects of the invention, the HA protein of the protein construct has also been altered by mutating specific locations to stabilize the trimeric structure. Examples of suitable locations include, but are not limited to, locations corresponding to a location in SEQ ID NO:4 selected from the group consisting of L331, N338, K396, L397, L400, 5438, N440, E448, T452, N461, G39, T46, N54 and T58, and wherein the protein construct is capable of forming a nanoparticle. Methods of replacing the HA protein head region, extending helix A, shortening or replacing the inter-helix region, and suitable site-specific mutations have been disclosed herein. In certain aspects of the invention, the nanoparticle comprises a protein construct comprising a first amino acid sequence from the stem region of a Group 2 influenza virus HA protein and a second amino acid sequence from the stem region of a Group 2 influenza virus HA protein, the first and second amino acid sequences being covalently linked by a linker sequence,

- wherein the first amino acid sequence comprises at least 20 contiguous amino acid residues from the amino acid sequence upstream of the amino-terminal end of the head region sequence;
- wherein the second amino acid sequence comprises at least 20 contiguous amino acid residues from the amino acid sequence downstream of the carboxyl-terminal end of the head region sequence; and,
- wherein the first or second amino acid sequence is joined to at least a portion of a monomeric subunit domain such that the protein construct is capable of forming a nanoparticle.

In certain aspects of the invention, the first amino acid sequence is from the stem region of a Group 2 influenza virus HA protein from a virus selected from the group consisting of an influenza H3 virus HA protein, an influenza H4 virus HA protein, an H7 influenza virus HA protein, an H10 influenza virus HA protein HA protein, an H14 influenza virus HA protein, and an H15 influenza virus HA protein. In certain aspects of the invention, the first amino acid sequence is from the stem region of an HA protein from a Group 2 virus listed in Table 2. In certain aspects of the invention, the first amino acid sequence is from the stem region of a Group 2 influenza HA protein having an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the first amino acid sequence is from the stem region of a Group 2 influenza HA protein comprising a sequence selected from the group consisting of SEQ ID NO:4-SEQ ID NO:26 and SEQ ID NO:47-SEQ ID NO:159.

In certain aspects of the invention, the second amino acid sequence is from the stem region of a Group 2 influenza HA protein from a virus selected from the group consisting of an influenza H3 virus, an influenza H4 virus, an H7 influenza virus, an H10 influenza virus, an H14 influenza virus, and an H15 influenza virus. In certain aspects of the invention, the second amino acid sequence is from the stem region of an HA protein from a Group 2 virus listed in Table 2. In certain aspects of the invention, the second amino acid sequence is from the stem region of a Group 2 influenza virus HA protein having an amino acid sequences at least 85%, at least 90%, at least 95% or at least 97% identical to a sequence selected from the group consisting of SEQ ID NO:4-SEQ ID NO:26 and SEQ ID NO:47-SEQ ID NO:159. In certain aspects of the invention, the second amino acid sequence is from the stem region of a Group 2 influenza virus HA protein comprising a sequence selected from the group consisting of SEQ ID NO:4-SEQ ID NO:26 and SEQ ID NO:47-SEQ ID NO:159.

As noted above, the first amino acid sequence comprises at least 20 contiguous amino acid residues from the amino acid sequence upstream of the amino-terminal end of the head region sequence. According to the present invention, the term upstream refers to the entirety of the amino acid sequence linked to the amino-terminal end of the first amino acid residue of the head region. Preferred upstream sequences are those that are immediately adjacent to the head region sequence.

In certain aspects of the invention, the amino-terminal end of the head region is located at the amino acid residue corresponding to Q60 of the HA protein of influenza A (Denmark/35/2005 (H3N2)) HA protein (SEQ ID NO:4) In certain aspects of the invention, the first amino acid sequence comprises at least 20 contiguous amino acid residues from the region of a Group 2 influenza virus HA protein corresponding to amino acid residues 1-59 of the HA protein of influenza A Denmark/35/2005 (H3N2)) represented by SEQ ID NO:4. In certain aspects of the invention, the first amino acid sequence comprises at least 20 contiguous amino acid residues from a sequence at least 85%, at least 90%, at least 95% or at least 97% identical to a sequence selected from the group consisting of SEQ ID NO:27, SEQ ID NO:28 and SEQ ID NO:29. In certain aspects of the invention, the first amino acid sequence comprises at least 20 contiguous amino acid residues from a sequence selected from the group consisting of SEQ ID NO:27, SEQ ID NO:28, and SEQ ID NO:29.

In certain aspects of the invention, the first amino acid sequence comprises at least 40 contiguous amino acid residues from the amino acid region of an HA protein corresponding to amino acid residues 1-59 of influenza A Denmark/35/2005 (H3N2)) HA protein (SEQ ID NO:4). In certain aspects of the invention, the first amino acid sequence comprises at least 40 contiguous amino acid residues from a sequence at least 85%, at least 90%, at least 95% or at least 97% identical to SEQ ID NO:27 or SEQ ID NO:28. In certain aspects of the invention, the first amino acid sequence comprises at least 40 contiguous amino acid residues from SEQ ID NO:27 or SEQ ID NO:28.

In certain aspects of the invention, the first amino acid sequence comprises a sequence at least 85%, at least 90%, at least 95% or at least 97% identical to SEQ ID NO:27. In certain aspects of the invention, the first amino acid sequence comprises SEQ ID NO:27.

As noted above, the second amino acid sequence comprises at least 20 contiguous amino acid residues from the amino acid sequence downstream of the carboxyl-terminal end of the head region sequence. According to the present invention, the term downstream refers to the entirety of the amino acid sequence linked to the carboxyl-terminal amino acid residue of the head region. Preferred upstream sequences are those that are immediately adjacent to the head region sequence. In certain aspects of the invention, the carboxyl-terminal end of the head region is located at the amino acid position corresponding to T329 of the HA protein of influenza A (Denmark/35/2005(H3N2)) HA protein represented by SEQ ID NO:4. Thus, in certain aspects of the invention, the second amino acid sequence comprises at least 20 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 20 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 20 contiguous amino acid residues from a sequence at least 85%, at least 90%, at least 95% or at least 97% identical to a sequence selected from the group consisting of SEQ ID NO:30, SEQ ID NO:31, SEQ ID NO:32 and SEQ ID NO:33. In certain aspects of the invention, the second amino acid sequence comprises at least 20 contiguous amino acid residues from a sequence selected from the group consisting of SEQ ID NO:30, SEQ ID NO:31, SEQ ID NO:32, and SEQ ID NO:33.

In certain aspects of the invention, the second amino acid sequence comprises at least 40 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 40 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40 contiguous amino acid residues from a sequence at least 85%, at least 90%, at least 95% or at least 97% identical to a sequence selected from the group consisting of SEQ ID NO:30, SEQ ID NO:31, and SEQ ID NO:32. In certain aspects of the invention, the second amino acid sequence comprises at least 20 contiguous amino acid residues from a sequence selected from the group consisting of SEQ ID NO:30, SEQ ID NO:31, and SEQ ID NO:32.

In certain aspects of the invention, the second amino acid sequence comprises an amino acid sequence at least 85%, at least 90%, at least 95% or at least 97% identical to SEQ ID NO:37. In certain aspects of the invention, the second amino acid sequence comprises SEQ ID NO:37.

In certain aspects of the invention, the second amino acid sequence comprises at least 60, at least 72, at least 75, at least 100, at least 150, at least 175, or at least 190 contiguous amino acids from a region of a Group 2 influenza HA protein corresponding to amino acid residues 330-519 of influenza A (Denmark/35/2005) (H3N2) HA protein. In certain aspects of the invention, the second amino acid sequence comprises at least 60, at least 72, at least 75, at least 100, at least 150, at least 175, or at least 190 contiguous amino acids from a region of a Group 2 influenza HA protein comprising amino acid residues 330-519 of influenza A (Denmark/35/2005(H3N2)) (SEQ ID NO:4). In certain aspects of the invention, the second amino acid sequence comprises at least 40, at least 60, at least 72, at least 75, at least 100, at least 150, at least 175, or at least 190 contiguous amino acid residues from a sequence at least 85%, at least 90%, at least 95% or at least 97% identical to SEQ ID NO:30. In certain aspects of the invention, the second amino acid sequence comprises at least 40, at least 60, at least 72, at least 75, at least 100, at least 150, at least 175, or at least 190 contiguous amino acid residues from SEQ ID NO:30.

In certain aspects of the invention, the nanoparticle comprises a protein construct comprising an amino acid sequence at least 80%, at least about 85%, at least about 90%, at least about 95%, at least about 97% or at least about 99% identical to a protein construct sequence recited in Table 2, wherein the nanoparticle is capable of selectively binding anti-influenza antibodies. In certain aspects of the invention, the nanoparticle comprises a protein construct comprising an amino acid sequence at least 80%, at least about 85%, at least about 90%, at least about 95%, at least about 97% or at least about 99% identical to a sequence selected from the group consisting of SEQ ID NO:47-159, wherein the nanoparticle is capable of selectively binding anti-influenza antibodies. In certain aspects of the invention, the nanoparticle comprises a protein construct comprising an amino acid sequence selected from the group consisting of SEQ ID NOs: 47-159.

Nanoparticles of the present invention can be used to elicit an immune response to influenza virus. One type of immune response is a B-cell response, which results in the production of antibodies against the antigen that elicited the immune response. Thus, in certain aspects of the invention the nanoparticle elicits antibodies that bind to the stem region of an influenza A HA protein from a virus selected from the group consisting of influenza A viruses, influenza B viruses and influenza C viruses. One embodiment of the present invention is a nanoparticle that elicits antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies that bind to the stem region of an influenza HA protein from a virus listed in Table 2.

While all antibodies are capable of binding to the antigen which elicited the immune response that resulted in antibody production, preferred antibodies are those that provide broad heterosubtypic protection against influenza virus. Thus, one embodiment of the present invention is a nanoparticle that elicits protective antibodies that bind to the stem region of influenza HA protein from a virus selected from the group consisting of influenza A viruses, influenza B viruses and influenza C viruses. One embodiment of the present invention is a nanoparticle that elicits protective antibodies that bind to the stem region of influenza HA protein selected from the group consisting of an H1 influenza virus HA protein, an H2 influenza virus HA protein, an influenza H3 virus HA protein, an influenza H4 virus HA protein, an influenza H5 virus HA protein, an influenza H6 virus HA protein, an H7 influenza virus HA protein, an H8 influenza virus HA protein, an H9 influenza virus HA protein, an H10 influenza virus HA protein HA protein, an H11 influenza virus HA protein, an H12 influenza virus HA protein, an H13 influenza virus HA protein, an H14 influenza virus HA protein, an H15 influenza virus HA protein, an H16 influenza virus HA protein, an H17 influenza virus HA protein, and an H18 influenza virus HA protein. One embodiment of the present invention is a nanoparticle that elicits antibodies that bind to the stem region of an influenza HA protein from a virus listed in Table 2. One embodiment of the present invention is a nanoparticle that elicits antibodies that bind to a protein comprising an amino acid sequence at least 80% identical to a sequence selected from the group consisting of SEQ ID NOs: 4-26. One embodiment of the present invention is a nanoparticle that elicits antibodies that bind to a protein comprising an amino acid sequence selected from the group consisting of SEQ ID NOs: 4-26.

Protective antibodies elicited by proteins of the present invention can protect against viral infections by affecting any step in the life cycle of the virus. For example, protective antibodies may prevent an influenza virus from attaching to a cell, entering a cell, releasing viral ribonucleoproteins into the cytoplasm, forming new viral particles in the infected cell and budding new viral particles from the infected host cell membrane. In certain aspects of the invention, protective antibodies elicited by proteins of the present invention prevent influenza virus from entering the host cell. In certain aspects of the invention, protective antibodies elicited by proteins of the present invention prevent fusion of viral membranes with endosomal membranes. In certain aspects of the invention, protective antibodies elicited by proteins of the present invention prevent release of ribonucleoproteins into the cytoplasm of the host cell. In certain aspects of the invention, protective antibodies elicited by proteins of the present invention prevent assembly of new virus in the infected host cell. In certain aspects of the invention, protective antibodies elicited by proteins of the present invention prevent release of newly formed virus from the infected host cell.

Because the amino acid sequence of the stem region of influenza virus is highly conserved, protective antibodies elicited by nanoparticles of the present invention may be broadly protective. That is, protective antibodies elicited by nanoparticles of the present invention may protect against influenza viruses of more than one type, subtype and/or strain. Thus, one embodiment of the present invention is a nanoparticle that elicits broadly protective antibodies that bind the stem region of influenza HA protein. One embodiment is a nanoparticle that elicits antibodies that bind the stem region of an HA protein from more than one type of influenza virus selected from the group consisting of influenza type A viruses, influenza type B viruses and influenza type C viruses. One embodiment is a nanoparticle that elicits antibodies that bind the stem region of an HA protein from more than one sub-type of influenza virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, and an H18 influenza virus. One embodiment is a nanoparticle that elicits antibodies that bind the stem region of an HA protein from more than strain of influenza virus. One embodiment of the present invention is a nanoparticle that elicits antibodies that bind more than one protein comprising an amino acid sequence at least 80% identical to a sequence selected from the group consisting of SEQ ID NO:4-SEQ ID NO:26. One embodiment of the present invention is a nanoparticle that elicits antibodies that bind to more than one protein comprising an amino acid sequence selected from the group consisting of SEQ ID NOs: 4-26.

As noted above, the HA sequence is linked to a portion of a monomeric subunit protein. As used herein, a monomeric subunit protein refers to a protein monomer that is capable of binding to other monomeric subunit proteins such that the monomeric subunit proteins self-assemble into a nanoparticle. Any monomeric subunit protein can be used to produce the protein construct of the present invention, so long as the protein construct is capable of forming a multimeric structure displaying HA protein on its surface. In certain aspects of the invention the monomeric subunit is ferritin.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. An example of the sequence of one such monomeric ferritin subunit is represented by SEQ ID NO 1. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled A, B, C, and D & E from the N-terminus respectively. The N-terminal sequence lies adjacent to the nanoparticle three-fold axis and extends to the surface, while the E helices pack together at the four-fold axis with the C-terminus extending into the particle core. The consequence of this packing creates two pores on the nanoparticle surface. It is expected that one or both of these pores represent the point by which the hydrated iron diffuses into and out of the nanoparticle. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Examples of such proteins include, but are not limited to SEQ ID NO:1 and SEQ ID NO:2 Amino acid sequences from monomeric ferritin subunits of any known ferritin protein can be used to produce protein constructs of the present invention, so long as the monomeric ferritin subunit is capable of self-assembling into a nanoparticle displaying HA on its surface. In certain aspects of the invention, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In certain aspects of the invention, the ferritin protein is from *Helicobacter pylori.*

Protein constructs of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

In certain aspects of the invention the Group 2 influenza virus HA protein is joined to at least 50, at least 100 or least 150 amino acids from ferritin, wherein the protein construct is capable of forming a nanoparticle. In certain aspects of the invention the Group 2 influenza virus HA protein is joined to at least 50, at least 100 or least 150 amino acids from SEQ ID NO:1 or SEQ ID NO:2, wherein the protein construct is capable of forming a nanoparticle. In certain aspects of the invention the Group 2 influenza virus HA protein is joined to a protein comprising an amino acid sequence at least 85%, at least 90% or at least 95% identical to the sequence of ferritin, wherein the protein construct is capable of forming a nanoparticle. In certain aspects of the invention the Group 2 influenza virus HA protein is joined to a protein comprising an amino acid sequence at least 85%, at least 90%, at least 95% identical to SEQ ID NO:1 or SEQ ID NO:2, wherein the protein construct is capable of forming a nanoparticle.

In certain aspects of the invention the monomeric subunit is lumazine synthase. In certain aspects of the invention the Group 2 influenza virus HA protein is joined to at least 50, at least 100 or least 150 amino acids from lumazine synthase, wherein the protein construct is capable of forming a nanoparticle. Thus, in certain aspects of the invention the Group 2 influenza virus HA protein is joined to a protein at least 85%, at least 90%, at least 95% identical to lumazine synthase, wherein the protein construct is capable of forming a nanoparticle.

As used herein, a nanoparticle of the present invention refers to a three-dimensional particle formed by self-assembly of protein constructs (fusion proteins) of the present invention. Nanoparticles of the present invention are generally spheroid in shape, although other shapes are not excluded, and are generally from about 20 nm to about 100 nm in diameter. Nanoparticles of the present invention may, but need not, comprise other molecules, such as proteins, lipids, carbohydrates, etc., than the protein constructs from which they are formed.

Because nanoparticles of the present invention can elicit an immune response to an influenza virus, they are useful as vaccines to protect individuals against infection by influenza virus. Thus, one embodiment of the present invention is a vaccine comprising a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the present invention is a nanoparticle vaccine that includes more than one influenza HA protein. Such a vaccine can include a combination of different influenza HA proteins, either on a single nanoparticle or as a mixture of nanoparticles, at least two of which have unique influenza HA proteins. A multivalent vaccine can comprise as many influenza HA proteins as necessary in order to result in production of the immune response necessary to protect against a desired breadth of virus strains. In certain aspects of the invention, the vaccine comprises an HA protein from at least two different influenza strains (bi-valent). In certain aspects of the invention, the vaccine comprises a HA protein from at least three different influenza strains (tri-valent). In certain aspects of the invention, the vaccine comprises an HA protein from at least four different influenza strains (tetra-valent). In certain aspects of the invention, the vaccine comprises an HA protein from at least five different influenza strains (penta-valent). In certain aspects of the invention, the vaccine comprises an HA protein from at least six different influenza strains (hexavalent). In various embodiments, a vaccine comprises an HA protein from each of 7, 8, 9, or 10 different strains of influenza virus. An example of such a combination is a nanoparticle vaccine that comprises influenza A group 1 HA protein, an influenza A group 2 HA protein, and an influenza B HA protein. In certain aspects of the invention, the influenza HA proteins are H1 HA, H3 HA, and B HA. Another example of a multivalent vaccine is a nanoparticle vaccine that comprises HA proteins from four different influenza viruses. In certain aspects of the invention, the multivalent vaccine comprises one or more HA proteins at least 80% identical, at least 85% identical, at least 90% identical, at least 95% identical, at least 97% identical or at least 99% identical to one or more HA proteins listed in Table 2. In certain aspects of the invention, the multivalent vaccine comprises one or more HA proteins listed in Table 2.

One embodiment of the present invention is a method to vaccinate an individual against influenza virus, the method comprising administering a nanoparticle to an individual such that an immune response against influenza virus is produced in the individual, wherein the nanoparticle comprises a monomeric subunit protein joined to a Group 2 influenza virus HA protein, and wherein the nanoparticle displays the influenza HA on its surface. In certain aspects of the invention, the nanoparticle is a monovalent nanoparticle. In certain aspects of the invention, the nanoparticle is multivalent nanoparticle. Another embodiment of the present invention is a method to vaccinate an individual against infection with influenza virus, the method comprising:

a) obtaining a nanoparticle comprising monomeric subunits, wherein the monomeric subunits are joined to an influenza hemagglutinin protein, and wherein the nanoparticle displays a Group 2 influenza virus HA protein on its surface; and, b) administering the nanoparticle to an individual such that an immune response against an influenza virus is produced.

One embodiment of the present invention is a method to vaccinate an individual against influenza virus, the method comprising administering a vaccine of the embodiments to an individual such that an immune response against influenza virus is produced in the individual, wherein the vaccine comprises at least one nanoparticle comprising a monomeric subunit joined to an influenza HA protein, and wherein the nanoparticle displays the influenza HA on its surface. In certain aspects of the invention, the vaccine is a monovalent vaccine. In certain aspects of the invention, the vaccine is multivalent vaccine. One embodiment of the present invention is a method to vaccinate an individual against infection with influenza virus, the method comprising:

a) obtaining a vaccine comprising at least one nanoparticle comprising a protein construct of the present invention, wherein the protein construct comprises a monomeric subunit protein joined to a Group 2 influenza virus HA protein, and wherein the nanoparticle displays the influenza HA on its surface; and, b) administering the vaccine to an individual such that an immune response against an influenza virus is produced.

Certain aspects of the invention, the nanoparticle is a monovalent nanoparticle. Certain aspects of the invention, the nanoparticle is multivalent nanoparticle.

Certain aspects of the invention, the nanoparticle has octahedral symmetry. Certain aspects of the invention, the influenza HA protein is capable of eliciting antibodies to an influenza virus. Certain aspects of the invention, the influenza HA protein is capable of eliciting broadly antibodies to an influenza virus. In preferred embodiments the elicited antibodies are protective antibodies. In a preferred embodiment, the elicited antibodies are broadly heterosubtypic protective.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. Certain aspects of the invention, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition The first and second vaccine compositions can be, but need not be, the same composition. Thus, certain aspects of the invention of the present invention, the step of administering the vaccine comprises administering a first vaccine composition, and then at a later time, administering a second vaccine composition. Certain aspects of the invention, the first vaccine composition comprises a nanoparticle of the present invention. Certain aspects of the invention, the first vaccine composition comprises a nanoparticle of the invention.

Certain aspects of the invention, the individual being vaccinated has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18$^{th}$ ed., 1990, Mack Publishing Co., Easton, PA. Vaccines may be administered by means including, but not limited to, traditional syringes, needleless injection devices, or micro-projectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

Certain aspects of the invention, vaccines, or nanoparticles, of the present invention can be used to protect an individual against infection by heterologous influenza virus. That is, a vaccine made using HA protein from one strain of influenza virus is capable of protecting an individual against infection by different strains of influenza. For example, a vaccine made using HA protein from influenza A/Denmark/35/2005)(H3N2), can be used to protect an individual against infection by an influenza virus recited in Table 2.

Certain aspects of the invention, vaccines, or nanoparticles, of the present invention can be used to protect an individual against infection by an antigenically divergent influenza virus. Antigenically divergent refers to the tendency of a strain of influenza virus to mutate over time, thereby changing the amino acids that are displayed to the immune system. Such mutation over time is also referred to as antigenic drift. Thus, for example, a vaccine made using HA protein from the influenza A/Denmark/35/2005)(H3N2) strain of influenza virus is capable of protecting an individual against infection by earlier, antigenically divergent Denmark strains of influenza, and by evolving (or diverging) influenza strains of the future.

Because nanoparticles of the present invention display Group 2 influenza virus HA proteins that are antigenically similar to an intact HA, they can be used in assays for detecting antibodies against influenza virus (anti-influenza antibodies).

Thus, one embodiment of the present invention is a method for detecting anti-influenza virus antibodies using nanoparticles of the present invention. A detection method of the present invention can generally be accomplished by:

a. contacting at least a portion of a sample being tested for the presence of anti-influenza antibodies with a nanoparticle of the present invention; and, b. detecting the presence of a nanoparticle/antibody complex;

wherein the presence of a nanoparticle/antibody complex indicates that the sample contains anti-influenza antibodies.

Certain aspects of the invention of the present invention, a sample is obtained, or collected, from an individual to be tested for the presence of anti-influenza virus antibodies. The individual may or may not be suspected of having anti-influenza antibodies or of having been exposed to influenza virus. A sample is any specimen obtained from the individual that can be used to test for the presence of anti-influenza virus antibodies. A preferred sample is a body fluid that can be used to detect the presence of anti-influenza virus antibodies. Examples of body fluids that may be used to practice the present method include, but are not limited to, blood, plasma, serum, lacrimal fluid and saliva. Those skilled in the art can readily identify samples appropriate for practicing the disclosed methods.

Blood, or blood-derived fluids such as plasma, serum, and the like, are particularly suitable as the sample. Such samples can be collected and prepared from individuals using methods known in the art. The sample may be refrigerated or frozen before assay.

Any nanoparticle of the present invention can be used to practice the disclosed method as long as the nanoparticle binds to anti-influenza virus antibodies. Useful nanoparticles, and methods of their production, have been described in detail herein. In a preferred embodiment, the nanoparticle comprises a protein construct, wherein the protein construct comprises at least 25, at least 50, at least 75, at least 100, or at least 150 contiguous amino acids from a monomeric subunit protein joined to (fused to) at least one epitope from a Group 2 influenza virus HA protein such that the nanoparticle comprises trimers of the Group 2 influenza virus HA protein epitope on its surface, and wherein the protein construct is capable of self-assembling into nanoparticles.

As used herein, the term contacting refers to the introduction of a sample being tested for the presence of anti-influenza antibodies to a nanoparticle of the present invention, for example, by combining or mixing the sample and the nanoparticle of the present invention, such that the nanoparticle is able to come into physical contact with antibodies in the sample, if present. When anti-influenza virus antibodies are present in the sample, an antibody/nanoparticle complex is then formed. Such complex formation refers to the ability of an anti-influenza virus antibodies to selectively bind to the HA portion of the protein construct in the nanoparticle in order to form a stable complex that can be detected. Binding of anti-influenza virus antibodies in the sample to the nanoparticle is accomplished under conditions suitable to form a complex. Such conditions (e.g., appropriate concentrations, buffers, temperatures, reaction times) as well as methods to optimize such conditions are known to those skilled in the art. Binding can be measured using a variety of methods standard in the art including, but not limited to, agglutination assays, precipitation assays, enzyme immunoassays (e.g., ELISA), immunoprecipitation assays, immunoblot assays and other immunoassays as described, for example, in Sambrook et al., Molecular Cloning: A Laboratory Manual, (Cold Spring Harbor Labs Press, 1989), and Harlow et al., Antibodies, a Laboratory Manual (Cold Spring Harbor Labs Press, 1988), both of which are incorporated by reference herein in their entirety. These references also provide examples of complex formation conditions.

As used herein, the phrases selectively binds HA, selective binding to HA, and the like, refer to the ability of an antibody to preferentially bind a HA protein as opposed to binding proteins unrelated to HA, or non-protein components in the sample or assay. An antibody that selectively binds HA is one that binds HA but does not significantly bind other molecules or components that may be present in the sample or assay. Significant binding, is considered, for example, binding of an anti-HA antibody to a non-HA molecule with an affinity or avidity great enough to interfere with the ability of the assay to detect and/or determine the level of, anti-influenza antibodies in the sample. Examples of other molecules and compounds that may be present in the sample, or the assay, include, but are not limited to, non-HA proteins, such as albumin, lipids and carbohydrates.

Certain aspects of the invention, an anti-influenza virus antibody/nanoparticle complex, also referred to herein as an antibody/nanoparticle complex, can be formed in solution. Certain aspects of the invention an antibody/nanoparticle complex can be formed in which the nanoparticle is immobilized on (e.g., coated onto) a substrate Immobilization techniques are known to those skilled in the art. Suitable substrate materials include, but are not limited to, plastic, glass, gel, celluloid, fabric, paper, and particulate materials. Examples of substrate materials include, but are not limited to, latex, polystyrene, nylon, nitrocellulose, agarose, cotton, PVDF (poly-vinylidene-fluoride), and magnetic resin. Suitable shapes for substrate material include, but are not limited to, a well (e.g., microtiter dish well), a microtiter plate, a dipstick, a strip, a bead, a lateral flow apparatus, a membrane, a filter, a tube, a dish, a celluloid-type matrix, a magnetic particle, and other particulates. Particularly preferred substrates include, for example, an ELISA plate, a dipstick, an immunodot strip, a radioimmunoassay plate, an agarose bead, a plastic bead, a latex bead, a cotton thread, a plastic chip, an immunoblot membrane, an immunoblot paper and a flow-through membrane. Certain aspects of the invention, a substrate, such as a particulate, can include a detectable marker. For descriptions of examples of substrate materials, see, for example, Kemeny, D. M. (1991) A Practical Guide to ELISA, Pergamon Press, Elmsford, NY pp 33-44, and Price, C. and Newman, D. eds. Principles and Practice of Immunoassay, 2nd edition (1997) Stockton Press, NY, NY, both of which are incorporated herein by reference in their entirety.

In accordance with the present invention, once formed, an anti-influenza virus antibody/nanoparticle complex is detected. Detection can be qualitative, quantitative, or semi-quantitative. As used herein, the phrases detecting complex formation, detecting the complex, and the like, refer to identifying the presence of anti-influenza virus antibody complexed with the nanoparticle. If complexes are formed, the amount of complexes formed can, but need not be, quantified. Complex formation, or selective binding, between a putative anti-influenza virus antibody and a nanoparticle can be measured (i.e., detected, determined) using a variety of methods standard in the art (see, for example, Sambrook et al. supra.), examples of which are disclosed herein. A complex can be detected in a variety of ways including, but not limited to use of one or more of the following assays: a hemagglutination inhibition assay, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG Immunodot System, Fribourg, Switzerland), and an immunoblot assay (e.g., a western blot), an phosphorescence assay, a flow-through assay, a chromatography assay, a PAGe-based assay, a surface plasmon resonance assay, a spectrophotometric assay, and an electronic sensory assay. Such assays are well known to those skilled in the art.

Assays can be used to give qualitative or quantitative results depending on how they are used. Some assays, such as agglutination, particulate separation, and precipitation assays, can be observed visually (e.g., either by eye or by a machines, such as a densitometer or spectrophotometer) without the need for a detectable marker.

In other assays, conjugation (i.e., attachment) of a detectable marker to the nanoparticle, or to a reagent that selectively binds to the nanoparticle, aids in detecting complex formation. A detectable marker can be conjugated to the nanoparticle, or nanoparticle-binding reagent, at a site that does not interfere with ability of the nanoparticle to bind to an anti-influenza virus antibody. Methods of conjugation are known to those of skill in the art. Examples of detectable markers include, but are not limited to, a radioactive label, a fluorescent label, a chemiluminescent label, a chromophoric label, an enzyme label, a phosphorescent label, an electronic label; a metal sol label, a colored bead, a physical label, or a ligand. A ligand refers to a molecule that binds selectively to another molecule. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

Certain aspects of the invention, an antibody/nanoparticle complex can be detected by contacting a sample with a specific compound, such as an antibody, that binds to an anti-influenza antibody, ferritin, or to the antibody/nanoparticle complex, conjugated to a detectable marker. A detectable marker can be conjugated to the specific compound in such a manner as not to block the ability of the compound to bind to the complex being detected. Preferred detectable markers include, but are not limited to, fluorescein, a radioisotope, a phosphatase (e.g., alkaline phosphatase), biotin, avidin, a peroxidase (e.g., horseradish peroxidase), beta-galactosidase, and biotin-related compounds or avidin-related compounds (e.g., streptavidin or ImmunoPure7 NeutrAvidin).

In another embodiment, a complex is detected by contacting the complex with an indicator molecule. Suitable indicator molecules include molecules that can bind to the anti-influenza virus antibody/nanoparticle complex, the anti-influenza virus antibody, or the nanoparticle. As such, an indicator molecule can comprise, for example, a reagent that binds the anti-influenza virus antibody, such as an antibody that recognizes immunoglobulins. Preferred indicator molecules that are antibodies include, for example, antibodies reactive with the antibodies from species of individual in which the anti-influenza virus antibodies are produced. An indicator molecule itself can be attached to a detectable marker of the present invention. For example, an antibody can be conjugated to biotin, horseradish peroxidase, alkaline phosphatase or fluorescein.

The present invention can further comprise one or more layers and/or types of secondary molecules or other binding molecules capable of detecting the presence of an indicator molecule. For example, an untagged (i.e., not conjugated to a detectable marker) secondary antibody that selectively binds to an indicator molecule can be bound to a tagged (i.e., conjugated to a detectable marker) tertiary antibody that selectively binds to the secondary antibody. Suitable secondary antibodies, tertiary antibodies and other secondary or tertiary molecules can be readily selected by those skilled in the art. Preferred tertiary molecules can also be selected by those skilled in the art based upon the characteristics of the secondary molecule. The same strategy can be applied for subsequent layers.

Preferably, the indicator molecule is conjugated to a detectable marker. A developing agent is added, if required, and the substrate is submitted to a detection device for analysis. In some protocols, washing steps are added after one or both complex formation steps in order to remove excess reagents. If such steps are used, they involve conditions known to those skilled in the art such that excess reagents are removed but the complex is retained.

Because assays of the present invention can detect anti-influenza virus antibodies in a sample, including a blood sample, such assays can be used to identify individuals having anti-influenza antibodies. Thus, one embodiment of the present invention is a method to identify an individual having anti-influenza virus antibodies, the method comprising:

a. contacting a sample from an individual being tested for anti-influenza antibodies with a nanoparticle of the present invention; and,
b. analyzing the contacted sample for the presence of a nanoparticle/antibody complex wherein the presence of a nanoparticle/antibody complex indicates the individual has anti-influenza antibodies.

Any of the disclosed assay formats can be used to conduct the disclosed method. Examples of useful assay formats include, but are not limited to, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG Immunodot System, Fribourg, Switzerland), and an immunoblot assay (e.g., a western blot), an phosphorescence assay, a flow-through assay, a chromatography assay, a PAGe-based assay, a surface plasmon resonance assay, bio-layer interferometry assay, a spectrophotometric assay, and an electronic sensory assay.

If no anti-influenza antibodies are detected in the sample, such a result indicates the individual does not have anti-influenza virus antibodies. The individual being tested may or may not be suspected of having antibodies to influenza virus. The disclosed methods may also be used to determine if an individual has been exposed to one or more specific type, group, sub-group or strain of influenza virus. To make such a determination, a sample is obtained from an individual that has tested negative for antibodies (i.e., lacked antibodies) to one or more specific type, group, sub-group or strain of influenza virus sometime in their past (e.g., greater than about 1 year, greater than about 2 years, greater than about 3 years, greater than about 4 years, greater than about 5 years, etc.). The sample is then tested for the presence of anti-influenza virus antibodies to one or more type, group, sub-group or strain, of influenza virus using a nanoparticle-based assay of the present invention. If the assay indicates the presence of such antibodies, the individual is then identified as having been exposed to one or more type, group sub-group or strain, of influenza virus sometime after the test identifying them as negative for anti-influenza antibodies. Thus, one embodiment of the present invention is method to identify an individual that has been exposed to influenza virus, the method comprising:

a. contacting at least a portion of a sample from an individual being tested for anti-influenza antibodies with a nanoparticle of the present invention; and,
b. analyzing the contacted sample for the presence or level of an antibody/nanoparticle complex, wherein the presence or level of antibody/nanoparticle complex indicates the presence or level of recent anti-influenza antibodies;

c. comparing the recent anti-influenza antibody level with a past anti-influenza antibody level;

wherein an increase in the recent anti-influenza antibody level over the past anti-influenza antibody level indicates the individual has been exposed to influenza virus subsequent to determination of the past anti-influenza antibody level.

Methods of the present invention are also useful for determining the response of an individual to a vaccine. Thus, one embodiment is a method for measuring the response of an individual to an influenza vaccine, the method comprising:

a. administering to the individual a vaccine for influenza virus;

b. contacting at least a portion of a sample from the individual with a nanoparticle of the present invention;

c. analyzing the contacted sample for the presence or level of an antibody/nanoparticle complex, wherein the presence or level of antibody/nanoparticle complex indicates the presence or level of recent anti-influenza antibodies wherein an increase in the level of antibody in the sample over the pre-vaccination level of antibody in the individual indicates the vaccine induced an immune response in the individual.

The influenza vaccine administered to the individual may, but need not, comprise a vaccine of the present invention, as long as the nanoparticle comprises an HA protein that can bind an anti-influenza antibody induced by the administered vaccine. Methods of administering influenza vaccines are known to those of skill in the art.

Analysis of the sample obtained from the individual may be performed using any of the disclosed assay formats. Certain aspects of the invention, analysis of the sample is performed using an assay format selected from the group consisting of, a radial diffusion assay, an enzyme-linked immunoassay, a competitive enzyme-linked immunoassay, a radioimmunoassay, a fluorescence immunoassay, a chemiluminescent assay, a lateral flow assay, a flow-through assay, a particulate-based assay (e.g., using particulates such as, but not limited to, magnetic particles or plastic polymers, such as latex or polystyrene beads), an immunoprecipitation assay, a BioCoreJ assay (e.g., using colloidal gold), an immunodot assay (e.g., CMG Immunodot System, Fribourg, Switzerland), and an immunoblot assay (e.g., a western blot), an phosphorescence assay, a flow-through assay, a chromatography assay, a PAGE-based assay, a surface plasmon resonance assay, bio-layer interferometry assay, a spectrophotometric assay, and an electronic sensory assay.

Certain aspects of the invention, the method includes a step of determining the level of anti-influenza antibody present in the individual prior to administering the vaccine. However, it is also possible to determine the level of anti-influenza antibody present in the individual from prior medical records, if such information is available.

While not necessary to perform the disclosed method, it may be preferable to wait some period of time between the step of administering the vaccine and the step of determining the level of anti-influenza antibody in the individual. Certain aspects of the invention, determination of the level of anti-influenza antibodies present in the individual is performed at least 1 day, at least 2 days, at least 3 days, at least 4 days, at least 5 days, at least 6 days, at least one week, at least two weeks, at least three weeks, at least four weeks, at least two months, at least three months or at least six months, following administration of the vaccine.

The present invention also includes kits suitable for detecting anti-influenza antibodies. Suitable means of detection include the techniques disclosed herein, utilizing nanoparticles of the present invention. Kits may also comprise a detectable marker, such as an antibody that selectively binds to the nanoparticle, or other indicator molecules. The kit can also contain associated components, such as, but not limited to, buffers, labels, containers, inserts, tubings, vials, syringes and the like.

EXAMPLES

This example characterizes the properties and activities of five H10 variants of Group 2 HA nanoparticles, designed using the parameters and methodology disclosed herein. All of the variants were based on the human A/Jiangxi/IPB13/2013(H10N8) strain. Nucleic acid molecules encoding the H10 variants were introduced into Expi293 cells, and the cells cultured under conditions suitable for expression of the encoded variant proteins. Expressed nanoparticles were purified from cell culture supernatant using lectin affinity chromatography followed by size exclusion chromatography (SEC). Chromatograms for the purified nanoparticles are shown in FIGS. 32A-32E.

The purified nanoparticles were analyzed by negative stain electron microscopy, which indicated that individual nanoparticles were formed with the HA stems projecting outward in a periodic arrangement. A representative electron micrograph for each variant is show in FIGS. 33A-33E.

The antigenicity of the H10ssF variants was evaluated in an ELISA format by measuring affinity to HA stem antibodies FI6, CT149 and CR8020. The results of this evaluation are shown in in FIGS. 34A-34D.

Figure 35A:
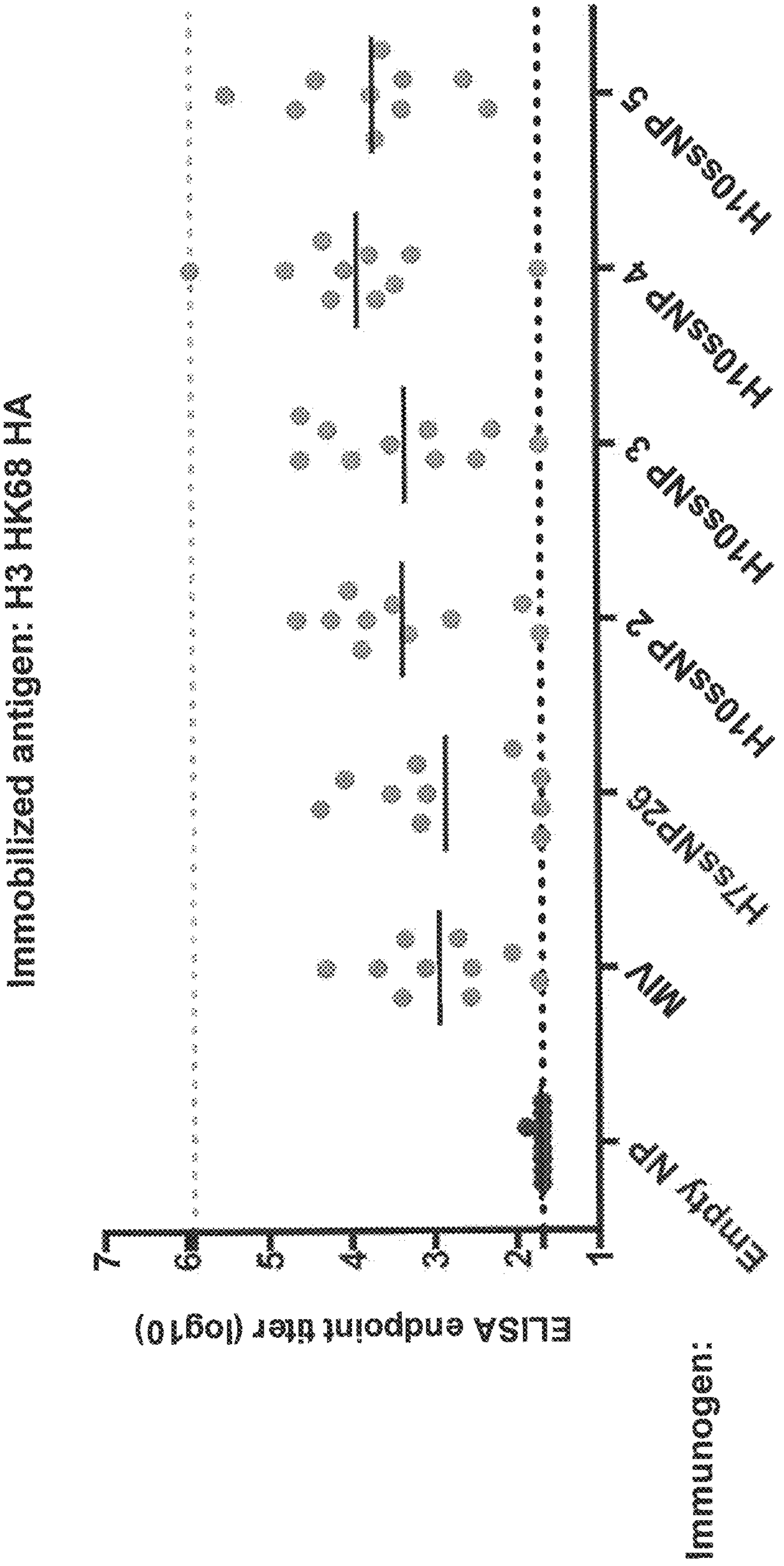
FIGS. 35A & 35B show immune responses of H10ssF-immunized mice to group 2 HAs. ELISA antibody endpoint titers of sera from BALB/c mice (n=10) immunized 3× with five different versions of S5AS-adjuvanted H10ssF (2 ug/mouse) to immobilized A/Hong Kong/1/1968 (H3N2) HA (FIG. 35A) and A/Anhui/1/2013 (H7N9) (FIG. 35B). Responses to sera from mice immunized with empty ferritin nanoparticle alone, H7N9 AH13 Monovalent inactivated vaccine (MIV) or H7ssF26 serve as controls. Geometric mean titers are shown by horizontal lines. The bottom dotted line indicates the baseline titer of 50 and the top dotted line indicates the highest value recorded.
Figure 35B:
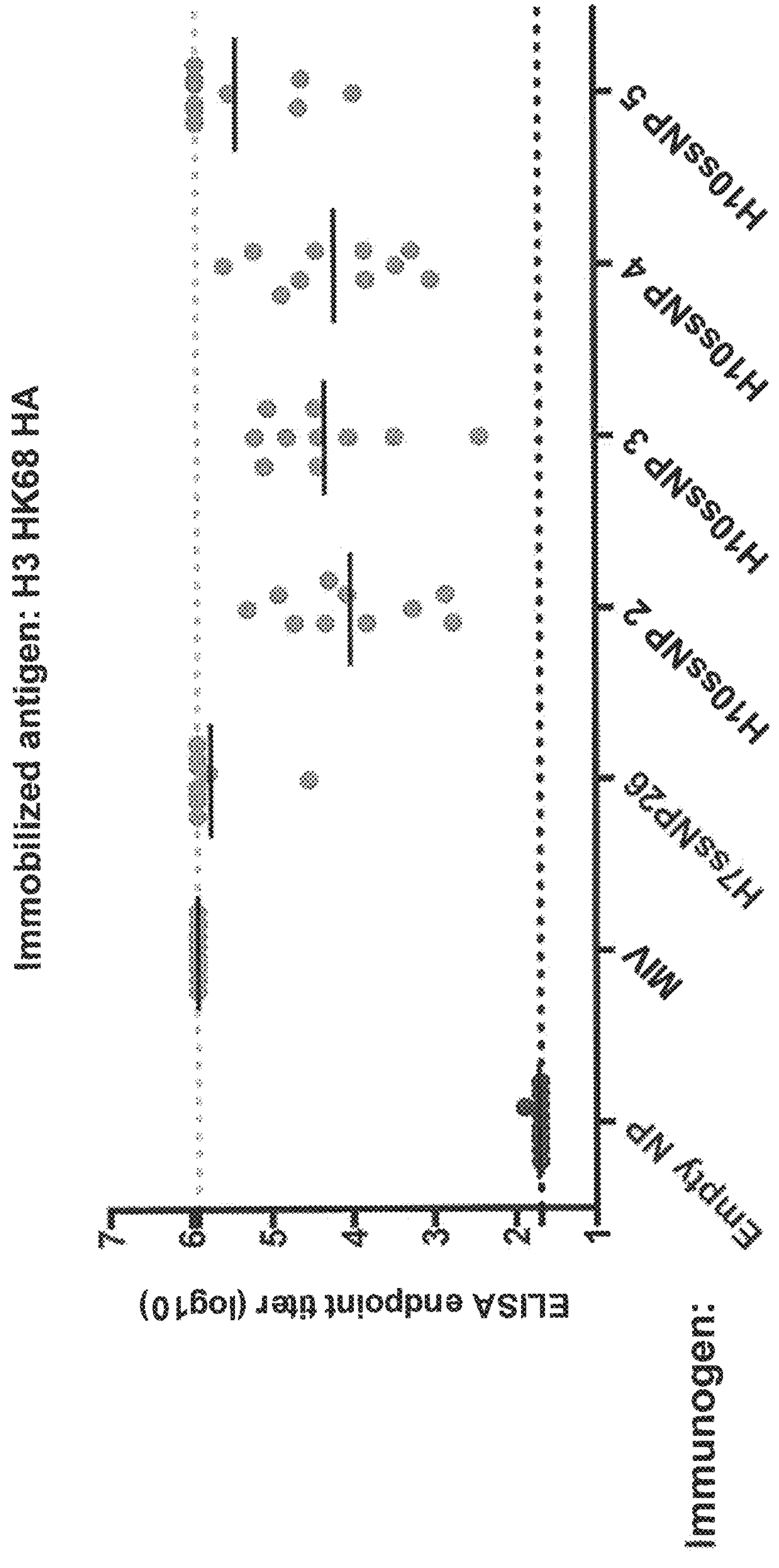
Figure 36A:
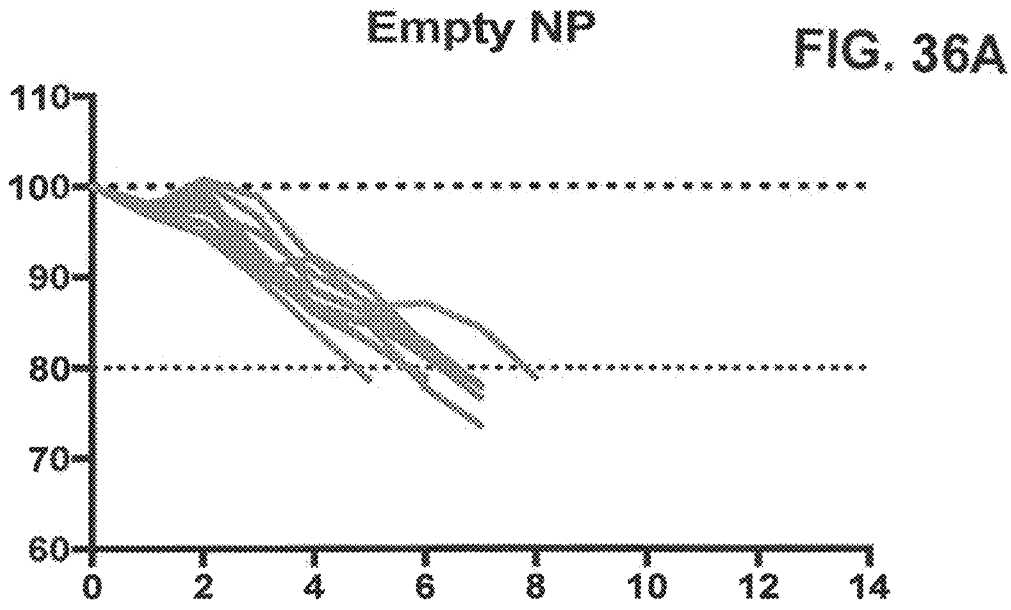
FIGS. 36A-36D show the responses of H10ssF-immunized mice to a lethal H3N2 challenge.
Figure 36B:
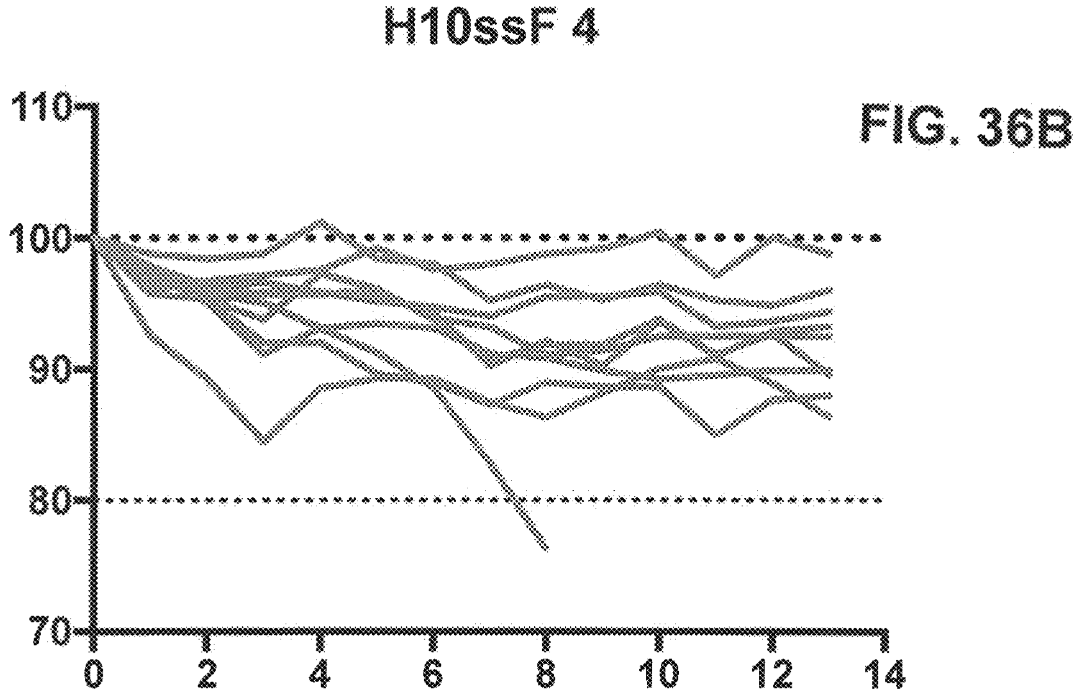
Figure 36C:
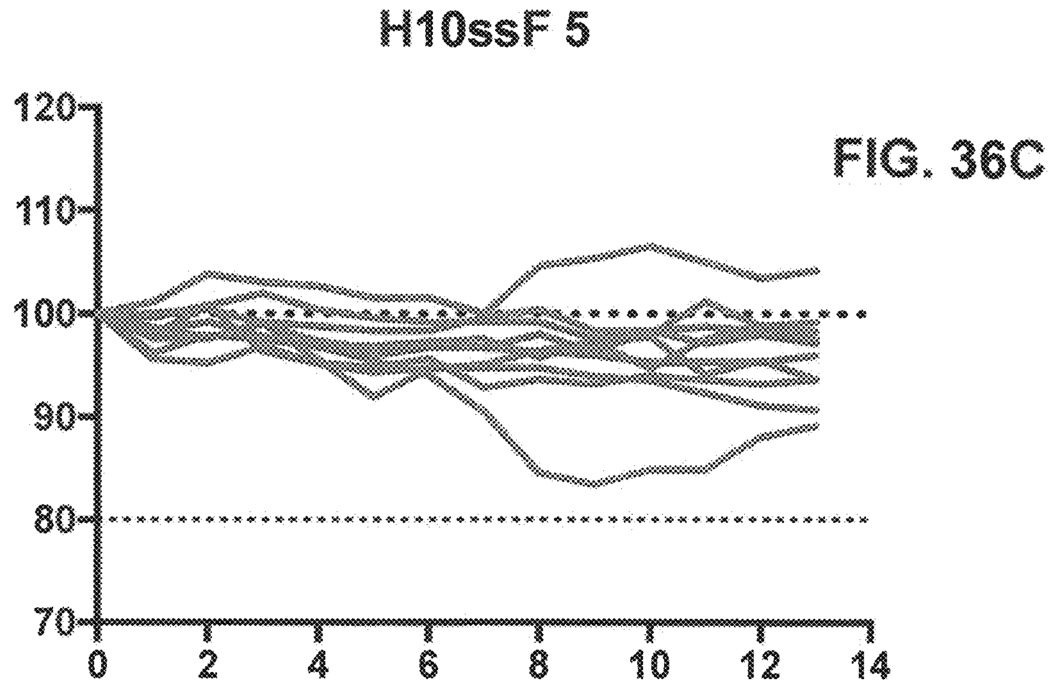
Figure 36D:
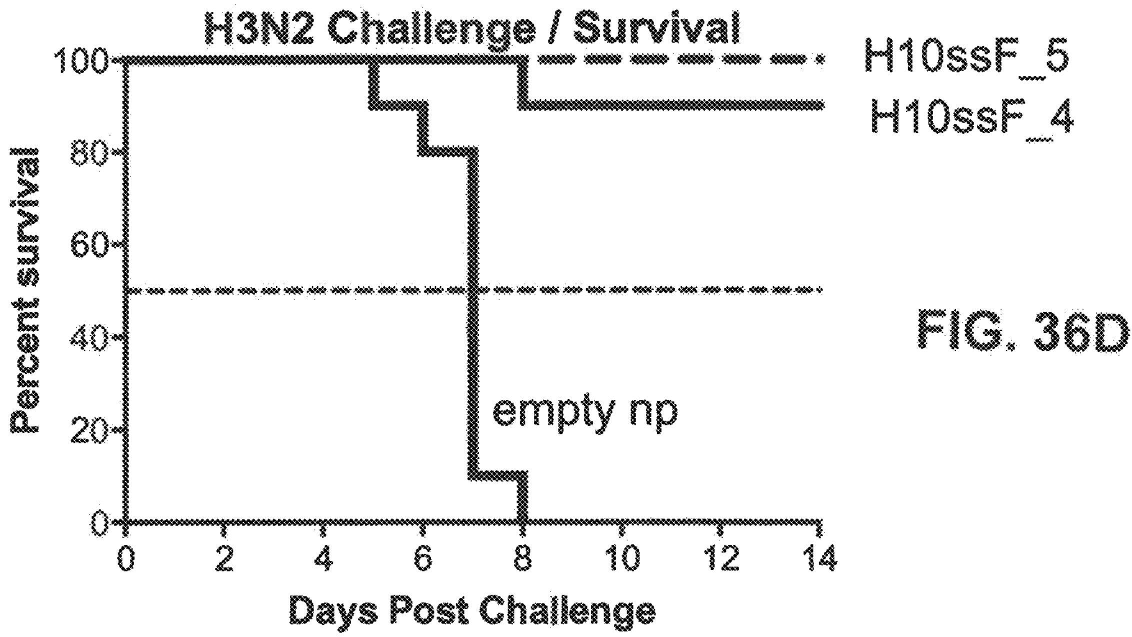
Figure 37A:
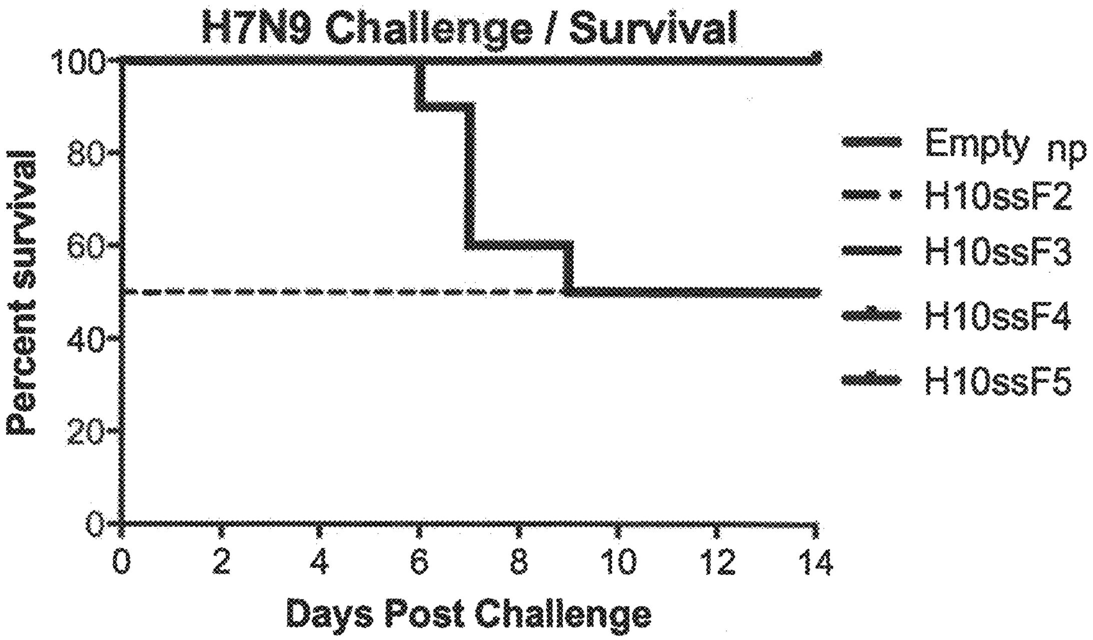
FIGS. 37A-37G show responses of H10ssF-immunized mice to a lethal H7N9 challenge.
Figure 37B:
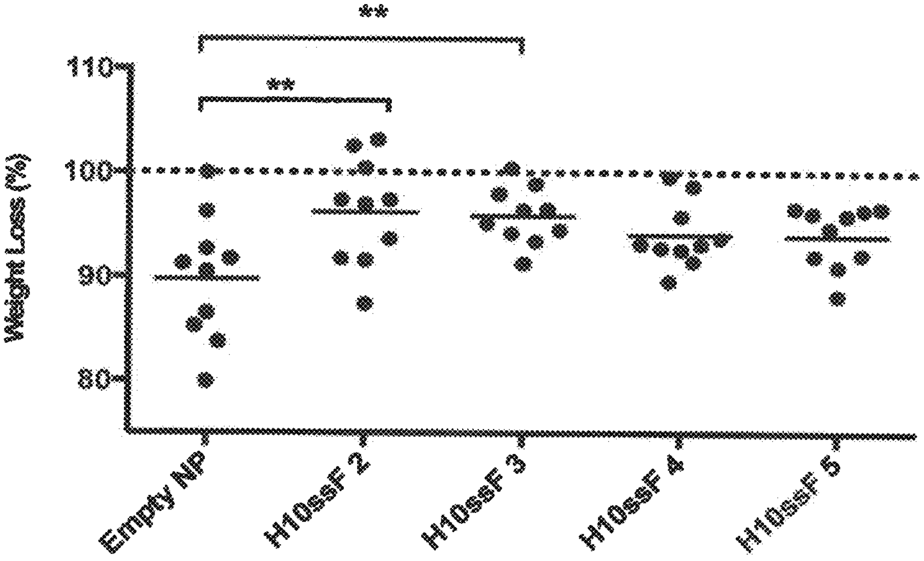
Figure 37C:
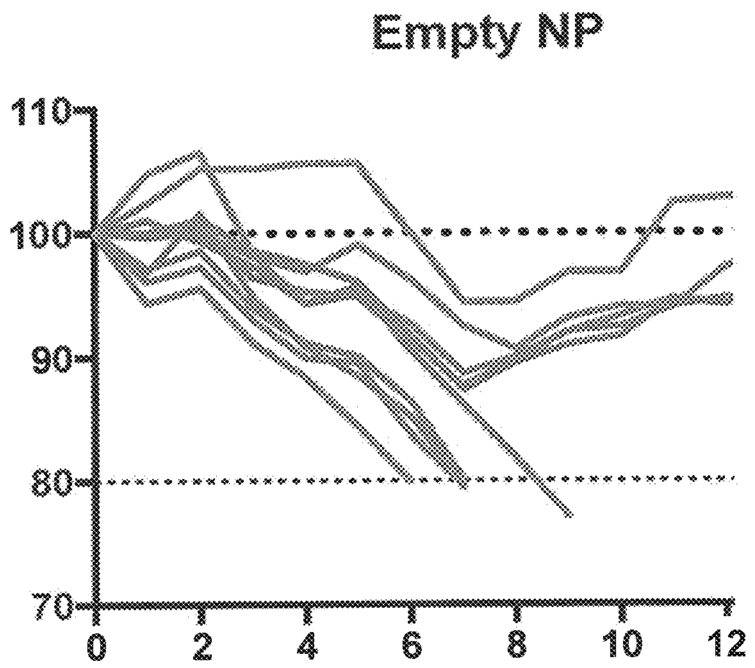
Figure 37D:
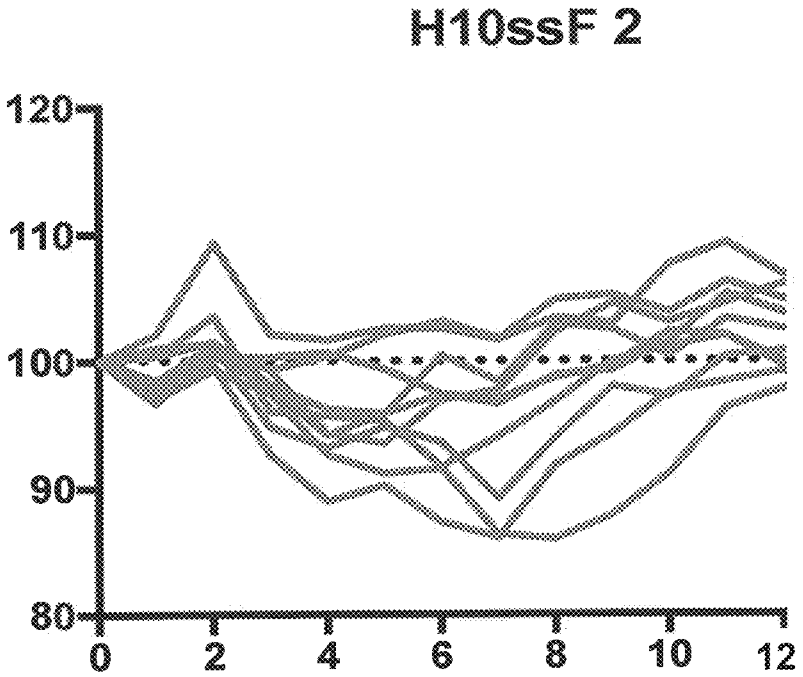
Figure 37E:
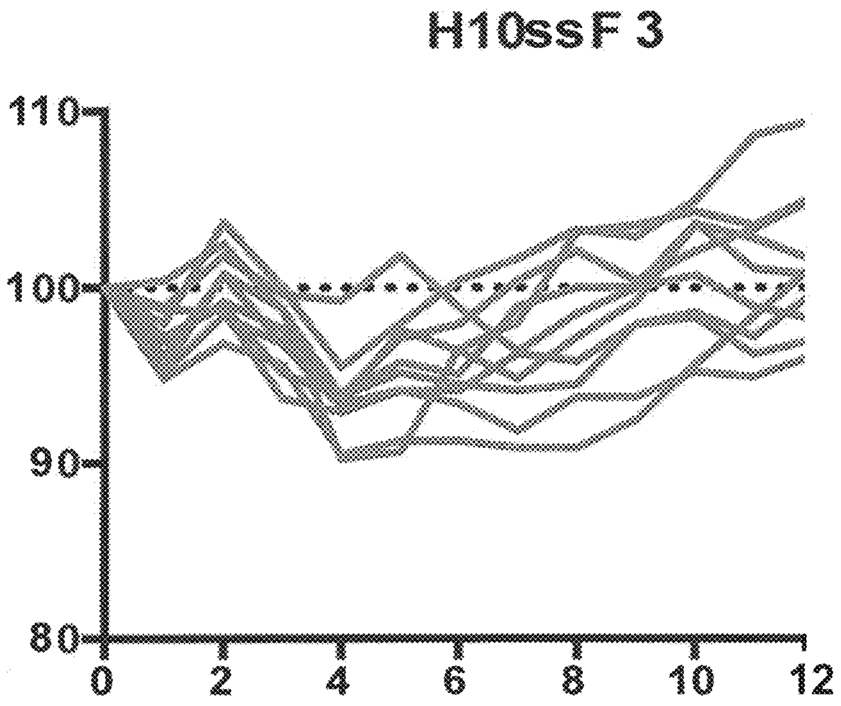
Figure 37F:
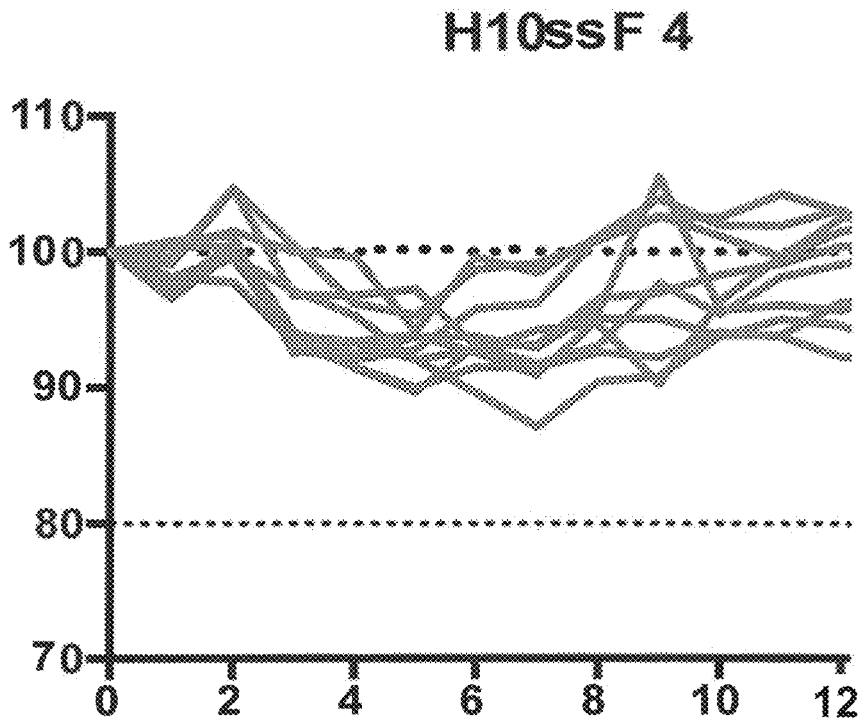
Figure 37G:
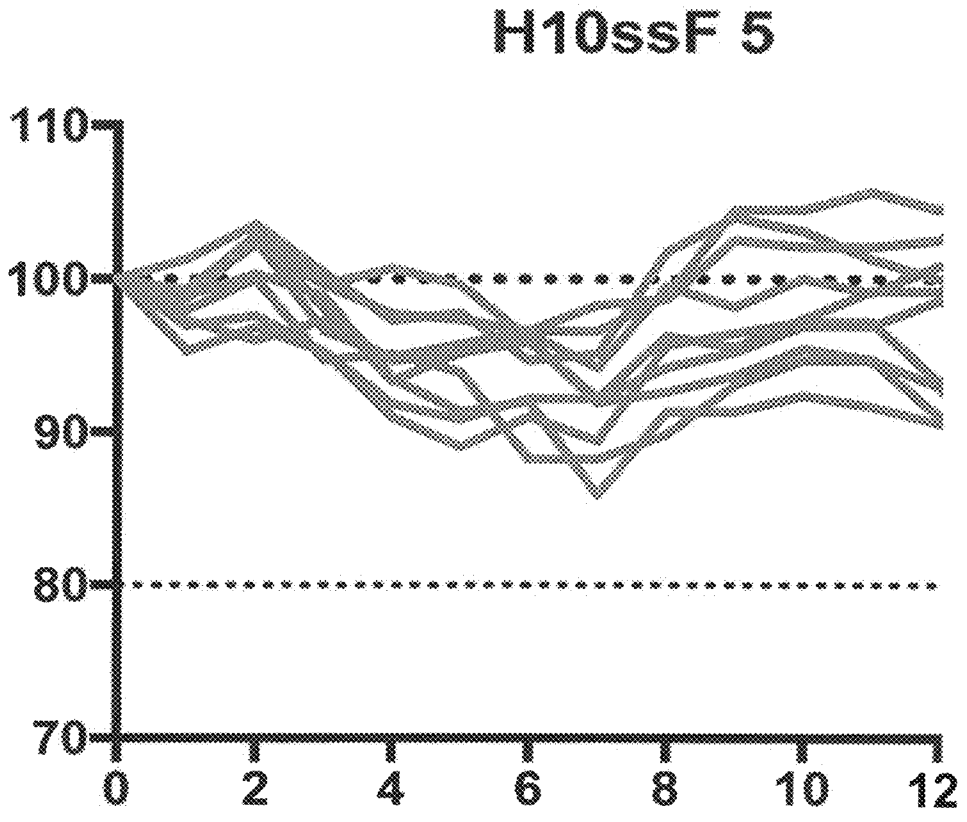
Figure 40A:
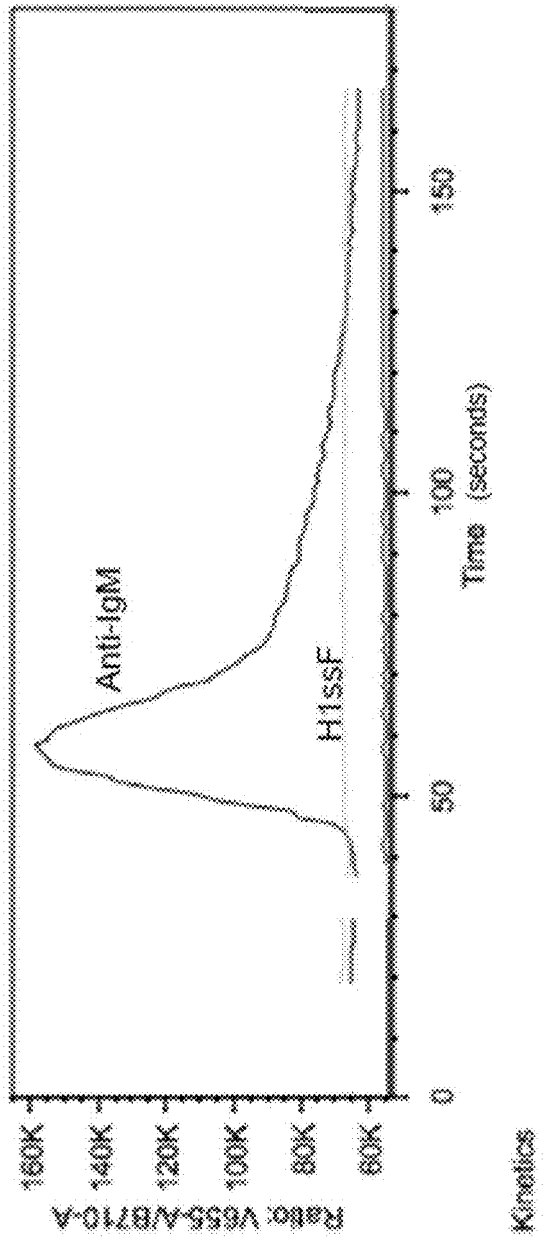
FIGS. 40A-40D show the ability of various protein constructs of the invention to activate B cells expressing germline-reverted 16.a.26 B cell receptors (BCRs). The graphs show calcium flux (indicating B-cell activation) resulting from contact of the B-cells with an anti-IgM positive control (and no activation using H1 negative control) (FIG. 40A), H3-ss-np protein constructs (FIG. 40B), H7-ss-np protein constructs (FIG. 40C), and H10ssF protein constructs (FIG. 40D).
Figure 40B:
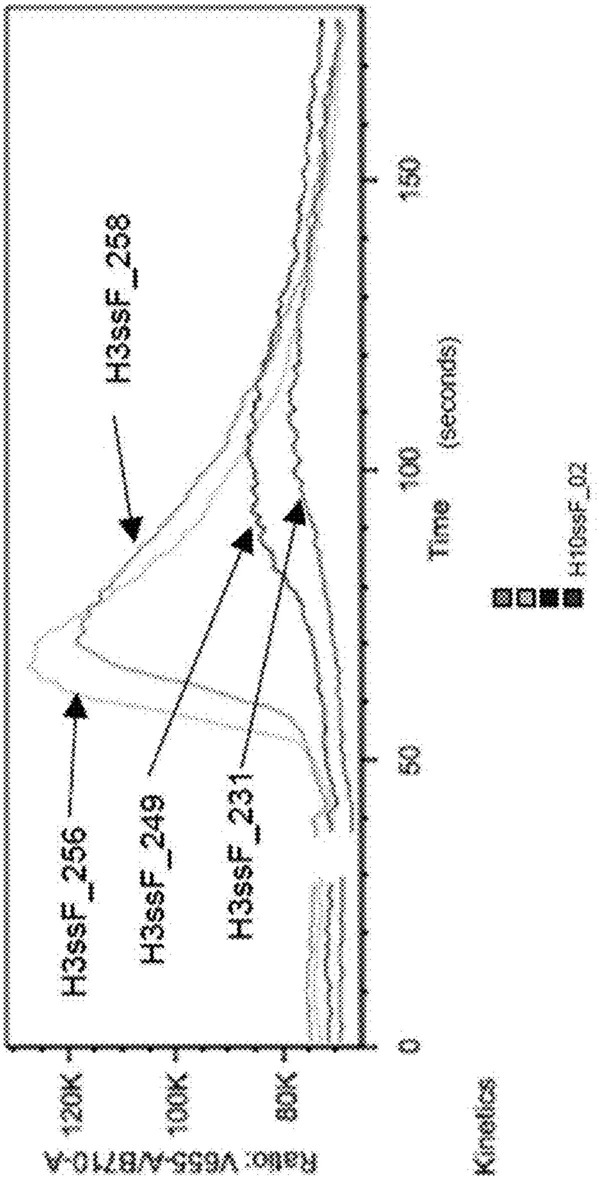
Figure 40C:
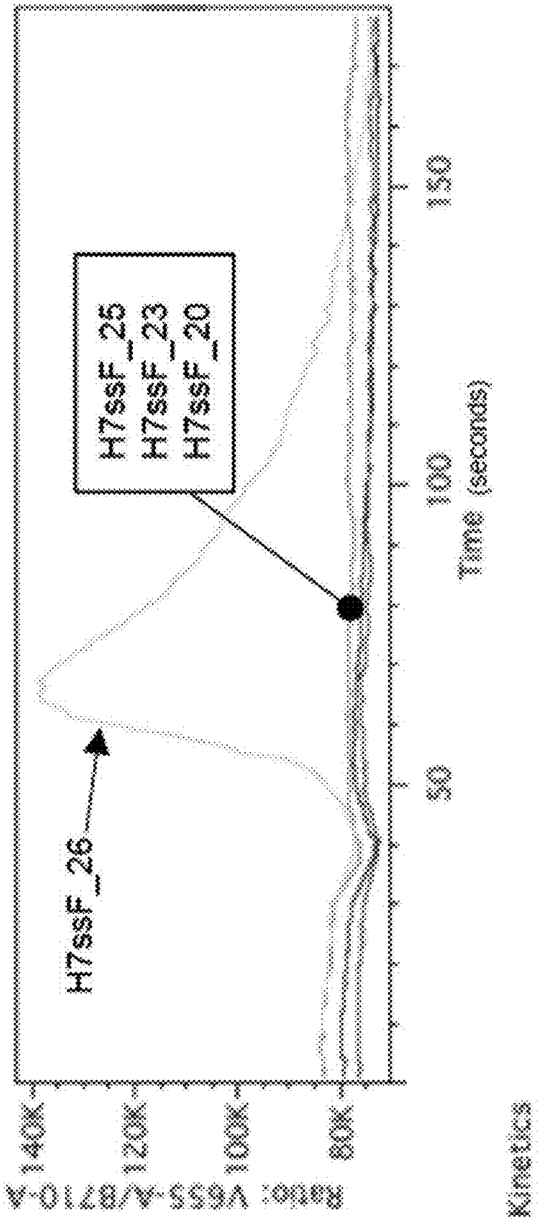
Figure 40D:
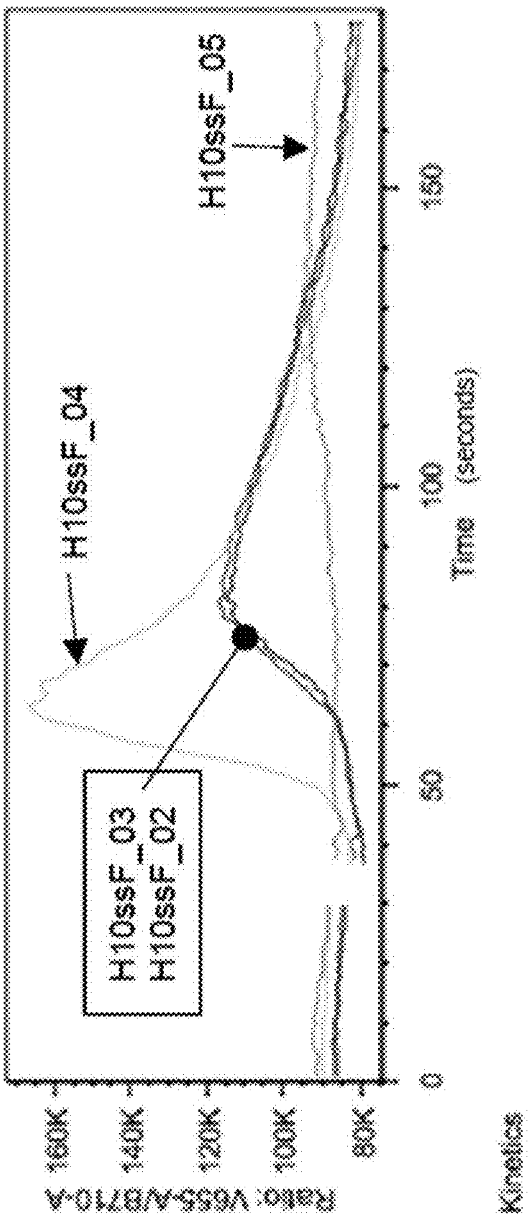

The nanoparticles were then tested for their ability to elicit an immune response against various influenza strains in mice. BALB/c mice (n=10) were immunized with 2 ug of one of the variant nanoparticles using SAS adjuvant. The immunization was repeated 2 more times at periodic intervals. 2 weeks after the last immunization, sera was collected and tested (by ELISA) for its ability to recognize HA protein from H3N2 and H7N9. The results, which are illustrated in FIGS. 35A & 35B, demonstrate that the sera was cross-reactive for both H3N2 and H7N9 HA protein.

The immunized mice were then challenged with a lethal dose of H3N2 (A/Philippines/1982) or H7N9 (A/Shanghai/2/2013-like), and weight loss and survival monitored. The results, which are shown in FIGS. 36A-36D and FIGS. 37A-37G, showed that immunization with the variants nanoparticles protected against both challenge strains without significant weight loss. These results demonstrate that H10ssF immunogens can provide heterosubtypic protection against H3N2 and H7N9 strains.

It has been shown that the human, broadly neutralizing stem monoclonal antibody (mAb) 16.a.26), which uses a VH1-18 v-gene, can potently neutralize both group 1 and group 2 influenza viruses. Thus, several HA-SS-np variants, including H3N2, H7N9 and H10N8 subtypes, were evaluated for their ability to activate B cells expressing a germline-reverted version of mAb 16.a.26. In the assay, activation of B-cells is indicated by Ca++ flux. The results of this evaluation, which are shown in FIG. 40, show that the variant nanoparticles H3ssF_256, H7ssF_26 and H10ssF_04 each resulted high levels of activation similar to that observed by the IgM positive control. As shown in FIG. 41, all three of these designs share the same helix A C-terminal extension (ELMEQ), suggesting that this particular motif is useful for eliciting a 16.a.26 bNAb response against influenza HA proteins.

What is claimed:

1. A protein construct comprising a Group 2 influenza hemagglutinin (HA) stabilized stem protein, wherein:
- a head region of the HA stabilized stem protein is replaced with a linker sequence;
- a helix A in a stem region of the HA stabilized stem protein is extended in length by the addition of helix-forming amino acid residues, thereby improving the stability of the HA stabilized stem protein; and
- the HA stabilized stem protein comprises an amino acid sequence at least 80% identical to the HA stabilized stem of SEQ ID NO: 49.

2. The protein construct of claim 1, wherein the linker sequence replacing the head region is less than 10 amino acids in length.

3. The protein construct of claim 1, wherein an inter-helix loop in the stem region of the HA stabilized stem protein is replaced with a linker sequence.

4. The protein construct of claim 3, wherein the linker sequence replacing the interhelix loop comprises the amino acid sequence set forth as GGPD (SEQ ID NO: 39).

5. The protein construct of claim 1, wherein the helix A in the stem region of the HA stabilized stem protein is extended in length by the addition of five helix-forming amino acid residues.

6. The protein construct of claim 5, wherein the helix A in the stem region of the HA stabilized stem protein is extended relative to helix A of a wild-type HA protein by the addition of ALMAQ (SEQ ID NO: 36) or ELMEQ (SEQ ID NO: 37).

7. The protein construct of claim 1, wherein the HA stabilized stem protein comprises one or more mutations that form, or strengthen, an ionic interaction or a salt bridge within the HA stabilized stem protein.

8. The protein construct of claim 1, wherein the HA stabilized stem protein comprises one or more mutations that increases hydrophobic packing within the HA stabilized stem protein.

9. The protein construct of claim 1, wherein the HA stabilized stem protein comprises an amino acid sequence at least 90% identical to the HA stabilized stem region of SEQ ID NO: 49.

10. The protein construct of claim 1, wherein the HA stabilized stem protein comprises an amino acid sequence at least 95% identical to the HA stabilized stem region of SEQ ID NO: 49.

11. The protein construct of claim 1, wherein the HA stabilized stem protein comprises an amino acid sequence set forth as any one of SEQ ID NO: 47-159.

12. A nanoparticle vaccine comprising the protein construct of claim 1.

13. A pharmaceutical composition comprising the protein construct of claim 1.

14. A method of vaccination, comprising administering a prophylactically or therapeutically effective amount of the protein construct of claim 1 to a subject.

15. The protein construct of claim 1, wherein the HA stabilized stem protein comprises an amino acid sequence at least 80% identical to the HA stabilized stem of SEQ ID NO: 49.

16. The protein construct of claim 1, wherein the HA stabilized stem protein comprises an amino acid sequence at least 99% identical to the HA stabilized stem of SEQ ID NO: 49.

* * * * *